(12) United States Patent

Kajino et al.

(10) Patent No.: US 8,933,105 B2
(45) Date of Patent: *Jan. 13, 2015

(54) PYRROLE COMPOUNDS

(75) Inventors: Masahiro Kajino, Osaka (JP); Haruyuki Nishida, Osaka (JP); Yasuyoshi Arikawa, Osaka (JP); Keizo Hirase, Osaka (JP); Koji Ono, Tsukuba (JP)

(73) Assignee: Takeda Pharmaceutical Company Limited, Osaka-Shi (JP)

( * ) Notice: Subject to any disclaimer, the term of this patent is extended or adjusted under 35 U.S.C. 154(b) by 1417 days.

This patent is subject to a terminal disclaimer.

(21) Appl. No.: 12/072,421

(22) Filed: Feb. 26, 2008

(65) Prior Publication Data

US 2008/0262042 A1    Oct. 23, 2008

(30) Foreign Application Priority Data

Feb. 28, 2007  (JP) ................. 2007-050326
Sep. 28, 2007  (JP) ................. 2007-256272

(51) Int. Cl.
*C07D 401/04*   (2006.01)
*A61K 31/4439*  (2006.01)

(52) U.S. Cl.
CPC .................. *C07D 401/04* (2013.01)
USPC .......................... 514/333; 546/256

(58) Field of Classification Search
USPC .......................... 546/256; 514/333
See application file for complete search history.

(56) References Cited

U.S. PATENT DOCUMENTS

| 5,286,742 | A | 2/1994 | Henegar et al. |
| 5,480,902 | A | 1/1996 | Addor et al. |
| 6,365,620 | B2 | 4/2002 | Eberle et al. |
| 2002/0193410 | A1 | 12/2002 | Burns et al. |
| 2007/0060623 | A1 | 3/2007 | Kajino et al. |
| 2008/0139639 | A1 | 6/2008 | Kajino et al. |

FOREIGN PATENT DOCUMENTS

| EP | 0259085 | 3/1988 |
| EP | 0464845 | 1/1992 |
| EP | 0538231 | 4/1993 |
| EP | 0597291 | 5/1994 |
| EP | 1061075 | 12/2000 |
| EP | 1176139 | 1/2002 |
| EP | 1284260 A1 | 2/2003 |
| EP | 1432693 | 6/2004 |
| EP | 1466902 A1 | 10/2004 |
| EP | 1477489 A1 | 11/2004 |
| EP | 1655284 | 5/2006 |
| EP | 1803709 | 7/2007 |
| EP | 1803709 A1 | 7/2007 |
| JP | 63-63678 | 3/1988 |
| JP | 08-119936 | 5/1996 |
| JP | 9-30967 | 2/1997 |
| JP | 11-209344 | 8/1999 |
| JP | 2004-315511 | 11/2004 |
| WO | WO 92/04025 | 3/1992 |
| WO | WO 93/09100 | 5/1993 |
| WO | WO 98/08815 | 3/1998 |
| WO | WO98/28269 | 7/1998 |
| WO | WO 00/58285 | 10/2000 |
| WO | WO 02/02524 | 1/2002 |
| WO | WO 02/02554 | 1/2002 |
| WO | WO 03/028641 | 4/2003 |
| WO | WO 03/040147 | 5/2003 |
| WO | WO03/044011 | 5/2003 |
| WO | WO 03/068738 | 8/2003 |
| WO | WO 03/068740 | 8/2003 |
| WO | WO 03/070729 | 8/2003 |
| WO | WO 03/106427 | 12/2003 |
| WO | WO 2004/014368 | 2/2004 |

(Continued)

OTHER PUBLICATIONS

Ichikawa, Junji, et al. "5-endo Heck-type cyclization of 2-(trifluoromethyl)allyl ketone oximes: synthesis of 4-difluoromethylene-substituted 1-pyrrolines", Chemical Communications, Nov. 13, 2006, No. 42, pp. 4425-4427, XP 002513503, ISSN: 1359-7345.

(Continued)

*Primary Examiner* — Patricia L Morris
(74) *Attorney, Agent, or Firm* — Edwards Wildman Palmer LLP; David G. Conlin

(57) ABSTRACT

The present invention provides a compound having a superior acid secretion inhibitory effect and showing an antiulcer activity, which is represented by the formula (I)

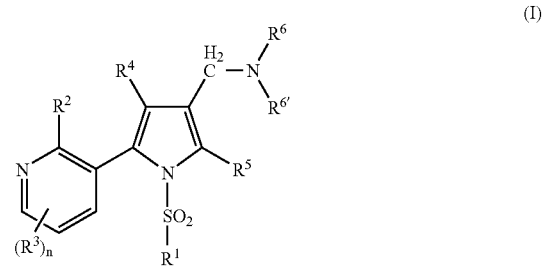

wherein $R^1$ is an optionally substituted cyclic group, $R^2$ is a substituent, $R^3$ is an optionally substituted alkyl group, an acyl group, an optionally substituted hydroxy group, an optionally substituted amino group, a halogen atom, a cyano group or a nitro group, $R^4$ and $R^5$ are each a hydrogen atom, an optionally substituted alkyl group, an acyl group, an optionally substituted hydroxy group, an optionally substituted amino group, a halogen atom, a cyano group or a nitro group, $R^6$ and $R^{6'}$ are each a hydrogen atom or an alkyl group, and n is an integer of 0-3, or a salt thereof.

9 Claims, No Drawings

(56) References Cited

FOREIGN PATENT DOCUMENTS

| WO | WO2004/103968 A1 | 12/2004 |
|---|---|---|
| WO | WO-2004103968 | 12/2004 |
| WO | WO-2006036024 | 4/2006 |
| WO | WO-2007/026916 | 3/2007 |
| WO | WO2007/114338 | 10/2007 |

OTHER PUBLICATIONS

Trost, Barry, et al. "A[3+2] and [4+3] Cycloaddition Approach to N-Heterocycles via Pd-Catalyzed TMM Reactions with Imines", J. Am. Chemical Soc., 1993, vol. 115, No. 15, pp. 6636-6645, XP 002141041, ISSN: 0002-7863.

Trost, Barry, et al. "A Selectivity Control Element for Palladium-Catalyzed Trimethylenemethane Cycloaddition" J. Am. Chemical Soc., 1991, vol. 113, pp. 9007-9009, XP 002513504, ISSN: 0002-7863.

Osipov, Sergej, at al. "A radical pathway to α-difluoromethylene containing prolines and α-aminoadipic acids" Tetrahedron Letters, 2000, vol. 41, No. 30, pp. 5659-5662, XP 004209533, ISSN: 0040-4039.

International Search Report for corresponding International Application No. PCT/JP2008/053890 (6" pages).

P. W. Shum, "A convenient method for the synthesis of unsymmetrical 3,4-disbustituted pyrroles," Tetrahedron Letters, vol. 31, No. 47, pp. 6785-6788 (1990).

K. Okabe et al., "The Second Generation Synthesis of a Tumor Promoter Pendolmycin," Tetrahedron, vol. 47, No. 36, pp. 7615-7624 (1991).

Banker, et al., "Modern Pharmaceutics, 3ed," Marcel Dekker, New York, 1996, pp. 451 and 596.

Wolff, Manfred E., "Burger's Medicinal Chemistry, 5ed, Part I" John Wiley & Sons, 1995, pp. 975-977.

Merck Manual about Stomach Cancer, Dec. 2007.

Medical Encyclopedia: Zollinger-Ellison syndrome [online], [retrieved on Aug. 27, 2007]. Retrieved from the Internet, URL; http://www.nlm.nih.gov/medlineplus/print/ency/article/000325.htm.

Stomach Cancer [online], [retrieved on Aug. 27, 2007]. Retrieved from the Internet, URL; http://www.nlm.nih.gov/medlineplus/print/stomachcancer.html.

http://en.wikipedia.org/wiki/Gastric_cancer [online], [retrieved on Dec. 28, 2006]. Retrieved from the Internet, URL; http://en.wikipedia.org/wiki/Sjogren's_syndrome.

Obach, R. Drug-Drug Interactions: An Important Negative Attribute in Drugs. Drugs of Today. (2003), 39, 301-338.

Artico, et al., "Strucutre-Based Design, Synthesis, and Biological Evaluation of Novel Pyrrolyl Aryl Sulfones: HIV-1 Non-Nucleoside Reverse Transcriptase Inhibitors Active at Nanomolar Concentrations," J. Med. Chem., XP002544396, 43:1886-1891 (2000).

PYRROLE COMPOUNDS

TECHNICAL FIELD

The present invention relates to pyrrole compounds having an acid secretion suppressive activity.

BACKGROUND ART

Proton pump inhibitors represented by omeprazole, which suppress secretion of gastric acid for the treatment of peptic ulcer, reflux esophagitis and the like, have been widely used in clinical situations. However, the existing proton pump inhibitors are associated with problems in terms of effect and side effects. To be specific, since the existing proton pump inhibitors are unstable under acidic conditions, they are often formulated as enteric preparations, in which case several hours are required before expression of the effect, and about 5 days to exhibit maximum efficacy by consecutive administration. In addition, since the existing proton pump inhibitors show inconsistent treatment effects due to metabolic enzyme polymorphism and drug interaction with pharmaceutical agents such as diazepam and the like, an improvement has been desired.

As pyrrole compounds having a proton pump inhibitory action, patent reference 1 describes a compound represented by the formula:

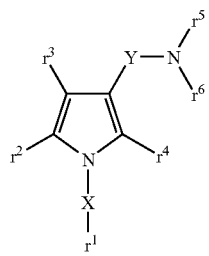

wherein X and Y are the same or different and each is a bond or a spacer having 1 to 20 atoms in the main chain, $r^1$ is an optionally substituted hydrocarbon group or an optionally substituted heterocyclic group, $r^2$, $r^3$ and $r^4$ are the same or different and each is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, and $r^5$ and $r^6$ are the same or different and each is a hydrogen atom or an optionally substituted hydrocarbon group.

In addition, as a therapeutic drug for neoplastic diseases or autoimmune diseases, patent reference 2 describes a compound represented by the formula:

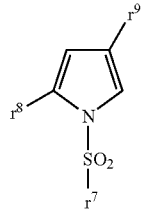

wherein $r^7$ is aryl, aralkyl, heteroaryl or the like, $r^8$ is aryl, heteroaryl or the like, and $r^9$ is aryl, heteroaryl, optionally substituted aminomethyl or the like.
[Patent reference 1] WO 2006/036024
[Patent reference 2] WO 2004/103968

DISCLOSURE OF THE INVENTION

Problems to be Solved by the Invention

A pharmaceutical agent that effectively suppresses gastric acid secretion as known proton pump inhibitors, which is improved in instability under acidic conditions, dispersion of effects due to metabolic enzyme polymorphism and drug interaction, which are problems of known proton pump inhibitors, is expected to show more superior treatment effect on peptic ulcer, reflux esophagitis and the like. As the situation stands, however, a proton pump inhibitor capable of sufficiently satisfying these requirements has not been found. It is therefore an object of the present invention to provide a compound having a superior acid secretion suppressive effect (particularly, proton pump inhibitory effect), which has been improved in these problems.

Means of Solving the Problems

The present inventors have conducted various studies and found that a compound represented by the formula (I):

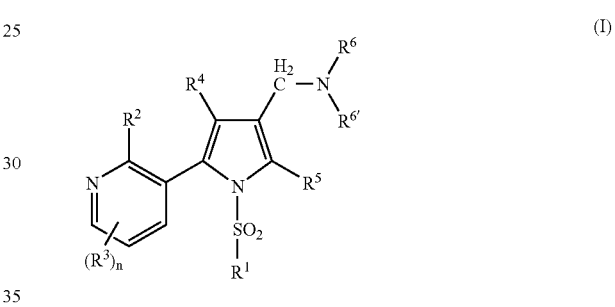

or a salt thereof [hereinafter to be sometimes abbreviated as compound (I)] unexpectedly has a very strong proton pump inhibitory effect, and is fully satisfactory as a pharmaceutical agent, which resulted in the completion of the present invention.

Accordingly, the present invention relates to the following.
[1] A compound represented by the formula (I)

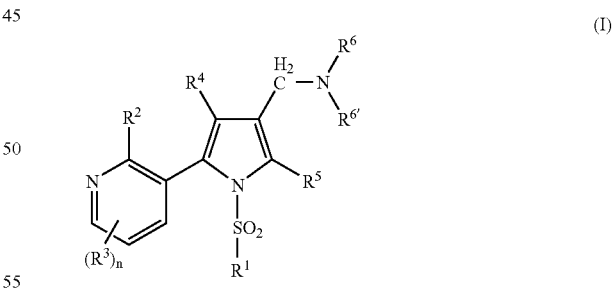

wherein $R^1$ is an optionally substituted cyclic group, $R^2$ is a substituent, $R^3$ is an optionally substituted alkyl group, an acyl group, an optionally substituted hydroxy group, an optionally substituted amino group, a halogen atom, a cyano group or a nitro group, $R^4$ and $R^5$ are the same or different and each is a hydrogen atom, an optionally substituted alkyl group, an acyl group, an optionally substituted hydroxy group, an optionally substituted amino group, a halogen atom, a cyano group or a nitro group, $R^6$ and $R^{6'}$ are the same or different and each is a hydrogen atom or an alkyl group, and n is an integer of 0 to 3, provided that 1-[5-(2-fluoropyridin- 3-yl)-1-(pyridin-3-ylsulfonyl)-1H-pyrrol-3-yl]-N-methyl-methanamine, 1-[5-(2-chloropyridin-3-yl)-1-(pyridin-3-yl-sulfonyl)-1H-pyrrol-3-yl]-N-methylmethanamine, 1-{5-(2-fluoropyridin-3-yl)-1-[(6-methoxypyridin-3-yl)sulfonyl]-1H-pyrrol-3-yl}-N-methylmethanamine, N-methyl-1-[5-(2-methylpyridin-3-yl)-1-(pyridin-3-ylsulfonyl)-1H-pyrrol-3-yl]methanamine, 1-{5-(2-fluoropyridin-3-yl)-1-[(6-methylpyridin-3-yl)sulfonyl]-1H-pyrrol-3-yl}-N-methylmethanamine, and 1-[4-chloro-5-(2-fluoropyridin-3-yl)-1-(pyridin-3-ylsulfonyl)-1H-pyrrol-3-yl]-N-methylmethanamine are excluded, or a salt thereof.

[2] The compound of the above-mentioned [1], wherein $R^1$ is an optionally substituted aryl group or an optionally substituted heteroaryl group, $R^2$ is a substituent, $R^3$ is an alkyl group optionally substituted by halogen, an acyl group, a halogen atom, a cyano group or a nitro group, $R^4$ and $R^5$ are the same or different and each is a hydrogen atom, an alkyl group optionally substituted by halogen, an acyl group, a halogen atom, a cyano group or a nitro group, $R^6$ is an alkyl group, $R^{6'}$ is a hydrogen atom, and n is an integer of 0 to 3.

[3] The compound of the above-mentioned [1], wherein $R^1$ is an optionally substituted phenyl group, an optionally substituted furyl group, an optionally substituted thienyl group, an optionally substituted pyridyl group, an optionally substituted pyrazolyl group, an optionally substituted imidazolyl group or an optionally substituted thiazolyl group.

[4] The compound of the above-mentioned [1], wherein $R^1$ is an optionally substituted furyl group, an optionally substituted pyridyl group or an optionally substituted pyrazolyl group.

[5] The compound of the above-mentioned [1], wherein $R^1$ is an optionally substituted pyridyl group.

[6] The compound of the above-mentioned [1], wherein the substituent for $R^2$ is an electron withdrawing group.

[7] The compound of the above-mentioned [6], wherein the electron withdrawing group is a halogen atom, a cyano group, an acyl group or a trifluoromethyl group.

[8] The compound of the above-mentioned [1], wherein $R^4$ and $R^5$ are the same or different and each is a hydrogen atom or a halogen atom.

[9] The compound of the above-mentioned [1], wherein $R^6$ is a methyl group.

[10] The compound of the above-mentioned [1], wherein n is 0.

[11] 1-[5-(2-Fluoropyridin-3-yl)-1-(phenylsulfonyl)-1H-pyrrol-3-yl]-N-methylmethanamine or a salt thereof, 1-[4-fluoro-5-(2-fluoropyridin-3-yl)-1-(pyridin-3-ylsulfonyl)-1H-pyrrol-3-yl]-N-methylmethanamine or a salt thereof, 1-[5-(2-chloropyridin-3-yl)-1-(phenylsulfonyl)-1H-pyrrol-3-yl]-N-methylmethanamine or a salt thereof, 3-{4-[(methylamino)methyl]-1-(phenylsulfonyl)-1H-pyrrol-2-yl}pyridine-2-carbonitrile or a salt thereof, or 1-{1-[(4-fluorophenyl)sulfonyl]-5-(2-fluoropyridin-3-yl)-1H-pyrrol-3-yl}-N-methylmethanamine or a salt thereof.

[12] 1-[4-Fluoro-5-(2-fluoropyridin-3-yl)-1-(phenylsulfonyl)-1H-pyrrol-3-yl]-N-methylmethanamine or a salt thereof, 1-[4-fluoro-5-(2-fluoropyridin-3-yl)-1-(3-furylsulfonyl)-1H-pyrrol-3-yl]-N-methylmethanamine or a salt thereof, 1-{4-fluoro-5-(2-fluoropyridin-3-yl)-1-[(2-methylfuran-3-yl)sulfonyl]-1H-pyrrol-3-yl}-N-methylmethanamine or a salt thereof, 1-[1-{[1-(difluoromethyl)-1H-pyrazol-4-yl]sulfonyl}-4-fluoro-5-(2-fluoropyridin-3-yl)-1H-pyrrol-3-yl]-N-methylmethanamine or a salt thereof, or 1-[4-fluoro-5-(2-fluoropyridin-3-yl)-1-(pyridin-2-ylsulfonyl)-1H-pyrrol-3-yl]-N-methylmethanamine or a salt thereof.

[13] A prodrug of the compound of the above-mentioned [1].

[14] A pharmaceutical composition comprising the compound of the above-mentioned [1] or a prodrug thereof.

[15] The pharmaceutical composition of the above-mentioned [14], which is an acid secretion inhibitor.

[16] The pharmaceutical composition of the above-mentioned [14], which is a potassium-competitive acid blocker.

[17] The pharmaceutical composition of the above-mentioned [14], which is an agent for the prophylaxis or treatment of peptic ulcer, Zollinger-Ellison syndrome, gastritis, reflux esophagitis, symptomatic gastroesophageal reflux disease (symptomatic GERD), Barrettesophagus, functional dyspepsia, gastric cancer, stomach MALT lymphoma, or ulcer caused by non-steroidal anti-inflammatory agent, gastric hyperacidity or ulcer due to postoperative stress; or an inhibitor of upper gastrointestinal hemorrhage due to peptic ulcer, acute stress ulcer, hemorrhagic gastritis or invasive stress.

[18] A method of treating or preventing peptic ulcer, Zollinger-Ellison syndrome, gastritis, reflux esophagitis, symptomatic gastroesophageal reflux disease (symptomatic GERD), Barrettesophagus, functional dyspepsia, gastric cancer, stomach MALT lymphoma, or ulcer caused by non-steroidal anti-inflammatory agent, gastric hyperacidity or ulcer due to postoperative stress; or a method of inhibiting upper gastrointestinal hemorrhage due to peptic ulcer, acute stress ulcer, hemorrhagic gastritis or invasive stress, which comprises administering an effective amount of the compound of the above-mentioned [1] or a prodrug thereof to a mammal.

[19] Use of the compound of the above-mentioned [1] or a prodrug thereof for the production of an agent for the prophylaxis or treatment of peptic ulcer, Zollinger-Ellison syndrome, gastritis, reflux esophagitis, symptomatic gastroesophageal reflux disease (symptomatic GERD), Barrettesophagus, functional dyspepsia, gastric cancer, stomach MALT lymphoma, or ulcer caused by non-steroidal anti-inflammatory agent, gastric hyperacidity or ulcer due to postoperative stress; or an inhibitor of upper gastrointestinal hemorrhage due to peptic ulcer, acute stress ulcer, hemorrhagic gastritis or invasive stress.

[20] The compound of the above-mentioned [1] or a prodrug thereof to be used for a method of treating or preventing peptic ulcer, Zollinger-Ellison syndrome, gastritis, reflux esophagitis, symptomatic gastroesophageal reflux disease (symptomatic GERD), Barrettesophagus, functional dyspepsia, gastric cancer, stomach MALT lymphoma, or ulcer caused by non-steroidal anti-inflammatory agent, gastric hyperacidity or ulcer due to postoperative stress; or a method of inhibiting upper gastrointestinal hemorrhage due to peptic ulcer, acute stress ulcer, hemorrhagic gastritis or invasive stress.

[21] A compound represented by the formula

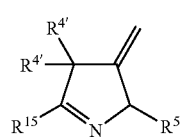

wherein $R^{4'}$ is a halogen atom, $R^5$ is a hydrogen atom, an optionally substituted alkyl group, an acyl group, an optionally substituted hydroxy group, an optionally substituted amino group, a halogen atom, a cyano group or a nitro group, and $R^{15}$ is an optionally substituted hydrocarbon group or an optionally substituted heterocyclic group, or a salt thereof.

[22] A compound represented by the formula

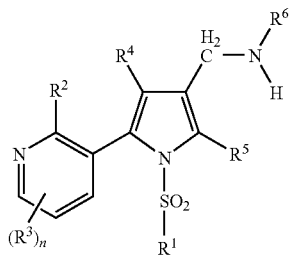

wherein $R^1$ is an optionally substituted aryl group or an optionally substituted heteroaryl group, $R^2$ is a substituent, $R^3$ is an alkyl group optionally substituted by halogen, an acyl group, a halogen atom, a cyano group or a nitro group, $R^4$ and $R^5$ are the same or different and each is a hydrogen atom, an alkyl group optionally substituted by halogen, an acyl group, a halogen atom, a cyano group or a nitro group, $R^6$ is an alkyl group, and n is an integer of 0 to 3, provided that 1-[5-(2-fluoropyridin-3-yl)-1-(pyridin-3-ylsulfonyl)-1H-pyrrol-3-yl]-N-methylmethanamine, 1-[5-(2-chloropyridin-3-yl)-1-(pyridin-3-ylsulfonyl)-1H-pyrrol-3-yl]-N-methylmethanamine, 1-{5-(2-fluoropyridin-3-yl)-1-[(6-methoxypyridin-3-yl)sulfonyl]-1H-pyrrol-3-yl}-N-methylmethanamine, N-methyl-1-[5-(2-methylpyridin-3-yl)-1-(pyridin-3-ylsulfonyl)-1H-pyrrol-3-yl]methanamine, 1-{5-(2-fluoropyridin-3-yl)-1-[(6-methylpyridin-3-yl)sulfonyl]-1H-pyrrol-3-yl}-N-methylmethanamine, and 1-[4-chloro-5-(2-fluoropyridin-3-yl)-1-(pyridin-3-ylsulfonyl)-1H-pyrrol-3-yl]-N-methylmethanamine are excluded, or a salt thereof.

Effect of the Invention

Compound (I) of the present invention shows a superior proton pump inhibitory effect. Conventional proton pump inhibitors such as omeprazole, lansoprazole and the like are converted to active forms in an acidic environment of stomach wall cells and form a covalent bond with a cysteine residue of $H^+/K^+$-ATPase, and irreversibly inhibit the enzyme activity. In contrast, compound (I) inhibits proton pump ($H^+/K^+$-ATPase) activity in a reversible and $K^+$ antagonist-like inhibitory manner, and consequently suppresses acid secretion. Therefore, it is sometimes called a potassium-competitive acid blocker (P-CAB), or an acid pump antagonist (APA). Compound (I) rapidly expresses the action and shows the maximum efficacy from the initial administration. Furthermore, it characteristically shows less influence of metabolic polymorphism (variation between patients), low cytotoxicity, weak cytochrome P450 (CYP) inhibitory activity, and long duration of action. Accordingly, the present invention can provide a clinically useful agent for the prophylaxis or treatment of peptic ulcer (e.g., gastric ulcer, duodenal ulcer, anastomotic ulcer, ulcer caused by non-steroidal anti-inflammatory agent, ulcer due to postoperative stress etc.), Zollinger-Ellison syndrome, gastritis, erosive esophagitis, reflux esophagitis, symptomatic gastroesophageal reflux disease (Symptomatic GERD), Barrettesophagus, functional dyspepsia, gastric cancer, stomach MALT lymphoma or hyperacidity; or a suppressant of upper gastrointestinal hemorrhage due to peptic ulcer, acute stress ulcer, hemorrhagic gastritis or invasive stress; and the like. Since compound (I) shows low toxicity and is superior in water-solubility, in vivo kinetics and efficacy expression, it is useful as a pharmaceutical composition. Since compound (I) is stable even under acidic conditions, it can be administered orally as a conventional tablet and the like without formulating into an enteric-coated preparation. This has an advantageous consequence that the preparation (tablet and the like) can be made smaller, and can be easily swallowed by patients having difficulty in swallowing, particularly the elderly and children. In addition, since it is free of a sustained release effect afforded by enteric-coated preparations, a gastric acid secretion-suppressive action is expressed rapidly, and symptoms such as pain and the like can be alleviated rapidly.

The present invention is explained in detail as follows.

In the formula (I), $R^1$ is an optionally substituted cyclic group. Examples of the "optionally substituted cyclic group" include an optionally substituted aryl group, an optionally substituted alicyclic hydrocarbon group or an optionally substituted heterocyclic group.

Examples of the aryl group in the "optionally substituted aryl group" for $R^1$ include a $C_{6-14}$ aryl group such as phenyl, 1-naphthyl, 2-naphthyl, 2-biphenylyl, 3-biphenylyl, 4-biphenylyl, 2-anthryl and the like.

Examples of the substituent of the aryl group include (1) a halogen atom (e.g., fluorine atom, chlorine atom, bromine atom, iodine atom etc.), (2) nitro, (3) cyano, (4) hydroxy, (5) $C_{1-6}$ alkoxy optionally having 1 to 5 (preferably 1 to 3) halogen atoms (e.g., fluorine, chlorine, bromine, iodine) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 5 (preferably 1 to 3) halogen atoms (e.g., fluorine, chlorine, bromine, iodine) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ arylcarbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkylcarbamoyl optionally substituted by hydroxyl (e.g., methylcarbamoyl, ethylcarbamoyl, 2-hydroxyethylcarbamoyl etc., preferably mono-$C_{1-6}$ alkyl-carbamoyl), (28) di-$C_{1-6}$ alkylcarbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxycarbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxycarbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 1,2,3-oxadiazolyl, 1,2,4-oxadiazolyl, 1,2,5-oxadiazolyl, 1,3,4-oxadiazolyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), which is optionally substituted by 1 to 3 $C_{1-6}$ alkyl groups (e.g., methyl, ethyl, n-propyl, isopropyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) a $C_{1-6}$ alkyl group optionally having 1 to 5 (preferably 1 to 3) halogen atoms (e.g., fluorine, chlorine, bromine, iodine) or hydroxy (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl, hydroxymethyl etc., preferably a $C_{1-6}$ alkyl group optionally having 1 to 5 (preferably 1 to 3) halogen atoms), (51) a $C_{2-6}$ alkenyl group (e.g., allyl, isopropenyl, isobutenyl, 1-methylallyl, 2-pentenyl, 2-hexenyl etc.) optionally having 1 to 5 halogen atoms (preferably 1 to 3) (e.g., fluorine, chlorine, bromine, iodine), (52) a $C_{2-6}$ alkynyl group (e.g., propargyl, 2-butynyl, 3-butynyl, 3-pentynyl, 3-hexynyl etc.), (53) a $C_{6-14}$ aryl group (e.g., phenyl etc.) optionally having 1 to 5 (preferably 1 to 3) halogen atoms (e.g., fluorine, chlorine, bromine, iodine), (54) $C_{7-16}$ aralkyl (e.g., benzyl, phenethyl etc.) optionally having 1 to 5 (preferably 1 to 3) halogen atoms (e.g., fluorine, chlorine, bromine, iodine), (55) oxo, and the like.

The substituent may be present at a substitutable position, and the number of the substituents is 1 to 5, preferably 1 to 3.

Examples of the alicyclic hydrocarbon group in the "optionally substituted alicyclic hydrocarbon group" for $R^1$ include a $C_{3-14}$ cycloalkyl group such as cyclopropyl, cyclobutyl, cyclopentyl, cyclohexyl, perhydronaphthyl, perhydroanthryl, bicyclo[2,2 μl]heptyl and the like (preferably a $C_{3-7}$ cycloalkyl group), a $C_{3-14}$ cycloalkenyl group such as cyclopropenyl, cyclobuten-1- or 3-yl, cyclopenten-1-, 3- or 4-yl, cyclohexen-1- or 3-yl and the like (preferably a $C_{3-7}$ cycloalkenyl group) and the like.

Examples of the substituent of the alicyclic hydrocarbon group include those similar to the substituents which the aforementioned aryl group in $R^1$ optionally has. The substituent may be present at a substitutable position, and the number of the substituents is 1 to 5, preferably 1 to 3.

Examples of the heterocyclic group in the "optionally substituted heterocyclic group" for $R^1$ include a 4- to 7-membered non-aromatic heterocyclic group (preferably, a 4- to 6-membered non-aromatic heterocyclic group) containing 1 to 3 hetero atoms selected from nitrogen atom, oxygen atom, sulfur atom and the like, such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, homomorpholine, homopiperazine and the like, and a heteroaryl group (preferably, a 5- or 6-membered aromatic heterocyclic group or a fused ring group thereof) such as pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazol-4-yl, 1,2,3-triazol-1-yl, 1,2,3-triazol-5-yl, 1,2,4-triazol-1-yl, 1,2,4-triazol-3-yl, 1,2,4-triazol-4-yl, 1,2,4-triazol-5-yl), tetrazolyl (e.g., tetrazol-1-, 2- or 5-yl), furyl (e.g., 2- or 3-furyl), thienyl (e.g., 2- or 3-thienyl), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), thiazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyridyl (e.g., 1-, 2-, 3- or 4-pyridyl), pyridazinyl (e.g., 1-, 3- or 4-pyridazinyl), pyrimidinyl (e.g., 1-, 2-, 4- or 5-pyrimidinyl), pyrazinyl (e.g., 1- or 2-pyrazinyl), benzofuryl (e.g., 2- or 3-benzofuryl), benzothienyl (e.g., 2- or 3-benzothienyl), isoindolyl (e.g., 1- or 3-isoindolyl), benzimidazolyl (e.g., 2-benzimidazolyl), benzoxazolyl (e.g., 2-benzoxazolyl), benzisoxazolyl (e.g., 3-benzisoxazolyl), benzothiazolyl (e.g., 2-benzothiazolyl), benzisothiazolyl (e.g., 3-benzisothiazolyl), cinnolinyl (e.g., 3- or 4-cinnolinyl), quinazolinyl (e.g., 2- or 4-quinazolinyl), quinoxalinyl (e.g., 2- or 3-quinoxalinyl), phthalazinyl (e.g., 1- or 4-phthalazinyl), pteridinyl, indolyl (e.g., 3H-indol-2-, 3-, 4-, 5-, 6- or 7-yl), quinolyl (e.g., 3-, 4-, 5-, 6-, 7- or 8-quinolyl), isoquinolyl (e.g., 1-, 3- or 4-isoquinolyl), pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), imidazo[1,2-a]pyridyl, imidazo[2,1-b]thiazolyl, imidazo[1,2-a]pyrimidinyl, imidazo[1,2-b]pyridazinyl, imidazo[1,2-a]imidazolyl, imidazo[2,1-b](1.3.4)thiadiazolyl, pyrazolo[1,5-a]pyrimidinyl, pyrazolo[5,1-b]thiazolyl or pyrazolo[1,5-a]pyridyl and the like.

Examples of the substituent of the heterocyclic group include those similar to the substituents which the aforementioned aryl group in $R^1$ optionally has. The substituent may be present at a substitutable position, and the number of the substituents is 1 to 5, preferably 1 to 3.

$R^1$ is preferably an "optionally substituted aryl group or an optionally substituted heteroaryl group".

$R^2$ is a substituent bonded to the 2-position of the 3-pyridyl group at the 5-position of the pyrrole ring of compound (I), and the position of substitution on the pyridyl group is extremely important for the expression of activity of the compound of the present invention.

Examples of the "substituent" for $R^2$ include an electron withdrawing group and an electron donating group, particularly preferably an electron withdrawing group.

Examples of the electron withdrawing group include a halogen atom (e.g., fluorine, chlorine, bromine, iodine), a cyano group, an acyl group, a halogenoalkyl group (e.g., a halogeno($C_{1-3}$)alkyl group such as fluoromethyl, chloromethyl, bromomethyl, iodomethyl, difluoromethyl, trifluoromethyl and the like etc.) and the like.

Examples of the aforementioned "acyl group" include an acyl group derived from an optionally substituted carboxylic acid, an optionally substituted oxycarboxylic acid, an optionally substituted sulfonic acid, an optionally substituted sulfinic acid and the like, and the like, for example, a group represented by the formula —$S(O)_p$—$R^7$ wherein p is 1 or 2, and $R^7$ is a hydroxyl group, a hydrocarbon group optionally having substituent(s) or a heterocyclic group optionally having substituent(s), a group represented by the formula —$COOR^8$ wherein $R^8$ is a hydrogen atom, a hydrocarbon group optionally having substituent(s) or a heterocyclic group optionally having substituent(s), a group represented by the formula —$CONR^9R^{10}$ wherein $R^9$ and $R^{10}$ are the same or different and each is a hydrogen atom, a hydrocarbon group optionally having substituent(s) or a heterocyclic group optionally having substituent(s), a group represented by the formula —$SO_2NH$—$R^{11}$ wherein $R^{11}$ is a hydrogen atom, a hydrocarbon group optionally having substituent(s) or a heterocyclic group optionally having substituent(s), a group represented by the formula —CO—$R^{12}$ wherein $R^{12}$ is a hydrogen atom, a hydrocarbon group optionally having substituent(s) or a heterocyclic group optionally having substituent(s), and the like.

When $R^2$ is a hydroxyl group, a tautomer thereof, that is, compound (I) wherein the pyridine ring bonded to the 5-position at the pyrrole ring is 2-pyridone ring is also encompassed in compound (I) of the present invention. Specific examples of the tautomer include the compounds of Examples 103, 104 and 105.

Examples of the "hydrocarbon group" of the "hydrocarbon group optionally having substituents" for $R^7$, $R^8$, $R^9$, $R^{10}$, $R^{11}$ or $R^{12}$ include a chain or cyclic hydrocarbon group (e.g., alkyl, alkenyl, alkynyl, cycloalkyl, aryl, aralkyl etc.). Of these, a chain or cyclic hydrocarbon group having 1 to 16 carbon atoms and the like are preferable.

Examples of the "alkyl" include $C_{1-6}$ alkyl (e.g., methyl, ethyl, propyl, isopropyl, butyl, isobutyl, sec-butyl, tert-butyl, pentyl, hexyl etc.) and the like.

Examples of the "alkenyl" include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) and the like.

Examples of the "alkynyl" include $C_{2-6}$ alkynyl (e.g., ethynyl, propargyl, 1-butynyl, 2-butynyl, 3-butynyl, 1-hexynyl etc.) and the like.

Examples of the "cycloalkyl" include $C_{3-7}$ cycloalkyl (e.g., cyclopropyl, cyclobutyl, cyclopentyl, cyclohexyl, cycloheptyl etc.) and the like.

Examples of the "aryl" include $C_{6-14}$ aryl (e.g., phenyl, 1-naphthyl, 2-naphthyl, 2-biphenylyl, 3-biphenylyl, 4-biphenylyl, 2-anthryl etc.) and the like.

Examples of the "aralkyl" include $C_{7-16}$ aralkyl (e.g., phenyl-$C_{1-6}$ alkyl, naphthyl-$C_{1-6}$ alkyl or diphenyl-$C_{1-4}$ alkyl etc. such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like) and the like.

When the above-mentioned hydrocarbon group is alkyl, alkenyl or alkynyl, the group may be substituted by 1 to 3 substituents selected from (1) a halogen atom (e.g., fluorine atom, chlorine atom, bromine atom, iodine atom etc.), (2) nitro, (3) cyano, (4) hydroxy, (5) $C_{1-6}$ alkoxy optionally having 1 to 3 halogen atoms (e.g., fluorine atom, chlorine atom, bromine atom, iodine atom) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 3 halogen atoms (e.g., fluorine atom, chlorine atom, bromine atom, iodine atom) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.) (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ arylcarbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxycarbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.) and the like.

In addition, when the above-mentioned hydrocarbon group is cycloalkyl, aryl or aralkyl, the group may be substituted by 1 to 5 (preferably 1 to 3) substituents selected from (1) halogen atom (e.g., fluorine atom, chlorine atom, bromine atom, iodine atom etc.), (2) nitro, (3) cyano, (4) hydroxy, (5) $C_{1-6}$ alkoxy optionally having 1 to 3 halogen atom (e.g., fluorine atom, chlorine atom, bromine atom, iodine atom) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 3 halogen atom (e.g., fluorine atom, chlorine atom, bromine atom, iodine atom) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ arylcarbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl optionally having 1 to 3 halogen atoms (e.g., fluorine atom, chlorine atom, bromine atom, iodine atom) (e.g., methylsulfonyl, ethylsulfonyl, trifluoromethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxycarbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) a $C_{1-6}$ alkyl group optionally having 1 to 3 halogen atoms (e.g., fluorine atom, chlorine atom, bromine atom, iodine atom) or hydroxy group (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.), (51) a $C_{2-6}$ alkenyl group optionally having 1 to 3 halogen atoms (e.g., fluorine atom, chlorine atom, bromine atom, iodine atom) (e.g., allyl, isopropenyl, isobutenyl, 1-methylallyl, 2-pentenyl, 2-hexenyl etc.), (52) $C_{2-6}$ alkynyl group (e.g., propargyl, 2-butynyl, 3-butynyl, 3-pentynyl, 3-hexynyl etc.), (53) mono-$C_{3-7}$ cycloalkyl-carbamoyl (e.g., cyclopropylcarbamoyl, cyclobutylcarbamoyl etc.), and (54) a 5- or 10-membered heterocyclyl-carbonyl containing, besides carbon atom, 1 or 2 kinds of 1 to 4 hetero atoms selected from a nitrogen atom, a sulfur atom and an oxygen atom (e.g., 4-morpholinocarbonyl etc.) and the like.

Examples of the "heterocyclic group" of the "heterocyclic group optionally having substituents" for $R^7$, $R^8$, $R^9$, $R^{10}$, $R^{11}$ or $R^{12}$ include a 3- to 8-membered heterocyclic group (preferably a 5- or 6-membered heterocyclic group) containing 1 to 4 hetero atoms selected from a nitrogen atom (optionally oxidized), an oxygen atom, a sulfur atom (optionally mono- or di-oxidized) and the like, or a group wherein a 3- or 8-membered heterocyclic group (preferably a 5- or 6-membered heterocyclic group) containing 1 to 4 hetero atoms selected from a nitrogen atom (optionally oxidized), an oxygen atom, a sulfur atom (optionally mono- or di-oxidized) and the like is condensed with a benzene ring or a 3- to 8-membered ring (preferably a 5- or 6-membered ring) containing 1 to 4 hetero atoms selected from a nitrogen atom (optionally oxidized), an oxygen atom, a sulfur atom (optionally mono- or di-oxidized) and the like, preferably a group wherein the 5- or 6-membered heterocyclic group is condensed with a 5- or 6-membered ring optionally containing 1 to 4 hetero atoms selected from a nitrogen atom (optionally oxidized), an oxygen atom, a sulfur atom (optionally mono- or di-oxidized) and the like.

Specific examples thereof include aziridinyl (e.g., 1- or 2-aziridinyl), azirinyl (e.g., 1- or 2-azirinyl), azetyl (e.g., 2-, 3- or 4-azetyl), azetidinyl (e.g., 1-, 2- or 3-azetidinyl), perhydroazepinyl (e.g., 1-, 2-, 3- or 4-perhydroazepinyl), perhydroazocinyl (e.g., 1-, 2-, 3-, 4- or 5-perhydroazocinyl), pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazol-1-, 4- or -5-yl, 1,2,4-triazol-1-, 3-, 4- or 5-yl), tetrazolyl (e.g., tetrazol-1-, 2- or 5-yl), furyl (e.g., 2- or 3-furyl), thienyl (e.g., 2- or 3-thienyl), thienyl wherein the sulfur atom is oxidized (e.g., 2- or 3-thienyl-1,1-dioxide), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), thiazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyrrolidinyl (e.g., 1-, 2- or 3-pyrrolidinyl), pyridyl (e.g., 2-, 3- or 4-pyridyl), pyridyl wherein the nitrogen atom is oxidized (e.g., 2-, 3- or 4-pyridyl-N-oxide), pyridazinyl (e.g., 3- or 4-pyridazinyl), pyridazinyl wherein one or both of the nitrogen atoms are oxidized (e.g., 3-, 4-, 5- or 6-pyridazinyl-N-oxide), pyrimidinyl (e.g., 2-, 4- or 5-pyrimidinyl), pyrimidinyl wherein one or both of the nitrogen atoms are oxidized (e.g., 2-, 4-, 5- or 6-pyrimidinyl-N-oxide), pyrazinyl, piperidinyl (e.g., 1-, 2-, 3- or 4-piperidinyl), piperazinyl (e.g., 1- or 2-piperazinyl), indolyl (e.g., 3H-indole-2-, 3-, 4-, 5-, 6- or 7-yl), pyranyl (e.g., 2-, 3- or 4-pyranyl), thiopyranyl (e.g., 2-, 3- or 4-thiopyranyl), thiopyranyl wherein the sulfur atom is oxidized (e.g., 2-, 3- or 4-thiopyranyl-1,1-dioxide), morpholinyl (e.g., 2-, 3- or 4-morpholinyl), thiomorpholinyl, quinolyl (e.g., 2-, 3-, 4-, 5-, 6-, 7- or 8-quinolyl), isoquinolyl, pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), chromenyl (e.g., 2H-chromen-2- or 3-yl), 2-benzo[b]thienyl, 3-benzo[b]thienyl, 2-benzo[b]furanyl, 3-benzo[b]furanyl and the like.

Examples of the "substituent" of the heterocyclic group include those similar to the substituents that the above-mentioned "hydrocarbon group" for $R^7$, $R^8$, $R^9$, $R^{10}$, $R^{11}$ or $R^{12}$ has when it is cycloalkyl, aryl or aralkyl. The number of the substituents is 1 to 5, preferably 1 to 3.

Of the above-mentioned group, the electron withdrawing group is preferably a halogen atom, a cyano group, an acyl group or a trifluoromethyl group.

Examples of the electron donating group include a $C_{1-6}$ alkyl group (e.g., methyl, ethyl, propyl, isopropyl, butyl, isobutyl, sec-butyl, tert-butyl, pentyl, hexyl etc.), a $C_{1-6}$ alkylthio group (e.g., methylthio, ethylthio, propylthio, isopropylthio, butylthio, pentylthio, hexylthio etc.), a $C_{1-6}$ alkoxy group (e.g., methoxy, ethoxy, propoxy, isopropoxy, butoxy, pentyloxy, hexyloxy etc.), a group represented by the —$NR^{13}R^{14}$ wherein $R^{13}$ and $R^{14}$ are the same or different and each is a hydrogen atom or an alkyl group, and a hydroxyl group and the like. Examples of the alkyl group for $R^{13}$ or $R^{14}$ include a $C_{1-6}$ alkyl group such as methyl, ethyl, propyl, isopropyl, butyl, isobutyl, sec-butyl, tert-butyl, pentyl, hexyl and the like, particularly preferably a $C_{1-3}$ alkyl group.

Of the above-mentioned group, the electron donating group is preferably a $C_{1-3}$ alkyl, a $C_{1-3}$ alkylthio, or a group represented by the formula —$NR^{13}R^{14}$ wherein each symbol is as defined above.

Of the aforementioned group, the "substituent" for $R^2$ is preferably, for example, an electron withdrawing group or electron donating group having not more than 7 atoms and comparatively low molecular weight shown below.

In the formula (I), $R^3$ is an optionally substituted alkyl group, an acyl group, an optionally substituted hydroxy group, an optionally substituted amino group, a halogen atom, a cyano group or a nitro group. $R^3$ is preferably an alkyl group optionally substituted by halogen, an acyl group, a halogen atom, a cyano group or a nitro group.

$R^4$ and $R^5$ are the same or different and each is a hydrogen atom, an optionally substituted alkyl group, an acyl group, an optionally substituted hydroxy group, an optionally substituted amino group, a halogen atom, a cyano group or a nitro group. Preferably, $R^4$ and $R^5$ are the same or different and each is a hydrogen atom, an alkyl group optionally substituted by halogen, an acyl group, a halogen atom, a cyano group or a nitro group.

Examples of the "alkyl group" in the "optionally substituted alkyl group" for $R^3$, $R^4$ or $R^5$ include a $C_{1-6}$ alkyl group such as methyl, ethyl, propyl, isopropyl, butyl, isobutyl, sec-butyl, tert-butyl, pentyl, hexyl and the like. Examples of the "substituent" of the alkyl include those similar to the substituents that the above-mentioned "hydrocarbon group" for $R^7$, $R^8$, $R^9$, $R^{10}$, $R^{11}$ or $R^{12}$ has when it is alkyl, alkenyl or alkynyl. The number of the substituents is 1 to 5, preferably 1 to 3.

Preferable examples of the substituent of the alkyl group for $R^3$, $R^4$ or $R^5$ include halogen (e.g., a fluorine atom, a chlorine atom, a bromine atom, an iodine atom). The number of the halogen atom as a substituent is 1 to 5, preferably 1 to 3.

Examples of the "acyl group" for $R^3$, $R^4$ or $R^5$ include acyl groups having 1 to 20 carbon atoms, which is derived from organic carboxylic acids, for example, $C_{1-7}$ alkanoyl groups (e.g., formyl; $C_{1-6}$ alkyl-carbonyl such as acetyl, propionyl, butyryl, isobutyryl, pentanoyl, hexanoyl, heptanoyl and the like; etc.), $C_{6-14}$ aryl-carbonyl groups (e.g., benzoyl, naphthalenecarbonyl etc.), $C_{1-6}$ alkoxy-carbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.), $C_{6-14}$ aryloxycarbonyl groups (e.g., phenoxycarbonyl group), $C_{7-19}$ aralkylcarbonyl groups (e.g., phenyl-$C_{1-4}$ alkylcarbonyl such as benzylcarbonyl, phenethylcarbonyl, phenylpropylcarbonyl and the like, naphthyl-$C_{1-4}$ alkylcarbonyl such as benzhydrylcarbonyl, naphthylethylcarbonyl and the like, etc.), $C_{7-19}$ aralkyloxycarbonyl groups (e.g., phenyl-$C_{1-4}$ alkyloxycarbonyl such as benzyloxycarbonyl and the like, etc.), 5- or 6-membered heterocyclyl-carbonyl groups or condensed heterocyclylcarbonyl groups thereof (e.g., pyrrolylcarbonyl such as 2- or 3-pyrrolylcarbonyl and the like; pyrazolylcarbonyl such as 3-, 4- or 5-pyrazolylcarbonyl and the like; imidazolylcarbonyl such as 2-, 4- or 5-imidazolylcarbonyl and the like; triazolylcarbonyl such as 1,2,3-triazol-4-ylcarbonyl, 1,2,4-triazol-3-ylcarbonyl and the like; tetrazolylcarbonyl such as 1H- or 2H-tetrazol-5-ylcarbonyl and the like; furylcarbonyl such as 2- or 3-furylcarbonyl and the like; thienylcarbonyl such as 2- or 3-thienylcarbonyl and the like; oxazolylcarbonyl such as 2-, 4- or 5-oxazolylcarbonyl and the like; isoxazolylcarbonyl such as 3-, 4- or 5-isoxazolylcarbonyl and the like; oxadiazolylcarbonyl such as 1,2,3-oxadiazol-4- or 5-ylcarbonyl, 1,2,4-oxadiazol-3- or 5-ylcarbonyl, 1,2,5-oxadiazol-3- or 4-ylcarbonyl, 1,3,4-oxadiazol-2-ylcarbonyl and the like; thiazolylcarbonyl such as 2-, 4- or 5-thiazolylcarbonyl and the like; isothiazolylcarbonyl such as 3-, 4- or 5-isothiazolylcarbonyl and the like; thiadiazolylcarbonyl such as 1,2,3-thiadiazol-4- or 5-ylcarbonyl, 1,2,4-thiadiazol-3- or 5-ylcarbonyl, 1,2,5-thiadiazol-3- or 4-ylcarbonyl, 1,3,4-thiadiazol-2-ylcarbonyl and the like; pyrrolidinylcarbonyl such as 2- or 3-pyrrolidinylcarbonyl and the like; pyridylcarbonyl such as 2-, 3- or 4-pyridylcarbonyl and the like; pyridylcarbonyl wherein the nitrogen atom is oxidized, such as 2-, 3- or 4-pyridyl-N-oxidocarbonyl and the like; pyridazinylcarbonyl such as 3- or 4-pyridazinylcarbonyl and the like; pyridazinyl wherein one or both of the nitrogen atoms are oxidized, such as 3-, 4-, 5- or 6-pyridazinyl-N-oxidocarbonyl and the like; pyrimidinylcarbonyl such as 2-, 4- or 5-pyrimidinylcarbonyl and the like; pyrimidinylcarbonyl wherein one or both of the nitrogen atoms are oxidized, such as 2-, 4-, 5- or 6-pyrimidinyl-N-oxidocarbonyl and the like; pyrazinylcarbonyl; piperidinylcarbonyl such as 2-, 3- or 4-piperidinylcarbonyl and the like; piperazinylcarbonyl; indolylcarbonyl such as 3H-indol-2- or 3-ylcarbonyl and the like; pyranylcarbonyl such as 2-, 3- or 4-pyranylcarbonyl and the like; thiopyranylcarbonyl such as 2-, 3- or 4-thiopyranylcarbonyl and the like; quinolylcarbonyl such as 3-, 4-, 5-, 6-, 7- or 8-quinolylcarbonyl and the like; isoquinolylcarbonyl; pyrido[2,3-d]pyrimidinylcarbonyl (e.g., pyrido[2,3-d]pyrimidin-2-ylcarbonyl); naphthyridinylcarbonyl (e.g., 1,5-naphthyridin-2- or 3-ylcarbonyl) such as 1,5-, 1,6-, 1,7-, 1,8-, 2,6- or 2,7-naphthyridinylcarbonyl and the like; thieno[2,3-d]pyridylcarbonyl (e.g., thieno[2,3-d]pyridin-3-ylcarbonyl); pyrazinoquinolylcarbonyl (e.g., pyrazino[2,3-b]quinolin-2-ylcarbonyl); 5- or 6-membered heterocyclylcarbonyl groups (e.g., chromenylcarbonyl (e.g., 2H-chromen-2- or 3-ylcarbonyl etc.) and the like) containing 1 to 4 hetero atoms such as a nitrogen atom (optionally oxidized), an oxygen atom, a sulfur atom (optionally mono- or di-oxidized) and the like), 5- or 6-membered heterocyclyl-acetyl groups (e.g., 5- or 6-membered heterocyclyl-acetyl groups containing 1 to 4 hetero atoms such as a nitrogen atom (optionally oxidized), an oxygen atom, a sulfur atom (optionally mono- or di-oxidized) and the like) such as 2-pyrrolylacetyl, 3-imidazolylacetyl, 5-isoxazolylacetyl and the like, and the like can be used.

As regards the substituent of acyl group, for example, when the above-mentioned acyl group is an alkanoyl group or an alkoxy-carbonyl group, it is optionally substituted by 1 to 3 substituents selected from an alkylthio group (e.g., $C_{1-4}$ alkylthio such as methylthio, ethylthio, n-propylthio, isopropylthio and the like, and the like), halogen (e.g., fluorine, chlorine, bromine, iodine), an alkoxy group (e.g., $C_{1-6}$ alkoxy such as methoxy, ethoxy, n-propoxy, tert-butoxy, n-hexyloxy and the like, and the like), a nitro group, an alkoxy-carbonyl group (e.g., $C_{1-6}$ alkoxy-carbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and the like, and the like), an alkylamino group (e.g., mono- or di-$C_{1-6}$ alkylamino such as methylamino, ethylamino, n-propylamino, n-butylamino, tert-butylamino, n-pentylamino, n-hexylamino, dimethylamino, diethylamino, methylethylamino, di-(n-propyl)amino, di-(n-butyl)amino and the like, and the like), an alkoxyimino group (e.g., $C_{1-6}$ alkoxyimino such as methoxyimino, ethoxyimino, n-propoxyimino, tert-butoxyimino, n-hexyloxy-imino and the like, and the like) and hydroxyimino.

When the above-mentioned acyl group is an aryl-carbonyl group, an aryloxy-carbonyl group, an aralkyl-carbonyl group, an aralkyloxycarbonyl group, a 5- or 6-membered heterocyclylcarbonyl group or a 5- or 6-membered heterocyclyl-acetyl group, it is optionally substituted by 1 to 5 (preferably 1 to 3) substituents selected from an alkyl group (e.g., $C_{1-6}$ alkyl such as methyl, ethyl, n-propyl, isopropyl, n-butyl, isobutyl, sec-butyl, tert-butyl, n-pentyl, sec-pentyl, isopentyl, neopentyl, n-hexyl, isohexyl and the like, $C_{3-6}$ cycloalkyl such as cyclohexyl and the like, and the like), an alkenyl group (e.g., $C_{2-6}$ alkenyl such as allyl, isopropenyl, isobutenyl, 1-methylallyl, 2-pentenyl, 2-hexenyl and the like, and the like), an alkynyl group (e.g., $C_{2-6}$ alkynyl such as propargyl, 2-butynyl, 3-butynyl, 3-pentynyl, 3-hexynyl and the like, and the like), an alkoxy group (e.g., $C_{1-6}$ alkoxy such as methoxy, ethoxy, n-propoxy, tert-butoxy, n-hexyloxy and the like, and the like), an acyl group [e.g., $C_{1-7}$ alkanoyl such as formyl, acetyl, propionyl, butyryl, isobutyryl, pentanoyl, hexanoyl, heptanoyl and the like; $C_{6-14}$ aryl-carbonyl such as benzoyl, naphthalenecarbonyl and the like; $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like; $C_{6-14}$ aryloxycarbonyl such as phenoxycarbonyl and the like; $C_{7-19}$ aralkylcarbonyl such as phenyl-$C_{1-4}$ alkyl-carbonyl (e.g., benzylcarbonyl, phenethylcarbonyl, phenylpropylcarbonyl and the like) and the like; $C_{7-19}$ aralkyloxy-carbonyl such as phenyl-$C_{1-4}$ alkyloxy-carbonyl (e.g., benzyloxycarbonyl and the like) and the like, and the like], nitro, amino, hydroxy, cyano, sulfamoyl, mercapto, halogen (e.g., fluorine, chlorine, bromine, iodine) and an alkylthio group ($C_{1-4}$ alkylthio such as methylthio, ethylthio, n-propylthio, isobutylthio and the like, and the like).

Examples of the "optionally substituted hydroxy group" for $R^3$, $R^4$ or $R^5$ include a group represented by —$OR^{16}$ wherein $R^{16}$ is a hydrogen atom, an optionally substituted hydrocarbon group, an optionally substituted heterocyclic group or an acyl group.

Examples of the "optionally substituted hydrocarbon group" for $R^{16}$ include those similar to the "optionally substituted hydrocarbon group" for the above-mentioned $R^7$, $R^8$, $R^9$, $R^{10}$, $R^{11}$ or $R^{12}$.

Examples of the "optionally substituted heterocyclic group" for $R^{16}$ include those similar to the "optionally substituted heterocyclic group" for the above-mentioned $R^7$, $R^8$, $R^9$, $R^{10}$, $R^{11}$ or $R^{12}$.

Examples of the "acyl group" for $R^{16}$ include those similar to the "acyl group" exemplified as the above-mentioned "substituent" for $R^2$.

Examples of the "optionally substituted amino group" for $R^3$, $R^4$ or $R^5$ include a group represented by —$NR^{17}R^{18}$ wherein $R^{17}$ and $R^{18}$ are the same or different and each is a hydrogen atom, an optionally substituted hydrocarbon group, an optionally substituted heterocyclic group or an acyl group.

Examples of the "optionally substituted hydrocarbon group" for $R^{17}$ or $R^{1a}$ include those similar to the "optionally substituted hydrocarbon group" for the above-mentioned $R^7$, $R^8$, $R^9$, $R^{10}$, $R^{11}$ or $R^{12}$.

Examples of the "optionally substituted heterocyclic group" for $R^{17}$ or $R^{18}$ include those similar to the "optionally substituted heterocyclic group" for the above-mentioned $R^7$, $R^8$, $R^9$, $R^{10}$, $R^{11}$ or $R^{12}$.

Examples of the "optionally substituted acyl group" for $R^{17}$ or $R^{18}$ include those similar to the "acyl group" exemplified as the above-mentioned "substituent" for $R^2$.

Examples of the "halogen atom" for $R^3$, $R^4$ or $R^5$ include fluorine, chlorine, bromine and iodine.

In the formula (I), $R^3$ is optionally substituted at any substitutable position of the pyridine ring. The number (i.e., n) of substituent $R^3$ is 0 to 3. When n is 2 or 3, each of $R^3$ is the same or different.

Preferably, n is 0.

Preferably, $R^4$ and $R^5$ are the same or different and each is a hydrogen atom or a halogen atom.

Examples of the "alkyl group" for $R^6$ or $R^{6'}$ include a $C_{1-6}$ alkyl group such as methyl, ethyl, propyl, isopropyl, butyl, isobutyl, sec-butyl, tert-butyl, pentyl, hexyl and the like, preferably a $C_{1-3}$ alkyl group, particularly preferably methyl.

Preferable embodiment of the partial structure of the formula (I):

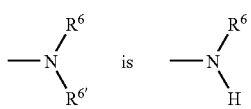

wherein $R^6$ is an alkyl group.

Compound (I) excluding 1-[5-(2-fluoropyridin-3-yl)-1-(pyridin-3-ylsulfonyl)-1H-pyrrol-3-yl]-N-methylmethanamine, 1-[5-(2-chloropyridin-3-yl)-1-(pyridin-3-ylsulfonyl)-1H-pyrrol-3-yl]-N-methylmethanamine, 1-{5-(2-fluoropyridin-3-yl)-1-[(6-methoxypyridin-3-yl)sulfonyl]-1H-pyrrol-3-yl}-N-methylmethanamine, N-methyl-1-[5-(2-methylpyridin-3-yl)-1-(pyridin-3-ylsulfonyl)-1H-pyrrol-3-yl]methanamine, 1-{5-(2-fluoropyridin-3-yl)-1-[(6-methylpyridin-3-yl)sulfonyl]-1H-pyrrol-3-yl}-N-methylmethanamine, and 1-[4-chloro-5-(2-fluoropyridin-3-yl)-1-(pyridin-3-ylsulfonyl)-1H-pyrrol-3-yl]-N-methylmethanamine and salts thereof is a novel compound.

As the preferable embodiment of compound (I), a compound represented by the following formula (Ia) can be mentioned. A compound represented by the formula (Ia)

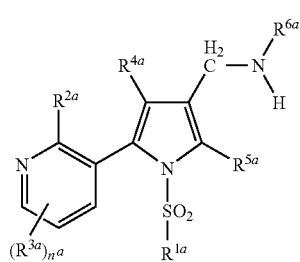

wherein $R^{1a}$ is an optionally substituted phenyl group, an optionally substituted furyl group, an optionally substituted thienyl group, an optionally substituted pyridyl group, an optionally substituted pyrazolyl group or an optionally substituted piperidyl group, $R^{2a}$ is a substituent selected from a halogen atom, cyano and a halogeno$C_{1-6}$ alkyl group, $R^{3a}$ is an alkyl group, $R^{4a}$ and $R^{5a}$ are the same or different and each is a hydrogen atom, an alkyl group or a halogen atom, $R^{6a}$ is an alkyl group, and $n^a$ is an integer of 0 to 3, or a salt thereof.

Preferable substituents for the formula (Ia) are similar to the corresponding substituents in the formula (I).

Examples of the substituent which phenyl group, furyl group, thienyl group, pyridyl group, pyrazolyl group or piperidyl group in $R^{1a}$ optionally has include those exemplified for the above-mentioned $R^1$. Of these, (1) a halogen atom (e.g., a fluorine atom, a chlorine atom, a bromine atom, an iodine atom etc.), (2) cyano, (3) $C_{1-6}$ alkoxy optionally having 1 to 5 (preferably 1 to 3) halogen atoms (e.g., fluorine, chlorine, bromine, iodine) (e.g., methoxy, ethoxy, propoxy, isopropoxy, butoxy, isobutoxy, sec-butoxy, pentyloxy, hexyloxy, fluoromethoxy etc.), (4) $C_{1-6}$ alkyl-carbonyl (e.g., acetyl, propionyl etc.), (5) $C_{1-6}$ alkylsulfonyl (e.g., methylsulfonyl, ethylsulfonyl etc.), (6) $C_{1-3}$ alkylenedioxy (e.g., methylenedioxy, ethylenedioxy etc.), (7) $C_{1-6}$ alkyl group optionally having 1 to 5 (preferably 1 to 3) halogen atoms (e.g., fluorine, chlorine, bromine, iodine) or hydroxyl (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl, hydroxymethyl etc.), (8) mono-$C_{1-6}$ alkylcarbamoyl optionally substituted by hydroxy (e.g., methylcarbamoyl, ethylcarbamoyl, 2-hydroxyethylcarbamoyl etc.), (9) $C_{1-6}$ alkyl-carbonyloxy (e.g., acetoxy etc.), (10) a 5- to 10-membered aromatic heterocyclic group (e.g., a 5- to 6-membered aromatic heterocyclic group such as 1,3,4-oxadiazolyl and the like) containing, besides carbon atom, 1 or 2 kinds of 1 to 4 hetero atoms selected from a nitrogen atom, a sulfur atom and an oxygen atom, which is optionally substituted by 1 to 3 $C_{1-6}$ alkyl groups (e.g., methyl, ethyl, n-propyl, isopropyl etc.), and the like are preferable.

In compound (Ia), another preferable embodiment is as follows.

Compound (Ia) wherein $R^{1a}$ is an optionally substituted phenyl group, an optionally substituted furyl group, an optionally substituted thienyl group or an optionally substituted pyridyl group, $R^{2a}$ is a substituent selected from a halogen atom, cyano and a $C_{1-6}$ alkyl group, $R^{3a}$ is an alkyl group, $R^{4a}$ and $R^{5a}$ are the same or different and each is a hydrogen atom, an alkyl group or a halogen atom, $R^{6a}$ is an alkyl group, and $n^a$ is an integer of 0 to 3, or a salt thereof.

The substituent which phenyl group, furyl group, thienyl group or pyridyl group in $R^{1a}$ optionally has is particularly preferably (1) a halogen atom (e.g., a fluorine atom, a chlorine atom, a bromine atom, an iodine atom etc.), (2) cyano, (3) $C_{1-6}$ alkoxy optionally having 1 to 5 (preferably 1 to 3) halogen atoms (e.g., fluorine, chlorine, bromine, iodine) (e.g., methoxy, ethoxy, propoxy, isopropoxy, butoxy, isobutoxy, sec-butoxy, pentyloxy, hexyloxy, fluoromethoxy etc.), (4) $C_{1-6}$ alkyl-carbonyl (e.g., acetyl, propionyl etc.), (5) $C_{1-6}$ alkylsulfonyl (e.g., methylsulfonyl, ethylsulfonyl etc.), (6) $C_{1-3}$ alkylenedioxy (e.g., methylenedioxy, ethylenedioxy etc.), (7) $C_{1-6}$ alkyl group optionally having 1 to 5 (preferably 1 to 3) halogen atoms (e.g., fluorine, chlorine, bromine, iodine) (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) and the like.

A compound represented by the formula

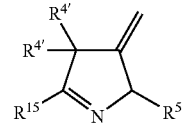

wherein $R^{4'}$ is a halogen atom, $R^{15}$ is an optionally substituted hydrocarbon group or an optionally substituted heterocyclic group, and $R^5$ is as defined in the above, or a salt thereof, which is a synthetic intermediate for compound (I), is a novel compound.

Examples of the "halogen atom" for $R^{4'}$ include fluorine, chlorine, bromine and iodine.

Examples of the "optionally substituted hydrocarbon group" for $R^{15}$ include those similar to the "optionally substituted hydrocarbon group" for the above-mentioned $R^7$, $R^8$, $R^9$, $R^{10}$, $R^{11}$ or $R^{12}$.

Examples of the "optionally substituted heterocyclic group" for $R^{15}$ include those similar to the "optionally substituted heterocyclic group" for the above-mentioned $R^7$, $R^8$, $R^9$, $R^{10}$, $R^{11}$ or $R^{12}$.

Examples of the salt of compound (I) include metal salt, ammonium salt, salts with organic bases, salts with inorganic bases, salts with organic acids, salts with basic or acidic amino acids and the like. Preferable examples of metal salt include alkali metal salts such as sodium salt, potassium salt and the like; alkaline earth metal salts such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysin, ornithine and the like. Preferable examples of the salt with acidic amino acid include a salt with aspartic acid, glutamic acid and the like.

Of these, pharmaceutically acceptable salts are preferable. For example, when a compound contains an acidic functional group, inorganic salts such as alkali metal salt (e.g., sodium salt, potassium salt etc.), alkaline earth metal salt (e.g., calcium salt, magnesium salt, barium salt etc.) and the like, ammonium salt and the like; and when a compound contains a basic functional group, for example, salts with inorganic acid such as hydrochloric acid, hydrobromic acid, nitric acid, sulfuric acid, phosphoric acid and the like, or salts with organic acid such as acetic acid, phthalic acid, fumaric acid, oxalic acid, tartaric acid, maleic acid, citric acid, succinic acid, methanesulfonic acid, p-toluenesulfonic acid and the like can be mentioned.

Compound (I) can be produced, for example, according to the methods described in WO 2006-036024, *Eur. J. Org. Chem.*, p. 2283 (2001), *J. Med. Chem.*, vol. 43, p. 1886 (2000), *J. Pharm. Pharmacol.*, vol. 46, p. 740 (1994), WO92/04025, *J. Heterocycl. Chem.*, vol. 25, p. 635 (1988), *J. Med. Chem.*, vol. 14, p. 328 (1971), *J. Med. Chem.*, vol. 35, p. 4195 (1992) or *Tetrahedron Lett.*, vol. 26, p. 4047 (1985), or a method analogous thereto.

The production methods of compound (I) in the present invention are explained.

The compounds (II)-(XXIV) in the formula may form salts, and as such salts, for example, those similar to the salts of compound (I) can be mentioned.

While the compounds obtained in respective steps can be used for the next reaction in the form of a reaction mixture or a crude product, they can also be easily isolated and purified from the reaction mixture by a known separation and purification means, such as recrystallization, distillation, chromatography and the like.

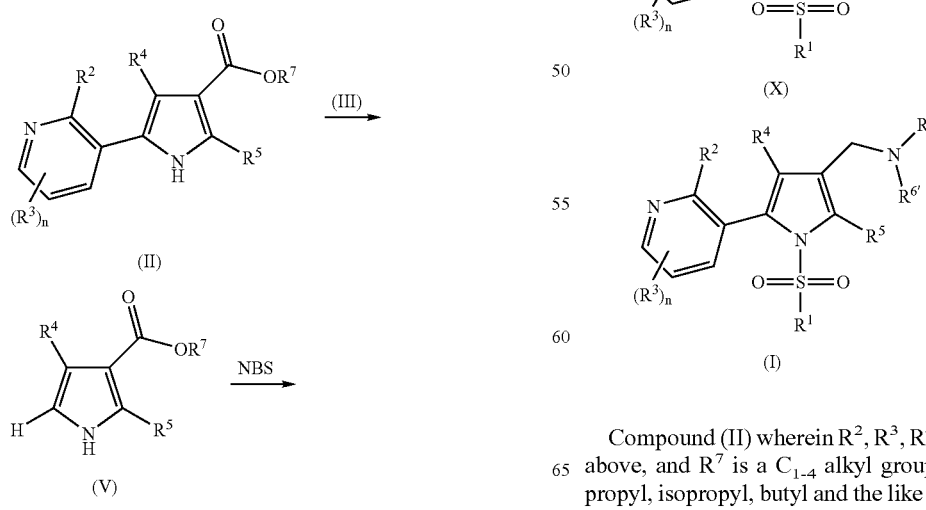

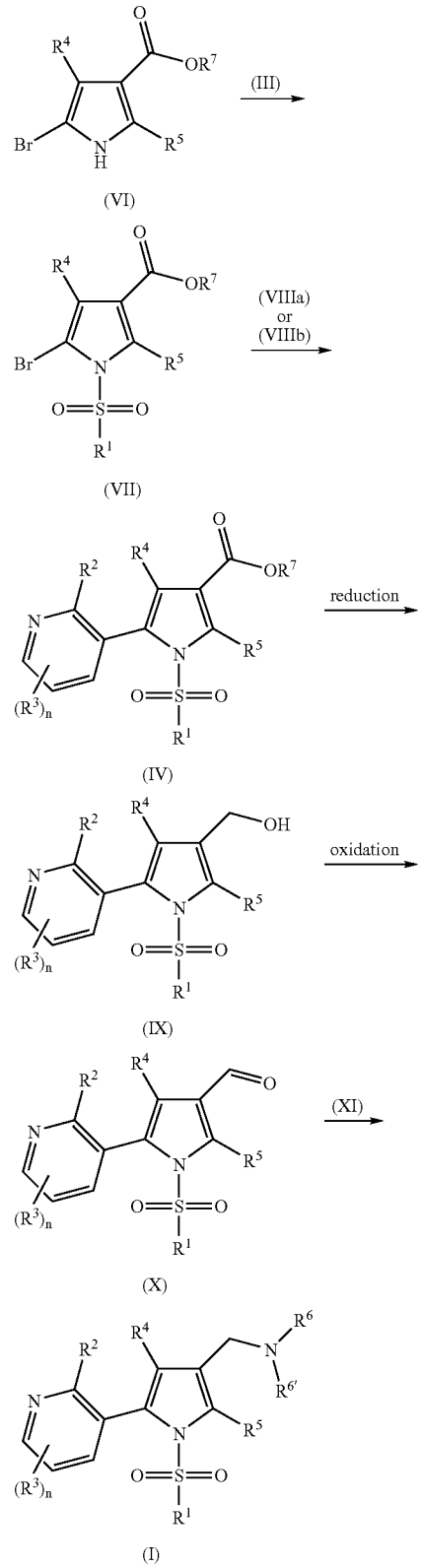

Compound (II) wherein $R^2$, $R^3$, $R^4$, $R^5$ and n are as defined above, and $R^7$ is a $C_{1-4}$ alkyl group such as methyl, ethyl, propyl, isopropyl, butyl and the like can be produced according to a method known per se, such as the method described in *Chem. Pharm. Bull.*, vol. 49, p. 1406 (2001), *Tetrahedron Letters*, vol. 35, p. 5989 (1994) and the like or a method analogous thereto.

Compound (IV) wherein each symbol is as defined above can be produced by reacting compound (II) with a compound represented by the formula (III)

wherein $R^1$ is as defined above.

This reaction is advantageously carried out using a solvent inert to the reaction. While the solvent is not particularly limited as long as the reaction proceeds, hydrocarbons such as benzene, toluene and the like, ethers such as tetrahydrofuran and the like, amides such as N,N-dimethylformamide, N,N-dimethylacetamide and the like, and the like or a mixed solvent thereof and the like are preferable.

Use of a base is effective for the reaction. As the base, for example, inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned. The amount of the base to be used is 0.8 to 10 mol, preferably 1 to 5 mol, per 1 mol of compound (II).

The reaction can also be carried out in the co-presence of a crown ether. As the crown ether, for example, 15-crown-5-ether, 18-crown-6-ether and the like can be mentioned. The amount of the crown ether to be used is 0.01 to 10 mol, preferably 1 to 5 mol, per 1 mol of compound (II).

While the reaction time varies depending on the reagents and solvent to be used, it is generally 1 min to 48 hr, preferably 10 min to 8 hr.

The reaction temperature is generally −20° C. to 100° C., preferably 0° C. to 50° C.

Compound (V) wherein each symbol in the formula is as defined above can be produced according to a method known per se, for example, the methods described in *Tetrahedron Letters*, vol. 13, p. 5337 (1972), *Heterocycles*, vol. 7, p. 77 (1977), *Chem. Pharm. Bull.*, vol. 27, p. 2857 (1979), *J. Org. Chem.*, vol. 62, p. 2649 (1997) and the like, or a method analogous thereto.

Compound (VI) wherein each symbol in the formula is as defined above can be produced by reacting compound (V) with N-bromosuccinimide (NBS).

N-Bromosuccinimide (NBS) is preferably used in about one equivalent relative to compound (V), and the reaction is preferably carried out under an inert gas atmosphere such as nitrogen, argon and the like.

This reaction is advantageously carried out using a solvent inert to the reaction. While the solvent is not particularly limited as long as the reaction proceeds, solvents such as ethers (e.g., tetrahydrofuran, diethyl ether and the like), amides (e.g., N,N-dimethylformamide, N,N-dimethylacetamide and the like) and the like, a mixed solvent thereof and the like are preferable.

While the reaction time varies depending on the reagents and solvent to be used, it is generally 10 min to 24 hr, preferably 5 to 12 hr.

The reaction temperature is generally −78° C. to 80° C., preferably −78° C. to 30° C.

Addition of a base is sometimes effective for the reaction. While the base to be used is not limited as long as the reaction proceeds, organic bases such as pyridine, picoline, lutidine and the like, and the like can be mentioned. The amount of the organic base to be used is 0.001 to 10 equivalents, preferably 0.001 to 0.1 equivalent, per 1 mol of compound (V).

Compound (VII) wherein each symbol in the formula is as defined above can be produced from compound (VI) according to a method similar to the method for producing compound (IV) from compound (II).

Compound (IV) wherein each symbol is as defined above can be also produced by reacting compound (VII) with a compound represented by the formula (VIIIa) (or various ester derivative of the formula (VIIIa))

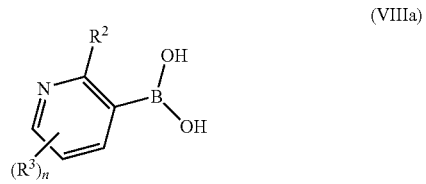

wherein each symbol is as defined above, according to a method described in Synthetic Communications, vol. 11, page 513 (1981), or a method analogous thereto.

Compound (IV) can be also produced by reacting compound (VII) with a compound represented by the formula (VIIIb)

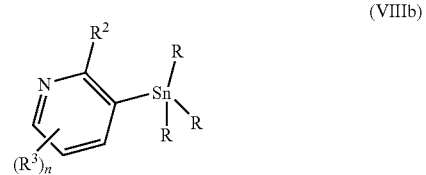

wherein R is an alkyl group or an allyl group, and the other symbol is as defined above, according to a method described in Synthesis, vol. 7, pages 564-565 (1986) or a method analogous thereto.

Compound (IX) wherein each symbol in the formula is as defined above can be produced by reducing compound (IV) with a reducing agent such as lithium aluminum hydride, diisobutyl aluminum hydride, sodium borohydride, calcium borohydride and the like. As the reducing agent, diisobutyl aluminum hydride is particularly preferable. The amount of the reducing agent to be used is 0.75 to 10 equivalents, preferably 1 to 5 equivalents, per 1 mol of compound (IV).

This reaction is advantageously carried out using a solvent inert to the reaction. While the solvent is not particularly limited as long as the reaction proceeds, solvents such as hydrocarbons (e.g., benzene, toluene and the like), ethers (e.g., tetrahydrofuran, diethyl ether and the like) and the like, a mixed solvent thereof and the like are preferable.

While the reaction time varies depending on the reagents and solvent to be used, it is generally 10 min to 24 hr, preferably 30 min to 8 hr.

The reaction temperature is generally -78° C. to 100° C., preferably -78° C. to 25° C.

Compound (X) wherein each symbol in the formula is as defined above can be produced by reacting compound (IX) with an oxidant such as chromic acid-pyridine complex, pyridinium chlorochromate, manganese dioxide, sulfur trioxide-pyridine complex, tetra-n-propylammonium perruthenate and the like. As the oxidant, manganese dioxide, sulfur trioxide-pyridine complex or tetra-n-propylammonium perruthenate is preferable. The oxidation reaction can be carried out, for example, according to the method described in *Synthesis*, p. 639 (1994).

Compound (I) wherein each symbol in the formula is as defined above can be produced by subjecting compound (X) and a compound represented by the formula (XI):

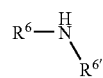

wherein $R^6$ and $R^{6'}$ are as defined above, to a reductive amination reaction, according to the methods described in *Shin Jikken Kagaku Koza*, Vols. 14-III, pp. 1380-1385 (Maruzen Press) and the like.

Compound (I) can also be produced by the following method.

Compound (XIII) wherein each symbol in the formula is as defined above can be produced from compound (XII) according to a method similar to the method for producing compound (X) from compound (IX).

Compound (XIV) wherein each symbol in the formula is as defined above can be produced from compound (XIII) according to a method similar to the method for producing compound (I) from compound (X).

Compound (XV) wherein $R^8$ is an amino-protecting group and other symbols are as defined above can be produced by protecting the amino group of compound (XIV) wherein $R^{6'}$ is a hydrogen atom. Examples of the amino-protecting group include a tert-butylcarbamate group (BOC group), a benzylcarbamate group (Cbz group) and the like. The protection reaction can be carried out according to a method known per se, for example, the method described in *Protective Groups in Organic Synthesis*, $3^{rd}$ Ed., Theodora W. Greene, Peter G. M. Wuts, pp. 494-653, Wiley-Interscience (1999) and the like.

Compound (XVI) wherein each symbol in the formula is as defined above can be produced from compound (XV) according to a method similar to the method for producing compound (IV) from compound (VII).

Compound (I) wherein each symbol is as defined above can be produced from compound (XIV) according to a method similar to the method for producing compound (IV) from compound (VII). Alternatively, compound (I) can be produced by removing the amino-protecting group from com-

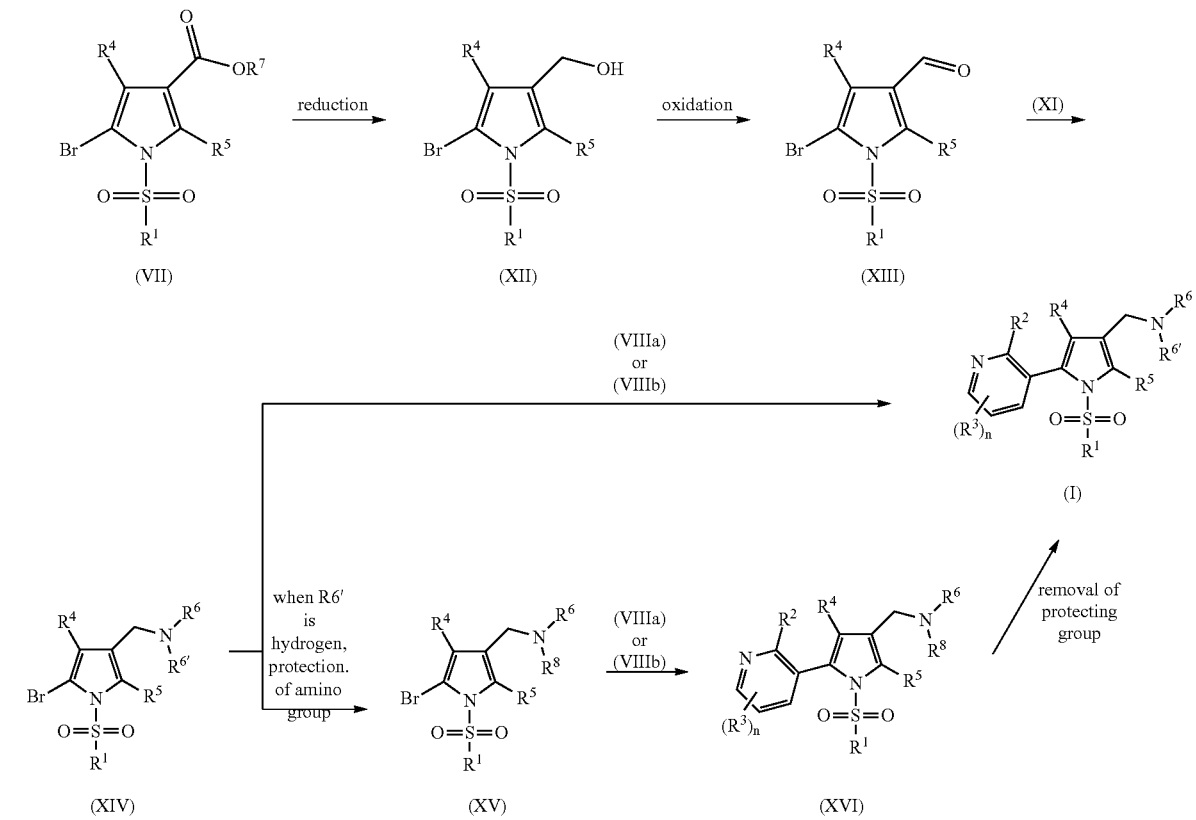

Compound (XII) wherein each symbol in the formula is as defined above can be produced from compound (VII) according to a method similar to the method for producing compound (IX) from compound (IV).

pound (XVI) by a method known per se, for example, the method described in *Protective Groups in Organic Synthesis*, 3rd Ed., Theodora W. Greene, Peter G. M. Wuts, pp. 494-653, Wiley-Interscience (1999) and the like.

Compounds (XVI) and (I) can also be produced by the following methods.

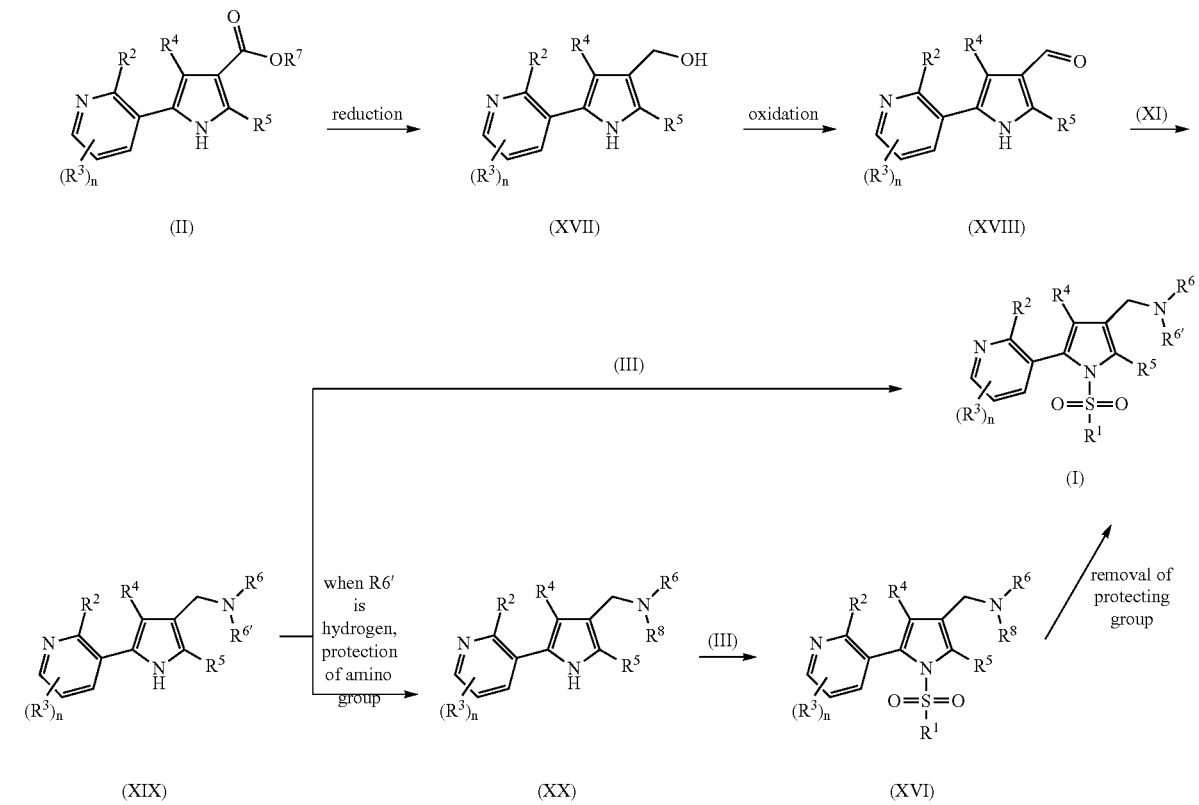

Compound (XVII) wherein each symbol in the formula is as defined above can be produced from compound (II) according to a method similar to the method for producing compound (IX) from compound (IV).

Compound (XVIII) wherein each symbol in the formula is as defined above can be produced from compound (XVII) according to a method similar to the method for producing compound (X) from compound (IX).

Compound (XIX) wherein each symbol in the formula is as defined above can be produced from compound (XVIII) according to a method similar to the method for producing compound (I) from compound (X).

Compound (XX) wherein each symbol in the formula is as defined above can be produced from compound (XIX) wherein $R^{6'}$ is a hydrogen atom according to a method similar to the method for producing compound (XV) from compound (XIV).

Compound (XVI) wherein each symbol in the formula is as defined above can be produced from compound (XX) according to a method similar to the method for producing compound (IV) from compound (II).

Compound (I) wherein each symbol is as defined above can be produced from compound (XIX) according to a method similar to the method for producing compound (IV) from compound (II). Alternatively, compound (I) can be produced by deprotecting compound (XVI) according to the aforementioned method.

Compounds (XIII), (X) and (I) can also be produced by the following methods.

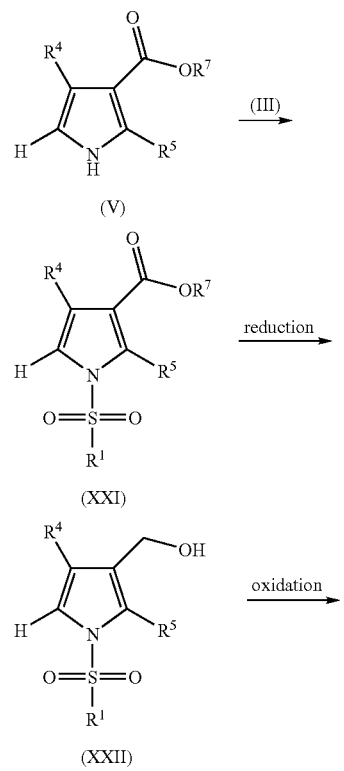

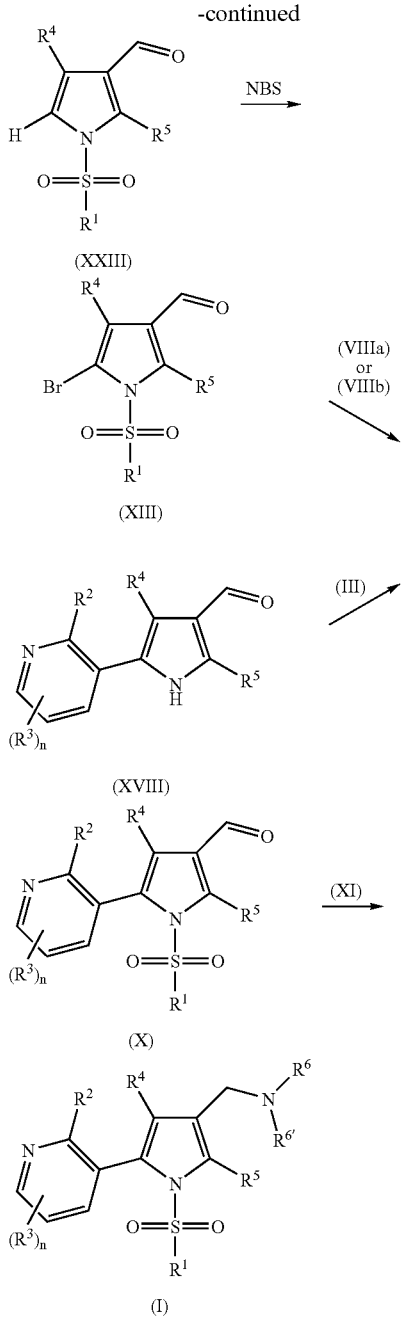

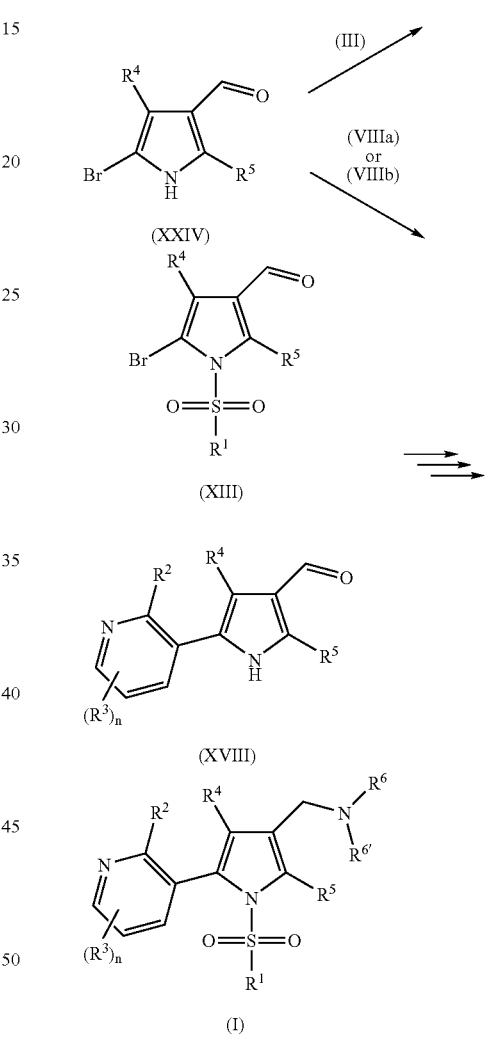

Compound (XXI) wherein each symbol in the formula is as defined above can be produced from compound (V) according to a method similar to the method for producing compound (IV) from compound (II).

Compound (XXII) wherein each symbol in the formula is as defined above can be produced from compound (XXI) according to a method similar to the method for producing compound (IX) from compound (IV).

Compound (XXIII) wherein each symbol in the formula is as defined above can be produced from compound (XXII) according to a method similar to the method for producing compound (X) from compound (IX).

Compound (XIII) wherein each symbol in the formula is as defined above can be produced from compound (XXIII) according to a method similar to the method for producing compound (VI) from compound (V).

Compound (X) wherein each symbol in the formula is as defined above can be produced from compound (XIII) according to a method similar to the method for producing compound (IV) from compound (VII), or from compound (XVIII) according to a method similar to the method for producing compound (IV) from compound (II). Furthermore, compound (I) can be produced according to a method similar to the aforementioned method.

Moreover, compound (XIII) and compound (XVIII) can also be synthesized by the following method, and compound (I) can be further produced by a method similar to the aforementioned method.

Compound (XXIV) wherein each symbol in the formula is as defined above can be produced according to a method known per se, for example, the method described in *J. Org. Chem.*, vol. 55, p. 6317 (1990) and the like, or a method analogous thereto.

Compound (XIII) wherein each symbol in the formula is as defined above can be produced from compound (XXIV) according to a method similar to the method for producing compound (IV) from compound (II).

Compound (XVIII) wherein each symbol in the formula is as defined above can be produced from compound (XXIV) according to a method similar to the method for producing compound (IV) from compound (VII).

Each of $R^2$, $R^3$, $R^4$ and $R^5$ of compounds (I) to (XXIV) in the formula can also be converted to different substituents by a substitution reaction and the like. Examples thereof include a conversion reaction of hydrogen into halogen using NBS, N-chlorosuccinic acid imide, N-fluoropyridinium salt and the like, and a conversion reaction of halogen into a cyano group using copper cyanide, zinc cyanide and the like. When $R^2$, $R^3$, $R^4$ and $R^5$ other than those in compound (I) are converted, each may be led to compound (I) according to the aforementioned methods.

Compound (XX) and compound (XIX) wherein $R^4$ is a halogen atom can also be produced by the following method. The method is particularly effective for the compounds wherein $R^4$ is a fluorine atom. Compound (I) can be produced according to a method similar to the aforementioned method.

Compound (XXVI) wherein $R^{4'}$, $R^5$ and $R^9$ are as defined above can be produced by reacting compound (XXV) with a base.

Examples of the base include inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, 1,8-diazabicyclo[5.4.0]undec-7-ene (DBU) and the like, and the like. The

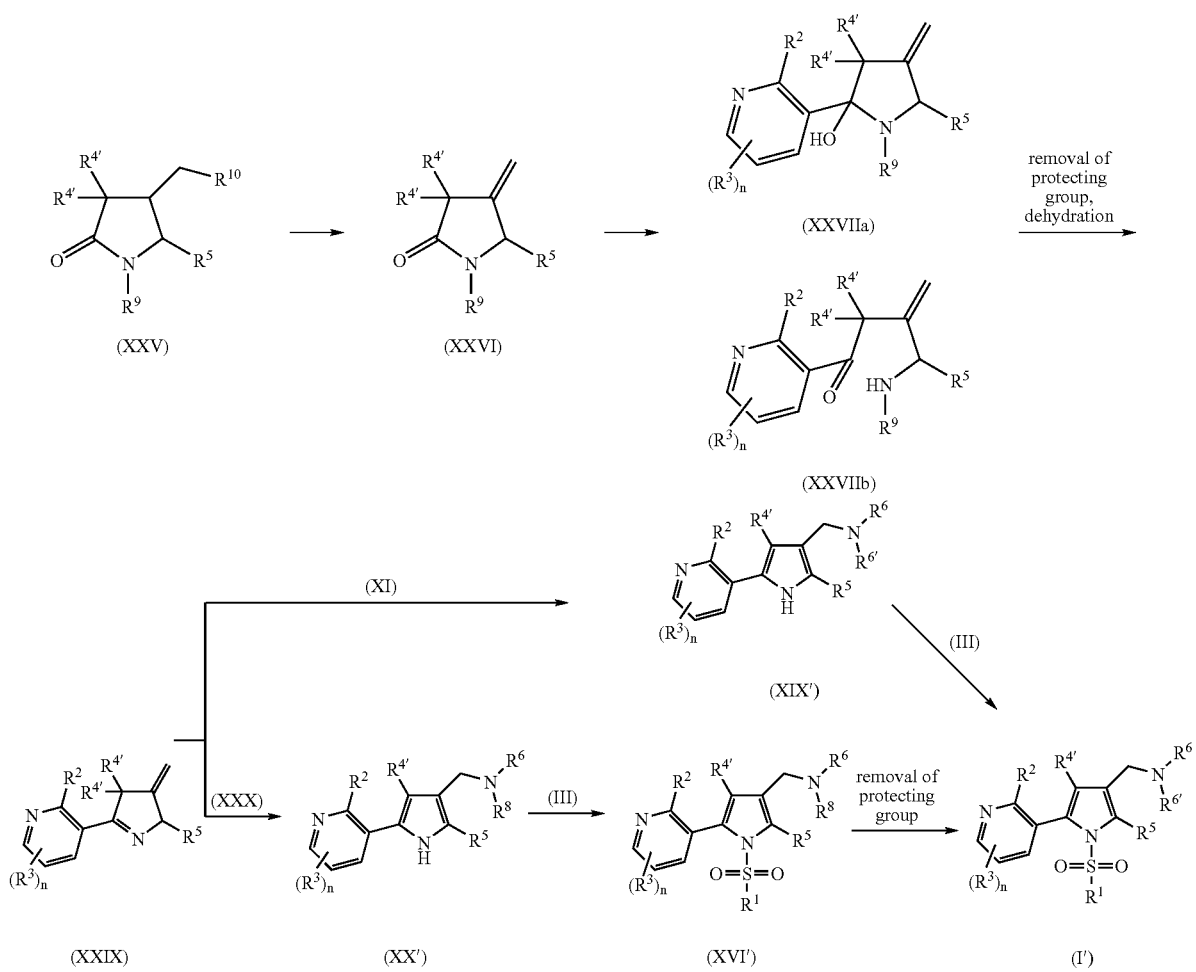

Compound (XXV) wherein $R^{4'}$ is a halogen atom such as fluorine, chlorine, bromine, iodine and the like, $R^5$ is as defined in the above, $R^9$ is an amide protecting group, and $R^{10}$ is a halogen atom such as chlorine, bromine, iodine and the like can be produced according to a method known per se, for example, the method described in J. Org. Chem., vol. 66, page 315 (2001) and the like or a method analogous thereto.

Examples of the amide protecting group for $R^9$ include a tert-butylcarbamate group (BOC group), a tosyl group, a benzyl group, an allyl group and the like can be mentioned, and are not particularly limited.

amount of the bases to be used is 0.8 to 10 mol, preferably 1 to 5 mol, per 1 mol of compound (XXV).

This reaction is advantageously carried out using a solvent inert to the reaction. While the solvent is not particularly limited as long as the reaction proceeds, hydrocarbons such as benzene, toluene and the like, ethers such as tetrahydrofuran and the like, amides such as N,N-dimethylformamide, N,N-dimethylacetamide and the like, and the like or a mixed solvent thereof and the like is preferable.

While the reaction time varies depending on the reagents and solvent to be used, it is generally 1 min to 48 hr, preferably 10 min to 8 hr.

The reaction temperature is generally −78° C. to 100° C., preferably −10° C. to 70° C.

Compound (XXVIIa) wherein each symbol is as defined above, or compound (XXVIIb) wherein each symbol is as defined above can be produced by reacting compound (XXVI) with a compound represented by the formula (XXVIII) wherein $R^2$ and $R^3$ are as defined above.

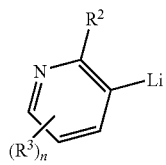
(XXVIII)

Compound (XXVIII) can be generated in a reaction system, for example, according to a method described in Tetrahedron Lett., vol. 21, page 4137 (1980), or Tetrahedron Lett., vol. 42, page 8697 (2001) or a method analogous thereto.

While the solvent used for this reaction is not particularly limited as long as the reaction proceeds, hydrocarbons such as n-hexane, toluene and the like, ethers such as tetrahydrofuran, diethyl ether and the like, and the like or a mixed solvent thereof and the like are preferable.

While the reaction time varies depending on the substrates and solvent to be used, it is generally 1 min to 48 hr, preferably 10 min to 24 hr.

The reaction temperature is generally −100° C. to 50° C., preferably −78° C. to 0° C.

Compound (XXIX) wherein $R^2$, $R^3$, $R^{4\prime}$ or $R^5$ is as defined above can be produced by subjecting compound (XXVIIa) or compound (XXVIIb) to deprotection and dehydrating reaction. While the reaction condition is not particularly limited, it varies depending on the kind of the protecting group and the solvent to be used. For example, the deprotection and the dehydrating reaction are continuously proceed by treating with an acid such as TFA and hydrochloric acid.

Compound (XX') wherein $R^2$, $R^3$, $R^{4\prime}$, $R^5$, $R^6$ or $R^8$ is as defined above and compound (XIX') wherein each symbol is as defined above can be produced by treating compounds represented by the formula (XXX) wherein $R^6$ and $R^8$ are defined above and the formula (XI), respectively, with a base such as sodium hydride, n-butyllithium and the like, and then reacting the resulting compound with compound (XXIX).

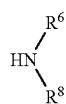
(XXX)

The protecting group for $R^8$ in this reaction is not particularly limited as long as it can be removed, benzyl group, 4-methoxybenzyl group, 2,4-dimethoxybenzyl group and the like are preferable.

While the solvent used for this reaction is not particularly limited as long as the reaction proceeds, hydrocarbons such as n-hexane, toluene and the like, ethers such as tetrahydrofuran, diethyl ether and the like, and the like or a mixed solvent thereof and the like are preferable.

While the reaction time varies depending on the substrates and solvent to be used, it is generally 1 min to 48 hr, preferably 10 min to 5 hr.

The reaction temperature is generally −100° C. to 100° C., preferably −78° C. to 30° C.

Each of $R^1$, $R^2$, $R^3$, $R^4$, $R^{4\prime}$ and $R^5$ of compounds (I) to (XXIX) in the formula can also be converted to different substituents by a substitution reaction, oxidation, reduction reaction and the like. When $R^1$, $R^2$, $R^3$, $R^4$, $R^{4\prime}$ and $R^5$ other than those in compound (I) are converted, each may be led to compound (I) or (I') according to the aforementioned methods.

The aforementioned compound (XXVI), and compound (XXXIa), compound (XXXIb) and (XXXII), which are introduced therefrom, are intermediates used for advantageously producing pyrrole compound (XXXIII).

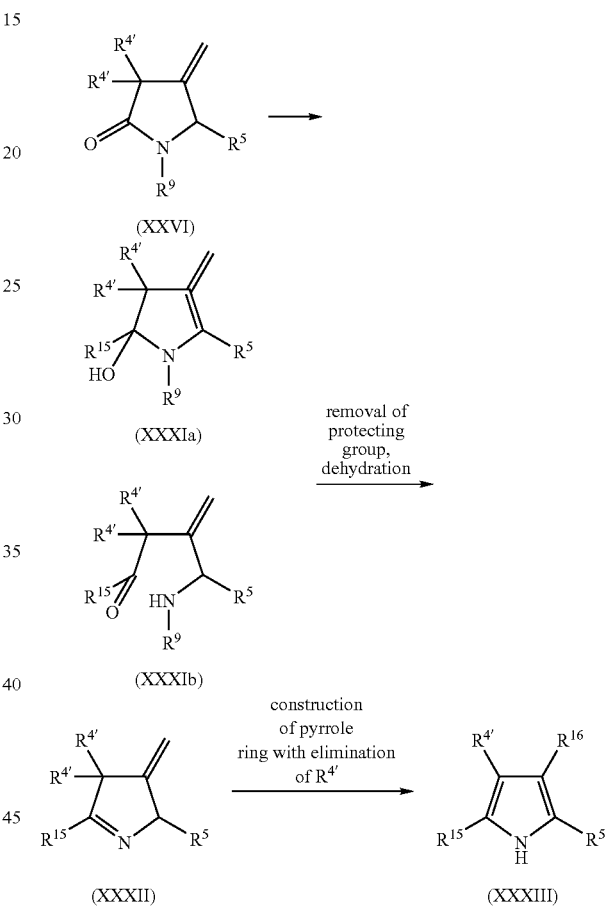

Compound (XXXIa) or compound (XXXIb) wherein $R^{15}$ is an optionally substituted hydrocarbon group or an optionally substituted heterocyclic group, and other symbols are as defined above) are can be produced by reacting compound (XXVI) with a compound represented by the formula (XXXIV)

$$R^{15}-X \qquad (XXXIV)$$

wherein $R^{15}$ is as defined above, and X is an atom or molecule capable of imparting nucleophilicity to $R^{15}$.

Examples of the "optionally substituted hydrocarbon group" for $R^{15}$ include those similar to the above-mentioned "optionally substituted hydrocarbon group" for $R^7$, $R^8$, $R^9$, $R^{10}$, $R^{11}$ or $R^{12}$.

Examples of the "optionally substituted heterocyclic group" for $R^{15}$ include those similar to the above-mentioned "optionally substituted heterocyclic group" for $R^7$, $R^8$, $R^9$, $R^{10}$, $R^{11}$ or $R^{12}$.

While X is not particularly limited as long as the reaction proceeds, Li, MgBr, MgCl and the like are preferable.

While the solvent used for this reaction is not particularly limited as long as the reaction proceeds, hydrocarbons such as n-hexane, toluene and the like, ethers such as tetrahydrofuran, diethyl ether and the like, and the like or a mixed solvent thereof and the like are preferable.

While the reaction time varies depending on the substrates and solvent to be used, it is generally 1 min to 48 hr, preferably 10 min to 24 hr.

The reaction temperature is generally −100° C. to 200° C., preferably −78° C. to 100° C.

Compound (XXXII) wherein each symbol is as defined above can be produced by subjecting compound (XXXIa) or compound (XXXIb) to deprotection and dehydrating reaction. While the reaction condition is not particularly limited, it varies depending on the kind of the protecting group and the solvent to be used. For example, the deprotection and the dehydrating reaction are continuously proceed by treating with an acid such as TFA and hydrochloric acid.

Compound (XXXIII) wherein $R^{16}$ is an optionally substituted aminomethyl group, and the other symbols are as defined above) can be produced by an elimination reaction of $R^{4'}$, which is accompanied by an addition reaction to the double bond of compound (XXXII).

While the elimination reaction of $R^{4'}$, accompanied by an addition reaction to the double bond of compound (XXXII), is not particularly limited, a method of reacting a compound with a nucleophilic agent, which is represented by a method of treating a compound represented by the formula (XXX)

(XXX)

wherein each symbol is as defined above, with a base such as sodium hydride, n-butyllithium and the like, and then reacting the resulting compound with compound (XXXII) to give a compound wherein $R^{16}$ is an aminomethyl group; a method of subjecting compound (XXXII) to a catalytic reduction to give a compound wherein $R^{16}$ is aminomethyl group, and the like are preferable.

While the solvent used for this reaction is not particularly limited as long as the reaction proceeds, hydrocarbons such as n-hexane, toluene and the like, ethers such as tetrahydrofuran, diethyl ether and the like, amides such as N,N-dimethylformamide, N,N-dimethylacetamide and the like, and the like or a mixed solvent thereof and the like are preferable.

While the reaction time varies depending on the substrates and solvent to be used, it is generally 1 min to 48 hr, preferably 10 min to 5 hr.

The reaction temperature is generally −100° C. to 200° C., preferably −78° C. to 100° C.

compound (I) can be isolated and purified by a known means such as phase transfer, concentration, solvent extraction, fractionation, liquid conversion, crystallization, recrystallization, chromatography and the like.

When compound (I) is obtained as a free compound, it can be converted to a desired salt by a method known per se or a method analogous thereto; conversely, when compound (I) is obtained as a salt, it can be converted into a free form or another desired salt by a method known per se or a method analogous thereto.

Compound (I) may be used as a prodrug. The prodrug of compound (I) means a compound which is converted to compound (I) under the physiological condition in the body by a reaction with an enzyme, gastric acid, or the like, that is, a compound which is converted to compound (I) by enzymatic oxidation, reduction, hydrolysis, and the like; a compound which is converted to compound (I) by hydrolysis with gastric acid, and the like.

The prodrug of compound (I) includes a compound wherein the amino group of compound (I) is modified with acyl, alkyl or phosphoryl (e.g., a compound wherein the amino group of compound (I) is modified with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl or t-butyl, etc.); a compound wherein the hydroxy group of compound (I) is modified with acyl, alkyl, phosphoric acid or boric acid (e.g., a compound wherein the hydroxy group of compound (I) is modified with acetyl, palmitoyl, propanoyl, pivaloyl, succinyl, fumaryl, alanyl or dimethylaminomethylcarbonyl, etc.); a compound wherein a carboxyl group of compound (I) is modified to ester or amide (e.g., a compound wherein a carboxyl group of compound (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide, etc.); and the like. These compounds can be produced from compound (I) by a method known per se.

In addition, the prodrug of compound (I) may be a compound, which is converted to compound (I) under the physiological conditions, as described in *Pharmaceutical Research and Development*, Vol. 7 (Molecule Design), pp. 163-198 (1990), published by Hirokawa Publishing Co.

When compound (I) contains an optical isomer, a stereoisomer, a regioisomer or a rotamer, either isomer and a mixture of these are also encompassed in compound (I). For example, when compound (I) has an optical isomer, an optical isomer resolved from a racemate is also encompassed in compound (I). These isomers can be obtained as single products according to synthesis and separation methods known per se (concentration, solvent extraction, column chromatography, recrystallization, etc.).

The compound (I) may be a crystal, and both a single crystal and crystal mixtures are encompassed in compound (I). Crystals can be produced by crystallization according to crystallization methods known per se.

The compound (I) may be a solvate (e.g., hydrate etc.) or a non-solvate, both of which are encompassed in the compound (I).

A compound labeled with an isotope (e.g., $^3$H, $^{14}$C, $^{35}$S, $^{125}$I and the like) and a deuterium conversion form wherein $^1$H has been converted to $^2$H(D) are also encompassed in the compound (I).

Compound (I) and a prodrug thereof of the present invention (hereinafter sometimes to be abbreviated as the compound of the present invention) have a proton pump inhibitory effect and effectively suppress gastric acid secretion. In addition, since they show low toxicity (e.g., acute toxicity, chronic toxicity, genetic toxicity, reproductive toxicity, cardiotoxicity, drug interaction, carcinogenicity and the like) and high water-solubility, and are superior in the stability, in vivo kinetics (absorbability, distribution, metabolism, excretion and the like), and efficacy expression, they are useful as pharmaceutical agents.

The compound of the present invention is useful for the treatment or prophylaxis of peptic ulcer (e.g., gastric ulcer, duodenal ulcer, anastomotic ulcer, ulcer caused by non-steroidal anti-inflammatory agent, ulcer due to postoperative stress etc.); Zollinger-Ellison syndrome; gastritis; erosive esophagitis; reflux esophagitis such as erosive reflux esophagitis and the like; symptomatic gastroesophageal reflux disease (Symptomatic GERD) such as nonerosive esophageal reflux, esophageal reflux unaccompanied by esophagitis and the like; Barrettesophagus; functional dyspepsia; gastric cancer (including gastric cancer associated with promoted production of interleukin-1β due to gene polymorphism of interleukin-1); stomach MALT lymphoma; hyperacidity; upper gastrointestinal hemorrhage caused by peptic ulcer, acute stress ulcer, hemorrhagic gastritis, invasive stress (e.g., stress caused by major surgery requiring post-operative intensive management, or cerebrovascular disorder, head trauma, multiple organ failure or extensive burn requiring intensive treatment) and the like; airway disorders; asthma; and the like in mammals (e.g., human, monkey, sheep, bovine, horse, dog, cat, rabbit, rat, mouse etc.), pre-anesthetic administration, eradication or assistant to eradication of *Helicobacter pylori* and the like.

As used herein, the above-mentioned reflux esophagitis and symptomatic gastroesophageal reflux disease (symptomatic GERD) are sometimes collectively referred to simply as GERD.

The content of a compound of the present invention in the pharmaceutical composition of the present invention is about 0.01 to 100% by weight relative to the entire composition. Though subject to change depending on the administration target, administration route, target disease and the like, its dose is about 0.5 to 1,500 mg/day, preferably about 5 to 150 mg/day, based on the active ingredient, when, for example, the compound is orally administered as an anti-ulcer agent to an adult human (60 kg). The compound of the present invention may be administered once daily or in 2 or 3 divided portions per day.

The compound of the present invention shows low toxicity and can be safely administered orally or parenterally (e.g., topical, rectal, intravenous administrations and the like) as it is or as a preparation containing a pharmaceutical composition containing a pharmacologically acceptable carrier admixed according to a method known per se, such as tablets (including sugar-coated tablets and film-coated tablets), powder, granule, capsule (including soft capsule), orally disintegrating tablet, orally disintegrating film, liquid, injection, suppository, sustained-release preparation, plaster and the like. Particularly, the compound of the present invention is preferably administered as an oral preparation in the form of tablet, granule, capsule and the like.

The pharmacologically acceptable carrier that may be used to produce the pharmaceutical composition of the present invention includes various organic or inorganic carrier substances in common use as pharmaceutical materials, including excipients, lubricants, binders, disintegrants, water-soluble polymers and basic inorganic salts for solid preparations; and solvents, solubilizing agents, suspending agents, isotonizing agents, buffers and soothing agents for liquid preparations and the like. Other ordinary pharmaceutical additives such as preservatives, anti-oxidants, colorants, sweetening agents, souring agents, bubbling agents and flavorings may also be used as necessary.

Such "excipients" include, for example, lactose, sucrose, D-mannitol, starch, cornstarch, crystalline cellulose, light anhydrous silicic acid, titanium oxide and the like.

Such "lubricants" include, for example, magnesium stearate, sucrose fatty acid esters, polyethylene glycol, talc, stearic acid and the like.

Such "binders" include, for example, hydroxypropyl cellulose, hydroxypropylmethyl cellulose, crystalline cellulose, starch, polyvinylpyrrolidone, gum arabic powder, gelatin, pullulan, low-substituted hydroxypropyl cellulose and the like.

Such "disintegrants" include (1) crosspovidone, (2) what is called super-disintegrants such as crosscarmellose sodium (FMC-Asahi Chemical) and carmellose calcium (Gotoku Yakuhin) etc, (3) sodium carboxymethyl starch (e.g., product of Matsutani Chemical), (4) low-substituted hydroxypropyl cellulose (e.g., product of Shin-Etsu Chemical), (5) corn starch, and so forth. Said "crosspovidone" may be any crosslinked polymer having the chemical name 1-ethenyl-2-pyrrolidinone homopolymer, including polyvinylpyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP), Polyplasdon INF-10 (produced by ISP) and the like.

Such "water-soluble polymers" include, for example, ethanol-soluble water-soluble polymers [e.g., cellulose derivatives such as hydroxypropyl cellulose (hereinafter also referred to as HPC) etc, polyvinylpyrrolidone and the like], ethanol-insoluble water-soluble polymers [e.g., cellulose derivatives such as hydroxypropylmethyl cellulose (hereinafter also referred to as HPMC) etc., methyl cellulose, carboxymethyl cellulose sodium and the like, sodium polyacrylate, polyvinyl alcohol, sodium alginate, guar gum and the like] and the like.

Such "basic inorganic salts" include, for example, basic inorganic salts of sodium, potassium, magnesium and/or calcium. Preferred are basic inorganic salts of magnesium and/or calcium. More preferred are basic inorganic salts of magnesium. Such basic inorganic salts of sodium include, for example, sodium carbonate, sodium hydrogen carbonate, disodium hydrogenphosphate and the like. Such basic inorganic salts of potassium include, for example, potassium carbonate, potassium hydrogencarbonate and the like. Such basic inorganic salts of magnesium include, for example, heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{16}.CO_3.4H_2O$], and aluminum magnesium hydroxide. Preferred are heavy magnesium carbonate, magnesium carbonate, magnesium oxide, magnesium hydroxide and the like. Such basic inorganic salts of calcium include, for example, precipitated calcium carbonate, calcium hydroxide, etc.

Such "solvents" include, for example, water for injection, alcohol, propylene glycol, macrogol, sesame oil, corn oil, olive oil and the like.

Such "solubilizing agents" include, for example, polyethylene glycol, propylene glycol, D-mannitol, benzyl benzoate, ethanol, trisaminomethane, cholesterol, triethanolamine, sodium carbonate, sodium citrate and the like.

Such "suspending agents" include, for example, surfactants such as stearyltriethanolamine, sodium lauryl sulfate, laurylaminopropionic acid, lecithin, benzalkonium chloride, benzethonium chloride, glyceryl monostearate etc; hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose etc., and the like.

Such "isotonizing agents" include, for example, glucose, D-sorbitol, sodium chloride, glycerol, D-mannitol and the like.

Such "buffers" include, for example, buffer solutions of phosphates, acetates, carbonates, citrates etc, and the like.

Such "soothing agents" include, for example, benzyl alcohol and the like.

Such "preservatives" include, for example, p-oxybenzoic acid esters, chlorobutanol, benzyl alcohol, phenethyl alcohol, dehydroacetic acid, sorbic acid and the like.

Such "antioxidants" include, for example, sulfites, ascorbic acid, α-tocopherol and the like.

Such "colorants" include, for example, food colors such as Food Color Yellow No. 5, Food Color Red No. 2, Food Color Blue No. 2 etc.; food lake colors, red ferric oxide and the like.

Such "sweetening agents" include, for example, saccharin sodium, dipotassium glycyrrhizinate, aspartame, stevia, thaumatin and the like.

Such "souring agents" include, for example, citric acid (citric anhydride), tartaric acid, malic acid and the like. Such "bubbling agents" include, for example, sodium bicarbonate and the like.

Such "flavorings" may be synthetic substances or naturally occurring substances, and include, for example, lemon, lime, orange, menthol, strawberry and the like.

The compound of the present invention may be prepared as a preparation for oral administration in accordance with a commonly-known method, by, for example, compression-shaping with a carrier such as an excipient, a disintegrant, a binder, a lubricant, or the like, and subsequently coating the preparation as necessary by a commonly known method for the purpose of taste masking, enteric dissolution or sustained release. For an enteric preparation, an intermediate layer may be provided by a commonly known method between the enteric layer and the drug-containing layer for the purpose of separation of the two layers.

For preparing the compound of the present invention as an orally disintegrating tablet, available methods include, for example, a method in which a core containing crystalline cellulose and lactose is coated with the compound of the present invention and, where necessary, a basic inorganic salt, and then further coated with a coating layer containing an water-soluble polymer to give a composition, which is coated with an enteric coating layer containing polyethylene glycol, further coated with an enteric coating layer containing triethyl citrate, still further coated with an enteric coating layer containing polyethylene glycol, and finally coated with mannitol to give fine granules, which are mixed with additives and shaped.

The above-mentioned "enteric coating layer" includes, for example, a layer consisting of a mixture of one or more kinds from aqueous enteric polymer substrates such as cellulose acetate phthalate (CAP), hydroxypropylmethyl cellulose phthalate, hydroxymethyl cellulose acetate succinate, methacrylic acid copolymers (e.g., Eudragit L30D-55 (trade name; produced by Rohm), Colicoat MAE30DP (trade name; produced by BASF), Polyquid PA30 (trade name; produced by Sanyo Chemical) etc.), carboxymethylethyl cellulose, shellac and the like; sustained-release substrates such as methacrylic acid copolymers (e.g., Eudragit NE30D (trade name), Eudragit RL30D (trade name), Eudragit RS30D (trade name), etc.) and the like; water-soluble polymers; plasticizers such as triethyl citrate, polyethylene glycol, acetylated monoglycerides, triacetin, castor oil and the like; and the like, and the like.

The above-mentioned "additive" includes, for example, water-soluble sugar alcohols (e.g., sorbitol, mannitol, maltitol, reduced starch saccharides, xylitol, reduced palatinose, erythritol, etc.), crystalline cellulose (e.g., Ceolas KG 801, Avicel PH 101, Avicel PH 102, Avicel PH 301, Avicel PH 302, Avicel RC-591 (crystalline cellulose.carmellose sodium) etc.), low-substituted hydroxypropyl cellulose (e.g., LH-22, LH-32, LH-23, LH-33 (Shin-Etsu Chemical), mixtures thereof etc.) and the like. Furthermore, binders, souring agents, bubbling agents, sweetening agents, flavorings, lubricants, colorants, stabilizers, excipients, disintegrants etc. are also used.

The compound of the present invention may be used in combination with 1 to 3 other active ingredients.

Such "other active ingredients" include, for example, anti-*Helicobacter pylori* active substances, imidazole compounds, bismuth salts, quinolone compounds, and so forth.

Examples of the "anti-*Helicobacter pylori* active substance" include penicillin antibiotic (e.g., amoxicillin, benzylpenicillin, piperacillin, mecillinam, ampicillin, temocillin, bacampicillin, aspoxicillin, sultamicillin, lenampicillin etc.), cephem antibiotic (e.g., cefixime, cefaclor etc.), macrolide antibiotic (e.g., erythromycin, clarithromycin, roxithromycin, rokitamycin, flurithromycin, telithromycin etc.), tetracycline antibiotic (e.g., tetracycline, minocycline, streptomycin etc.), aminoglycoside antibiotic (e.g., gentamicin, amikacin etc.), imipenem and the like. Of these, penicillin antibiotic, macrolide antibiotic and the like are preferable.

Such "imidazole compounds" include, for example, metronidazole, miconazole and the like.

Such "bismuth salts" include, for example, bismuth acetate, bismuth citrate, bismuth subsalicylate and the like.

Such "quinolone compounds" include, for example, ofloxacin, ciploxacin and the like.

For eradication of *Helicobacter pylori*, a compound (I) or a salt thereof of the present invention with antibiotic penicillin (e.g., amoxicillin and the like) and antibiotic erythromycin (e.g., clarithromycin and the like) is preferably used.

For the purpose of eradication of *Helicobacter pylori*, while the compound of the present invention has an anti-*H. pylori* action (bacteriostatic action or eradication action) by itself, it can enhance antibacterial action of other antibiotics based on the pH controlling action in the stomach and the like, and also provides an assistant effect such as an eradication effect based on the action of the antibiotics to be used in combination.

Such "other active ingredients" and the compound (I) or a salt thereof of the present invention may be mixed, prepared as a single pharmaceutical composition [e.g., tablets, powders, granules, capsules (including soft capsules), liquids, injectable preparations, suppositories, sustained-release preparations, etc.], in accordance with a commonly known method, and used in combination, and may also be prepared as separate preparations and administered to the same subject simultaneously or at a time interval.

In addition, the compound of the present invention may be used in combination with a gastric motility enhancer, a drug acting on lower esophageal sphincter (e.g., temporary lower esophageal sphincter relaxation suppressant etc.), ClC-2 channel opener (intestinal juice secretion enhancer), a histamine H2 receptor antagonist, an antacid, a sedative, a stomachic digestant or a non-steroidal anti-inflammatory drug (NSAID).

As the "gastric motility enhancer", for example, domperidone, metoclopramide, mosapride, itopride, tegaserod and the like can be mentioned.

As the "a drug acting on lower esophageal sphincter", for example, GABA-B receptor agonists such as baclofen, an optically active form thereof and the like, glutamine receptor antagonists and the like can be mentioned.

As the "ClC-2 channel opener (intestinal juice secretion enhancer)", lubiprostone and the like can be mentioned.

As the "histamine H2 receptor antagonist", cimetidine, ranitidine, famotidine, roxatidine, nizatidine, lafutidine and the like can be mentioned.

As the "antacid", sodium hydrogen carbonate, aluminum hydroxide and the like can be mentioned.

As the "sedatives", diazepam, chlordiazepoxide and the like can be mentioned.

As the "stomachic digestant", gentiana, *swertia japonica*, diastase and the like can be mentioned.

As the "non-steroidal anti-inflammatory drug", for example, aspirin, indomethacin, ibuprofen, mefenamic acid, diclofenac, etodorac, piroxicam, celecoxib and the like can be mentioned.

A gastric motility enhancer, a drug acting on lower esophageal sphincter, a ClC-2 channel opener (intestinal juice secretion enhancer), a histamine H2 receptor antagonist, an antacid, a sedative, a stomachic digestant or a non-steroidal anti-inflammatory drug and compound (I) or a salt thereof of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a staggered manner.

The compound of the present invention may be used in combination with the following drugs.

(i) proton pump inhibitor, for example, omeprazole, esomeprazole, pantoprazole, rabeprazole, tenatoprazole, ilaprazole and lansoprazole;

(ii) oral antacid combination agent, for example, Maalox, Aludrox and Gaviscon;

(iii) mucous membrane protector, for example, polaprezinc, ecabe sodium, rebamipide, teprenone, cetraxate, sucralfate, chloropylline-copper and plaunotol;

(iv) antigastric agent, for example, anti-gastrin vaccine, itriglumide and Z-360;

(v) 5-HT$_3$ antagonist, for example, dolasetron, palonosetron, alosetron, azasetron, ramosetron, mitrazapine, granisetron, tropisetron, E-3620, ondansetron and indisetron;

(vi) 5-HT$_4$ agonist, for example, tegaserod, mosapride, cinitapride and oxtriptane;

(vii) laxative agent, for example, Trifyba, Fybogel, Konsyl, Isogel, Regulan, Celevac and Normacol;

(viii) GABA$_B$ agonist, for example, baclofen and AZD-3355;

(ix) GABA$_B$ antagonist, for example, GAS-360 and SGS-742;

(x) calcium channel blocker, for example, aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xi) dopamine antagonist, for example, metoclopramide, domperidone and levosulpiride;

(xii) tachykinin (NK) antagonist, particularly, NK-3, NK-2 and NK-1 antagonist, for example, nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenylpiperidine (2S,3S);

(xiii) nitric monoxide synthase inhibitor, for example, GW-274150, tilarginine, P54, guanidioethyldisulfide and nitroflurbiprofen;

(xiv) vanilloid receptor 1 antagonist, for example, AMG-517 and GW-705498;

(xv) ghrelin agonist, for example, capromorelin and TZP-101;

(xvi) AchE release stimulant, for example, Z-338 and KW-5092.

The above-mentioned drugs (i)-(xvi) and compound (I) or a salt thereof of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a staggered manner.

EXAMPLES

The present invention is explained in detail in the following by referring to Reference Examples, Examples and Experimental Examples, which are not to be construed as limitative.

In the following Reference Examples and Examples, the "room temperature" generally means about 10° C. to about 35° C., but it is not particularly strictly limited. The mixing ratio of liquids shows a volume ratio. Unless otherwise specified, "%" means weight %. The yield is in mol/mol %. Silica gel column chromatography was performed using silica gel 60 (0.063-0.200 mm) manufactured by MERCK, Fuji Silysia Chemical Ltd. Chromatorex (trade name) NH (described as basic silica gel column chromatography) or Purif-Pack manufactured by MORITEX (described as silica gel column chromatography or basic silica gel column chromatography). The melting point was measured using Yanagimoto trace melting point measurement apparatus or Buechi trace melting point measurement apparatus (B-545), and shown without amendment. For $^1$H-NMR spectrum, tetramethylsilane was used as the internal standard, and Varian Gemini-200 (200 MHz), Mercury-300 (300 MHz) spectrometer, Bruker AVANCE AV300 (300 MHz) and JNM-AL400 (400 MHz) nuclear magnetic resonance apparatuses JEOL DATUM (JEOL DATUM LTD.) were used for the measurement. The following abbreviations are used for showing the measurement results.

s: singlet, d: doublet, dd: double doublet, ddd: triple doublet, dt: double triplet, t: triplet, q: quartet, dq: double quartet, m: multiplet, br: broad, brs: broad singlet, J: coupling constant, Hz: Hertz.

Reference Example 1

5-bromo-1H-pyrrole-3-carbaldehyde

A solution of 1H-pyrrole-3-carbaldehyde (19.1 g) in tetrahydrofuran (300 mL) was cooled to −70° C., and a solution of N-bromosuccinimide (35.8 g) in N,N-dimethylformamide (100 mL) was added dropwise. After stirring at the same temperature for 1 hr, the mixture was warmed to −10° C. over 2 hr, and further stirred for 30 min. Ice water was added to the reaction mixture at 0° C., and the mixture was warmed to room temperature and extracted with ethyl acetate. The extract was washed with 10% aqueous citric acid solution, 6% aqueous sodium hydrogen carbonate solution and saturated brine, dried over anhydrous sodium sulfate, and concentrated under reduced pressure. The crystals obtained as a residue were washed with diisopropyl ether to give the title compound as colorless crystals (yield 17.7 g, 51%).
¹H-NMR (CDCl₃) δ: 6.65-6.66 (1H, m), 7.37-7.38 (1H, m), 8.80 (1H, br), 9.70 (1H, s).

Reference Example 2

5-bromo-1-(phenylsulfonyl)-1H-pyrrole-3-carbaldehyde

To a solution of 5-bromo-1H-pyrrole-3-carbaldehyde (3.50 g) in tetrahydrofuran (70 mL) was added sodium hydride (60% in oil, 1.21 g) at room temperature, and the mixture was stirred for 10 min. Benzenesulfonyl chloride (4.27 g) was added, and the mixture was further stirred for 1 hr, diluted with water, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→7:3) and crystallized from diisopropyl ether to give the title compound as colorless crystals (yield 5.4 g, 85%).
¹H-NMR (CDCl₃) δ: 6.73 (1H, d, J=2.0 Hz), 7.58-7.63 (2H, m), 7.70-7.75 (1H, m), 7.98-8.01 (2H, m), 8.10 (1H, d, J=2.0 Hz), 9.77 (1H, s).

Reference Example 3

5-(2-fluoropyridin-3-yl)-1-(phenylsulfonyl)-1H-pyrrole-3-carbaldehyde 5-bromo-1-(phenylsulfonyl)-1H-pyrrole-3-carbaldehyde (3.15 g), (2-fluoropyridin-3-yl)boronic acid (2.83 g), sodium hydrogen carbonate (2.53 g) and tetrakis(triphenylphosphine)palladium (870 mg) were added to a deaerated mixture of 1,2-dimethoxyethane (80 mL) and water (20 mL), and the mixture was stirred under a nitrogen atmosphere at 80° C. for 5 hr. The reaction mixture was cooled, saturated aqueous sodium hydrogen carbonate solution was added, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→2:3) to give the title compound as a colorless oil (yield 2.25 g, 68%).
¹H-NMR (CDCl₃) δ: 6.71 (1H, d, J=1.7 Hz), 7.24-7.28 (1H, m), 7.42-7.48 (4H, m), 7.62-7.68 (1H, m), 7.70-7.76 (1H, m), 8.14 (1H, d, J=1.9 Hz), 8.28-8.31 (1H, m), 9.90 (1H, s).

Reference Example 4

5-(2-fluoropyridin-3-yl)-1H-pyrrole-3-carbaldehyde 5-(2-Fluoropyridin-3-yl)-1-(phenylsulfonyl)-1H-pyrrole-3-carbaldehyde (2.25 g) was dissolved in methanol (20 mL) and tetrahydrofuran (20 mL), 8 mol/L aqueous sodium hydroxide solution (20 mL) was added dropwise at room temperature and the mixture was stirred for 1 hr. The reaction mixture was diluted with saturated brine, and extracted with ethyl acetate. The extract was washed with saturated brine, dried over anhydrous magnesium sulfate, and concentrated under reduced pressure. Ethyl acetate was added to the residue, and insoluble crystals were collected by filtration to give the title compound as pale-brown crystals (yield 1.03 g, 79%).
¹H-NMR (DMSO-d₆) δ: 6.99 (1H, d, J=1.5 Hz), 7.43-7.48 (1H, m), 7.88 (1H, s), 8.12-8.15 (1H, m), 8.27-8.34 (1H, m), 9.77 (1H, s), 12.28 (1H, brs).

Reference Example 5

1-[(2-fluorophenyl)sulfonyl]-5-(2-fluoropyridin-3-yl)-1H-pyrrole-3-carbaldehyde

To a solution of 5-(2-fluoropyridin-3-yl)-1H-pyrrole-3-carbaldehyde (80 mg) in tetrahydrofuran (8 mL) was added sodium hydride (60% in oil, 34 mg) at room temperature, and the mixture was stirred for 10 min. 15-Crown-5 (186 mg) was added dropwise, and the mixture was stirred for 5 min. 2-Fluorobenzenesulfonyl chloride (123 mg) was added, and the mixture was further stirred for 1 hr. The reaction mixture was diluted with saturated brine, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→1:1) to give the title compound as a colorless oil (yield 120 mg, 82%).
¹H-NMR (CDCl₃) δ: 6.73 (1H, d, J=1.5 Hz), 7.12-7.29 (4H, m), 7.64-7.74 (2H, m), 8.21 (1H, d, J=1.9 Hz), 8.24-8.26 (1H, m), 9.92 (1H, s).

Reference Example 6

5-(2-fluoropyridin-3-yl)-1-(2-furylsulfonyl)-1H-pyrrole-3-carbaldehyde

To a solution of 5-(2-fluoropyridin-3-yl)-1H-pyrrole-3-carbaldehyde (220 mg) in tetrahydrofuran (30 mL) was added sodium hydride (60% in oil, 84 mg) at room temperature and the mixture was stirred for 10 min. 15-Crown-5 (464 mg) was added dropwise, and the mixture was stirred for 5 min. Furan-2-sulfonyl chloride (263 mg) was added, and the mixture was further stirred for 30 min. The reaction mixture was diluted with saturated aqueous sodium hydrogen carbonate solution, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:1) and crystallized from diethyl ether to give the title compound as colorless crystals (yield 280 mg, 83%).
¹H-NMR (CDCl₃) δ: 6.51 (1H, dd, J=3.7 Hz, 1.8 Hz), 6.76 (1H, d, J=1.9 Hz), 6.84 (1H, dd, J=3.7 Hz, 0.7 Hz), 7.26-7.30 (1H, m), 7.60 (1H, dd, J=1.7 Hz, 1.0 Hz), 7.76-7.82 (1H, m), 8.10 (1H, d, J=1.7 Hz), 8.30-8.33 (1H, m), 9.90 (1H, s).

Reference Example 7

5-(2-fluoropyridin-3-yl)-1-{[3-(methylsulfonyl)phenyl]sulfonyl}-1H-pyrrole-3-carbaldehyde To a solution of 5-(2-fluoropyridin-3-yl)-1H-pyrrole-3-carbaldehyde (200 mg) in tetrahydrofuran (30 mL) was added sodium hydride (60% in oil, 84 mg) at room temperature and the mixture was stirred for 10 min. 15-Crown-5 (464 mg) was added dropwise, and the mixture was stirred for 5 min. 3-(Methylsulfonyl)benzenesulfonyl chloride (402 mg) was added, and the mixture was further stirred for 30 min. The reaction mixture was diluted with saturated aqueous sodium hydrogen carbonate solution, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:1→1:4) and crystallized from diethyl ether to give the title compound as colorless crystals (yield 280 mg, 65%).

$^1$H-NMR (CDCl$_3$) δ: 3.13 (3H, s), 6.75 (1H, d, J=1.9 Hz), 7.33-7.37 (1H, m), 7.70-7.86 (3H, m), 7.91 (1H, t, J=1.7 Hz), 8.16 (1H, d, J=1.9 Hz), 8.19-8.23 (1H, m), 8.31-8.34 (1H, m), 9.92 (1H, s).

Reference Example 8

5-(2-fluoropyridin-3-yl)-1-(2-thienylsulfonyl)-1H-pyrrole-3-carbaldehyde

To a solution of 5-(2-fluoropyridin-3-yl)-1H-pyrrole-3-carbaldehyde (200 mg) in tetrahydrofuran (30 mL) was added sodium hydride (60% in oil, 84 mg) at room temperature and the mixture was stirred for 10 min. 15-Crown-5 (464 mg) was added dropwise, and the mixture was stirred for 5 min. 3-(Methylsulfonyl)benzenesulfonyl chloride (402 mg) was added, and the mixture was further stirred for 30 min. The reaction mixture was diluted with saturated aqueous sodium hydrogen carbonate solution, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=3:2→2:3) and crystallized from diisopropyl ether to give the title compound as colorless crystals (yield 170 mg, 48%).

$^1$H-NMR (CDCl$_3$) δ: 6.74 (1H, d, J=1.9 Hz), 7.04 (1H, dd, J=4.9 Hz, 3.8 Hz), 7.27-7.31 (2H, m), 7.72 (1H, dd, J=4.9 Hz, 1.5 Hz), 7.77-7.83 (1H, m), 8.09 (1H, d, J=1.5 Hz), 8.30-8.33 (1H, m), 9.89 (1H, s).

Reference Example 9

1-(1,3-benzodioxol-5-ylsulfonyl)-5-(2-fluoropyridin-3-yl)-1H-pyrrole-3-carbaldehyde To a solution of 5-(2-fluoropyridin-3-yl)-1H-pyrrole-3-carbaldehyde (200 mg) in tetrahydrofuran (20 mL) was added sodium hydride (60% in oil, 64 mg) at room temperature and the mixture was stirred for 10 min. 15-Crown-5 (348 mg) was added dropwise, and the mixture was stirred for 5 min. 1,3-Benzodioxole-5-sulfonyl chloride (250 mg) was added, and the mixture was further stirred for 30 min. The reaction mixture was diluted with saturated aqueous sodium hydrogen carbonate solution, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=3:2→2:3) and crystallized from diethyl ether to give the title compound as colorless crystals (yield 250 mg, 64%).

$^1$H-NMR (CDCl$_3$) δ: 6.10 (2H, s), 6.71-6.82 (3H, m), 6.96 (1H, dd, J=8.3 Hz, 2.1 Hz), 7.28-7.31 (1H, m), 7.76-7.82 (1H, m), 8.09 (1H, d, J=1.7 Hz), 8.29-8.32 (1H, m), 9.89 (1H, s).

Reference Example 10

4-chloro-5-(2-fluoropyridin-3-yl)-1H-pyrrole-3-carbaldehyde 5-(2-Fluoropyridin-3-yl)-1H-pyrrole-3-carbaldehyde (610 mg) was dissolved in N,N-dimethylformamide (20 mL), N-chlorosuccinimide (641 mg) was added, and the mixture was stirred at 80° C. for 40 min. After cooling the reaction mixture, water was added, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=3:2→1:1) to give the title compound as colorless crystals (yield 320 mg, 44%).

$^1$H-NMR (DMSO-d$_6$) δ: 7.49-7.54 (1H, m), 7.86 (1H, d, J=2.3 Hz), 8.12-8.19 (1H, m), 8.30-8.32 (1H, m), 9.80 (1H, s), 12.48 (1H, brs).

Reference Example 11

4-chloro-5-(2-fluoropyridin-3-yl)-1-{[3-(methylsulfonyl)phenyl]sulfonyl}-1H-pyrrole-3-carbaldehyde To a solution of 4-chloro-5-(2-fluoropyridin-3-yl)-1H-pyrrole-3-carbaldehyde (250 mg) in tetrahydrofuran (25 mL) was added sodium hydride (60% in oil, 89 mg) at room temperature and the mixture was stirred for 5 min. 15-Crown-5 (490 mg) was added dropwise, and the mixture was stirred for 5 min. 3-(Methylsulfonyl)benzenesulfonyl chloride (426 mg) was added, and the mixture was further stirred for 1 hr. The reaction mixture was diluted with saturated aqueous sodium hydrogen carbonate solution, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:1) to give the title compound as a pale-yellow oil (yield 280 mg, 57%).

$^1$H-NMR (CDCl$_3$) δ: 3.15 (3H, s), 7.40-7.44 (1H, m), 7.72-7.89 (4H, m), 8.16 (1H, s), 8.22-8.25 (1H, m), 8.39 (1H, d, J=4.9 Hz), 9.97 (1H, s).

Reference Example 12

4-fluoro-5-(2-fluoropyridin-3-yl)-1H-pyrrole-3-carbaldehyde 5-(2-Fluoropyridin-3-yl)-1H-pyrrole-3-carbaldehyde (660 mg) was dissolved in acetonitrile (30 mL) and tetrahydrofuran (30 mL), 1-fluoro-2,6-dichloropyridinium triflate (1.32 g) was added, and the mixture was stirred for 2 hr. The reaction mixture was diluted with saturated aqueous sodium hydrogen carbonate solution, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=3:2→3:7) to give the title compound as pale-yellow crystals (yield 110 mg, 15%).

$^1$H-NMR (CDCl$_3$) δ: 7.30-7.36 (2H, m), 8.11-8.12 (1H, m), 8.25-8.32 (1H, m), 9.21 (1H, brs), 9.90 (1H, s).

Reference Example 13

4-fluoro-5-(2-fluoropyridin-3-yl)-1-(pyridin-3-ylsulfonyl)-1H-pyrrole-3-carbaldehyde To a solution of 4-fluoro-5-(2-fluoropyridin-3-yl)-1H-pyrrole-3-carbaldehyde (110 mg) in tetrahydrofuran (11 mL) was added sodium hydride (60% in oil, 43 mg) at room temperature and the mixture was stirred for 5 min. 15-Crown-5 (233 mg) was added dropwise, and the mixture was stirred for 5 min. Pyridine-3-sulfonyl chloride (141 mg) was added, and the mixture was further stirred for 1 hr. The reaction mixture was diluted with saturated aqueous sodium hydrogen carbonate solution, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:1→1:4) to give the title compound as a colorless oil (yield 90 mg, 49%).

$^1$H-NMR (CDCl$_3$) δ: 7.33-7.38 (1H, m), 7.41-7.46 (1H, m), 7.68-7.72 (1H, m), 7.79-7.86 (1H, m), 8.00 (1H, d, J=4.5 Hz), 8.37-8.39 (1H, m), 8.65 (1H, d, J=2.3 Hz), 8.88 (1H, dd, J=4.7 Hz, 1.7 Hz), 9.92 (1H, s).

Reference Example 14

5-(2-chloropyridin-3-yl)-1H-pyrrole-3-carbaldehyde

5-Bromo-1-(phenylsulfonyl)-1H-pyrrole-3-carbaldehyde (2.67 g), (2-chloropyridin-3-yl)boronic acid (2.00 g), sodium hydrogen carbonate (2.15 g) and tetrakis(triphenylphosphine)palladium (738 mg) were added to a deaerated mixture of 1,2-dimethoxyethane (40 mL) and water (10 mL), and the mixture was stirred under a nitrogen atmosphere at 80° C. for 5 hr. The reaction mixture was allowed to cool, saturated aqueous sodium hydrogen carbonate solution was added, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→1:1). The obtained pale-yellow oil was dissolved in methanol (15 mL) and tetrahydrofuran (15 mL), 8 mol/L aqueous sodium hydroxide solution (15 mL) was added dropwise at room temperature and the mixture was stirred for 30 min. The reaction mixture was diluted with saturated brine, and extracted with ethyl acetate. The extract was washed with saturated brine, dried over anhydrous magnesium sulfate, and concentrated under reduced pressure. Ethyl acetate was added to the residue and insoluble crystals were collected by filtration to give the title compound as brown crystals (yield 578 mg, 33%).

$^1$H-NMR (DMSO-d$_6$) δ: 7.00-7.02 (1H, m), 7.53 (1H, dd, J=7.8 Hz, 4.7 Hz), 7.87 (1H, dd, J=3.3 Hz, 1.6 Hz), 8.06 (1H, dd, J=7.8 Hz, 1.8 Hz), 8.37 (1H, dd, J=4.7 Hz, 1.8 Hz), 9.77 (1H, s), 12.21 (1H, brs).

Reference Example 15

5-(2-chloropyridin-3-yl)-1-[(6-methylpyridin-3-yl)sulfonyl]-1H-pyrrole-3-carbaldehyde To a solution of 5-(2-chloropyridin-3-yl)-1H-pyrrole-3-carbaldehyde (207 mg) in tetrahydrofuran (20 mL) was added sodium hydride (60% in oil, 100 mg) at room temperature and the mixture was stirred for 10 min. 15-Crown-5 (552 mg) was added dropwise, and the mixture was stirred for 5 min. 6-Methylpyridine-3-sulfonyl chloride (250 mg) was added, and the mixture was further stirred for 1 hr. The reaction mixture was diluted with saturated aqueous sodium hydrogen carbonate solution, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=3:7→1:4) to give the title compound as a colorless oil (yield 90 mg, 25%).

$^1$H-NMR (CDCl$_3$) δ: 2.65 (3H, s), 6.73 (1H, d, J=1.5 Hz), 7.23 (1H, d, J=8.3 Hz), 7.37 (1H, dd, J=7.6 Hz, 4.5 Hz), 7.53 (1H, dd, J=8.3 Hz, 2.3 Hz), 7.75 (1H, dd, J=7.6 Hz, 1.9 Hz), 8.14 (1H, d, J=1.9 Hz), 8.49 (1H, d, J=1.9 Hz), 8.51 (1H, d, J=1.9 Hz), 9.92 (1H, s).

Reference Example 16

5-(2-chloropyridin-3-yl)-1-[(3-fluorophenyl)sulfonyl]-1H-pyrrole-3-carbaldehyde

To a solution of 5-(2-chloropyridin-3-yl)-1H-pyrrole-3-carbaldehyde (250 mg) in tetrahydrofuran (25 mL) was added sodium hydride (60% in oil, 73 mg) at room temperature and the mixture was stirred for 15 min. 3-Fluorobenzenesulfonyl chloride (310 mg) was added to the reaction mixture, and the mixture was further stirred for 30 min. The reaction mixture was diluted with saturated brine, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:1) to give the title compound as a colorless oil (yield 420 mg, 95%).

$^1$H-NMR (CDCl$_3$) δ: 6.74 (1H, d, J=1.9 Hz), 7.10-7.14 (1H, m), 7.21-7.24 (1H, m), 7.33-7.38 (2H, m), 7.42-7.49 (1H, m), 7.73 (1H, dd, J=7.6 Hz, 1.9 Hz), 8.14 (1H, d, J=1.9 Hz), 8.49 (1H, dd, J=4.7 Hz, 2.0 Hz), 9.92 (1H, s).

Reference Example 17

3-{1-[(3-fluorophenyl)sulfonyl]-4-formyl-1H-pyrrol-2-yl}pyridine-2-carbonitrile 5-(2-Chloropyridin-3-yl)-1-[(3-fluorophenyl)sulfonyl]-1H-pyrrole-3-carbaldehyde (420 mg), copper (I) cyanide (516 mg), tris(dibenzylideneacetone)dipalladium (0) (53 mg) and 1,1'-bis(diphenylphosphino)ferrocene (96 mg) were mixed in 1,4-dioxane (20 mL), and the mixture was heated under reflux for 3 hr. The reaction mixture was cooled to around room temperature, copper (I) cyanide (516 mg), tris(dibenzylideneacetone)dipalladium (0) (53 mg) and 1,1'-bis(diphenylphosphino)ferrocene (96 mg) were added and the mixture was heated under reflux for 60 hr. The reaction mixture was allowed to cool, water and ethyl acetate were added and the mixture was filtered. The obtained ethyl acetate layer was washed with saturated brine, dried over anhydrous magnesium sulfate, and concentrated under reduced pressure. The residue was purified by silica gel column chromatography (eluent: hexane-ethyl acetate=7:3→3:2) to give the title compound as a colorless oil (yield 70 mg, 17%).

$^1$H-NMR (CDCl$_3$) δ: 6.89 (1H, d, J=1.9 Hz), 7.06-7.10 (1H, m), 7.18-7.21 (1H, m), 7.36-7.50 (2H, m), 7.60-7.64 (1H, m), 7.94 (1H, dd, J=8.0 Hz, 1.5 Hz), 8.18 (1H, d, J=1.9 Hz), 8.77-8.79 (1H, m), 9.93 (1H, s).

Reference Example 18 tert-butyl [(5-bromo-1H-pyrrol-3-yl)methyl]methylcarbamate

To a solution of 5-bromo-1H-pyrrole-3-carbaldehyde (10.5 g) in tetrahydrofuran (100 mL) were added 40% methylamine methanol solution (60 mL) and methanol (100 mL), and the mixture was stirred at room temperature for 1 hr. Sodium borohydride (25.8 g) was added to the reaction mixture, and the mixture was further stirred for 30 min and concentrated under reduced pressure. Saturated aqueous sodium hydrogen carbonate solution was added to the residue, and the mixture was extracted with ethyl acetate. The extract was washed with saturated aqueous sodium hydrogen carbonate solution, water and saturated brine, and dried over anhydrous sodium sulfate. The solvent was concentrated under reduced pressure and the residue was dissolved in tetrahydrofuran (100 mL), di-tert-butyl dicarbonate (14.0 mL) was added at 0° C., and the mixture was stirred at room temperature for 30 min. Water was added to the reaction mixture, and the mixture was extracted with ethyl acetate. The extract was washed with saturated aqueous sodium hydrogen carbonate solution, water and saturated brine, and dried over anhydrous sodium sulfate. The solvent was concentrated under reduced pressure and the residue was purified by silica gel column chromatography (eluent: hexane-ethyl acetate=4:1) to give the title compound as a yellow oil (yield 12.6 g, 73%).

$^1$H-NMR (CDCl$_3$) δ: 1.48 (9H, s), 2.80 (3H, brs), 4.22 (2H, brs), 6.09 (1H, brs), 6.63 (1H, brs), 8.17 (1H, brs).

Reference Example 19 tert-butyl ({5-bromo-1-[(3-methoxyphenyl)sulfonyl]-1H-pyrrol-3-yl}methyl)methylcarbamate Sodium hydride (60% in oil, 432 mg) was washed twice with hexane, and suspended in tetrahydrofuran (20 mL). A solution of tert-butyl [(5-bromo-1H-pyrrol-3-yl)methyl]methylcarbamate (2.55 g) in tetrahydrofuran (10 mL) was added at 0° C., and the mixture was stirred at the same temperature for 30 min. 15-Crown-5 (2.2 mL), then a solution of 3-methoxybenzenesulfonyl chloride (2.16 g) in tetrahydrofuran (5 mL) were added at the same temperature, and the mixture was stirred at room temperature for 1 hr. Water was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent: hexane-ethyl acetate=4:1) to give the title compound as a brown oil (yield 3.87 g, 96%).

$^1$H-NMR (CDCl$_3$) δ: 1.47 (9H, s), 2.79 (3H, brs), 3.85 (3H, s), 4.17 (2H, brs), 6.24 (1H, brs), 7.13-7.17 (1H, m), 7.33 (1H, brs), 7.40-7.50 (3H, m).

Reference Example 20 tert-butyl ({5-(2-fluoropyridin-3-yl)-1-[(3-methoxyphenyl)sulfonyl]-1H-pyrrol-3-yl}methyl)methylcarbamate tert-butyl ({5-bromo-1-[(3-methoxyphenyl)sulfonyl]-1H-pyrrol-3-yl}methyl)methylcarbamate (459 mg), (2-fluoropyridin-3-yl)boronic acid (169 mg), sodium carbonate (254 mg), and tetrakis(triphenylphosphine)palladium (173 mg) were suspended in 1,2-dimethoxyethane (10 mL) and water (4 mL), and the mixture was stirred at 105° C. for 2 hr. The reaction mixture was cooled to room temperature, water was added and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=4:1→2:1) to give the title compound as a pale-yellow oil (yield 303 mg, 64%).

$^1$H-NMR (CDCl$_3$) δ: 1.46 (9H, s), 2.81 (3H, s), 3.74 (3H, s), 4.23 (2H, br), 6.26 (1H, brs), 6.85-6.87 (1H, m), 6.99-7.09 (2H, m), 7.20-7.40 (3H, m), 7.70-7.79 (1H, m), 8.22-8.23 (1H, m).

Reference Example 21 tert-butyl ({5-bromo-1-[(3-fluorophenyl)sulfonyl]-1H-pyrrol-3-yl}methyl)methylcarbamate Sodium hydride (60% in oil, 440 mg) was washed twice with hexane, and suspended in tetrahydrofuran (20 mL). A solution of tert-butyl [(5-bromo-1H-pyrrol-3-yl)methyl]methylcarbamate (2.58 g) in tetrahydrofuran (10 mL) was added at 0° C., and the mixture was stirred at the same temperature for 30 min. 15-Crown-5 (2.2 mL), then a solution of 3-fluorobenzenesulfonyl chloride (1.96 g) in tetrahydrofuran (5 mL) were added at the same temperature, and the mixture was stirred at room temperature for 1 hr. Water was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent: hexane-ethyl acetate=5:1) to give the title compound as a brown oil (yield 3.62 g, 91%).

$^1$H-NMR (CDCl$_3$) δ: 1.47 (9H, s), 2.80 (3H, brs), 4.18 (2H, brs), 6.27 (1H, brs), 7.33-7.38 (2H, m), 7.48-7.64 (2H, m), 7.71-7.74 (1H, m).

Reference Example 22 tert-butyl ({1-[(3-fluorophenyl)sulfonyl]-5-(2-fluoropyridin-3-yl)-1H-pyrrol-3-yl}methyl)methylcarbamate Under an argon atmosphere, a suspension of tert-butyl ({5-bromo-1-[(3-fluorophenyl)sulfonyl]-1H-pyrrol-3-yl}methyl)methylcarbamate (455 mg), 2-fluoropyridin-3-yl)boronic acid (173 mg), tetrakis(triphenylphosphine)palladium (178 mg) and sodium carbonate (258 mg) in 1,2-dimethoxyethane (10 mL) and water (5 mL) was stirred at 105° C. for 3 hr. The reaction mixture was cooled to room temperature, water was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent: hexane-ethyl acetate=3:1) to give the title compound as a pale-yellow oil (yield 214 mg, 45%).

$^1$H-NMR (CDCl$_3$) δ: 1.46 (9H, s), 2.83 (3H, s), 4.24 (2H, brs), 6.28 (1H, s), 7.10-7.14 (1H, m), 7.19-7.33 (4H, m), 7.37-7.44 (1H, m), 7.71-7.77 (1H, m), 8.25-8.27 (1H, m).

Reference Example 23 tert-butyl{[5-bromo-1-(pyridin-3-ylsulfonyl)-1H-pyrrol-3-yl]methyl}methylcarbamate To a suspension of sodium hydride (60% in oil, 7.4 g) in tetrahydrofuran (300 mL) was added a solution of tert-butyl [(5-bromo-1H-pyrrol-3-yl)methyl]methylcarbamate (44.5 g) in tetrahydrofuran (60 mL) at 0° C., and 15-crown-5 (40.7 g) and pyridine-3-sulfonyl chloride (30.1 g) were added at the same temperature. The mixture was stirred at room temperature for 30 min, water was added and the mixture was concentrated under reduced pressure. The residue was extracted with ethyl acetate. The extract was washed with saturated brine, dried over anhydrous sodium sulfate, and concentrated under reduced pressure. The residue was washed with a mixed solvent of diisopropyl ether-hexane=1:1 to give the title compound as colorless crystals (yield 45.2 g, 68%).

$^1$H-NMR (CDCl$_3$) δ: 1.47 (9H, s), 2.80 (3H, brs), 4.18 (2H, brs), 6.28 (1H, brs), 7.35 (1H, brs), 7.48-7.52 (1H, m), 8.18-8.22 (1H, m), 8.85-8.88 (1H, m), 9.12-9.13 (1H, m).

Reference Example 24 tert-butyl {[5-(2-fluoro-6-methylpyridin-3-yl)-1-(pyridin-3-ylsulfonyl)-1H-pyrrol-3-yl]methyl}methylcarbamate tert-butyl {[5-bromo-1-(pyridin-3-ylsulfonyl)-1H-pyrrol-3-yl]methyl}methylcarbamate (431 mg), (2-fluoro-6-methylpyridin-3-yl)boronic acid (233 mg), sodium hydrogen carbonate (253 mg) and tetrakis(triphenylphosphine)palladium (88 mg) were added to a deaerated mixture of 1,2-dimethoxyethane (8 mL) and water (2 mL), and the mixture was stirred under a nitrogen atmosphere at 100° C. for 2 hr. The reaction mixture was allowed to cool, saturated aqueous sodium hydrogen carbonate solution was added, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=2:3→1:4) to give the title compound as a colorless oil (yield 400 mg, 87%).

$^1$H-NMR (CDCl$_3$) δ: 1.46 (9H, s), 2.56 (3H, s), 2.81 (3H, s), 4.23 (2H, s), 6.26 (1H, s), 7.09 (1H, d, J=7.2 Hz), 7.33-7.39 (2H, m), 7.57-7.72 (2H, m), 8.68 (1H, d, J=2.3 Hz), 8.79 (1H, dd, J=4.7 Hz, 1.3 Hz).

Reference Example 25 tert-butyl {[5-(2-chloropyridin-3-yl)-1-(pyridin-3-ylsulfonyl)-1H-pyrrol-3-yl]methyl}methylcarbamate tert-Butyl {[5-bromo-1-(pyridin-3-ylsulfonyl)-1H-pyrrol-3-yl]methyl}methylcarbamate (430 mg), (2-chloropyridin-3-yl)boronic acid (189 mg), sodium carbonate (254 mg), and tetrakis(triphenylphosphine)palladium (116 mg) were suspended in 1,2-dimethoxyethane (10 mL) and water (4 mL), and the mixture was stirred at 105° C. for 2 hr. The reaction mixture was cooled to room temperature, water was added and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=2:1→1:4) to give the title compound as a pale-yellow oil (yield 195 mg, 42%).

$^1$H-NMR (CDCl$_3$) δ: 1.47 (9H, s), 2.84 (3H, brs), 4.26 (2H, brs), 6.29 (1H, brs), 7.29-7.38 (3H, m), 7.63-7.72 (2H, m), 8.43-8.45 (1H, m), 8.66 (1H, d, J=2.4 Hz), 8.78-8.80 (1H, m).

Reference Example 26 tert-butyl 3-[5-(2-cyanopyridin-3-yl)-1-(pyridin-3-ylsulfonyl)-1H-pyrrol-3-yl]-2-methylcarbamate A suspension of tert-butyl {[5-(2-chloropyridin-3-yl)-1-(pyridin-3-ylsulfonyl)-1H-pyrrol-3-yl]methyl}methylcarbamate (195 mg), zinc cyanide (98.9 mg) and tetrakis(triphenylphosphine)palladium (97.3 mg) in N,N-dimethylformamide (5 mL) was heated under an argon atmosphere at 120° C. for 8 hr. After cooling to room temperature, water and ethyl acetate were added and the mixture was filtered through celite. The organic layer of the filtrate was washed with water and saturated brine, dried over anhydrous sodium sulfate, and concentrated under reduced pressure. The residue was purified by silica gel column chromatography (eluent: hexane-ethyl acetate=9:1→4:1) to give the title compound as a pale-yellow oil (yield 109 mg, 57%).

$^1$H-NMR (CDCl$_3$) δ: 1.47 (9H, s), 2.83 (3H, brs), 4.27 (2H, brs), 6.48 (1H, brs), 7.38-7.43 (2H, m), 7.55-7.67 (2H, m), 7.93 (1H, d, J=7.5 Hz), 8.60-8.61 (1H, m), 8.71-8.73 (1H, m), 8.81-8.83 (1H, m).

Reference Example 27 tert-butyl {[5-bromo-1-(phenylsulfonyl)-1H-pyrrol-3-yl]methyl}methylcarbamate

Sodium hydride (60% in oil, 1.69 g) was washed twice with hexane, and suspended in tetrahydrofuran (100 mL). A solution of tert-butyl [(5-bromo-1H-pyrrol-3-yl)methyl]methylcarbamate (10.4 g) in tetrahydrofuran (15 mL) was added at 0° C., and the mixture was stirred at the same temperature for 15 min. 15-Crown-5 (8.0 mL), then a solution of benzenesulfonyl chloride (5.1 mL) in tetrahydrofuran (10 mL) were added at the same temperature, and the mixture was stirred at room temperature for 30 min. Water was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent: hexane-ethyl acetate=4:1) to give the title compound as a brown oil (yield 15.2 g, 98%).

$^1$H-NMR (CDCl$_3$) δ: 1.48 (9H, s), 2.79 (3H, brs), 4.17 (2H, brs), 6.24 (1H, brs), 7.35 (1H, brs), 7.51-7.57 (2H, m), 7.62-7.68 (1H, m), 7.90-7.94 (2H, m).

Reference Example 28 tert-butyl {[5-(2-chloropyridin-3-yl)-1-(phenylsulfonyl)-1H-pyrrol-3-yl]methyl}methylcarbamate Under a nitrogen atmosphere, to a solution of diisopropylamine (8.3 g) in tetrahydrofuran (70 mL) was added a 1.6 mol/L hexane solution (50 mL) of n-butyllithium at −78° C., and the mixture was stirred at the same temperature for 15 min. A solution of 2-chloropyridine (6.6 g) in tetrahydrofuran (10 mL) was added dropwise, and the mixture was stirred at the same temperature for 2 hr. To the obtained reaction mixture was added dropwise a solution of triisopropoxyborane (15.1 g) in tetrahydrofuran (10 mL) at the same temperature, and the mixture was stirred for 30 min. Methanol (10 mL) was added to the reaction mixture, and the mixture was concentrated under reduced pressure. Under an argon atmosphere, a suspension of the obtained residue, tert-butyl ({[5-bromo-1-(phenylsulfonyl)-1H-pyrrol-3-yl]methyl}methylcarbamate (7.94 g), tetrakis(triphenylphosphine)palladium (3.21 g) and sodium carbonate (19.7 g) in 1,2-dimethoxyethane (80 mL) and water (40 mL) was stirred at 105° C. for 4 hr. The reaction mixture was cooled to room temperature, water was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent: hexane-ethyl acetate=4:1→2:1) to give the title compound as a pale-yellow oil (yield 1.88 g, yield from 2-chloropyridine 7%).

¹H-NMR (CDCl₃) δ: 1.47 (9H, s), 2.83 (3H, s), 4.26 (2H, brs), 6.26 (1H, d, J=1.8 Hz), 7.26-7.31 (1H, m), 7.37 (1H, d, J=1.8 Hz), 7.40-7.42 (4H, m), 7.55-7.60 (1H, m), 7.68-7.71 (1H, m), 8.40-8.43 (1H, m).

Reference Example 29 tert-butyl {[5-(2-cyanopyridin-3-yl)-1-(phenylsulfonyl)-1H-pyrrol-3-yl]methyl}methylcarbamate By an operation similar to that in Reference Example 26 and using tert-butyl {[5-(2-chloropyridin-3-yl)-1-(phenylsulfonyl)-1H-pyrrol-3-yl]methyl}methylcarbamate (378 mg), the title compound was obtained as colorless crystals (yield 250 mg, 67%).

¹H-NMR (CDCl₃) δ: 1.47 (9H, s), 2.82 (3H, brs), 4.27 (2H, brs), 6.44 (1H, brs), 7.33-7.45 (5H, m), 7.52-7.63 (2H, m), 7.94-7.96 (1H, m), 8.67-8.69 (1H, m).

Reference Example 30 tert-butyl {[5-(2-fluoropyridin-3-yl)-1-(pyridin-3-ylsulfonyl)-1H-pyrrol-3-yl]methyl}methylcarbamate A suspension of tert-butyl {[5-bromo-1-(pyridin-3-ylsulfonyl)-1H-pyrrol-3-yl]methyl}methylcarbamate (430 mg), (2-fluoropyridin-3-yl)boronic acid (221 mg), sodium carbonate (254 mg) and tetrakis(triphenylphosphine)palladium (173 mg) in 1,2-dimethoxyethane (10 mL) and water (5 mL) was stirred at 105° C. for 1 hr. The reaction mixture was cooled to room temperature, water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=6:1→1:1) to give the title compound as a pale-yellow oil (yield 310 mg, 69%).

¹H-NMR (CDCl₃) δ: 1.46 (9H, s), 2.82 (3H, s), 4.23 (2H, brs), 6.29 (1H, brs), 7.23-7.27 (1H, m), 7.34-7.39 (2H, m), 7.66-7.73 (2H, m), 8.25-8.27 (1H, m), 8.66 (1H, d, J=2.4 Hz), 8.78-8.80 (1H, m).

Reference Example 31 tert-butyl {[5-(2-fluoropyridin-3-yl)-1H-pyrrol-3-yl]methyl}methylcarbamate tert-Butyl {[5-(2-fluoropyridin-3-yl)-1-(pyridin-3-ylsulfonyl)-1H-pyrrol-3-yl]methyl}methylcarbamate (4.78 g) was dissolved in tetrahydrofuran (20 mL) and methanol (10 mL), 8 mol/L aqueous sodium hydroxide solution (4 mL) was added under ice-cooling. After stirring at room temperature for 4 hr, about half of the solvent was evaporated under reduced pressure, water was added to the residue and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=19:1→ethyl acetate) to give the title compound as a pale-yellow oil (yield 2.84 g, 87%).

¹H-NMR (CDCl₃) δ: 1.50 (9H, s), 2.84 (3H, brs), 4.30 (2H, brs), 6.63 (1H, brs), 6.84 (1H, brs), 7.17-7.22 (1H, m), 7.93-8.01 (2H, m), 8.95 (1H, brs).

Reference Example 32 tert-butyl {[5-(2-fluoropyridin-3-yl)-1-(3-thienylsulfonyl)-1H-pyrrol-3-yl]methyl}methylcarbamate To a suspension of sodium hydride (97.9 mg, 60% in oil) in tetrahydrofuran (10 mL) were added a solution of tert-butyl {[5-(2-fluoropyridin-3-yl)-1H-pyrrol-3-yl]methyl}methylcarbamate (311 mg) in tetrahydrofuran (3 mL), 15-crown-5 (449 mg), and thiophene-3-sulfonyl chloride (280 mg) under ice-cooling. The mixture was stirred at room temperature for 30 min, water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=6:1→3:1) to give the title compound as a pale-yellow oil (yield 433 mg, 94%).

¹H-NMR (CDCl₃) δ: 1.47 (9H, s), 2.83 (3H, s), 4.24 (2H, brs), 6.28 (1H, brs), 6.97-6.99 (1H, m), 7.20-7.26 (1H, m), 7.32-7.35 (2H, m), 7.58-7.60 (1H, m), 7.72-7.77 (1H, m), 8.22-8.24 (1H, m).

Reference Example 33 tert-butyl ({1-[(3-cyanophenyl)sulfonyl]-5-(2-fluoropyridin-3-yl)-1H-pyrrol-3-yl}methyl)methylcarbamate By an operation similar to that in Reference Example 32 and using tert-butyl {[5-(2-fluoropyridin-3-yl)-1H-pyrrol-3-yl]methyl}methylcarbamate (305 mg), and 3-cyanobenzenesulfonyl chloride (318 mg), the title compound was obtained as a colorless oil (yield 447 mg, 95%).

¹H-NMR (CDCl₃) δ: 1.47 (9H, s), 2.84 (3H, s), 4.25 (2H, brs), 6.30 (1H, brs), 7.25-7.33 (2H, m), 7.54-7.63 (2H, m), 7.66-7.77 (2H, m), 7.83-7.86 (1H, m), 8.27-8.29 (1H, m).

Reference Example 34 tert-butyl ({1-[(3-acetylphenyl)sulfonyl]-5-(2-fluoropyridin-3-yl)-1H-pyrrol-3-yl}methyl)methylcarbamate To a solution of tert-butyl ({1-[(3-cyanophenyl)sulfonyl]-5-(2-fluoropyridin-3-yl)-1H-pyrrol-3-yl}methyl)methylcarbamate (431 mg) in diethyl ether (4 mL) was added a 1.0 mol/L solution (2.4 mL) of methyllithium in diethyl ether at −78° C., and the mixture was stirred at room temperature for 1 hr. Water was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent: hexane-ethyl acetate=1:1) to give the title compound as a brown oil (yield 110 mg, 25%).

¹H-NMR (CDCl₃) δ: 1.45 (9H, s), 2.55 (3H, s), 2.81 (3H, s), 4.23 (2H, brs), 6.26 (1H, s), 7.25-7.27 (1H, m), 7.34-7.35 (1H, m), 7.51-7.56 (1H, s), 7.60-7.64 (1H, m), 7.70-7.79 (1H, m), 7.91-7.94 (1H, m), 8.11-8.15 (1H, m), 8.23-8.25 (1H, m).

Reference Example 35 tert-butyl ({1-[(4-fluorophenyl)sulfonyl]-5-(2-fluoropyridin-3-yl)-1H-pyrrol-3-yl}methyl)methylcarbamate By an operation similar to that in Reference Example 32 and using tert-butyl {[5-(2-fluoropyridin-3-yl)-1H-pyrrol-3- yl]methyl}methylcarbamate (305 mg), and 4-fluorobenzenesulfonyl chloride (292 mg), the title compound was obtained as a colorless oil (yield 436 mg, 94%).

$^1$H-NMR (CDCl$_3$) δ: 1.46 (9H, s), 2.82 (3H, brs), 4.23 (2H, brs), 6.26 (1H, brs), 7.03-7.11 (2H, m), 7.21-7.25 (1H, m), 7.32 (1H, brs), 7.40-7.45 (2H, m), 7.72-7.77 (1H, m), 8.24-8.25 (1H, m).

Reference Example 36 tert-butyl ({1-[(2,3-difluorophenyl)sulfonyl]-5-(2-fluoropyridin-3-yl)-1H-pyrrol-3-yl}methyl)methylcarbamate Sodium hydride (60% in oil, 86.2 mg) was washed twice with hexane, and suspended in tetrahydrofuran (5 mL). A solution of tert-butyl {[5-(2-fluoropyridin-3-yl)-1H-pyrrol-3-yl]methyl}methylcarbamate (298 mg) in tetrahydrofuran (3 mL) was added at 0° C., and the mixture was stirred at the same temperature for 15 min. 15-Crown-5 (0.43 mL), then a solution of 2,3-difluorophenylsulfonyl chloride (472 mg) in tetrahydrofuran (3 mL) were added at the same temperature, and the mixture was stirred for 30 min. Water was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by basic silica gel column chromatography (eluent: hexane-ethyl acetate=2:1) to give the title compound as a brown oil (yield 447 mg, 95%).

$^1$H-NMR (CDCl$_3$) δ: 1.47 (9H, s), 2.86 (3H, brs), 4.27 (2H, brs), 6.30 (1H, brs), 7.02-7.13 (2H, m), 7.20-7.24 (1H, m), 7.38-7.47 (2H, m), 7.70-7.76 (1H, m), 8.21-8.23 (1H, m).

Reference Example 37 tert-butyl ({1-[(3,4-difluorophenyl)sulfonyl]-5-(2-fluoropyridin-3-yl)-1H-pyrrol-3-yl}methyl)methylcarbamate Sodium hydride (60% in oil, 83.8 mg) was washed twice with hexane, and suspended in tetrahydrofuran (5 mL). A solution of tert-butyl {[5-(2-fluoropyridin-3-yl)-1H-pyrrol-3-yl]methyl}methylcarbamate (307 mg) in tetrahydrofuran (2 mL) was added at 0° C., and the mixture was stirred at the same temperature for 30 min. 15-Crown-5 (0.4 mL), then a solution of 3,4-difluorophenylsulfonyl chloride (0.27 mL) in tetrahydrofuran (2 mL) were added at the same temperature, and the mixture was stirred at room temperature for 30 min. Water was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent: hexane-ethyl acetate=2:1) to give the title compound as a brown oil (yield 472 mg, 97%).

$^1$H-NMR (CDCl$_3$) δ: 1.47 (9H, s), 2.83 (3H, s), 4.24 (2H, brs), 6.30 (1H, brs), 7.19-7.31 (5H, m), 7.73-7.78 (1H, m), 8.27-8.28 (1H, m).

Reference Example 38 tert-butyl ({1-[(3-fluoro-4-methylphenyl)sulfonyl]-5-(2-fluoropyridin-3-yl)-1H-pyrrol-3-yl}methyl)methylcarbamate Sodium hydride (60% in oil, 82.8 mg) was washed twice with hexane, and suspended in tetrahydrofuran (5 mL). A solution of tert-butyl {[5-(2-fluoropyridin-3-yl)-1H-pyrrol-3-yl]methyl}methylcarbamate (306 mg) in tetrahydrofuran (2 mL) was added at 0° C., and the mixture was stirred at the same temperature for 15 min. 15-Crown-5 (0.4 mL), then a solution of 3-fluoro-4-methylphenylsulfonyl chloride (418 mg) in tetrahydrofuran (2 mL) were added at the same temperature, and the mixture was stirred at room temperature for 1 hr. Water was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by basic silica gel column chromatography (eluent: hexane-ethyl acetate=3:1) to give the title compound as a brown oil (yield 289 mg, 60%).

$^1$H-NMR (CDCl$_3$) δ: 1.46 (9H, s), 2.31 (3H, d, J=2.4 Hz), 2.82 (3H, s), 4.23 (2H, brs), 6.27 (1H, s), 7.04-7.10 (2H, m), 7.20-7.26 (2H, m), 7.31 (1H, s), 7.72-7.78 (1H, m), 8.25-8.26 (1H, m).

Reference Example 39 tert-butyl ({1-[(2,5-difluorophenyl)sulfonyl]-5-(2-fluoropyridin-3-yl)-1H-pyrrol-3-yl}methyl)methylcarbamate By an operation similar to that in Reference Example 32 and using tert-butyl {[5-(2-fluoropyridin-3-yl)-1H-pyrrol-3-yl]methyl}methylcarbamate (305 mg), and 2,5-difluorobenzenesulfonyl chloride (319 mg), the title compound was obtained as a colorless oil (yield 160 mg, 33%).

$^1$H-NMR (CDCl$_3$) δ: 1.47 (9H, s), 2.85 (3H, brs), 4.26 (2H, brs), 6.29 (1H, brs), 6.93-6.99 (1H, m), 7.10-7.17 (1H, m), 7.20-7.31 (2H, m), 7.39 (1H, brs), 7.68-7.74 (1H, m), 8.22-8.24 (1H, m).

Reference Example 40

1-(2-fluoropyridin-3-yl)propan-1-ol

To a solution of diisopropylamine (15.8 g) in tetrahydrofuran (100 mL) was added dropwise a 1.6 mol/L hexane solution (95 mL) of n-butyllithium at −78° C., and the mixture was stirred for 15 min. A solution of 2-fluoropyridine (11.6 g) in tetrahydrofuran (10 mL) was added dropwise at −78° C., and the mixture was stirred at the same temperature for 30 min. To the obtained mixture was added a solution of propionaldehyde (11.2 mL) in tetrahydrofuran (10 mL) at the same temperature, and the mixture was further stirred for 1 hr. Water was added to the reaction mixture, and the mixture was extracted with ethyl acetate. The extract was washed with water and saturated brine, dried over anhydrous magnesium sulfate, and concentrated under reduced pressure. The residue was purified by silica gel column chromatography (eluent: hexane-ethyl acetate=2:1) to give the title compound as a brown oil (yield 12.4 g, 67%).

$^1$H-NMR (CDCl$_3$) δ: 0.97 (3H, t, J=7.5 Hz), 1.74-1.87 (2H, m), 2.02 (1H, brs), 4.88-4.94 (1H, m), 7.19-7.24 (1H, m), 7.89-7.96 (1H, m), 8.11-8.13 (1H, m).

Reference Example 41

1-(2-fluoropyridin-3-yl)propan-1-one

To a mixture of 1-(2-fluoropyridin-3-yl)propan-1-ol (12.3 g), dimethyl sulfoxide (130 mL) and triethylamine (65 mL) was added a sulfur trioxide-pyridine complex (25.6 g), and the mixture was stirred at room temperature for 14 hr. Water was added to the reaction mixture, and the mixture was extracted with ethyl acetate. The extract was washed with water and saturated brine, dried over anhydrous magnesium sulfate, and concentrated under reduced pressure. The residue was purified by silica gel column chromatography (eluent: hexane-ethyl acetate=4:1) to give the title compound as a brown oil (yield 10.6 g, 87%).

$^1$H-NMR (CDCl$_3$) δ: 1.22 (3H, t, J=7.2 Hz), 3.01-3.09 (2H, m), 7.30-7.35 (1H, m), 8.31-8.39 (2H, m).

Reference Example 42

2-bromo-1-(2-fluoropyridin-3-yl)propan-1-one

To a mixture of 1-(2-fluoropyridin-3-yl)propan-1-one (12.9 g) and 25% solution (70 mL) of hydrogen bromide in acetic acid was added dropwise bromine (4.4 mL), and the obtained mixture was stirred at room temperature for 3 hr. The reaction mixture was concentrated under reduced pressure to give the title compound as a red-brown oil (yield 29.6 g, quantitative).

$^1$H-NMR (CDCl$_3$) δ: 1.91 (3H, d, J=6.6 Hz), 5.30-5.37 (1H, m), 7.35-7.40 (1H, m), 8.35-8.44 (2H, m).

Reference Example 43

Ethyl 2-cyano-4-(2-fluoropyridin-3-yl)-3-methyl-4-oxobutanoate

To a solution of diisopropylethylamine (45 mL) and ethyl cyanoacetate (11.5 g) in tetrahydrofuran (50 mL) was added dropwise a solution of 2-bromo-1-(2-fluoropyridin-3-yl)propan-1-one (29.6 g) in tetrahydrofuran (50 mL), and the mixture was stirred at room temperature for 14 hr. Insoluble materials were filtered off, and filtrate was concentrated under reduced pressure. Water was added to the residue, and the mixture was extracted with ethyl acetate. The extract was washed with water and saturated brine, dried over anhydrous magnesium sulfate, and concentrated under reduced pressure. The residue was purified by silica gel column chromatography (eluent: hexane-ethyl acetate=2:1) to give the title compound as a brown oil (yield 18.8 g, 85%).

$^1$H-NMR (CDCl$_3$) δ: 1.24-1.39 (3H, m), 1.44-1.48 (3H, m), 3.75-4.34 (4H, m), 7.36-7.41 (1H, m), 8.32-8.40 (1H, m), 8.44-8.46 (1H, m).

Reference Example 44

Ethyl 2-chloro-5-(2-fluoropyridin-3-yl)-4-methyl-1H-pyrrole-3-carboxylate

To a solution of ethyl 2-cyano-4-(2-fluoropyridin-3-yl)-3-methyl-4-oxobutanoate (19.4 g) in ethyl acetate (20 mL) was added 4 mol/L hydrogen chloride-ethyl acetate solution (90 mL), and the mixture was stirred for 18 hr, and concentrated under reduced pressure. Water was added to the residue, and the mixture was extracted with ethyl acetate. The extract was washed with water, saturated aqueous sodium hydrogen carbonate solution and saturated brine, dried over anhydrous magnesium sulfate, and concentrated under reduced pressure. The residue was recrystallized from ethyl acetate-hexane to give the title compound as yellow crystals (yield 14.3 g, 69%).

$^1$H-NMR (CDCl$_3$) δ: 1.39 (3H, t, J=7.2 Hz), 2.37 (3H, s), 4.34 (2H, q, J=7.2 Hz), 7.26-7.31 (1H, m), 7.82-7.89 (1H, m), 8.15-8.18 (1H, m), 8.87 (1H, brs).

Reference Example 45

Ethyl 5-(2-fluoropyridin-3-yl)-4-methyl-1H-pyrrole-3-carboxylate

To a solution of ethyl 2-chloro-5-(2-fluoropyridin-3-yl)-4-methyl-1H-pyrrole-3-carboxylate (10.0 g) and triethylamine (5.5 mL) in ethanol (250 mL) was added 10% palladium carbon (50% containing water, 1.43 g), and the mixture was stirred under a hydrogen atmosphere at 60° C. for 3 hr. After cooling, the reaction mixture was filtrated, and the filtrate was concentrated under reduced pressure. Water was added to the residue, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was recrystallized from ethyl acetate-hexane to give the title compound as colorless crystals (yield 7.93 g, 90%).

$^1$H-NMR (CDCl$_3$) δ: 1.36 (3H, t, J=7.2 Hz), 2.44 (3H, s), 4.30 (2H, q, J=7.2 Hz), 7.26-7.30 (1H, m), 7.52-7.54 (1H, m), 7.87-7.93 (1H, m), 8.12-8.15 (1H, m), 8.92 (1H, brs).

Reference Example 46

[5-(2-fluoropyridin-3-yl)-4-methyl-1H-pyrrol-3-yl]methanol

A solution of ethyl 5-(2-fluoropyridin-3-yl)-4-methyl-1H-pyrrole-3-carboxylate (5.01 g) in tetrahydrofuran (50 mL) was cooled to −78° C., a 1.5 mol/L toluene solution (45 mL) of diisobutylaluminum hydride was added dropwise, and the mixture was stirred at 0° C. for 1 hr. Water was added to the reaction mixture, insoluble materials were filtered off, and the filtrate was extracted with ethyl acetate. The extract was washed with water, dried over anhydrous sodium sulfate, and concentrated under reduced pressure. The residue was washed with diisopropyl ether to give the title compound as colorless crystals (yield 1.72 g, 41%).

$^1$H-NMR (CDCl$_3$) δ: 1.32 (1H, brs, J=4.5 Hz), 2.29 (3H, s), 4.62 (2H, d, J=4.5 Hz), 6.91-6.92 (1H, m), 7.23-7.28 (1H, m), 7.88-7.95 (1H, m), 8.06-8.09 (1H, m), 8.57 (1H, brs).

Reference Example 47

5-(2-fluoropyridin-3-yl)-4-methyl-1H-pyrrole-3-carbaldehyde

To a suspension of [5-(2-fluoropyridin-3-yl)-4-methyl-1H-pyrrol-3-yl]methanol (1.70 g) in acetonitrile (35 mL) were added tetra-n-propylammonium perruthenate (103 mg), N-methylmorpholine N-oxide (1.44 g) and molecular sieves 4A powder (0.89 g), and the mixture was stirred at room temperature for 2 days. The reaction mixture was filtrated and the filtrate was concentrated under reduced pressure. The residue was purified by silica gel column chromatography (eluent: hexane-ethyl acetate=1:2) to give the title compound as colorless crystals (yield 527 mg, 31%).

$^1$H-NMR (CDCl$_3$) δ: 2.50 (3H, s), 7.26-7.33 (1H, m), 7.49-7.50 (1H, m), 7.90-7.97 (1H, m), 8.16-8.18 (1H, m), 9.00 (1H, brs), 9.93 (1H, s).

Reference Example 48

5-(2-fluoropyridin-3-yl)-4-methyl-1-(pyridin-3-ylsulfonyl)-1H-pyrrole-3-carbaldehyde Sodium hydride (60% in oil, 99.6 mg) was washed twice with hexane, and suspended in tetrahydrofuran (5 mL). A solution of 5-(2-fluoropyridin-3-yl)-4-methyl-1H-pyrrole-3-carbaldehyde (213 mg) in tetrahydrofuran (5 mL) was added at 0° C. The mixture was stirred at 0° C. for 30 min, 15-crown-5 (0.5 mL), then a solution of pyridine-3-sulfonyl chloride (375 mg) in tetrahydrofuran (2 mL) were added at the same temperature, and the mixture was stirred at room temperature for 1 hr. Water was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent: hexane-ethyl acetate=1:2) to give the title compound as colorless crystals (yield 218 mg, 61%).

$^1$H-NMR (CDCl$_3$) δ: 2.04 (3H, m), 7.31-7.35 (1H, m), 7.38-7.43 (1H, m), 7.64-7.77 (2H, m), 8.09 (1H, s), 8.33-8.36 (1H, m), 8.61-8.63 (1H, m), 8.84-8.86 (1H, m), 9.98 (1H, s).

Reference Example 49

5-(2-fluoropyridin-3-yl)-4-methyl-1-(phenylsulfonyl)-1H-pyrrole-3-carbaldehyde

Sodium hydride (60% in oil, 99.8 mg) was washed twice with hexane, and suspended in tetrahydrofuran (5 mL). A solution of 5-(2-fluoropyridin-3-yl)-4-methyl-1H-pyrrole-3-carbaldehyde (214 mg) in tetrahydrofuran (5 mL) was added at 0° C. The mixture was stirred at 0° C. for 30 min, 15-crown-5 (0.5 mL), then benzenesulfonyl chloride (0.28 mL) were added at the same temperature, and the mixture was stirred at room temperature for 1 hr. Water was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent: hexane-ethyl acetate=2:1) to give the title compound as a yellow oil (yield 221 mg, 61%).

$^1$H-NMR (CDCl$_3$) δ: 2.03 (3H, m), 7.26-7.32 (1H, m), 7.36-7.46 (4H, m), 7.60-7.66 (1H, m), 7.70-7.76 (1H, m), 8.10 (1H, s), 8.29-8.32 (1H, m), 9.97 (1H, s).

Reference Example 50

N-allyl-2-bromo-2,2-difluoroacetamide

Ethyl bromodifluoroacetate (100 g) was cooled to 0° C., and allylamine (39 mL) was added dropwise. The mixture was stirred at room temperature for 14 hr, and concentrated under reduced pressure. Water was added to the residue, and the mixture was extracted with ethyl acetate. The extract was washed successively with 1 mol/L hydrochloric acid, water, saturated aqueous sodium hydrogen carbonate solution, and saturated brine, dried over anhydrous magnesium sulfate, and concentrated under reduced pressure to give the title compound as a colorless oil (yield 105 g, 100%).

$^1$H-NMR (CDCl$_3$) δ: 3.99 (2H, dd, J=6.1, 5.7 Hz), 5.22-5.26 (1H, m), 5.26-5.33 (1H, m), 5.77-5.94 (1H, m), 6.31 (1H, brs).

Reference Example 51 tert-butyl allyl[bromo(difluoro)acetyl]carbamate

To a solution of N-allyl-2-bromo-2,2-difluoroacetamide (154 g) and 4-dimethylaminomethylpyridine (8.82 g) in acetonitrile (750 mL) was added dropwise di-tert-butyl dicarbonate (173 g) at 0° C. The mixture was stirred at room temperature for 14 hr, and concentrated under reduced pressure. Water was added to the residue, and the mixture was extracted with ethyl acetate. The extract was washed successively with water and saturated brine, dried over anhydrous magnesium sulfate, and concentrated under reduced pressure to give the title compound as a brown oil (yield 211 g, 93%).

$^1$H-NMR (CDCl$_3$) δ: 1.54 (9H, s), 4.29 (2H, ddd, J=5.7, 1.5, 1.1 Hz), 5.23 (1H, ddt, J=10.2, 1.1, 1.5 Hz), 5.25 (1H, ddt, J=17.0, 1.5, 1.1 Hz), 5.85 (1H, ddt, J=17.0, 10.2, 5.7 Hz).

Reference Example 52 tert-butyl 4-(bromomethyl)-3,3-difluoro-2-oxopyrrolidine-1-carboxylate

Under a nitrogen atmosphere, a suspension of tert-butyl allyl[bromo(difluoro)acetyl]carbamate (50.0 g) and copper bromide (6.91 g) in 1,2-dichloroethane (500 mL) was heated to 80° C. 2,2'-Bipyridyl (7.51 g) was added, and the obtained mixture was stirred at 80° C. for 24 hr. After cooling, the reaction mixture was concentrated under reduced pressure. The residue was suspended in tetrahydrofuran (150 mL), insoluble materials were filtered off, and the filtrate was concentrated under reduced pressure. The residue was purified by silica gel column chromatography (eluent: hexane:ethyl acetate=4:1), and washed with diisopropyl ether to give the title compound as white crystals (yield 32.3 g, 65%).

$^1$H-NMR (CDCl$_3$) δ: 1.57 (9H, s), 2.82-3.06 (1H, m), 3.40 (1H, dd, J=10.7, 10.0 Hz), 3.48 (1H, ddd, J=11.3, 8.1, 0.8 Hz), 3.67 (1H, dd, J=10.7, 4.9 Hz), 4.09 (1H, dd, J=11.3, 8.1 Hz).

Reference Example 53 tert-butyl 3,3-difluoro-4-methylene-2-oxopyrrolidine-1-carboxylate

To a solution of tert-butyl 4-(bromomethyl)-3,3-difluoro-2-oxopyrrolidine-1-carboxylate (50.1 g) in tetrahydrofuran (400 mL) was added dropwise 1,8-diazabicyclo[5.4.0]undec-7-ene (25.0 mL) at 0° C. over 15 min. After the completion of the dropwise addition, the mixture was stirred at room temperature for 1 hr. Insoluble materials were filtered off and the filtrate was concentrated under reduced pressure. The residue was purified by silica gel column chromatography (eluent: hexane:ethyl acetate=4:1). The obtained crystals were washed with diisopropyl ether to give the title compound as colorless crystals (yield 28.1 g, 76%).

$^1$H-NMR (CDCl$_3$) δ: 1.57 (9H, s), 4.32-4.39 (2H, m), 5.69-5.76 (1H, m), 5.92-6.06 (1H, m).

Reference Example 54 tert-butyl 3,3-difluoro-2-(2-fluoropyridin-3-yl)-2-hydroxy-4-methylenepyrrolidine-1-carboxylate Under a nitrogen atmosphere, to a solution of diisopropylamine (23.9 g) in anhydrous tetrahydrofuran (175 mL) was added dropwise a 1.61 mol/L hexane solution (136 mL) of n-butyllithium at −78° C., and the mixture was stirred at the same temperature for 15 min. To the obtained solution was added dropwise a solution of 2-fluoropyridine (21.9 g) in anhydrous tetrahydrofuran (25 mL) at the same temperature over 30 min, and the mixture was stirred for 2 hr. To the obtained suspension was added dropwise a solution of tert-butyl 3,3-difluoro-4-methylene-2-oxopyrrolidine-1-carboxylate (25.0 g) in anhydrous tetrahydrofuran (50 mL) at the same temperature, and the mixture was stirred for 3 hr. Saturated aqueous ammonium chloride solution was added, and the mixture was extracted with ethyl acetate. The extract was washed successively with saturated aqueous sodium hydrogen carbonate solution, water and saturated brine, dried over anhydrous magnesium sulfate, and concentrated under reduced pressure. The residue was purified by silica gel column chromatography (eluent: hexane:ethyl acetate=2:1). The obtained crystals were washed with diisopropyl ether to give the title compound as colorless crystals (yield 23.7 g, 67%).

$^1$H-NMR (CDCl$_3$) δ: 1.16 (3.6H, brs), 1.44 (5.4H, brs), 3.55 (0.40H, brs), 4.19-4.40 (2H, m), 4.75 (0.60H, brs), 5.56 (1H, s), 5.78 (1H, s), 7.28 (1H, ddd, J=7.5, 2.8, 1.9 Hz), 8.13 (1H, ddd, J=9.8, 7.5, 1.9 Hz), 8.19-8.26 (1H, m).

Reference Example 55 tert-butyl {3,3-difluoro-2-methylene-4-oxo-4-[2-(trifluoromethyl)pyridin-3-yl]butyl}carbamate Under a nitrogen atmosphere, to a solution of 2,2,6,6-tetramethylpiperidine (10.2 g) in anhydrous tetrahydrofuran (100 mL) was added dropwise a 1.61 mol/L hexane solution (40.5 mL) of n-butyllithium at −78° C., and the mixture was stirred at the same temperature for 15 min. To the obtained solution was added dropwise a solution of 2-(trifluoromethyl)pyridine (10.2 g) in anhydrous tetrahydrofuran (10 mL) at the same temperature over 30 min, and the mixture was stirred for 2 hr. A solution of tert-butyl 3,3-difluoro-4-methylene-2-oxopyrrolidine-1-carboxylate (7.65 g) in anhydrous tetrahydrofuran (10 mL) solution was added dropwise to the obtained suspension at the same temperature, and the mixture was stirred for 2 hr. Saturated aqueous ammonium chloride solution was added, and the mixture was extracted with ethyl acetate. The extract was washed successively with saturated aqueous sodium hydrogen carbonate solution, water and saturated brine, dried over anhydrous magnesium sulfate, and concentrated under reduced pressure. The residue was purified by silica gel column chromatography (eluent: hexane:ethyl acetate=3:1) to give the title compound as a yellow oil (yield 10.8 g, 87%).

$^1$H-NMR (CDCl$_3$) δ: 1.45 (9H, s), 3.93 (2H, brd, J=5.7 Hz), 4.82 (1H, brs), 5.63-5.66 (2H, m), 7.56-7.60 (1H, m), 7.94-7.97 (1H, m), 8.84-8.86 (1H, m).

Reference Example 56

3-(4,4-difluoro-3-methylene-3,4-dihydro-2H-pyrrol-5-yl)-2-fluoropyridine

To a solution of tert-butyl 3,3-difluoro-2-(2-fluoropyridin-3-yl)-2-hydroxy-4-methylenepyrrolidine-1-carboxylate (20.0 g) in acetic acid (70 mL) was added dropwise concentrated hydrochloric acid (20 mL). The obtained mixture was stirred at room temperature for 1 hr, and concentrated under reduced pressure. Saturated aqueous sodium hydrogen carbonate solution was added to the residue, and the mixture was extracted with ethyl acetate. The extract was washed successively with saturated aqueous sodium hydrogen carbonate solution, water and saturated brine, dried over anhydrous magnesium sulfate, and concentrated under reduced pressure. The residue was purified by silica gel column chromatography (eluent: hexane:ethyl acetate=2:1) to give the title compound as a yellow oil (yield 11.6 g, 90%).

$^1$H-NMR (CDCl$_3$) δ: 4.79 (2H, ddd, J=4.9, 2.6, 2.5 Hz), 5.58-5.65 (1H, m), 5.84-5.93 (1H, m), 7.33 (1H, ddd, J=7.5, 4.9, 1.7 Hz), 8.32-8.45 (2H, m).

Reference Example 57

3-(4,4-difluoro-3-methylene-3,4-dihydro-2H-pyrrol-5-yl)-2-(trifluoromethyl)pyridine To a solution of tert-butyl {3,3-difluoro-2-methylene-4-oxo-4-[2-(trifluoromethyl)pyridin-3-yl]butyl}carbamate (3.25 g) in acetic acid (10 mL) was added dropwise concentrated hydrochloric acid (3 mL). The obtained mixture was stirred at room temperature for 2 hr, and concentrated under reduced pressure. Saturated aqueous sodium hydrogen carbonate solution was added to the residue, and the mixture was extracted with ethyl acetate. The extract was washed successively with saturated aqueous sodium hydrogen carbonate solution, water and saturated brine, dried over anhydrous magnesium sulfate, and concentrated under reduced pressure. The residue was purified by silica gel column chromatography (eluent: hexane:ethyl acetate=3:1) to give the title compound as a yellow oil (yield 1.85 g, 83%).

$^1$H-NMR (CDCl$_3$) δ: 4.76-4.77 (2H, m), 5.65-5.67 (1H, m), 5.89-5.92 (1H, m), 7.57-7.62 (1H, m), 7.96-7.99 (1H, m), 8.83-8.84 (1H, m).

Reference Example 58

2-chloro-3-(4,4-difluoro-3-methylene-3,4-dihydro-2H-pyrrol-5-yl)pyridine

Under a nitrogen atmosphere, to a solution of diisopropylamine (30.8 g) in anhydrous tetrahydrofuran (300 mL) was added dropwise a 1.61 mol/L hexane solution (160 mL) of n-butyllithium at −78° C., and the mixture was stirred at the same temperature for 15 min. To the obtained solution was added a solution of 2-chloropyridine (30.9 g) in anhydrous tetrahydrofuran (30 mL) at the same temperature over 30 min, and the mixture was stirred for 2 hr. To the obtained suspension was added dropwise a solution of tert-butyl 3,3-difluoro-4-methylene-2-oxopyrrolidine-1-carboxylate (30.1 g) in anhydrous tetrahydrofuran (30 mL) at the same temperature, and the mixture was stirred for 3 hr. Saturated aqueous ammonium chloride solution was added, and the mixture was extracted with ethyl acetate. The extract was washed successively with saturated aqueous sodium hydrogen carbonate solution, water and saturated brine, dried over anhydrous magnesium sulfate, and concentrated under reduced pressure. The residue was purified by silica gel column chromatography (eluent: hexane:ethyl acetate=3:1) to give a mixture of tert-butyl [4-(2-chloropyridin-3-yl)-3,3-difluoro-2-methylene-4-oxobutyl]carbamate and tert-butyl 2-(2-chloropyridin-3-yl)-3,3-difluoro-2-hydroxy-4-methylenepyrrolidine-1-carboxylate (yield 23.8 g). To a solution of the obtained mixture (23.7 g) in acetic acid (70 mL) was added dropwise concentrated hydrochloric acid (18 mL). The obtained mixture was stirred at room temperature for 1 hr, and concentrated under reduced pressure. Saturated aqueous sodium hydrogen carbonate solution was added to the residue, and the mixture was extracted with ethyl acetate. The extract was washed successively with saturated aqueous sodium hydrogen carbonate solution, water and saturated brine, dried over anhydrous magnesium sulfate, and concentrated under reduced pressure. The residue was purified by silica gel column chromatography (eluent: hexane:ethyl acetate=3:1) to give the title compound as a yellow oil (yield 12.1 g, 2 step yield 41%).

$^1$H-NMR (CDCl$_3$) δ: 4.78-4.82 (2H, m), 5.63-5.66 (1H, m), 5.87-5.91 (1H, m), 7.33-7.37 (1H, m), 7.94-7.97 (1H, m), 8.49-8.52 (1H, m).

Reference Example 59

1-(2,4-dimethoxyphenyl)-N-methylmethanamine 2,4-Dimethoxybenzaldehyde (5.0 g) was dissolved in methanol (60 mL), and a 40% methanol solution (9.3 mL) of methylamine was added at room temperature. The mixture was stirred at room temperature for 1 hr, and sodium borohydride (1.37 g) was added by small portions under ice-cooling. The mixture was stirred at room temperature for 3 hr, treated with 1 mol/L hydrochloric acid under ice-cooling, and methanol was evaporated under reduced pressure. The residue was diluted with ethyl acetate, basified with saturated aqueous sodium hydrogen carbonate solution, and extracted with ethyl acetate. The extract was washed with saturated brine, dried over anhydrous sodium sulfate, and concentrated under reduced pressure. The residue was purified by basic silica gel column chromatography (eluent: hexane:ethyl acetate=4: 1→2:1) to give the title compound as a colorless oil (yield 4.41 g, 81%).

$^1$H-NMR (CDCl$_3$) δ: 2.40 (3H, s), 3.67 (2H, s), 3.80 (3H, s), 3.81 (3H, s), 6.40-6.45 (2H, m), 7.11 (1H, d, J=7.8 Hz), 1H not detected.

Reference Example 60

1-(2,4-dimethoxyphenyl)-N-{[4-fluoro-5-(2-fluoropyridin-3-yl)-1H-pyrrol-3-yl]methyl}-N-methylmethanamine Sodium hydride (60% in oil, 2.23 g) was washed twice with hexane and suspended in tetrahydrofuran (180 mL). To the suspension was added dropwise a solution of 1-(2,4-dimethoxyphenyl)-N-methylmethanamine (9.09 g) in tetrahydrofuran (10 mL) at 0° C. After the completion of the dropwise addition, the mixture was stirred at 60° C. for 18 hr. The reaction mixture was cooled to 0° C., a solution of 3-(4, 4-difluoro-3-methylene-3,4-dihydro-2H-pyrrol-5-yl)-2-fluoropyridine (9.64 g) in tetrahydrofuran (10 mL) was added dropwise, and the mixture was stirred at the same temperature for 1 hr. Ice water and saturated brine were added, and the mixture was extracted with ethyl acetate. The extract was washed successively with saturated aqueous ammonium chloride solution, saturated aqueous sodium hydrogen carbonate solution, water and saturated brine, dried over anhydrous sodium sulfate, and concentrated under reduced pressure. The residue was purified by basic silica gel column chromatography (eluent: ethyl acetate) to give the title compound as a yellow oil (yield 16.8 g, 97%).

$^1$H-NMR (CDCl$_3$) δ: 2.24 (3H, s), 3.51 (2H, s), 3.54 (2H, s), 3.79 (3H, s), 3.80 (3H, s), 6.45 (1H, s), 6.42-6.50 (1H, m), 6.68 (1H, dd, J=4.7, 3.6 Hz), 7.18-7.29 (2H, m), 7.98 (1H, ddd, J=4.5, 1.9, 1.5 Hz), 8.25 (1H, ddd, J=10.2, 8.0, 1.9 Hz), 8.67 (1H, s).

Reference Example 61

1-(2,4-dimethoxyphenyl)-N-({4-fluoro-5-[2-(trifluoromethyl)pyridin-3-yl]-1H-pyrrol-3-yl}methyl)-N-methylmethanamine Sodium hydride (60% in oil, 1.00 g) was washed twice with hexane, and suspended in tetrahydrofuran (50 mL). To the suspension was added dropwise a solution of 1-(2,4-dimethoxyphenyl)-N-methylmethanamine (3.99 g) in tetrahydrofuran (10 mL) at 0° C. After the completion of the dropwise addition, the mixture was stirred at 60° C. for 18 hr. The reaction mixture was cooled to 0° C., a solution of 3-(4, 4-difluoro-3-methylene-3,4-dihydro-2H-pyrrol-5-yl)-2-(trifluoromethyl)pyridine (5.29 g) in tetrahydrofuran (10 mL) was added dropwise, and the mixture was stirred at the same temperature for 1 hr. Ice water and saturated brine were added, and the mixture was extracted with ethyl acetate. The extract was washed successively with saturated aqueous ammonium chloride solution, saturated aqueous sodium hydrogen carbonate solution, water and saturated brine, dried over anhydrous sodium sulfate, and concentrated under reduced pressure. The residue was purified by basic silica gel column chromatography (eluent: hexane:ethyl acetate=1:2) to give the title compound as a yellow oil (yield 8.36 g, 98%).

$^1$H-NMR (CDCl$_3$) δ: 2.24 (3H, s), 3.52 (2H, s), 3.53 (2H, s), 3.79 (3H, s), 3.80 (3H, s), 6.45-6.48 (2H, s), 6.68-6.71 (1H, m), 7.22-7.25 (1H, m), 7.50-7.54 (1H, m), 8.02-8.10 (2H, m), 8.57-8.58 (1H, m).

Reference Example 62

1-[5-(2-chloropyridin-3-yl)-4-fluoro-1H-pyrrol-3-yl]-N-(2,4-dimethoxybenzyl)-N-methylmethanamine Sodium hydride (60% in oil, 2.89 g) was washed twice with hexane, and suspended in tetrahydrofuran (100 mL). To the suspension was added dropwise a solution of 1-(2,4-dimethoxyphenyl)-N-methylmethanamine (11.4 g) in tetrahydrofuran (10 mL) at 0° C. After the completion of the dropwise addition, the mixture was stirred at 60° C. for 16 hr. The reaction mixture was cooled to 0° C., a solution of 2-chloro-3-(4,4-difluoro-3-methylene-3,4-dihydro-2H-pyrrol-5-yl)pyridine (11.0 g) in tetrahydrofuran (10 mL) was added dropwise, and the mixture was stirred at the same temperature for 30 min. Water and saturated brine were added, and the mixture was extracted with ethyl acetate. The extract was washed successively with saturated aqueous ammonium chloride solution, saturated aqueous sodium hydrogen carbonate solution, water and saturated brine, dried over anhydrous sodium sulfate, and concentrated under reduced pressure. The residue was purified by basic silica gel column chromatography (eluent: hexane:ethyl acetate=1:1) to give the title compound as a yellow oil (yield 17.8 g, 95%).

$^1$H-NMR (CDCl$_3$) δ: 2.25 (3H, s), 3.52 (2H, s), 3.53 (2H, s), 3.79-3.80 (6H, m), 6.45-6.48 (2H, m), 6.69-6.72 (1H, m), 7.23-7.30 (2H, m), 8.07-8.10 (1H, m), 8.21-8.23 (1H, m), 8.85 (1H, brs).

Reference Example 63

1-(2,4-dimethoxyphenyl)-N-{[4-fluoro-5-(2-fluoropyridin-3-yl)-1-(pyridin-3-ylsulfonyl)-1H-pyrrol-3-yl]methyl}-N-methylmethanamine To a suspension of sodium hydride (60% in oil, 1.57 g) in tetrahydrofuran (100 mL) was added dropwise a solution of 1-(2,4-dimethoxyphenyl)-N-{[4-fluoro-5-(2-fluoropyridin-3-yl)-1H-pyrrol-3-yl]methyl}-N-methylmethanamine (9.8 g) in tetrahydrofuran (30 mL) under ice-cooling. The reaction mixture was stirred at the same temperature for 10 min, and 15-crown-5 (8.66 g) was added dropwise. After further stirring for 10 min, pyridine-3-sulfonyl chloride (6.98 g) was added dropwise. After stirring for 15 min at the same temperature, ice water was added and the reaction mixture was extracted with ethyl acetate. The aqueous layer was weakly basified with saturated aqueous sodium hydrogen carbonate solution (100 mL), and extracted again with ethyl acetate. The combined extract was washed successively with saturated aqueous sodium hydrogen carbonate solution and saturated brine, dried over anhydrous sodium sulfate, and concentrated under reduced pressure. The residue was purified by basic silica gel column chromatography (eluent: hexane:ethyl acetate=6:1→3:1), and washed with diisopropyl ether to give the title compound as colorless crystals (yield 9.25 g, 69%).

$^1$H-NMR (CDCl$_3$) δ: 2.22 (3H, s), 3.45 (2H, s), 3.47 (2H, s), 3.81 (3H, s), 3.84 (3H, s), 6.44-6.50 (2H, m), 7.15-7.22 (1H, m), 7.27-7.37 (2H, m), 7.40 (1H, d, J=5.3 Hz), 7.67 (1H, ddd, J=8.1, 2.3, 1.7 Hz), 7.81 (1H, ddd, J=9.2, 7.3, 1.9 Hz), 8.30 (1H, ddd, J=4.9, 1.9, 0.9 Hz), 8.67 (1H, d, J=1.9 Hz), 8.78 (1H, dd, J=4.9, 1.5 Hz).

Reference Example 64

1-(2,4-dimethoxyphenyl)-N-{[4-fluoro-5-(2-fluoropyridin-3-yl)-1-(phenylsulfonyl)-1H-pyrrol-3-yl]methyl}-N-methylmethanamine To a solution of 1-(2,4-dimethoxyphenyl)-N-{[4-fluoro-5-(2-fluoropyridin-3-yl)-1H-pyrrol-3-yl]methyl}-N-methylmethanamine (2.98 g) in tetrahydrofuran (20 mL) was added sodium hydride (60% in oil, 421 mg) under ice-cooling. After stirring at the same temperature for 30 min, 15-crown-5 (1.80 mL) was added dropwise. After further stirring for 15 min, benzenesulfonyl chloride (1.15 mL) was added dropwise. After stirring for 1 hr at the same temperature, saturated aqueous ammonium chloride solution and water were added, and the mixture was extracted with ethyl acetate. The extract was washed with saturated brine, dried over anhydrous magnesium sulfate, and concentrated under reduced pressure. The residue was purified by basic silica gel column chromatography (eluent: hexane:ethyl acetate=9:1→7:3) to give the title compound as a yellow oil (yield 2.95 g, 72%).

$^1$H-NMR (CDCl$_3$) δ: 2.21 (3H, s), 3.45 (2H, s), 3.47 (2H, s), 3.81 (3H, s), 3.84 (3H, s), 6.47 (1H, dd, J=6.6, 2.5 Hz), 6.48 (1H, s), 7.16-7.23 (1H, m), 7.24-7.31 (1H, m), 7.32-7.44 (5H, m), 7.52-7.59 (1H, m), 7.82 (1H, ddd, J=9.0, 7.5, 2.1 Hz), 8.27 (1H, ddd, J=4.9, 1.9, 0.9 Hz).

Reference Example 65

1-(2,4-dimethoxyphenyl)-N-({4-fluoro-1-(phenylsulfonyl)-5-[2-(trifluoromethyl)pyridin-3-yl]-1H-pyrrol-3-yl}methyl)-N-methylmethanamine Sodium hydride (60% in oil, 286 mg) was washed twice with hexane, and suspended in tetrahydrofuran (15 mL). To the suspension was added dropwise a solution of 1-(2,4-dimethoxyphenyl)-N-({4-fluoro-5-[2-(trifluoromethyl)pyridin-3-yl]-1H-pyrrol-3-yl}methyl)-N-methylmethanamine (1.99 g) in tetrahydrofuran (5 mL) under ice-cooling. After stirring at the same temperature for 30 min, 15-crown-5 (1.42 mL), then benzenesulfonyl chloride (0.91 mL) were added dropwise. After stirring at the same temperature for 30 min, water was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by basic silica gel column chromatography (eluent: hexane:ethyl acetate=1:1) to give the title compound as a yellow oil (yield 1.98 g, 75%).

$^1$H-NMR (CDCl$_3$) δ: 2.23 (3H, s), 3.43-3.56 (4H, s), 3.81 (3H, s), 3.84 (3H, s), 6.45-6.48 (2H, m), 7.19-7.22 (2H, m), 7.37-7.42 (4H, m), 7.52-7.59 (2H, m), 7.76-7.79 (1H, m), 8.77-8.88 (1H, m).

Reference Example 66

1-[5-(2-chloropyridin-3-yl)-4-fluoro-1-(phenylsulfonyl)-1H-pyrrol-3-yl]-N-(2,4-dimethoxybenzyl)-N-methylmethanamine Sodium hydride (60% in oil, 2.95 g) was washed twice with hexane, and suspended in tetrahydrofuran (200 mL). To the suspension was added dropwise a solution of 1-[5-(2-chloropyridin-3-yl)-4-fluoro-1H-pyrrol-3-yl]-N-(2,4-dimethoxybenzyl)-N-methylmethanamine (19.1 g) in tetrahydrofuran (20 mL) under ice-cooling. After stirring at the same temperature for 15 min, 15-crown-5 (16.3 g), then a solution of benzenesulfonyl chloride (13.1 g) in tetrahydrofuran (20 mL) were added dropwise. After stirring at the same temperature for 30 min, ice was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by basic silica gel column chromatography (eluent: hexane:ethyl acetate=1:1) to give the title compound as a yellow oil (yield 20.2 g, 78%).

$^1$H-NMR (CDCl$_3$) δ: 2.23 (3H, s), 3.42-3.55 (4H, m), 3.81 (3H, s), 3.84 (3H, s), 6.45-6.48 (2H, m), 7.19-7.22 (1H, m), 7.30-7.41 (5H, m), 7.53-7.60 (2H, m), 7.72-7.78 (1H, m), 8.42-8.44 (1H, m).

Reference Example 67 tert-butyl ({4-fluoro-1-(phenylsulfonyl)-5-[2-(trifluoromethyl)pyridin-3-yl]-1H-pyrrol-3-yl}methyl)methylcarbamate To a solution of 1-(2,4-dimethoxyphenyl)-N-({4-fluoro-1-(phenylsulfonyl)-5-[2-(trifluoromethyl)pyridin-3-yl]-1H-pyrrol-3-yl}methyl)-N-methylmethanamine (1.98 g) in tetrahydrofuran (20 mL) were added 1-chloroethyl chlorocarbonate (0.41 mL) at 0° C., and the mixture was stirred for 1 hr. Triethylamine (1.6 mL) was added at the same temperature, and the obtained mixture was stirred at 80° C. for 14 hr. The reaction mixture was cooled to room temperature, and concentrated under reduced pressure. Water was added to the residue, and the mixture was extracted with ethyl acetate. The extract was washed with water and saturated brine, dried over anhydrous sodium sulfate, and concentrated under reduced pressure. Ethanol (20 mL) was added to the residue, and the mixture was stirred at 50° C. for 3 hr. The reaction mixture was cooled to room temperature, and concentrated under reduced pressure. Saturated aqueous sodium hydrogen carbonate solution was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure. The residue was dissolved in ethyl acetate (15 mL), di-tert-butyl dicarbonate (0.87 mL) was added, and the mixture was stirred at room temperature for 2 days. Saturated aqueous sodium hydrogen carbonate solution was added, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent: hexane:ethyl acetate=2:1) to give the title compound as a yellow oil (yield 1.39 g, 77%).

$^1$H-NMR (CDCl$_3$) δ: 1.48 (9H, s), 2.87 (3H, brs), 4.27 (2H, brs), 7.25-7.43 (5H, m), 7.53-7.62 (2H, m), 7.77-7.80 (1H, m), 8.78 (1H, d, J=5.4 Hz).

Reference Example 68 tert-butyl {[5-(2-chloropyridin-3-yl)-4-fluoro-1-(phenylsulfonyl)-1H-pyrrol-3-yl]methyl}methylcarbamate To a solution of 1-[5-(2-chloropyridin-3-yl)-4-fluoro-1-(phenylsulfonyl)-1H-pyrrol-3-yl]-N-(2,4-dimethoxybenzyl)-N-methylmethanamine (20.2 g) in tetrahydrofuran (200 mL) was added dropwise 1-chloroethyl chlorocarbonate (4.6 mL) at 0° C., and the mixture was stirred for 1 hr. Triethylamine (12.3 g) was added at the same temperature, and the obtained mixture was refluxed for 14 hr. The reaction mixture was cooled to 0° C., and the obtained solid was filtrated. The filtrate was concentrated under reduced pressure. Water was added to the residue, and the mixture was extracted with ethyl acetate. The extract was washed with water and saturated brine, dried over anhydrous sodium sulfate, and concentrated under reduced pressure. Ethanol (250 mL) was added to the residue, and the mixture was stirred at 50° C. for 3 hr. The reaction mixture was cooled to room temperature, and concentrated under reduced pressure. Saturated aqueous sodium hydrogen carbonate solution was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure. The residue was dissolved in ethyl acetate (200 mL), di-tert-butyl dicarbonate (9.02 g) was added and the mixture was stirred at room temperature for 1 hr. Water was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent: hexane:ethyl acetate=2:1) to give the title compound as a yellow oil (yield 13.1 g, 72%).

$^1$H-NMR (CDCl$_3$) δ: 1.49 (9H, s), 2.87 (3H, s), 4.26 (2H, brs), 7.31-7.44 (6H, m), 7.57-7.59 (1H, m), 7.75-7.78 (1H, m), 8.43-8.45 (1H, m).

Reference Example 69 tert-butyl {[5-(2-cyanopyridin-3-yl)-4-fluoro-1-(phenylsulfonyl)-1H-pyrrol-3-yl]methyl}methylcarbamate A suspension of tert-butyl {[5-(2-chloropyridin-3-yl)-4-fluoro-1-(phenylsulfonyl)-1H-pyrrol-3-yl]methyl}methylcarbamate (7.24 g), zinc cyanide (3.55 g) and tetrakis(triphenylphosphine)palladium (0) (3.56 g) in N,N-dimethylformamide (80 mL) was stirred at 120° C. for 20 hr. The reaction mixture was cooled to room temperature, and insoluble materials were filtered off. Water was added to the filtrate, and the mixture was extracted with ethyl acetate. The extract washed with saturated aqueous sodium hydrogen carbonate solution, water and saturated brine, dried over anhydrous magnesium sulfate, and concentrated under reduced pressure. The residue was purified by silica gel column chromatography (eluent: hexane:ethyl acetate=2:1) to give a mixture of tert-butyl {[5-(2-chloropyridin-3-yl)-4-fluoro-1-(phenylsulfonyl)-1H-pyrrol-3-yl]methyl}methylcarbamate and the title compound. A suspension of the obtained mixture, zinc cyanide (3.56 g) and tetrakis(triphenylphosphine)palladium (0) (3.38 g) in N,N-dimethylformamide (80 mL) was stirred at 120° C. for 12 hr. The reaction mixture was cooled to room temperature, and insoluble materials were filtered off. Water was added to the filtrate, and the mixture was extracted with ethyl acetate. The extract washed with saturated aqueous sodium hydrogen carbonate solution, water and saturated brine, dried over anhydrous magnesium sulfate, and concentrated under reduced pressure. The residue was purified by silica gel column chromatography (eluent: hexane:ethyl acetate=2:1) to give the title compound as a yellow oil (yield 5.84 g, 82%).

$^1$H-NMR (CDCl$_3$) δ: 1.49 (9H, s), 2.86 (3H, s), 4.29 (2H, s), 7.32-7.46 (5H, m), 7.57-7.65 (2H, m), 7.95-7.98 (1H, m), 8.71-8.73 (1H, m).

Reference Example 70 tert-butyl ({4-fluoro-5-[2-(trifluoromethyl)pyridin-3-yl]-1H-pyrrol-3-yl}methyl)methylcarbamate To a solution of tert-butyl ({4-fluoro-1-(phenylsulfonyl)-5-[2-(trifluoromethyl)pyridin-3-yl]-1H-pyrrol-3-yl}methyl)methylcarbamate (938 mg) in tetrahydrofuran (4 mL) and methanol (1 mL) was added a 8 mol/L aqueous sodium hydroxide solution (0.6 mL) at 0° C., and the mixture was stirred at room temperature for 1 hr. The reaction mixture was concentrated under reduced pressure. Water was added to the residue, and the mixture was extracted with ethyl acetate. The extract washed with saturated aqueous sodium hydrogen carbonate solution, water and saturated brine, dried over anhydrous sodium sulfate, and concentrated under reduced pressure. The residue was purified by basic silica gel column chromatography (eluent: hexane:ethyl acetate=4:1) to give the title compound as a yellow oil (yield 423 mg, 62%).

$^1$H-NMR (CDCl$_3$) δ: 1.49 (9H, s), 2.88 (3H, brs), 4.31 (2H, brs), 6.68 (1H, brs), 7.51-7.55 (1H, m), 7.99-8.02 (1H, m), 8.08 (1H, brs), 8.60-8.61 (1H, m).

Reference Example 71 tert-butyl {[5-(2-chloropyridin-3-yl)-4-fluoro-1H-pyrrol-3-yl]methyl}methylcarbamate To a mixture of tert-butyl {[5-(2-chloropyridin-3-yl)-4-fluoro-1-(phenylsulfonyl)-1H-pyrrol-3-yl]methyl}methylcarbamate (5.50 g), tetrahydrofuran (25 mL), 2-propanol (25 mL) and methanol (20 mL) was added a 1 mol/L aqueous sodium hydroxide solution (50 mL), and the mixture was stirred at room temperature for 1 hr. The reaction mixture was concentrated under reduced pressure. Water was added to the residue, and the mixture was extracted with ethyl acetate. The extract washed with saturated aqueous sodium hydrogen carbonate solution, water and saturated brine, dried over anhydrous sodium sulfate, and concentrated under reduced pressure. The residue was purified by basic silica gel column chromatography (eluent: hexane:ethyl acetate=1:1) to give the title compound as a yellow solid (yield 3.59 g, 92%).

$^1$H-NMR (CDCl$_3$) δ: 1.49 (9H, s), 2.88 (3H, brs), 4.31 (2H, brs), 6.69 (1H, brs), 7.26-7.30 (1H, m), 8.03-8.06 (1H, m), 8.22-8.24 (1H, m), 8.87 (1H, brs).

Reference Example 72 tert-butyl {[5-(2-cyanopyridin-3-yl)-4-fluoro-1H-pyrrol-3-yl]methyl}methylcarbamate To a mixture of tert-butyl {[5-(2-cyanopyridin-3-yl)-4-fluoro-1-(phenylsulfonyl)-1H-pyrrol-3-yl]methyl}methylcarbamate (5.43 g), tetrahydrofuran (50 mL), and methanol (13 mL) was added a 8 mol/L aqueous sodium hydroxide solution (2 mL) at 0° C., and the mixture was stirred at the same temperature for 30 min. The reaction mixture was concentrated under reduced pressure. Water was added to the residue, and the mixture was extracted with ethyl acetate. The extract washed with saturated aqueous sodium hydrogen carbonate solution, water and saturated brine, dried over anhydrous sodium sulfate, and concentrated under reduced pressure. The residue was purified by basic silica gel column chromatography (eluent: hexane:ethyl acetate=1:1), and further by silica gel column chromatography (eluent: hexane:ethyl acetate=1:1) to give the title compound as a yellow oil (yield 2.18 g, 57%).
$^1$H-NMR (CDCl$_3$) δ: 1.49 (9H, s), 2.88 (3H, s), 4.30 (2H, brs), 6.79 (1H, brs), 7.48-7.52 (1H, m), 8.18-8.21 (1H, m), 8.48-8.49 (1H, m), 9.06 (1H, brs).

Reference Example 73 tert-butyl ({4-fluoro-1-(pyridin-3-ylsulfonyl)-5-[2-(trifluoromethyl)pyridin-3-yl]-1H-pyrrol-3-yl}methyl)methylcarbamate Sodium hydride (60% in oil, 69.7 mg) was washed twice with hexane, and suspended in tetrahydrofuran (10 mL). To the suspension was added dropwise a solution of tert-butyl ({4-fluoro-5-[2-(trifluoromethyl)pyridin-3-yl]-1H-pyrrol-3-yl}methyl)methylcarbamate (422 mg) in tetrahydrofuran (2 mL) under ice-cooling. After stirring at the same temperature for 30 min, 15-crown-5 (0.36 mL) and a solution of pyridine-3-sulfonyl chloride (332 mg) in tetrahydrofuran (2 mL) were added dropwise. The mixture was stirred at room temperature for 40 min, water was added, and the mixture was extracted with ethyl acetate. The extract was washed successively with saturated aqueous sodium hydrogen carbonate solution, water and saturated brine, dried over anhydrous sodium sulfate, and concentrated under reduced pressure. The residue was purified by silica gel column chromatography (eluent: hexane:ethyl acetate=1:2) to give the title compound as a yellow oil (yield 510 mg, 88%).
$^1$H-NMR (CDCl$_3$) δ: 1.49 (9H, s), 2.88 (3H, brs), 4.29 (2H, brs), 7.25-7.39 (2H, m), 7.57-7.62 (2H, m), 7.79-7.82 (1H, m), 8.59-8.61 (1H, m), 8.80-8.82 (2H, m).

Reference Example 74 tert-butyl {[4-fluoro-5-(2-fluoropyridin-3-yl)-1-(pyridin-3-ylsulfonyl)-1H-pyrrol-3-yl]methyl}methylcarbamate To a solution of 1-[4-fluoro-5-(2-fluoropyridin-3-yl)-1-(pyridin-3-ylsulfonyl)-1H-pyrrol-3-yl]-N-methylmethanamine (500 mg) obtained in Example 27 in tetrahydrofuran (5 mL) was added di-tert-butyl dicarbonate (329 mg) at room temperature and the mixture was stirred for 5 min. The reaction mixture was concentrated under reduced pressure, and the obtained residue was purified by silica gel column chromatography (eluent: hexane-ethyl acetate=4:1→2:1) to give the title compound as a colorless oil (yield 383 mg, 60%).
$^1$H-NMR (CDCl$_3$) δ: 1.48 (9H, s), 2.86 (3H, s), 4.26 (2H, s), 7.25-7.39 (3H, m), 7.62-7.65 (1H, m), 7.77-7.82 (1H, m), 8.29-8.31 (1H, m), 8.63-8.64 (1H, m), 8.79-8.81 (1H, m).

Reference Example 75 tert-butyl {[4-fluoro-5-(2-fluoropyridin-3-yl)-1H-pyrrol-3-yl]methyl}methylcarbamate tert-Butyl {[4-fluoro-5-(2-fluoropyridin-3-yl)-1-(pyridin-3-ylsulfonyl)-1H-pyrrol-3-yl]methyl}methylcarbamate (1.0 g) was dissolved in tetrahydrofuran (8 mL) and 2-propanol (2 mL), and 1 mol/L aqueous sodium hydroxide solution (5 mL) was added under ice-cooling. After stirring at room temperature for 18 hr, the solvent evaporated under reduced pressure, water was added to the residue and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=4:1→2:1) to give the title compound as a pale-yellow oil (yield 752 mg, quantitative).
$^1$H-NMR (CDCl$_3$) δ: 1.49 (9H, s), 2.88 (3H, s), 4.31 (2H, s), 6.67 (1H, br), 7.21-7.26 (1H, m), 7.98-8.00 (1H, m), 8.19-8.26 (1H, m), 9.65 (1H, br)

Reference Example 76 tert-butyl ({4-fluoro-5-(2-fluoropyridin-3-yl)-1-[(3-methoxyphenyl)sulfonyl]-1H-pyrrol-3-yl}methyl)methylcarbamate To a suspension of sodium hydride (60% in oil, 60 mg) in tetrahydrofuran (5 mL) was added a solution of tert-butyl {[4-fluoro-5-(2-fluoropyridin-3-yl)-1H-pyrrol-3-yl]methyl}methylcarbamate (323 mg) in tetrahydrofuran (5 mL) at 0° C., and 15-crown-5 (330 mg) and 3-methoxybenzenesulfonyl chloride (310 mg) were added at the same temperature. The mixture was stirred at room temperature for 30 min, water was added and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=7:1→3:1) to give the title compound as a colorless oil (yield 551 mg, quantitative).
$^1$H-NMR (CDCl$_3$) δ: 1.47 (9H, s), 2.85 (3H, s), 3.73 (3H, s), 4.25 (2H, s), 6.82-6.83 (1H, m), 6.95-6.99 (1H, m), 7.07-7.11 (1H, m), 7.20-7.34 (3H, m), 7.78-7.84 (1H, m), 8.26-8.28 (1H, m).

Reference Example 77 tert-butyl ({4-fluoro-1-[(3-fluorophenyl)sulfonyl]-5-(2-fluoropyridin-3-yl)-1H-pyrrol-3-yl}methyl)methylcarbamate To a suspension of sodium hydride (60% in oil, 60 mg) in tetrahydrofuran (5 mL) was added a solution of tert-butyl {[4-fluoro-5-(2-fluoropyridin-3-yl)-1H-pyrrol-3-yl]methyl}methylcarbamate (323 mg) in tetrahydrofuran (5 mL) at 0° C., 15-crown-5 (330 mg) and 3-fluorobenzenesulfonyl chloride (292 mg) were added at the same temperature. The mixture was stirred at room temperature for 30 min, water was added and the mixture was extracted with ethyl acetate. The extract was washed with saturated brine, dried over anhydrous is sodium sulfate, and concentrated under reduced pressure. The residue was purified by silica gel column chromatography (eluent: hexane-ethyl acetate=7:1→3:1) to give the title compound as a colorless oil (yield 527 mg, quantitative).
$^1$H-NMR (CDCl$_3$) δ: 1.48 (9H, s), 2.87 (3H, s), 4.26 (2H, s), 7.07-7.11 (1H, m), 7.15-7.17 (1H, m), 7.20-7.32 (3H, m), 7.37-7.44 (1H, m), 7.78-7.83 (1H, m), 8.29-8.30 (1H, m).

Reference Example 78 tert-butyl ({5-(2-chloropyridin-3-yl)-4-fluoro-1-[(3-methoxyphenyl)sulfonyl]-1H-pyrrol-3-yl}methyl) methylcarbamate To a suspension of sodium hydride (60% in oil, 60 mg) in tetrahydrofuran (5 mL) were added dropwise a solution of tert-butyl {[5-(2-chloropyridin-3-yl)-4-fluoro-1H-pyrrol-3-yl]methyl}methylcarbamate (340 mg) in tetrahydrofuran (5 mL), 15-crown-5 (330 mg) and 3-methoxybenzenesulfonyl chloride (310 mg) under ice-cooling and the mixture was stirred for 45 min. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→2:1) to give the title compound as a pale-yellow oil (yield 501 mg, 98%).
$^1$H-NMR (CDCl$_3$) δ: 1.48 (9H, s), 2.88 (3H, s), 3.74 (3H, s), 4.27 (2H, brs), 6.82 (1H, t, J=2.1 Hz), 6.96-6.99 (1H, m), 7.09 (1H, dd, J=7.8, 2.1 Hz), 7.28-7.35 (3H, m), 7.77 (1H, dd, J=7.5, 1.8 Hz), 8.44 (1H, dd, J=4.5, 1.8 Hz).

Reference Example 79 tert-butyl ({5-(2-chloropyridin-3-yl)-4-fluoro-1-[(3-fluorophenyl)sulfonyl]-1H-pyrrol-3-yl}methyl)methylcarbamate To a suspension of sodium hydride (60% in oil, 60 mg) in tetrahydrofuran (5 mL) were added dropwise a solution of tert-butyl {[5-(2-chloropyridin-3-yl)-4-fluoro-1H-pyrrol-3-yl]methyl}methylcarbamate (340 mg) in tetrahydrofuran (5 mL), 15-crown-5 (330 mg) and 3-fluorobenzenesulfonyl chloride (292 mg) under ice-cooling and the mixture was stirred for 10 min. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→2:1) to give the title compound as a pale-yellow oil (yield 477 mg, 96%).
$^1$H-NMR (CDCl$_3$) δ: 1.48 (9H, s), 2.89 (3H, s), 4.29 (2H, brs), 7.04-7.13 (1H, m), 7.17 (1H, d, J=8.3 Hz), 7.29-7.47 (4H, m), 7.78 (1H, dd, J=7.7, 1.9 Hz), 8.47 (1H, dd, J=4.7, 1.9 Hz).

Reference Example 80 tert-butyl {[5-(2-chloropyridin-3-yl)-4-fluoro-1-(pyridin-3-ylsulfonyl)-1H-pyrrol-3-yl]methyl}methylcarbamate To a suspension of sodium hydride (60% in oil, 60 mg) in tetrahydrofuran (5 mL) were added tert-butyl {[5-(2-chloropyridin-3-yl)-4-fluoro-1H-pyrrol-3-yl] methyl}methylcarbamate, 15-crown-5 (330 mg) and pyridine-3-sulfonyl chloride (266 mg) under ice-cooling and the mixture was stirred for 15 min. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→1:1) to give the title compound as a pale-yellow oil (yield 465 mg, 97%).
$^1$H-NMR (CDCl$_3$) δ: 1.48 (9H, s), 2.88 (3H, s), 4.30 (2H, brs), 7.29-7.44 (3H, m), 7.63 (1H, d, J=7.9 Hz), 7.79 (1H, dd, J=7.7, 1.9 Hz), 8.48 (1H, dd, J=4.9, 1.9 Hz), 8.65 (1H, d, J=2.1 Hz), 8.82 (1H, dd, J=4.7, 1.5 Hz).

Reference Example 81 tert-butyl ({5-(2-chloropyridin-3-yl)-1-[(3-cyanophenyl)sulfonyl]-4-fluoro-1H-pyrrol-3-yl}methyl)methylcarbamate To a suspension of sodium hydride (60% in oil, 60 mg) in tetrahydrofuran (5 mL) were added dropwise a solution (5 mL) of tert-butyl {[5-(2-chloropyridin-3-yl)-4-fluoro-1H-pyrrol-3-yl]methyl}methylcarbamate (340 mg) in tetrahydrofuran, 15-crown-5 (330 mg) and 3-cyanobenzenesulfonyl chloride (302 mg) under ice-cooling and the mixture was stirred for 3 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=6:1→3:1) to give the title compound as a pale-yellow oil (yield 490 mg, 97%).
$^1$H-NMR (CDCl$_3$) δ: 1.50 (9H, s), 2.90 (3H, s), 4.30 (2H, brs), 7.32 (1H, brs), 7.39 (1H, dd, J=7.6, 4.8 Hz), 7.55-7.61 (2H, m), 7.64 (1H, q, J=1.3 Hz), 7.82 (1H, dd, J=7.6, 1.8 Hz), 7.85-7.91 (1H, m), 8.51 (1H, dd, J=4.7, 1.9 Hz).

Reference Example 82 tert-butyl ({5-(2-cyanopyridin-3-yl)-4-fluoro-1-[(3-methoxyphenyl)sulfonyl]-1H-pyrrol-3-yl}methyl) methylcarbamate To a suspension of sodium hydride (60% in oil, 60 mg) in tetrahydrofuran (5 mL) were added dropwise a solution (5 mL) of tert-butyl {[5-(2-cyanopyridin-3-yl)-4-fluoro-1H-pyrrol-3-yl]methyl}methylcarbamate (330 mg) in tetrahydrofuran, 15-crown-5 (330 mg) and 3-methoxybenzenesulfonyl chloride (310 mg) under ice-cooling and the mixture was stirred for 15 min. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→2:1) to give the title compound as a pale-yellow oil (yield 477 mg, 95%).
$^1$H-NMR (CDCl$_3$) δ: 1.49 (9H, s), 2.87 (3H, s), 3.75 (3H, s), 4.31 (2H, s), 6.68-6.85 (1H, m), 6.85-7.00 (1H, m), 7.05-

7.18 (1H, m), 7.33 (2H, t, J=8.0 Hz), 7.60 (1H, dd, J=8.0, 4.8 Hz), 7.97 (1H, dd, J=8.1, 1.5 Hz), 8.73 (1H, dd, J=4.7, 1.5 Hz).

Reference Example 83 tert-butyl ({5-(2-cyanopyridin-3-yl)-4-fluoro-1-[(3-fluorophenyl)sulfonyl]-1H-pyrrol-3-yl}methyl)methylcarbamate To a suspension of sodium hydride (60% in oil, 60 mg) in tetrahydrofuran (5 mL) were added dropwise a solution (5 mL) of tert-butyl {[5-(2-cyanopyridin-3-yl)-4-fluoro-1H-pyrrol-3-yl]methyl}methylcarbamate (330 mg) in tetrahydrofuran, 15-crown-5 (330 mg) and 3-fluorobenzenesulfonyl chloride (292 mg) under ice-cooling and the mixture was stirred for 3 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→2:1) to give the title compound as a pale-yellow oil (yield 445 mg, 91%).
$^1$H-NMR (CDCl$_3$) δ: 1.49 (9H, s), 2.88 (3H, s), 4.25-4.37 (2H, m), 7.04-7.10 (1H, m), 7.14 (1H, d, J=8.1 Hz), 7.35 (2H, t, J=5.7 Hz), 7.40-7.51 (1H, m), 7.62 (1H, dd, J=7.9, 4.7 Hz), 7.96 (1H, dd, J=8.1, 1.5 Hz), 8.76 (1H, dd, J=4.7, 1.5 Hz).

Reference Example 84 tert-butyl {[1-[(3-cyanophenyl)sulfonyl]-5-(2-cyanopyridin-3-yl)-4-fluoro-1H-pyrrol-3-yl]methyl}methylcarbamate To a suspension of sodium hydride (60% in oil, 60 mg) in tetrahydrofuran (5 mL) were added dropwise a solution (5 mL) of tert-butyl {[5-(2-cyanopyridin-3-yl)-4-fluoro-1H-pyrrol-3-yl]methyl}methylcarbamate (330 mg) in tetrahydrofuran, 15-crown-5 (330 mg) and 3-cyanobenzenesulfonyl chloride (302 mg) under ice-cooling and the mixture was stirred for 15 min. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→2:1) to give the title compound as a pale-yellow oil (yield 401 mg, 81%).
$^1$H-NMR (CDCl$_3$) δ: 1.49 (9H, s), 2.89 (3H, s), 4.31 (2H, brs), 7.29-7.44 (1H, m), 7.48-7.75 (4H, m), 7.82-8.04 (2H, m), 8.79 (1H, dd, J=4.7, 1.5 Hz).

Reference Example 85 tert-butyl {[5-(2-cyanopyridin-3-yl)-4-fluoro-1-(pyridin-3-ylsulfonyl)-1H-pyrrol-3-yl]methyl}methylcarbamate To a suspension of sodium hydride (60% in oil, 60 mg) in tetrahydrofuran (4 mL) were added dropwise a solution (2 mL) of tert-butyl {[5-(2-cyanopyridin-3-yl)-4-fluoro-1H-pyrrol-3-yl]methyl}methylcarbamate (330 mg) in tetrahydrofuran, 15-crown-5 (330 mg) and pyridine-3-sulfonyl chloride (266 mg) under ice-cooling and the mixture was stirred for 1 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→3:2) to give the title compound as a pale-yellow oil (yield 421 mg, 89%).
$^1$H-NMR (CDCl$_3$) δ: 1.49 (9H, s), 2.87 (3H, s), 4.23-4.36 (2H, m), 7.43 (2H, dd, J=8.1, 4.9 Hz), 7.56-7.69 (2H, m), 7.96 (1H, dd, J=8.1, 1.5 Hz), 8.61 (1H, d, J=2.1 Hz), 8.77 (1H, dd, J=4.7, 1.5 Hz), 8.85 (1H, dd, J=4.6, 1.2 Hz).

Reference Example 86 tert-butyl {[1-[(3-cyanophenyl)sulfonyl]-4-fluoro-5-(2-fluoropyridin-3-yl)-1H-pyrrol-3-yl]methyl}methylcarbamate To a suspension of sodium hydride (60% in oil, 60 mg) in tetrahydrofuran (5 mL) were added dropwise a solution (5 mL) of tert-butyl {[4-fluoro-5-(2-fluoropyridin-3-yl)-1H-pyrrol-3-yl]methyl}methylcarbamate (323 mg) in tetrahydrofuran, 15-crown-5 (330 mg) and 3-cyanobenzenesulfonyl chloride (302 mg) under ice-cooling and the mixture was stirred for 17 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→2:1) to give the title compound as a pale-yellow oil (yield 446 mg, 91%).
$^1$H-NMR (CDCl$_3$) δ: 1.49 (9H, s), 2.88 (3H, s), 4.28 (2H, s), 7.30-7.39 (2H, m), 7.59 (2H, d, J=4.9 Hz), 7.66 (1H, s), 7.75-7.93 (2H, m), 8.34 (1H, d, J=4.7 Hz).

Reference Example 87 tert-butyl [(4-fluoro-5-(2-fluoropyridin-3-yl)-1-{[3-(methylsulfonyl)phenyl]sulfonyl}-1H-pyrrol-3-yl)methyl]methylcarbamate To a suspension of sodium hydride (60% in oil, 60 mg) in tetrahydrofuran (5 mL) were added dropwise a solution (3 mL) of tert-butyl {[4-fluoro-5-(2-fluoropyridin-3-yl)-1H-pyrrol-3-yl]methyl}methylcarbamate (323 mg) in tetrahydrofuran, 15-crown-5 (330 mg) and 3-(methylsulfonyl)benzenesulfonyl chloride (307 mg) under ice-cooling and the mixture was stirred for 1 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→1:1) to give the title compound as a pale-yellow oil (yield 504 mg, 96%).
$^1$H-NMR (CDCl$_3$) δ: 1.49 (9H, s), 2.88 (3H, s), 3.10 (3H, s), 4.27 (2H, s), 7.30 (1H, d, J=5.3 Hz), 7.36 (1H, ddd, J=7.2, 5.2, 1.6 Hz), 7.64-7.76 (2H, m), 7.82-7.92 (2H, m), 8.14-8.20 (1H, m), 8.32 (1H, d, J=4.0 Hz).

Reference Example 88 benzyl 3-{[4-{[(tert-butoxycarbonyl)(methyl)amino]methyl}-3-fluoro-2-(2-fluoropyridin-3-yl)-1H-pyrrol-1-yl]sulfonyl}benzoate To a solution of 3-(chlorosulfonyl)benzoyl chloride (1.5 g) in tetrahydrofuran (12 mL) were added benzyl alcohol (712 mg) and pyridine (370 mg) at room temperature, and the mixture was stirred for 1 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=19:16:1) to give benzyl 3-(chlorosulfonyl)benzoate as a colorless oil (yield 1.70 g, 87%). To a suspension of sodium hydride (60% in oil, 120 mg) in tetrahydrofuran (8 mL) were added dropwise a solution (12 mL) of tert-butyl {[4-fluoro-5-(2-fluoropyridin-3-yl)-1H-pyrrol-3-yl]methyl}methylcarbamate (646 mg) in tetrahydrofuran, 15-crown-5 (660 mg) and benzyl 3-(chlorosulfonyl)benzoate (684 mg) under ice-cooling and the mixture was stirred for 1 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→3:2) to give the title compound as a pale-yellow oil (yield 1.09 g, 91%).

$^1$H-NMR (CDCl$_3$) δ: 1.46 (9H, s), 2.83 (3H, s), 4.24 (2H, brs), 5.37 (2H, s), 7.16 (1H, t, J=5.3 Hz), 7.27 (1H, brs), 7.34-7.47 (5H, m), 7.47-7.64 (2H, m), 7.77 (1H, t, J=8.2 Hz), 8.01 (1H, s), 8.16 (1H, d, J=4.0 Hz), 8.27 (1H, dt, J=7.5, 1.4 Hz)

Reference Example 89

3-{[4-{[(tert-butoxycarbonyl)(methyl)amino]methyl}-3-fluoro-2-(2-fluoropyridin-3-yl)-1H-pyrrol-1-yl]sulfonyl}benzoic acid To a solution of benzyl 3-{[4-{[(tert-butoxycarbonyl)(methyl)amino]methyl}-3-fluoro-2-(2-fluoropyridin-3-yl)-1H-pyrrol-1-yl]sulfonyl}benzoate (1.03 g) in ethanol (5 mL) was added 10% palladium carbon (50% containing water, 200 mg), and the mixture was stirred for 1 hr under a hydrogen atmosphere. The reaction mixture was filtrated, and concentrated under reduced pressure to give the title compound as a colorless solid (yield 866 mg, 99%).

$^1$H-NMR (CDCl$_3$) δ: 1.48 (9H, s), 2.87 (3H, s), 4.28 (2H, brs), 7.31-7.39 (2H, m), 7.55 (1H, t, J=7.7 Hz), 7.59-7.68 (1H, m), 7.88 (1H, ddd, J=9.2, 7.4, 1.9 Hz), 8.04 (1H, s), 8.29-8.38 (2H, m), 1H not detected.

Reference Example 90 tert-butyl ({4-fluoro-5-(2-fluoropyridin-3-yl)-1-[(3-{[(2-hydroxyethyl)amino]carbonyl}phenyl)sulfonyl]-1H-pyrrol-3-yl}methyl)methylcarbamate To a solution of 3-{[4-{[(tert-butoxycarbonyl)(methyl)amino]methyl}-3-fluoro-2-(2-fluoropyridin-3-yl)-1H-pyrrol-1-yl]sulfonyl}benzoic acid (300 mg) in dimethylformamide (1.5 mL) were added 1-ethyl-3-(3-dimethylaminopropyl)carbodiimide hydrochloride (136 mg), then a solution of 2-aminoethanol (40 mg) in dimethylformamide (0.5 mL) at room temperature, and the mixture was stirred for 2 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (ethyl acetate) to give the title compound as a pale-yellow oil (yield 116 mg, 36%).

$^1$H-NMR (CDCl$_3$) δ: 1.47 (9H, s), 2.86 (3H, brs), 3.57-3.69 (2H, m), 3.81-3.93 (2H, m), 4.24 (2H, brs), 7.27 (1H, d, J=5.3 Hz), 7.36 (1H, t, J=5.4 Hz), 7.46-7.64 (3H, m), 7.88 (1H, brs), 8.09 (1H, d, J=6.0 Hz), 8.30 (1H, d, J=3.8 Hz), 2H not detected.

Reference Example 91 tert-butyl [(4-fluoro-5-(2-fluoropyridin-3-yl)-1-{[3-(hydroxymethyl)phenyl]sulfonyl}-1H-pyrrol-3-yl)methyl]methylcarbamate To a solution of 3-{[4-{[(tert-butoxycarbonyl)(methyl)amino]methyl}-3-fluoro-2-(2-fluoropyridin-3-yl)-1H-pyrrol-1-yl]sulfonyl}benzoic acid (256 mg) in tetrahydrofuran (2 mL) was added a 1.9 mol/L toluene solution (0.53 mL) of borane dimethylsulfide complex at room temperature, and the mixture was stirred for 24 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→2:3) to give the title compound as a pale-yellow oil (yield 207 mg, 83%).

$^1$H-NMR (CDCl$_3$) δ: 1.47 (9H, s), 2.59 (1H, brs), 2.86 (3H, s), 4.24 (2H, brs), 4.64 (2H, d, J=4.5 Hz), 7.30 (4H, brs), 7.39 (1H, t, J=8.0 Hz), 7.56 (1H, d, J=7.6 Hz), 7.86 (1H, t, J=8.0 Hz), 8.29 (1H, d, J=4.2 Hz).

Reference Example 92 tert-butyl {[1-{[3-(chloromethyl)phenyl]sulfonyl}-4-fluoro-5-(2-fluoropyridin-3-yl)-1H-pyrrol-3-yl]methyl}methylcarbamate To a solution of tert-butyl [(4-fluoro-5-(2-fluoropyridin-3-yl)-1-{[3-(hydroxymethyl)phenyl]sulfonyl}-1H-pyrrol-3-yl)methyl]methylcarbamate (683 mg) in tetrahydrofuran (5 mL) were added methanesulfonyl chloride (174 mg) and diisopropylethylamine (215 mg) under ice-cooling, and the mixture was stirred at room temperature for 60 hr. The solvent was concentrated under reduced pressure, and the residue was purified by silica gel column chromatography (eluent: hexane-ethyl acetate=9:1→3:1) to give the title compound as a pale-yellow oil (yield 386 mg, 55%).

$^1$H-NMR (CDCl$_3$) δ: 1.49 (9H, s), 2.85 (3H, s), 4.26 (2H, brs), 4.55 (2H, s), 7.28-7.39 (2H, m), 7.47 (1H, t, J=7.6 Hz), 7.55-7.68 (2H, m), 8.01 (1H, d, J=8.1 Hz), 8.30 (1H, s), 8.62 (1H, d, J=4.7 Hz).

Reference Example 93 tert-butyl {[4-fluoro-5-(2-fluoropyridin-3-yl)-1-({3-[(methylthio)methyl]phenyl}sulfonyl)-1H-pyrrol-3-yl]methyl}methylcarbamate To a solution of tert-butyl {[1-{[3-(chloromethyl)phenyl]sulfonyl}-4-fluoro-5-(2-fluoropyridin-3-yl)-1H-pyrrol-3-yl]methyl}methylcarbamate (386 mg) in tetrahydrofuran (3 mL) were added sodium thiomethoxide (58 mg) and potassium iodide (125 mg) and the mixture was stirred for 21 hr. Dimethylformamide (3 mL) was added and the mixture was stirred at 100° C. for 76 hr. Water was added to the reaction mixture and the mixture was extracted with ethyl acetate. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=9:1→4:1) to give the title compound as a yellow oil (yield 291 mg, 74%).

$^1$H-NMR (CDCl$_3$) δ: 1.48 (9H, s), 1.92 (3H, s), 2.85 (3H, s), 3.60 (2H, s), 4.26 (2H, brs), 7.27-7.32 (4H, m), 7.36 (1H, t, J=7.6 Hz), 7.55 (1H, d, J=7.5 Hz), 7.84 (1H, t, J=8.2 Hz), 8.28 (1H, d, J=5.5 Hz).

Reference Example 94 tert-butyl {[4-fluoro-5-(2-fluoropyridin-3-yl)-1-({3-[(methylsulfonyl)methyl]phenyl}sulfonyl)-1H-pyrrol-3-yl]methyl}methylcarbamate To a solution of tert-butyl {[4-fluoro-5-(2-fluoropyridin-3-yl)-1-({3-[(methylthio)methyl]phenyl}sulfonyl)-1H-pyrrol-3-yl]methyl}methylcarbamate (235 mg) in ethyl acetate (3 mL) was added dropwise a solution of 3-chloroperbenzoic acid (620 mg) in ethyl acetate (2 mL) under ice-cooling, and the mixture was stirred for 2 hr. Saturated aqueous sodium thiosulfate solution was added, and the mixture was extracted with ethyl acetate. The separated organic layer was washed with saturated aqueous sodium hydrogen carbonate solution. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=4:1→2:3) to give the title compound as a pale-yellow oil (yield 231 mg, 92%).

$^1$H-NMR (CDCl$_3$) δ: 1.48 (9H, s), 2.79 (3H, s), 2.87 (3H, s), 4.20 (2H, s), 4.26 (2H, s), 7.27-7.35 (2H, m), 7.38 (1H, s), 7.41-7.54 (2H, m), 7.70 (1H, d, J=7.2 Hz), 7.85 (1H, t, J=9.0 Hz), 8.29 (1H, d, J=4.9 Hz).

Reference Example 95 tert-butyl {[4-fluoro-5-(2-fluoropyridin-3-yl)-1-(3-furylsulfonyl)-1H-pyrrol-3-yl]methyl}methylcarbamate To a suspension of sodium hydride (60% in oil, 48 mg) in tetrahydrofuran (2 mL) were added dropwise a solution of tert-butyl {[4-fluoro-5-(2-fluoropyridin-3-yl)-1H-pyrrol-3-yl]methyl}methylcarbamate (259 mg) in tetrahydrofuran (1 mL), 15-crown-5 (266 mg) and furan-3-sulfonyl chloride (147 mg) under ice-cooling and the mixture was stirred for 30 min. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→3:2) to give the title compound as a pale-yellow oil (yield 335 mg, 92%).

$^1$H-NMR (CDCl$_3$) δ: 1.48 (9H, s), 2.89 (3H, s), 4.28 (2H, brs), 6.30 (1H, brs), 7.15-7.25 (1H, m), 7.27-7.32 (1H, m), 7.38-7.44 (1H, m), 7.58 (1H, dd, J=1.5, 0.9 Hz), 7.78-7.90 (1H, m), 8.27-8.32 (1H, m).

Reference Example 96 tert-butyl {[5-(2-fluoropyridin-3-yl)-1-(3-furylsulfonyl)-1H-pyrrol-3-yl]methyl}methylcarbamate To a suspension of sodium hydride (60% in oil, 48 mg) in tetrahydrofuran (2 mL) were added dropwise a solution of tert-butyl {[5-(2-fluoropyridin-3-yl)-1H-pyrrol-3-yl]methyl}methylcarbamate (244 mg) in tetrahydrofuran (1 mL), 15-crown-5 (266 mg) and furan-3-sulfonyl chloride (147 mg) under ice-cooling and the mixture was stirred for 1.5 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→3:1) to give the title compound as a pale-yellow oil (yield 253 mg, 73%).

$^1$H-NMR (CDCl$_3$) δ: 1.47 (9H, s), 2.84 (3H, s), 4.25 (2H, brs), 6.31 (1H, s), 6.35 (1H, d, J=1.1 Hz), 7.21-7.26 (1H, m), 7.28 (1H, d, J=1.9 Hz), 7.41 (1H, t, J=1.7 Hz), 7.59 (1H, dd, J=1.5, 0.8 Hz), 7.78 (1H, t, J=9.1 Hz), 8.25 (1H, d, J=4.9 Hz).

Reference Example 97 tert-butyl [(4-fluoro-5-(2-fluoropyridin-3-yl)-1-{[3-(5-methyl-1,3,4-oxadiazol-2-yl)phenyl]sulfonyl}-1H-pyrrol-3-yl)methyl]methylcarbamate To a suspension of sodium hydride (60% in oil, 18 mg) in tetrahydrofuran (0.5 mL) were added dropwise a solution of tert-butyl {[4-fluoro-5-(2-fluoropyridin-3-yl)-1H-pyrrol-3-yl]methyl}methylcarbamate (97 mg) in tetrahydrofuran (0.5 mL), 15-crown-5 (100 mg) and 3-(5-methyl-1,3,4-oxadiazol-2-yl)benzenesulfonyl chloride (85 mg) under ice-cooling and the mixture was stirred for 2 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→1:1) to give the title compound as a pale-yellow oil (yield 85 mg, 52%).

$^1$H-NMR (CDCl$_3$) δ: 1.43-1.50 (9H, m), 2.63-2.69 (3H, m), 2.83-2.90 (3H, m), 4.26 (2H, brs), 7.30-7.39 (2H, m), 7.48-7.65 (2H, m), 7.79-7.92 (1H, m), 7.98-8.12 (1H, m), 8.23-8.35 (2H, m).

Reference Example 98

3-{[2-(2-chloropyridin-3-yl)-4-formyl-1H-pyrrol-1-yl]sulfonyl}benzonitrile

To a solution of 5-(2-chloropyridin-3-yl)-1H-pyrrole-3-carbaldehyde (110 mg) in tetrahydrofuran (11 mL) was added sodium hydride (60% in oil, 64 mg) at room temperature and the mixture was stirred for 10 min. 3-Cyanobenzenesulfonyl chloride (215 mg) was added and the mixture was further stirred for 15 min. The reaction mixture was diluted with saturated aqueous sodium hydrogen carbonate solution, and extracted with ethyl acetate. The obtained extract was washed with saturated brine, dried over anhydrous magnesium sulfate, and concentrated under reduced pressure. The residue was crystallized from diethyl ether to give the title compound as colorless crystals (yield 150 mg, 76%).

¹H-NMR (CDCl₃) δ: 6.76 (1H, d, J=1.7 Hz), 7.41 (1H, dd, J=7.6, 4.8 Hz), 7.62-7.64 (3H, m), 7.78 (1H, dd, J=7.6, 2.0 Hz), 7.91-7.94 (1H, m), 8.16 (1H, d, J=1.9 Hz), 8.54 (1H, dd, J=4.8, 2.0 Hz), 9.94 (1H, s).

Reference Example 99 tert-butyl {[1-(cyclohexylsulfonyl)-4-fluoro-5-(2-fluoropyridin-3-yl)-1H-pyrrol-3-yl]methyl}methylcarbamate To a solution of tert-butyl {[4-fluoro-5-(2-fluoropyridin-3-yl)-1H-pyrrol-3-yl]methyl}methylcarbamate (324 mg) in tetrahydrofuran (20 mL) was added sodium hydride (60% in oil, 121 mg) and the mixture was stirred at room temperature for 15 min. 15-Crown-5 (664 mg) was added dropwise, and the mixture was stirred for 5 min. Cyclohexanesulfonyl chloride (367 mg) was added and the mixture was further stirred for 2 hr. The reaction mixture was diluted with water, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→1:1) to give the title compound as a colorless oil (yield 420 mg, 89%).
¹H-NMR (CDCl₃) δ: 1.08-1.42 (5H, m), 1.48 (9H, s), 1.64-1.85 (5H, m), 2.77-2.88 (1H, m), 2.91 (3H, s), 4.30 (2H, brs), 7.10 (1H, d, J=4.9 Hz), 7.28-7.36 (1H, m), 7.85-7.93 (1H, m), 8.29 (1H, d, J=4.5 Hz).

Reference Example 100 tert-butyl {[4-fluoro-5-(2-fluoropyridin-3-yl)-1-(piperidin-1-ylsulfonyl)-1H-pyrrol-3-yl]methyl}methylcarbamate To a solution of tert-butyl {[4-fluoro-5-(2-fluoropyridin-3-yl)-1H-pyrrol-3-yl]methyl}methylcarbamate (324 mg) in tetrahydrofuran (20 mL) was added sodium hydride (60% in oil, 121 mg) at room temperature and the mixture was stirred for 15 min. 15-Crown-5 (664 mg) was added dropwise, and the mixture was stirred for 5 min. Piperidine-1-sulfonyl chloride (240 mg) was added, and the mixture was further stirred for 3 hr. The reaction mixture was diluted with water, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:4→1:1) to give the title compound as a colorless oil (yield 210 mg, 45%).
¹H-NMR (CDCl₃) δ: 1.45 (6H, br), 1.49 (9H, s), 2.88 (4H, br), 2.91 (3H, s), 4.29 (2H, brs), 7.12 (1H, d, J=4.9 Hz), 7.25-7.30 (1H, m), 7.86-7.98 (1H, m), 8.26 (1H, d, J=4.2 Hz).

Reference Example 101 tert-butyl ({1-[(2,6-difluorophenyl)sulfonyl]-4-fluoro-5-(2-fluoropyridin-3-yl)-1H-pyrrol-3-yl}methyl)methylcarbamate To a solution of tert-butyl {[4-fluoro-5-(2-fluoropyridin-3-yl)-1H-pyrrol-3-yl]methyl}methylcarbamate (324 mg) in tetrahydrofuran (20 mL) was added sodium hydride (60% in oil, 121 mg) at room temperature and the mixture was stirred for 15 min. 15-Crown-5 (664 mg) was added dropwise, and the mixture was stirred for 5 min. 2,6-Difluorobenzenesulfonyl chloride (320 mg) was added, and the mixture was further stirred for 30 min. The reaction mixture was diluted with water, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:4→2:3) to give the title compound as a colorless oil (yield 430 mg, 86%).
¹H-NMR (CDCl₃) δ: 1.49 (9H, s), 2.90 (3H, s), 4.30 (2H, brs), 6.93 (2H, t, J=8.5 Hz), 7.25-7.30 (1H, m), 7.36 (1H, d, J=5.7 Hz), 7.50-7.63 (1H, m), 7.81-7.90 (1H, m), 8.26 (1H, d, J=4.9 Hz).

Reference Example 102

4-chloro-5-(2-fluoropyridin-3-yl)-1-[(1-methyl-1H-pyrazol-4-yl)sulfonyl]-1H-pyrrole-3-carbaldehyde To a solution of 4-chloro-5-(2-fluoropyridin-3-yl)-1H-pyrrole-3-carbaldehyde (150 mg) in tetrahydrofuran (20 mL) was added sodium hydride (60% in oil, 81 mg) at room temperature and the mixture was stirred for 15 min. 15-Crown-5 (442 mg) was added dropwise and the mixture was stirred for 5 min. 1-methyl-1H-pyrazole-4-sulfonyl chloride (242 mg) was added and the mixture was further stirred for 30 min. The reaction mixture was diluted with water, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:1→1:4) to give the title compound as a colorless oil (yield 160 mg, 65%).
¹H-NMR (CDCl₃) δ: 3.91 (3H, s), 7.34-7.41 (1H, m), 7.44 (1H, s), 7.46 (1H, s), 7.81-7.93 (1H, m), 8.05 (1H, s), 8.38-8.44 (1H, m), 9.95 (1H, s).

Reference Example 103 tert-butyl {[4-fluoro-5-(2-fluoropyridin-3-yl)-1-(2-thienylsulfonyl)-1H-pyrrol-3-yl]methyl}methylcarbamate To a suspension of sodium hydride (60% in oil, 37 mg) in tetrahydrofuran (2 mL) were added dropwise a solution of tert-butyl {[5-(2-fluoropyridin-3-yl)-4-fluoro-1H-pyrrol-3-yl]methyl}methylcarbamate (200 mg) in tetrahydrofuran (1 mL), 15-crown-5 (205 mg) and 2-thiophenesulfonyl chloride (136 mg) at room temperature and the mixture was stirred for 1 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=6:1→3:2) to give the title compound as a colorless oil (yield 276 mg, 95%).
¹H-NMR (CDCl₃) δ: 1.48 (9H, s), 2.87 (3H, s), 4.27 (2H, brs), 7.19-7.33 (3H, m), 7.63 (1H, dd, J=5.0, 1.0 Hz), 7.84 (1H, ddd, J=9.2, 7.4, 1.9 Hz), 8.25-8.32 (1H, m).

Reference Example 104 tert-butyl {[4-fluoro-5-(2-fluoropyridin-3-yl)-1-(2-furylsulfonyl)-1H-pyrrol-3-yl]methyl}methylcarbamate To a suspension of sodium hydride (60% in oil, 37 mg) in tetrahydrofuran (2 mL) were added dropwise a solution of tert-butyl {[5-(2-fluoropyridin-3-yl)-4-fluoro-1H-pyrrol-3-yl]methyl}methylcarbamate (200 mg) in tetrahydrofuran (1 mL), 15-crown-5 (205 mg) and 2-furansulfonyl chloride (132 mg) under ice-cooling and the mixture was stirred for 1 hr and half. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=6:1→2:1) to give the title compound as a pale-yellow oil (yield 243 mg, 87%).

$^1$H-NMR (CDCl$_3$) δ: 1.48 (9H, s), 2.89 (3H, s), 4.28 (2H, brs), 6.45 (1H, dd, J=3.6, 1.9 Hz), 6.76 (1H, d, J=3.6 Hz), 7.21-7.33 (2H, m), 7.49-7.56 (1H, m), 7.83 (1H, ddd, J=9.2, 7.4, 2.0 Hz), 8.26-8.33 (1H, m).

Reference Example 105 tert-butyl {[4-fluoro-5-(2-fluoropyridin-3-yl)-1-(3-thienylsulfonyl)-1H-pyrrol-3-yl]methyl}methylcarbamate To a suspension of sodium hydride (60% in oil, 37 mg) in tetrahydrofuran (2 mL) were added a solution of tert-butyl {[5-(2-fluoropyridin-3-yl)-4-fluoro-1H-pyrrol-3-yl]methyl}methylcarbamate in tetrahydrofuran (1 mL), 15-crown-5 (205 mg) and 3-thiophenesulfonyl chloride (136 mg) at room temperature and the mixture was stirred for 2 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=6:1→3:2) to give the title compound as a pale-yellow oil (yield 264 mg, 91%).

$^1$H-NMR (CDCl$_3$) δ: 1.48 (9H, s), 2.88 (3H, s), 4.27 (2H, brs), 6.95 (1H, dd, J=5.1, 1.1 Hz), 7.23-7.31 (2H, m), 7.35 (1H, dd, J=5.1, 3.2 Hz), 7.58 (1H, dd, J=3.0, 1.3 Hz), 7.82 (1H, t, J=9.0 Hz), 8.26-8.31 (1H, m).

Reference Example 106 tert-butyl ({4-fluoro-5-(2-fluoropyridin-3-yl)-1-[(1-methyl-1H-pyrazol-4-yl)sulfonyl]-1H-pyrrol-3-yl}methyl)methylcarbamate To a solution of tert-butyl {[4-fluoro-5-(2-fluoropyridin-3-yl)-1H-pyrrol-3-yl]methyl}methylcarbamate (324 mg) in tetrahydrofuran (20 mL) was added sodium hydride (60% in oil, 121 mg) at room temperature and the mixture was stirred for 15 min. 15-Crown-5 (664 mg) was added dropwise and the mixture was stirred for 5 min. 1-Methyl-1H-pyrazole-4-sulfonyl chloride (362 mg) was added, and the mixture was further stirred for 30 min. The reaction mixture was diluted with saturated aqueous sodium hydrogen carbonate, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:1) to give the title compound as a colorless oil (yield 460 mg, 98%).

$^1$H-NMR (CDCl$_3$) δ: 1.48 (9H, s), 2.88 (3H, s), 3.87 (3H, s), 4.27 (2H, brs), 7.21 (1H, d, J=4.9 Hz), 7.30 (1H, t, J=6.1), 7.41 (1H, br), 7.42 (1H, s), 7.86 (1H, t, J=8.1 Hz), 8.29 (1H, d, J=4.9 Hz).

Reference Example 107

Methyl 5-{[4-{[(tert-butoxycarbonyl)(methyl)amino]methyl}-3-fluoro-2-(2-fluoropyridin-3-yl)-1H-pyrrol-1-yl]sulfonyl}-2-furoate To a suspension of sodium hydride (60% in oil, 64.3 mg) in tetrahydrofuran (2 mL) was added a solution of tert-butyl {[5-(2-fluoropyridin-3-yl)-4-fluoro-1H-pyrrol-3-yl]methyl}methylcarbamate (400 mg) in tetrahydrofuran (1 mL) at room temperature and the mixture was stirred for 15 min. 15-Crown-5 (354 mg) and methyl 5-(chlorosulfonyl)-2-furoate were added dropwise and the mixture was further stirred at room temperature for 30 min. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→2:1) to give the title compound as a pale-yellow oil (yield 522 mg, 83%).

$^1$H-NMR (CDCl$_3$) δ: 1.47 (9H, s), 2.89 (3H, s), 3.92 (3H, s), 4.29 (2H, brs), 6.84 (1H, d, J=3.6 Hz), 7.11 (1H, d, J=3.8 Hz), 7.24 (1H, d, J=5.5 Hz), 7.31 (1H, ddd, J=7.3, 5.0, 1.6 Hz), 7.89 (1H, ddd, J=9.3, 7.4, 2.0 Hz), 8.29-8.34 (1H, m).

Reference Example 108 tert-butyl [(4-fluoro-5-(2-fluoropyridin-3-yl)-1-{[5-(hydroxymethyl)-2-furyl]sulfonyl}-1H-pyrrol-3-yl)methyl]methylcarbamate To a solution of methyl 5-{[4-{[(tert-butoxycarbonyl)(methyl)amino]methyl}-3-fluoro-2-(2-fluoropyridin-3-yl)-1H-pyrrol-1-yl]sulfonyl}-2-furoate (825 mg) in tetrahydrofuran (8 mL) was added dropwise a 1.5 mol/L solution (5.38 mL) of diisobutylaluminum hydride in toluene under ice-cooling and the mixture was stirred for 1 hr. Hydrochloric acid was added to the reaction mixture and the mixture was further stirred for 1 hr and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→1:2) to give the title compound as a colorless oil (yield 565 mg, 53%).

$^1$H-NMR (CDCl$_3$) δ: 1.50 (9H, s), 2.90 (3H, s), 4.27 (2H, brs), 4.56 (2H, d, J=6.6 Hz), 6.33 (1H, d, J=3.6 Hz), 6.74 (1H, d, J=3.6 Hz), 7.22 (1H, brs), 7.27-7.34 (1H, m), 7.85 (1H, t, J=8.3 Hz), 8.29 (1H, d, J=4.9 Hz), 1H not detected.

Reference Example 109 tert-butyl {[4-fluoro-1-{[5-(fluoromethyl)-2-furyl]sulfonyl}-5-(2-fluoropyridin-3-yl)-1H-pyrrol-3-yl]methyl}methylcarbamate To a solution of tert-butyl [(4-fluoro-5-(2-fluoropyridin-3-yl)-1-{[5-(hydroxymethyl)-2-furyl]sulfonyl}-1H-pyrrol-3-yl)methyl]methylcarbamate (223 mg) in dichloromethane (5 mL) was added diethylaminosulfur trifluoride (78.7 mg) under ice-cooling, and the mixture was stirred at room temperature for 18 hr. Saturated aqueous sodium hydrogen carbonate solution was added and the mixture was extracted with ethyl acetate. The organic layer was washed with saturated brine, dried over anhydrous magnesium sulfate, and concentrated under reduced pressure. The residue was purified by silica gel column chromatography (eluent: hexane-ethyl acetate=4:1→2:1) to give the title compound as a pale-yellow oil (yield 166 mg, 57%).

$^1$H-NMR (CDCl$_3$) δ: 1.48 (9H, s), 2.89 (3H, s), 4.29 (2H, brs), 5.23 (2H, d, J=47.8 Hz), 6.52 (1H, t, J=3.8 Hz), 6.77 (1H, dd, J=3.6, 0.9 Hz), 7.24 (1H, d, J=5.7 Hz), 7.27-7.33 (1H, m), 7.84 (1H, ddd, J=9.3, 7.4, 2.0 Hz), 8.30 (1H, ddd, J=4.9, 1.9, 0.9 Hz).

Reference Example 110 tert-butyl {[1-{[5-(aminocarbonyl)-2-furyl]sulfonyl}-4-fluoro-5-(2-fluoropyridin-3-yl)-1H-pyrrol-3-yl]methyl}methylcarbamate To a solution of methyl 5-{[4-{[(tert-butoxycarbonyl)(methyl)amino]methyl}-3-fluoro-2-(2-fluoropyridin-3-yl)-1H-pyrrol-1-yl]sulfonyl}-2-furoate (443 mg) in methanol (5 mL) was added 8 mol/L ammonia methanol solution (1 mL) at room temperature and the mixture was stirred for 3 hr. The reaction mixture was concentrated under reduced pressure, and the residue was purified by silica gel column chromatography (eluent: hexane-ethyl acetate=4:1→2:3) to give the title compound as a pale-yellow oil (yield 330 mg, 77%).

$^1$H-NMR (CDCl$_3$) δ: 1.48 (9H, s), 2.92 (3H, s), 4.28 (2H, s), 5.61 (1H, brs), 6.91 (1H, brs), 7.13 (1H, d, J=3.6 Hz), 7.20 (1H, d, J=5.5 Hz), 7.28-7.37 (1H, m), 7.82 (1H, brs), 8.32 (1H, d, J=4.0 Hz), 1H not detected.

Reference Example 111 tert-butyl {[1-[(5-cyano-2-furyl)sulfonyl]-4-fluoro-5-(2-fluoropyridin-3-yl)-1H-pyrrol-3-yl]methyl}methylcarbamate To a solution of tert-butyl {[1-{[5-(aminocarbonyl)-2-furyl]sulfonyl}-4-fluoro-5-(2-fluoropyridin-3-yl)-1H-pyrrol-3-yl]methyl}methylcarbamate (285 mg) in tetrahydrofuran (2.5 mL) were added pyridine (181 mg) and trifluoroacetic anhydride (211 mg) under ice-cooling, and the mixture was stirred for 2 hr. The reaction mixture was concentrated under reduced pressure, and the residue was purified by silica-gel column chromatography (eluent: hexane-ethyl acetate=6:1→3:2) to give the title compound as a pale-yellow oil (yield 258 mg, 94%).

$^1$H-NMR (CDCl$_3$) δ: 1.49 (9H, s), 2.92 (3H, s), 4.31 (2H, brs), 6.84 (1H, d, J=3.8 Hz), 7.09 (1H, d, J=3.8 Hz), 7.21-7.25 (1H, m), 7.32 (1H, ddd, J=7.2, 5.1, 1.7 Hz), 7.82 (1H, ddd, J=9.3, 7.4, 1.9 Hz), 8.26-8.36 (1H, m).

Reference Example 112 tert-butyl {[1-{[5-(1,3-dioxolan-2-yl)-2-furyl]sulfonyl}-4-fluoro-5-(2-fluoropyridin-3-yl)-1H-pyrrol-3-yl]methyl}methylcarbamate To a suspension of sodium hydride (60% in oil, 155 mg) in tetrahydrofuran (10 mL) was added tert-butyl {[5-(2-fluoropyridin-3-yl)-4-fluoro-1H-pyrrol-3-yl]methyl}methylcarbamate (1.04 g) under ice-cooling and the mixture was stirred for 15 min. 15-Crown-5 (354 mg) and a solution of methyl 5-(chlorosulfonyl)-2-furoate in tetrahydrofuran (2 mL) were added dropwise and the mixture was further stirred at room temperature for 1.5 hr. The reaction mixture was concentrated under reduced pressure, and the residue was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→1:1) to give the title compound as a brown oil (yield 1.33 g, 78%).

$^1$H-NMR (CDCl$_3$) δ: 1.48 (9H, s), 2.88 (3H, s), 3.96-4.05 (4H, m), 4.29 (2H, brs), 5.86 (1H, s), 6.44 (1H, d, J=3.4 Hz), 6.72 (1H, d, J=3.6 Hz), 7.14-7.36 (2H, m), 7.84 (1H, ddd, J=9.2, 7.4, 2.1 Hz), 8.20-8.37 (1H, m).

Reference Example 113 tert-butyl ({4-fluoro-5-(2-fluoropyridin-3-yl)-1-[(5-formyl-2-furyl)sulfonyl]-1H-pyrrol-3-yl}methyl)methylcarbamate To a solution of tert-butyl {[1-{[5-(1,3-dioxolan-2-yl)-2-furyl]sulfonyl}-4-fluoro-5-(2-fluoropyridin-3-yl)-1H-pyrrol-3-yl]methyl}methylcarbamate (1.23 g) in tetrahydrofuran (5 mL) was added 2 mol/L hydrochloric acid (5 mL) at room temperature and the mixture was stirred for 40 hr. A half of the reaction mixture was evaporated under reduced pressure, and extracted with ethyl acetate. The separated organic layer was washed with saturated aqueous sodium hydrogen carbonate solution and saturated brine, dried over anhydrous magnesium sulfate, and concentrated under reduced pressure. The residue was purified by silica gel column chromatography (eluent: hexane-ethyl acetate=9:1→2:1) to give the title compound as a brown oil (yield 661 mg, 59%).

$^1$H-NMR (CDCl$_3$) δ: 1.48 (9H, s), 2.90 (3H, s), 4.29 (2H, brs), 6.91 (1H, d, J=3.4 Hz), 7.17 (1H, d, J=3.8 Hz), 7.23-7.26 (1H, m), 7.33 (1H, ddd, J=7.3, 5.2, 1.5 Hz), 7.88 (1H, ddd, J=9.2, 7.5, 1.9 Hz), 8.32 (1H, d, J=4.9 Hz), 9.71 (1H, s).

Reference Example 114 tert-butyl {[1-{[5-(difluoromethyl)-2-furyl]sulfonyl}-4-fluoro-5-(2-fluoropyridin-3-yl)-1H-pyrrol-3-yl]methyl}methylcarbamate To a solution of tert-butyl ({4-fluoro-5-(2-fluoropyridin-3-yl)-1-[(5-formyl-2-furyl)sulfonyl]-1H-pyrrol-3-yl}methyl)methylcarbamate (197 mg) in dichloromethane (2 mL) was added diethylaminosulfur trifluoride (197 mg) under ice-cooling, and the mixture was stirred at room temperature for 5 hr. Water and calcium chloride were added to the reaction mixture and the mixture was stirred for 5 min and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→2:1) to give the title compound as a pale-yellow oil (yield 154 mg, 75%).

$^1$H-NMR (CDCl$_3$) δ: 1.48 (9H, s), 2.89 (3H, s), 4.29 (2H, brs), 6.57 (1H, t, J=53.8 Hz), 6.67-6.73 (1H, m), 6.82 (1H, d, J=3.8 Hz), 7.23 (1H, d, J=5.5 Hz), 7.30 (1H, ddd, J=7.2, 5.1, 1.7 Hz), 7.83 (1H, ddd, J=9.3, 7.4, 2.0 Hz), 8.28-8.35 (1H, m).

Reference Example 115 tert-butyl [(4-fluoro-5-(2-fluoropyridin-3-yl)-1-{[5-(1-hydroxyethyl)-2-furyl]sulfonyl}-1H-pyrrol-3-yl)methyl]methylcarbamate To a solution of tert-butyl ({4-fluoro-5-(2-fluoropyridin-3-yl)-1-[(5-formyl-2-furyl)sulfonyl]-1H-pyrrol-3-yl}methyl)

methylcarbamate (464 mg) in tetrahydrofuran (5 mL) was added a 1.0 mol/L solution (1.3 mL) of methylmagnesium bromide in tetrahydrofuran under ice-cooling and the mixture was stirred for 2 hr. 1 mol/L Hydrochloric acid was added to the reaction mixture and the mixture was further stirred for 1 hr and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→3:2) to give the title compound as a pale-yellow oil (yield 410 mg, 86%).

$^1$H-NMR (CDCl$_3$) δ: 1.49 (12H, m), 2.90 (3H, s), 4.27 (2H, brs), 4.81 (1H, dq, J=6.5, 6.2 Hz), 6.28 (1H, d, J=3.4 Hz), 6.73 (1H, d, J=3.6 Hz), 7.23 (1H, brs), 7.27-7.34 (1H, m), 7.86 (1H, t, J=7.7 Hz), 8.25-8.32 (1H, m), 1H not detected.

Reference Example 116 tert-butyl {[1-[(5-acetyl-2-furyl)sulfonyl]-4-fluoro-5-(2-fluoropyridin-3-yl)-1H-pyrrol-3-yl]methyl}methylcarbamate To a solution of tert-butyl [(4-fluoro-5-(2-fluoropyridin-3-yl)-1-{[5-(1-hydroxyethyl)-2-furyl]sulfonyl}-1H-pyrrol-3-yl)methyl]methylcarbamate (234 mg) in dimethyl sulfoxide (3 mL) were added triethylamine (3 mL) and sulfur trioxide pyridine complex (449 mg), and the mixture was stirred at 60° C. for 3 days. 1 mol/L Hydrochloric acid was added, and the mixture was extracted with ethyl acetate. The separated aqueous layer was extracted again with ethyl acetate. The combined organic layer was washed with saturated aqueous sodium hydrogen carbonate solution and saturated brine, dried over anhydrous magnesium sulfate, and concentrated under reduced pressure. The residue was purified by silica gel column chromatography (eluent: hexane-ethyl acetate=9:1→3:2) to give the title compound as a pale-yellow oil (yield 180 mg, 77%).

$^1$H-NMR (CDCl$_3$) δ: 1.47 (9H, s), 2.47 (3H, s), 2.89 (3H, s), 4.29 (2H, brs), 6.88 (1H, d, J=3.8 Hz), 7.09 (1H, d, J=3.8 Hz), 7.23-7.26 (1H, m), 7.32 (1H, ddd, J=7.2, 5.1, 1.6 Hz), 7.88 (1H, ddd, J=9.1, 7.5, 1.9 Hz), 8.32 (1H, d, J=4.0 Hz).

Reference Example 117 tert-butyl ({4-fluoro-5-(2-fluoropyridin-3-yl)-1-[(2-methyl-3-furyl)sulfonyl]-1H-pyrrol-3-yl}methyl)methylcarbamate To a suspension of sodium hydride (60% in oil, 34 mg) in tetrahydrofuran (4 mL) were added dropwise 15-crown-5 (0.17 mL), a solution of tert-butyl {[4-fluoro-5-(2-fluoropyridin-3-yl)-1H-pyrrol-3-yl]methyl}methylcarbamate (210 mg) in tetrahydrofuran (1 mL) and 2-methylfuran-3-sulfonyl chloride (176 mg) under ice-cooling, and the mixture was stirred for 0.5 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→2:3) and basic silica gel column chromatography (eluent: hexane-ethyl acetate=17:3→1:1) to give the title compound as a pale-yellow oil (yield 187 mg, 61%).

$^1$H-NMR (CDCl$_3$) δ: 1.48 (9H, s), 2.13 (3H, s), 2.90 (3H, s), 4.28 (2H, brs), 6.08 (1H, d, J=1.9 Hz), 7.19 (1H, d, J=1.5 Hz), 7.23-7.33 (2H, m), 7.80-7.89 (1H, m), 8.26-8.31 (1H, m).

Reference Example 118 tert-butyl {[1-[(5-chloro-2-thienyl)sulfonyl]-4-fluoro-5-(2-fluoropyridin-3-yl)-1H-pyrrol-3-yl]methyl}methylcarbamate To a suspension of sodium hydride (60% in oil, 24.0 mg) in tetrahydrofuran (2 mL) was added tert-butyl {[5-(2-fluoropyridin-3-yl)-4-fluoro-1H-pyrrol-3-yl]methyl}methylcarbamate (150 mg) under ice-cooling, and the mixture was stirred for 15 min. 15-Crown-5 (133 mg) and a solution of 5-chlorothiophene-2-sulfonyl chloride in tetrahydrofuran (1 mL) were added dropwise and the mixture was further stirred at room temperature for 1 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→2:1) to give the title compound as a colorless oil (yield 229 mg, 98%).

$^1$H-NMR (CDCl$_3$) δ: 1.48 (9H, s), 2.89 (3H, s), 4.28 (2H, brs), 6.84 (1H, d, J=4.1 Hz), 7.01 (1H, d, J=4.1 Hz), 7.20 (1H, brs), 7.30 (1H, ddd, J=7.3, 5.2, 1.7 Hz), 7.83 (1H, ddd, J=9.1, 7.5, 2.0 Hz), 8.31 (1H, d, J=4.7 Hz).

Reference Example 119 tert-butyl {[1-[(5-bromo-2-thienyl)sulfonyl]-4-fluoro-5-(2-fluoropyridin-3-yl)-1H-pyrrol-3-yl]methyl}methylcarbamate To a suspension of sodium hydride (60% in oil, 26.0 mg) in tetrahydrofuran (3 mL) was added tert-butyl {[5-(2-fluoropyridin-3-yl)-4-fluoro-1H-pyrrol-3-yl]methyl}methylcarbamate (156 mg) at room temperature, and the mixture was stirred for 10 min. 15-Crown-5 (143 mg) and 5-bromothiophene-2-sulfonyl chloride (196 mg) were added and the mixture was stirred at room temperature for 15 min. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→3:2) to give the title compound as a colorless oil (yield 248 mg, 90%).

$^1$H-NMR (CDCl$_3$) δ: 1.48 (9H, s), 2.89 (3H, s), 4.27 (2H, brs), 6.94-7.01 (2H, m), 7.20 (1H, brs), 7.30 (1H, ddd, J=7.3, 5.2, 1.7 Hz), 7.83 (1H, ddd, J=9.1, 7.4, 1.9 Hz), 8.31 (1H, dt, J=3.9, 0.8 Hz).

Reference Example 120 tert-butyl {[1-[(4-bromo-3-thienyl)sulfonyl]-4-fluoro-5-(2-fluoropyridin-3-yl)-1H-pyrrol-3-yl]methyl}methylcarbamate To a suspension of sodium hydride (60% in oil, 106 mg) in tetrahydrofuran (10 mL) was added tert-butyl {[5-(2-fluoropyridin-3-yl)-4-fluoro-1H-pyrrol-3-yl]

methyl}methylcarbamate (659 mg) under ice-cooling, and the mixture was stirred for 10 min. 15-Crown-5 (584 mg) and 5-bromothiophene-2-sulfonyl chloride (800 mg) were added and the mixture was stirred for 1 hr under ice-cooling. Saturated aqueous ammonium chloride solution was added, and the mixture was concentrated under reduced pressure. The residue was extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→3:2) to give the title compound as a pale-yellow oil (yield 1.09 g, 98%).

$^1$H-NMR (CDCl$_3$) δ: 1.49 (9H, s), 2.90 (3H, s), 4.30 (2H, brs), 7.04 (1H, d, J=5.3 Hz), 7.23-7.30 (1H, m), 7.46 (1H, d, J=4.9 Hz), 7.50 (1H, d, J=5.3 Hz), 7.85 (1H, ddd, J=9.2, 7.3, 2.1 Hz), 8.22-8.28 (1H, m).

Reference Example 121 tert-butyl {[1-[(4-cyano-3-thienyl)sulfonyl]-4-fluoro-5-(2-fluoropyridin-3-yl)-1H-pyrrol-3-yl]methyl}methylcarbamate To a solution of tert-butyl {[1-[(4-bromo-3-thienyl)sulfonyl]-4-fluoro-5-(2-fluoropyridin-3-yl)-1H-pyrrol-3-yl]methyl}methylcarbamate (229 mg) in dimethylformamide (3 mL) was added zinc cyanide (74.6 mg) at room temperature, and the mixture was sufficiently deaerated under an argon atmosphere. Tetrakis(triphenylphosphine)palladium (0) (145 mg) was added and the mixture was further deaerated and stirred at 120° C. for 2 hr. The reaction mixture was diluted with ethyl acetate and filtrated. The filtrate was washed with water, and separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→3:2) to give the title compound as a pale-yellow oil (yield 181 mg, 88%).

$^1$H-NMR (CDCl$_3$) δ: 1.48 (9H, s), 2.90 (3H, s), 4.31 (2H, brs), 7.29-7.36 (2H, m), 7.42 (1H, brs), 7.68 (1H, d, J=5.1 Hz), 7.88 (1H, ddd, J=9.2, 7.4, 2.0 Hz), 8.31 (1H, d, J=4.5 Hz).

Reference Example 122

Methyl 3-{[4-{[(tert-butoxycarbonyl)(methyl)amino]methyl}-3-fluoro-2-(2-fluoropyridin-3-yl)-1H-pyrrol-1-yl]sulfonyl}thiophene-2-carboxylate To a suspension of sodium hydride (60% in oil, 14.8 mg) in tetrahydrofuran (3 mL) was added tert-butyl {[5-(2-fluoropyridin-3-yl)-4-fluoro-1H-pyrrol-3-yl]methyl}methylcarbamate (100 mg) under ice-cooling, and the mixture was stirred for 5 min. 15-Crown-5 (81.7 mg) and methyl 3-(chlorosulfonyl)thiophene-2-carboxylate were added dropwise and the mixture was further stirred under ice-cooling for 2 hr. The reaction mixture was concentrated under reduced pressure, diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→2:1) to give the title compound as a pale-yellow oil (yield 158 mg, 97%).

$^1$H-NMR (CDCl$_3$) δ: 1.49 (9H, s), 2.92 (3H, s), 3.87 (3H, s), 4.32 (2H, brs), 6.60 (1H, d, J=5.3 Hz), 7.20-7.26 (1H, m), 7.33 (1H, d, J=5.3 Hz), 7.49 (1H, d, J=4.3 Hz), 7.83 (1H, ddd, J=9.2, 7.4, 1.9 Hz), 8.22 (1H, ddd, J=4.8, 1.9, 0.8 Hz).

Reference Example 123 tert-butyl ({5-(2-fluoropyridin-3-yl)-1-[(5-isoxazol-5-yl-2-thienyl)sulfonyl]-1H-pyrrol-3-yl}methyl)methylcarbamate To a solution of tert-butyl {[5-(2-fluoropyridin-3-yl)-1H-pyrrol-3-yl]methyl}methylcarbamate (200 mg) in tetrahydrofuran (10 mL) was added sodium hydride (60% in oil, 53 mg) under ice-cooling, and the mixture was stirred for 20 min. After stirring, 15-crown-5 (290 mg) was added. 5-Isoxazol-5-ylthiophene-2-sulfonyl chloride (246 mg) was added and the mixture was further stirred under ice-cooling for 1 hr. The reaction mixture was diluted with saturated aqueous sodium hydrogen carbonate solution, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:1) to give the title compound as a colorless oil (yield 80 mg, 24%).

$^1$H-NMR (CDCl$_3$) δ: 1.50 (9H, s), 2.88 (3H, s), 4.29 (2H, brs), 6.37 (1H, s), 6.55 (1H, d, J=1.9 Hz), 7.23-7.38 (4H, m), 7.79-7.87 (1H, m), 8.30-8.33 (1H, m), 8.34 (1H, d, J=1.9 Hz).

Reference Example 124 tert-butyl {[1-[(1-ethyl-1H-pyrazol-4-yl)sulfonyl]-4-fluoro-5-(2-fluoropyridin-3-yl)-1H-pyrrol-3-yl]methyl}methylcarbamate To a solution of tert-butyl {[4-fluoro-5-(2-fluoropyridin-3-yl)-1H-pyrrol-3-yl]methyl}methylcarbamate (200 mg) in tetrahydrofuran (10 mL) was added sodium hydride (60% in oil, 50 mg) at room temperature, and the mixture was stirred for 5 min. 15-Crown-5 (273 mg) was added. Then 1-ethyl-1H-pyrazole-4-sulfonyl chloride (181 mg) was added and the mixture was further stirred for 30 min. The reaction mixture was diluted with water, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:1) to give the title compound as a colorless oil (yield 290 mg, 97%).

$^1$H-NMR (CDCl$_3$) δ: 1.44-1.49 (12H, m), 2.88 (3H, s), 4.08-4.17 (2H, m), 4.27 (2H, brs), 7.23 (1H, d, J=4.9 Hz), 7.27-7.33 (1H, m), 7.39 (1H, brs), 7.44 (1H, s), 7.83-7.91 (1H, m), 8.28-8.31 (1H, m).

Reference Example 125 tert-butyl {[1-[(1,5-dimethyl-1H-pyrazol-4-yl)sulfonyl]-4-fluoro-5-(2-fluoropyridin-3-yl)-1H-pyrrol-3-yl]methyl}methylcarbamate To a solution of tert-butyl {[4-fluoro-5-(2-fluoropyridin-3-yl)-1H-pyrrol-3-yl]methyl}methylcarbamate (200 mg) in tetrahydrofuran (10 mL) was added sodium hydride (60% in oil, 50 mg) at room temperature, and the mixture was stirred for 5 min. 15-Crown-5 (273 mg) was added. Then 1,5-dimethyl-1H-pyrazole-4-sulfonyl chloride (181 mg) was added and the mixture was further stirred for 30 min. The reaction mixture was diluted with water, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:1) to give the title compound as a colorless oil (yield 290 mg, 97%).

$^1$H-NMR (CDCl$_3$) δ: 1.49 (9H, s), 2.12 (3H, s), 2.89 (3H, s), 3.74 (3H, s), 4.28 (2H, s), 7.17 (1H, s), 7.26-7.32 (2H, m), 7.82-7.91 (1H, m), 8.24-8.30 (1H, m).

Reference Example 126 tert-butyl {[1-{[1-(difluoromethyl)-1H-pyrazol-4-yl]sulfonyl}-4-fluoro-5-(2-fluoropyridin-3-yl)-1H-pyrrol-3-yl]methyl}methylcarbamate To a solution of tert-butyl {[4-fluoro-5-(2-fluoropyridin-3-yl)-1H-pyrrol-3-yl]methyl}methylcarbamate (324 mg) in tetrahydrofuran (10 mL) was added sodium hydride (60% in oil, 80 mg) at room temperature, and the mixture was stirred for 10 min. 15-Crown-5 (442 mg) was added. Then 1-(difluoromethyl)-1H-pyrazole-4-sulfonyl chloride (181 mg) was added and the mixture was further stirred for 1 hr. The reaction mixture was diluted with saturated aqueous sodium hydrogen carbonate solution, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→1:1) to give the title compound as a colorless oil (yield 380 mg, 75%).

$^1$H-NMR (CDCl$_3$) δ: 1.48 (9H, s), 2.89 (3H, s), 4.28 (2H, s), 6.95-7.36 (3H, m), 7.59 (1H, s), 7.82 (1H, t, J=7.8 Hz), 7.91 (1H, s), 8.32 (1H, d, J=4.2 Hz).

Reference Example 127 tert-butyl ({4-fluoro-5-(2-fluoropyridin-3-yl)-1-[(1-methyl-1H-imidazol-2-yl)sulfonyl]-1H-pyrrol-3-yl}methyl)methylcarbamate To a suspension of sodium hydride (60% in oil, 26 mg) in tetrahydrofuran (4 mL) were added dropwise 15-crown-5 (0.13 mL), a solution of tert-butyl {[4-fluoro-5-(2-fluoropyridin-3-yl)-1H-pyrrol-3-yl]methyl}methylcarbamate (162 mg) in tetrahydrofuran (1 mL) and 1-methyl-1H-imidazole-2-sulfonyl chloride (136 mg) under ice-cooling, and the mixture was stirred for 0.5 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→ethyl acetate) to give the title compound as a pale-yellow oil (yield 229 mg, 98%).

$^1$H-NMR (CDCl$_3$) δ: 1.48 (9H, s), 2.90 (3H, s), 3.61 (3H, s), 4.31 (2H, brs), 6.93-6.94 (1H, m), 7.03-7.08 (1H, m), 7.21-7.30 (1H, m), 7.33 (1H, d, J=5.5 Hz), 7.75-7.87 (1H, m), 8.22-8.30 (1H, m).

Reference Example 128 tert-butyl {[5-(2-fluoropyridin-3-yl)-1-(1,3-thiazol-2-ylsulfonyl)-1H-pyrrol-3-yl]methyl}methylcarbamate To a suspension of sodium hydride (60% in oil, 31 mg) in tetrahydrofuran (4 mL) were added dropwise 15-crown-5 (0.16 mL), a solution of tert-butyl {[5-(2-fluoropyridin-3-yl)-1H-pyrrol-3-yl]methyl}methylcarbamate (183 mg) in tetrahydrofuran (1 mL) and 1,3-thiazole-2-sulfonyl chloride (160 mg) under ice-cooling, and the mixture was stirred for 0.5 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→ethyl acetate) to give the title compound as a pale-yellow oil (yield 168 mg, 62%).

$^1$H-NMR (CDCl$_3$) δ: 1.46 (9H, s), 2.82 (3H, s), 4.24 (2H, brs), 6.33 (1H, s), 7.21-7.27 (1H, m), 7.36-7.40 (1H, m), 7.64 (1H, d, J=3.0 Hz), 7.78-7.86 (1H, m), 7.93 (1H, d, J=3.0 Hz), 8.22-8.29 (1H, m).

Reference Example 129 tert-butyl ({4-fluoro-5-(2-fluoropyridin-3-yl)-1-[(6-methoxypyridin-3-yl)sulfonyl]-1H-pyrrol-3-yl}methyl)methylcarbamate To a suspension of sodium hydride (60% in oil, 26 mg) in tetrahydrofuran (4 mL) were added dropwise 15-crown-5 (129 μL), a solution of tert-butyl {[4-fluoro-5-(2-fluoropyridin-3-yl)-1H-pyrrol-3-yl]methyl}methylcarbamate (162 mg) in tetrahydrofuran (1 mL) and 6-methoxypyridine-3-sulfonyl chloride (129 mg) under ice-cooling, and the mixture was stirred for 0.5 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→4:6) to give the title compound as a pale-yellow oil (yield 247 mg, 100%).

$^1$H-NMR (CDCl$_3$) δ: 1.48 (9H, s), 2.87 (3H, s), 3.97 (3H, s), 4.26 (2H, brs), 6.70 (1H, d, J=8.5 Hz), 7.22-7.36 (2H, m), 7.46 (1H, dd, J=8.8, 2.5 Hz), 7.77-7.89 (1H, m), 8.19 (1H, d, J=2.3 Hz), 8.30 (1H, dd, J=4.0, 0.9 Hz).

Reference Example 130 tert-butyl {[4-fluoro-5-(2-fluoropyridin-3-yl)-1-(pyridin-2-ylsulfonyl)-1H-pyrrol-3-yl]methyl}methylcarbamate To a suspension of sodium hydride (60% in oil, 26 mg) in tetrahydrofuran (4 mL) were added dropwise 15-crown-5 (0.13 mL), a solution of tert-butyl {[4-fluoro-5-(2-fluoropyridin-3-yl)-1H-pyrrol-3-yl]methyl}methylcarbamate (162 mg) in tetrahydrofuran (1 mL) and pyridine-2-sulfonyl chloride (133 mg) under ice-cooling, and the mixture was stirred for 0.5 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→ethyl acetate) to give the title compound as a pale-yellow oil (yield 221 mg, 95%).

$^1$H-NMR (CDCl$_3$) δ: 1.48 (9H, s), 2.87 (3H, s), 4.27 (2H, br), 7.23-7.31 (1H, m), 7.34 (1H, d, J=5.3 Hz), 7.47-7.55 (1H, m), 7.60 (1H, d, J=8.0 Hz), 7.79-7.90 (2H, m), 8.23-8.29 (1H, m), 8.58-8.64 (1H, m).

Reference Example 131 tert-butyl {1-[(2-chloropyridin-3-yl)sulfonyl]-4-fluoro-5-(2-fluoropyridin-3-yl)-1H-pyrrol-3-yl]methyl}methylcarbamate To a suspension of sodium hydride (60% in oil, 39 mg) in tetrahydrofuran (6 mL) were added dropwise 15-crown-5 (0.19 mL), a solution of tert-butyl {[4-fluoro-5-(2-fluoropyridin-3-yl)-1H-pyrrol-3-yl]methyl}methylcarbamate (243 mg) in tetrahydrofuran (1 mL) and 2-chloropyridine-3-sulfonyl chloride (239 mg) under ice-cooling, and the mixture was stirred for 0.5 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→3:7) to give the title compound as a pale-yellow oil (yield 340 mg, 91%).

$^1$H-NMR (CDCl$_3$) δ: 1.49 (9H, s), 2.92 (3H, s), 4.32 (2H, brs), 7.18 (1H, dd, J=7.9, 4.9 Hz), 7.22-7.30 (1H, m), 7.47 (1H, brs), 7.56 (1H, dd, J=7.9, 1.9 Hz), 7.73-7.83 (1H, m), 8.21-8.27 (1H, m), 8.57 (1H, dd, J=4.7, 1.9 Hz).

Reference Example 132 tert-butyl {1-[(2-cyanophenyl)sulfonyl]-4-fluoro-5-(2-fluoropyridin-3-yl)-1H-pyrrol-3-yl]methyl}methylcarbamate To a suspension of sodium hydride (60% in oil, 26 mg) in tetrahydrofuran (4 mL) were added dropwise 15-crown-5 (0.13 mL), a solution of tert-butyl {[4-fluoro-5-(2-fluoropyridin-3-yl)-1H-pyrrol-3-yl]methyl}methylcarbamate (162 mg) in tetrahydrofuran (1 mL) and 2-cyanobenzenesulfonyl chloride (151 mg) under ice-cooling, and the mixture was stirred for 0.5 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=7:3→1:4) to give the title compound as a pale-yellow oil (yield 238 mg, 98%).

$^1$H-NMR (CDCl$_3$) δ: 1.48 (9H, s), 2.91 (3H, s), 4.32 (2H, brs), 7.27-7.36 (2H, m), 7.49-7.62 (2H, m), 7.68-7.77 (1H, m), 7.79-7.90 (2H, m), 8.25-8.31 (1H, m).

Reference Example 133 tert-butyl {1-{[4-(benzyloxy)phenyl]sulfonyl}-4-fluoro-5-(2-fluoropyridin-3-yl)-1H-pyrrol-3-yl]methyl}methylcarbamate To a solution of tert-butyl {[4-fluoro-5-(2-fluoropyridin-3-yl)-1H-pyrrol-3-yl]methyl}methylcarbamate (200 mg) in tetrahydrofuran (10 mL) was added sodium hydride (60% in oil, 50 mg), and the mixture was stirred at room temperature for 10 min. 4-(Benzyloxy)benzenesulfonyl chloride (210 mg) was added and the mixture was further stirred for 30 min. The reaction mixture was diluted with water, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→1:1) to give the title compound as a colorless oil (yield 360 mg, quantitative).

$^1$H-NMR (CDCl$_3$) δ: 1.46 (9H, s), 2.84 (3H, s), 4.24 (2H, brs), 5.06 (2H, s), 6.85-6.93 (2H, m), 7.21-7.42 (9H, m), 7.75-7.83 (1H, m), 8.23-8.28 (1H, m).

Reference Example 134 tert-butyl ({4-fluoro-5-(2-fluoropyridin-3-yl)-1-[(4-hydroxyphenyl)sulfonyl]-1H-pyrrol-3-yl}methyl)methylcarbamate To a solution of tert-butyl {[1-{[4-(benzyloxy)phenyl]sulfonyl}-4-fluoro-5-(2-fluoropyridin-3-yl)-1H-pyrrol-3-yl]methyl}methylcarbamate (360 mg) in ethyl acetate (30 mL) was added 10% palladium carbon (50% containing water, 350 mg) under a nitrogen atmosphere, and the mixture was stirred for 1 hr under a hydrogen atmosphere. The reaction mixture was filtrated, and the filtrate was concentrated under reduced pressure to give the title compound as a colorless oil (yield 300 mg, quantitative).

$^1$H-NMR (CDCl$_3$) δ: 1.51 (9H, s), 2.89 (3H, s), 4.29 (2H, brs), 6.84 (2H, d, J=8.3 Hz), 7.18-7.37 (4H, m), 7.91 (1H, brs), 8.29 (1H, dd, J=4.9, 1.5 Hz) 9.00 (1H, brs).

Reference Example 135 tert-butyl {[5-(2-fluoropyridin-3-yl)-1-(1,3-thiazol-2-ylsulfonyl)-1H-pyrrol-3-yl]methyl}methylcarbamate To a suspension of sodium hydride (60% in oil, 31 mg) in tetrahydrofuran (4 mL) were added dropwise 15-crown-5 (0.16 mL), a solution of tert-butyl {[5-(2-fluoropyridin-3-yl)-1H-pyrrol-3-yl]methyl}methylcarbamate (183 mg) in tetrahydrofuran (1 mL) and 1,3-thiazole-2-sulfonyl chloride (160 mg) under ice-cooling, and the mixture was stirred for 0.5 hr. The reaction mixture was diluted with water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=4:1→ethyl acetate) to give the title compound as a pale-yellow oil (yield 168 mg, 62%).

$^1$H-NMR (CDCl$_3$) δ: 1.46 (9H, s), 2.82 (3H, s), 4.24 (2H, brs), 6.33 (1H, s), 7.21-7.27 (1H, m), 7.36-7.40 (1H, m), 7.64 (1H, d, J=3.0 Hz), 7.78-7.86 (1H, m), 7.93 (1H, d, J=3.0 Hz), 8.22-8.29 (1H, m).

Reference Example 136 tert-butyl {[4-fluoro-5-(2-fluoropyridin-3-yl)-1-(morpholin-4-ylsulfonyl)-1H-pyrrol-3-yl]methyl}methylcarbamate To a solution of tert-butyl {[4-fluoro-5-(2-fluoropyridin-3-yl)-1H-pyrrol-3-yl]methyl}methylcarbamate (324 mg) in tetrahydrofuran (20 mL) was added sodium hydride (60% in oil, 121 mg) at room temperature, and the mixture was stirred for 10 min. 15-Crown-5 (664 mg) was added, morpholine-4-sulfonyl chloride (250 mg) was added and the mixture was further stirred for 2 hr. The reaction mixture was diluted with water, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→3:2) to give the title compound as a colorless oil (yield 370 mg, 78%).

$^1$H-NMR (CDCl$_3$) δ: 1.48 (9H, s), 2.92 (7H, br), 3.57 (4H, t, J=4.7 Hz), 4.30 (2H, s), 7.13 (1H, br), 7.26-7.30 (1H, m), 7.83-7.96 (1H, m), 8.27 (1H, d, J=4.5 Hz).

Reference Example 137 tert-butyl {[4-fluoro-5-(2-fluoropyridin-3-yl)-1-(pyrrolidin-1-ylsulfonyl)-1H-pyrrol-3-yl]methyl}methylcarbamate To a solution of tert-butyl {[4-fluoro-5-(2-fluoropyridin-3-yl)-1H-pyrrol-3-yl]methyl}methylcarbamate (200 mg) in tetrahydrofuran (20 mL) was added sodium hydride (60% in oil, 75 mg) at room temperature, and the mixture was stirred for 15 min. 15-Crown-5 (410 mg) was added, pyrrolidine-1-sulfonyl chloride (210 mg) was added and the mixture was further stirred for 6 hr. The reaction mixture was diluted with saturated aqueous sodium hydrogen carbonate solution, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→1:1) to give the title compound as a colorless oil (yield 260 mg, 92%).

$^1$H-NMR (CDCl$_3$) δ: 1.48 (9H, s), 1.73-1.79 (4H, m), 2.91 (3H, s), 2.98 (4H, brs), 4.29 (2H, brs), 7.17 (1H, d, J=5.7 Hz), 7.23-7.33 (1H, m), 7.91-7.98 (1H, m), 8.27 (1H, d, J=4.5 Hz).

Reference Example 138 tert-butyl {[5-(2-cyanopyridin-3-yl)-1-(2-furylsulfonyl)-1H-pyrrol-3-yl]methyl}methylcarbamate To a suspension of sodium hydride (60% in oil, 26.0 mg) in tetrahydrofuran (3 mL) was added tert-butyl {[5-(2-cyanopyridin-3-yl)-1H-pyrrol-3-yl]methyl}methylcarbamate (150 mg) at room temperature, and the mixture was stirred for 15 min. After stirring, 15-crown-5 (143 mg) and furan-2-sulfonyl chloride (125 mg) were added dropwise and the mixture was further stirred at room temperature for 2 hr. Saturated aqueous ammonium chloride solution was added, and the mixture was concentrated under reduced pressure. The residue was extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→3:2) to give the title compound as a colorless oil (yield 193 mg, 91%).

$^1$H-NMR (CDCl$_3$) δ: 1.47 (9H, s), 2.84 (3H, brs), 4.28 (2H, brs), 6.47 (1H, dd, J=3.6, 1.9 Hz), 6.49 (1H, brs), 6.77 (1H, d, J=3.2 Hz), 7.36 (1H, s), 7.51-7.60 (2H, m), 7.96 (1H, dd, J=8.1, 1.5 Hz), 8.71 (1H, dd, J=4.8, 1.4 Hz).

Reference Example 139 tert-butyl {[5-(2-cyanopyridin-3-yl)-1-(3-furylsulfonyl)-1H-pyrrol-3-yl]methyl}methylcarbamate To a suspension of sodium hydride (60% in oil, 26.0 mg) in tetrahydrofuran (3 mL) was added tert-butyl {[5-(2-cyanopyridin-3-yl)-1H-pyrrol-3-yl]methyl}methylcarbamate (150 mg) at room temperature, and the mixture was stirred for 15 min. After stirring, 15-crown-5 (143 mg) and furan-3-sulfonyl chloride (125 mg) were added dropwise and the mixture was further stirred at room temperature for 2 hr. Saturated aqueous ammonium chloride solution was added, and the mixture was concentrated under reduced pressure. The residue was extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→3:2) to give the title compound as a colorless oil (yield 175 mg, 82%).

$^1$H-NMR (CDCl$_3$) δ: 1.48 (9H, s), 2.85 (3H, s), 4.29 (2H, brs), 6.33 (1H, d, J=1.3 Hz), 6.50 (1H, s), 7.37 (1H, s), 7.44 (1H, t, J=1.7 Hz), 7.51-7.59 (2H, m), 7.95 (1H, d, J=7.0 Hz), 8.71 (1H, dd, J=4.7, 1.5 Hz).

Reference Example 140 tert-butyl {[5-(2-cyanopyridin-3-yl)-1-(2-thienylsulfonyl)-1H-pyrrol-3-yl]methyl}methylcarbamate To a suspension of sodium hydride (60% in oil, 26.0 mg) in tetrahydrofuran (3 mL) was added tert-butyl {[5-(2-cyanopyridin-3-yl)-1H-pyrrol-3-yl]methyl}methylcarbamate (150 mg) at room temperature, and the mixture was stirred for 15 min. After stirring, 15-crown-5 (143 mg) and thiophene-2-sulfonyl chloride (137 mg) were added-dropwise and the mixture was further stirred at room temperature for 2 hr. Saturated aqueous ammonium chloride solution was added, and the mixture was concentrated under reduced pressure. The residue was extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→3:2) to give the title compound as a colorless oil (yield 195 mg, 89%).

$^1$H-NMR (CDCl$_3$) δ: 1.48 (9H, s), 2.84 (3H, brs), 4.28 (2H, brs), 6.48 (1H, s), 7.02 (1H, dd, J=5.0, 3.9 Hz), 7.20 (1H, dd, J=3.9, 1.4 Hz), 7.40 (1H, s), 7.56 (1H, dd, J=8.1, 4.7 Hz), 7.66 (1H, dd, J=5.0, 1.4 Hz), 7.98 (1H, dd, J=8.1, 1.7 Hz), 8.71 (1H, dd, J=4.7, 1.5 Hz).

Reference Example 141 tert-butyl {[5-(2-cyanopyridin-3-yl)-1-(3-thienylsulfonyl)-1H-pyrrol-3-yl]methyl}methylcarbamate To a suspension of sodium hydride (60% in oil, 26.0 mg) in tetrahydrofuran (3 mL) was added tert-butyl {[5-(2-cyanopyridin-3-yl)-1H-pyrrol-3-yl]methyl}methylcarbamate (156 mg) at room temperature, and the mixture was stirred for 10 min. After stirring, 15-crown-5 (143 mg) and thiophene-3-sulfonyl chloride (138 mg) were added dropwise and the mixture was further stirred at room temperature for 15 min. Saturated aqueous ammonium chloride solution was added, and the mixture was concentrated under reduced pressure. The residue was extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=6:1→3:2) to give the title compound as a pale-yellow oil (yield 201 mg, 88%).

¹H-NMR (CDCl₃) δ: 1.48 (9H, s), 2.84 (3H, s), 4.28 (2H, brs), 6.47 (1H, s), 6.96 (1H, dd, J=5.1, 1.3 Hz), 7.39 (1H, dd, J=5.2, 3.1 Hz), 7.42 (1H, s), 7.50-7.60 (2H, m), 7.96 (1H, dd, J=7.8, 1.2 Hz), 8.70 (1H, dd, J=4.8, 1.6 Hz).

Reference Example 142 tert-butyl ({5-(2-cyanopyridin-3-yl)-1-[(2,6-difluorophenyl)sulfonyl]-1H-pyrrol-3-yl}methyl)methylcarbamate To a suspension of sodium hydride (60% in oil, 26.0 mg) in tetrahydrofuran (3 mL) was added tert-butyl {[5-(2-cyanopyridin-3-yl)-1H-pyrrol-3-yl]methyl}methylcarbamate (156 mg) at room temperature, and the mixture was stirred for 15 min. After stirring, 15-crown-5 (143 mg) and 2,6-difluorobenzenesulfonyl chloride (159 mg) were added dropwise and the mixture was further stirred at room temperature for 2 hr. Saturated aqueous ammonium chloride solution was added, and the mixture was concentrated under reduced pressure. The residue was extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→3:2) to give the title compound as a colorless oil (yield 213 mg, 87%).
¹H-NMR (CDCl₃) δ: 1.48 (9H, s), 2.85 (3H, brs), 4.30 (2H, brs), 6.47 (1H, brs), 6.86-6.99 (2H, m), 7.49 (1H, s), 7.51-7.64 (2H, m), 7.99 (1H, dd, J=8.0, 1.6 Hz), 8.68 (1H, dd, J=4.7, 1.7 Hz).

Reference Example 143 tert-butyl ({5-(2-cyanopyridin-3-yl)-1-[(2,4-difluorophenyl)sulfonyl]-1H-pyrrol-3-yl}methyl)methylcarbamate To a suspension of sodium hydride (60% in oil, 26.0 mg) in tetrahydrofuran (3 mL) was added tert-butyl {[5-(2-cyanopyridin-3-yl)-1H-pyrrol-3-yl]methyl}methylcarbamate (156 mg) at room temperature, and the mixture was stirred for 15 min. After stirring, 15-crown-5 (143 mg) and 2,4-difluorobenzenesulfonyl chloride (159 mg) were added dropwise and the mixture was further stirred at room temperature for 1 hr. Saturated aqueous ammonium chloride solution was added, and the mixture was concentrated under reduced pressure. The residue was extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→2:1) to give the title compound as a colorless oil (yield 208 mg, 85%).
¹H-NMR (CDCl₃) δ: 1.48 (9H, s), 2.85 (3H, brs), 4.29 (2H, brs), 6.46 (1H, brs), 6.80-6.88 (1H, m), 6.93 (1H, ddd, J=10.2, 8.1, 2.4 Hz), 7.20 (1H, ddd, J=8.8, 8.0, 5.8 Hz), 7.46 (1H, s), 7.55 (1H, dd, J=7.9, 4.7 Hz), 7.93 (1H, dd, J=8.0, 1.6 Hz), 8.69 (1H, dd, J=4.7, 1.7 Hz).

Reference Example 144 tert-butyl ({5-(2-cyanopyridin-3-yl)-1-[(2-methylphenyl)sulfonyl]-1H-pyrrol-3-yl}methyl)methylcarbamate To a suspension of sodium hydride (60% in oil, 26.0 mg) in tetrahydrofuran (3 mL) was added tert-butyl {[5-(2-cyanopyridin-3-yl)-1H-pyrrol-3-yl]methyl}methylcarbamate (156 mg) at room temperature, and the mixture was stirred for 15 min. After stirring, 15-crown-5 (143 mg) and 2-methylbenzenesulfonyl chloride (203 mg) were added dropwise and the mixture was further stirred at room temperature for 1 hr. Saturated aqueous ammonium chloride solution was added, and the mixture was concentrated under reduced pressure. The residue was extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→2:1) to give the title compound as a pale-yellow oil (yield 202 mg, 87%).
¹H-NMR (CDCl₃) δ: 1.48 (9H, s), 2.36 (3H, s), 2.88 (3H, brs), 4.32 (2H, s), 6.43 (1H, brs), 6.96 (1H, t, J=7.6 Hz), 7.02-7.09 (1H, m), 7.29 (1H, d, J=7.7 Hz), 7.40-7.47 (1H, m), 7.49 (1H, dd, J=8.0, 4.8 Hz), 7.57 (1H, s), 7.95 (1H, dd, J=8.1, 1.7 Hz), 8.58 (1H, dd, J=4.8, 1.6 Hz).

Reference Example 145 tert-butyl {[1-[(2-chlorophenyl)sulfonyl]-5-(2-cyanopyridin-3-yl)-1H-pyrrol-3-yl]methyl}methylcarbamate To a suspension of sodium hydride (60% in oil, 26.0 mg) in tetrahydrofuran (3 mL) was added tert-butyl {[5-(2-cyanopyridin-3-yl)-1H-pyrrol-3-yl]methyl}methylcarbamate (156 mg) at room temperature, and the mixture was stirred for 15 min. After stirring, 15-crown-5 (143 mg) and 2-chlorobenzenesulfonyl chloride (214 mg) were added dropwise and the mixture was further stirred at room temperature for 1 hr. Saturated aqueous ammonium chloride solution was added, and the mixture was concentrated under reduced pressure. The residue was extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→2:1) to give the title compound as a pale-yellow oil (yield 211 mg, 87%).
¹H-NMR (CDCl₃) δ: 1.48 (9H, s), 2.87 (3H, brs), 4.32 (2H, brs), 6.45 (1H, brs), 7.06-7.21 (2H, m), 7.45-7.55 (3H, m), 7.59 (1H, s), 7.93 (1H, dd, J=8.1, 1.7 Hz), 8.62 (1H, dd, J=4.8, 1.6 Hz).

Reference Example 146 tert-butyl ({5-(2-cyanopyridin-3-yl)-1-[(2-fluorophenyl)sulfonyl]-1H-pyrrol-3-yl}methyl)methylcarbamate To a suspension of sodium hydride (60% in oil, 26.0 mg) in tetrahydrofuran (3 mL) was added tert-butyl {[5-(2-cyanopyridin-3-yl)-1H-pyrrol-3-yl]methyl}methylcarbamate (156 mg) at room temperature, and the mixture was stirred for 10 min. After stirring, 15-crown-5 (143 mg) and 2-fluorobenzenesulfonyl chloride (146 mg) were added dropwise and the mixture was further stirred at room temperature for 20 min. Saturated aqueous ammonium chloride solution was added, and the mixture was concentrated under reduced pressure. The residue was extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→2:1) to give the title compound as a pale-yellow oil (yield 218 mg, 93%).

$^1$H-NMR (CDCl$_3$) δ: 1.48 (9H, s), 2.85 (3H, brs), 4.30 (2H, brs), 6.45 (1H, brs), 7.06-7.23 (3H, m), 7.49 (1H, s), 7.53 (1H, dd, J=8.0, 4.8 Hz), 7.58-7.68 (1H, m), 7.93 (1H, dd, J=8.0, 1.6 Hz), 8.67 (1H, dd, J=4.7, 1.5 Hz).

Reference Example 147 tert-butyl {[1-[(2-cyanophenyl)sulfonyl]-5-(2-cyanopyridin-3-yl)-1H-pyrrol-3-yl]methyl}methylcarbamate To a suspension of sodium hydride (60% in oil, 26 mg) in tetrahydrofuran (4 mL) were added dropwise a solution of tert-butyl {[5-(2-cyanopyridin-3-yl)-1H-pyrrol-3-yl]methyl}methylcarbamate (156 mg) in tetrahydrofuran (2 mL) solution, 15-crown-5 (0.13 mL) and 2-cyanobenzenesulfonyl chloride (151 mg) under ice-cooling, and the mixture was stirred for 30 min. The reaction mixture was diluted with ice water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=7:3→ethyl acetate) to give the title compound as a pale-yellow oil (yield 239 mg, 100%).

$^1$H-NMR (CDCl$_3$) δ: 1.47 (9H, s), 2.86 (3H, s), 4.32 (2H, brs), 6.49 (1H, brs), 7.24-7.31 (1H, m), 7.55-7.64 (2H, m), 7.66-7.69 (1H, m), 7.74 (1H, t, J=7.0 Hz), 7.82-7.87 (1H, m), 8.00 (1H, dd, J=8.1, 1.7 Hz), 8.68-8.74 (1H, m).

Reference Example 148 tert-butyl ({5-(2-cyanopyridin-3-yl)-1-[(6-methoxypyridin-3-yl)sulfonyl]-1H-pyrrol-3-yl}methyl)methylcarbamate To a suspension of sodium hydride (60% in oil, 26 mg) in tetrahydrofuran (4 mL) were added dropwise a solution of tert-butyl {[5-(2-cyanopyridin-3-yl)-1H-pyrrol-3-yl]methyl}methylcarbamate (156 mg) in tetrahydrofuran (2 mL), 15-crown-5 (0.13 mL) and 6-methoxypyridine-3-sulfonyl chloride (135 mg) under ice-cooling, and the mixture was stirred for 30 min. The reaction mixture was diluted with ice water, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by silica gel column chromatography (eluent: hexane-ethyl acetate=9:1→2:3) to give the title compound as a pale-yellow oil (yield 235 mg, 97%).

$^1$H-NMR (CDCl$_3$) δ: 1.47 (9H, s), 2.84 (3H, brs), 3.97 (3H, s), 4.27 (2H, brs), 6.46 (1H, s), 6.73 (1H, d, J=8.9 Hz), 7.40 (1H, s), 7.47 (1H, dd, J=8.9, 2.6 Hz), 7.53-7.63 (1H, m), 7.96 (1H, dd, J=8.0, 1.0 Hz), 8.13 (1H, d, J=2.6 Hz), 8.72 (1H, dd, J=4.7, 1.5 Hz).

Reference Example 149 tert-butyl methyl{[5-(1-methyl-2-oxo-1,2-dihydropyridin-3-yl)-1-(phenylsulfonyl)-1H-pyrrol-3-yl]methyl}carbamate To a solution of tert-butyl {[5-(2-fluoropyridin-3-yl)-1-(phenylsulfonyl)-1H-pyrrol-3-yl]methyl}methylcarbamate (214 mg) in 1,2-dichloroethane (8 mL) was added dropwise dimethyl sulfate (273 μL) under ice-cooling, and the mixture was stirred at 80° C. for 18 hr. The reaction mixture was cooled to room temperature, triethylamine (1.41 mL), acetic acid (0.94 mL) and ethanol (0.94 mL) were added, and the mixture was heated under reflux for 2 hr. After cooling, the mixture was diluted with ethyl acetate and saturated aqueous sodium hydrogen carbonate solution, and extracted with ethyl acetate. The separated aqueous layer was extracted again with ethyl acetate. The combined organic layer was washed with saturated brine, dried over anhydrous sodium sulfate, and concentrated under reduced pressure. The residue was purified by basic silica gel column chromatography (eluent: methanol-ethyl acetate=1:99→3:17) (basic TLC:R$_f$=0.4 (chloroform:methanol=10:1)) to give the title compound as a pale-yellow oil (yield 9.9 mg, 4.5%).

$^1$H-NMR (CDCl$_3$) δ: 1.44 (9H, s), 2.77 (3H, brs), 3.51 (3H, s), 4.20 (2H, brs), 6.16 (1H, t, J=6.7 Hz), 6.23 (1H, d, J=1.3 Hz), 7.16-7.28 (2H, m), 7.32 (1H, dd, J=6.7, 2.0 Hz), 7.37-7.46 (2H, m), 7.51-7.59 (1H, m), 7.62-7.68 (2H, m).

Reference Example 150

2-(benzylthio)-6-fluoropyridine

Sodium hydride (60% in oil, 0.76 g) was washed twice with hexane and suspended in tetrahydrofuran (20 mL). To the suspension was added dropwise a solution of benzylmercaptan (1.9 mL) in tetrahydrofuran (5 mL) at 0° C. and the mixture was stirred for 1 hr. A solution of 2,6-difluoropyridine (2.00 g) in tetrahydrofuran (5 mL) was added dropwise at 0° C. The reaction mixture was stirred at room temperature for 12 hr, water was added, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent: hexane-ethyl acetate=15:1) to give the title compound as a pale-red oil (yield 3.45 g, 96%).

$^1$H-NMR (CDCl$_3$) δ: 4.39 (2H, s), 6.56-6.60 (1H, m), 7.00-7.03 (1H, m), 7.20-7.32 (4H, m), 7.38-7.42 (1H, m), 7.50-7.58 (1H, m).

Reference Example 151

2-(benzylthio)-6-methoxypyridine 2-(Benzylthio)-6-fluoropyridine (199 mg) and 28% sodium methoxide methanol solution (2 mL) were stirred at 60° C. for 2 hr. The reaction mixture was concentrated under reduced pressure, water was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure to give the title compound as a yellow oil (yield 182 mg, 86%).

$^1$H-NMR (CDCl$_3$) δ: 3.93 (3H, s), 4.43 (2H, s), 6.41-6.43 (1H, m), 6.74-6.77 (1H, m), 7.19-7.40 (6H, m).

Reference Example 152

2-(benzylthio)-6-methylpyridine

2-Chloro-6-methylpyridine (1.30 g), potassium carbonate (2.12 g) and benzylmercaptan (1.8 mL) were stirred in dimethyl sulfoxide (10 mL) at 150° C. for 3 hr. The reaction mixture was cooled to room temperature, water was added, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent: hexane-ethyl acetate=15:1) to give the title compound as a pale-red oil (yield 1.90 g, 87%).

$^1$H-NMR (CDCl$_3$) δ: 2.52 (3H, s), 4.41 (2H, s), 6.81-6.83 (1H, m), 6.93-6.95 (1H, m), 7.20-7.42 (6H, m).

Reference Example 153

6-methoxypyridine-2-sulfonyl chloride

To a suspension of 2-(benzylthio)-6-methoxypyridine (176 mg) in acetic acid (2 mL) and water (1 mL) was added N-chlorosuccinimide (410 mg), and the mixture was stirred at room temperature for 4 hr. The reaction mixture was concentrated under reduced pressure, water was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent: hexane-ethyl acetate=6:1) to give the title compound as a colorless oil (yield 81.5 mg, 52%).

$^1$H-NMR (CDCl$_3$) δ: 4.06 (3H, s), 7.08 (1H, dd, J=8.1, 0.6 Hz), 7.65 (1H, dd, J=6.9, 0.6 Hz), 7.08-7.86 (1H, m).

Reference Example 154

6-methylpyridine-2-sulfonyl chloride

To a suspension of 2-(benzylthio)-6-methylpyridine (632 mg) in acetic acid (8 mL) and water (4 mL) was added N-chlorosuccinimide (1.58 g), and the mixture was stirred at room temperature for 1 hr. The reaction mixture was concentrated under reduced pressure, water was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent: hexane-ethyl acetate=6:1) to give the title compound as a colorless oil (yield 164 mg, 29%).

$^1$H-NMR (CDCl$_3$) δ: 2.72 (3H, s), 49-7.52 (1H, m), 7.86-7.90 (2H, m).

Reference Example 155 tert-butyl ({4-fluoro-5-(2-fluoropyridin-3-yl)-1-[(6-fluoropyridin-2-yl)sulfonyl]-1H-pyrrol-3-yl}methyl)methylcarbamate To a suspension of 2-(benzylthio)-6-fluoropyridine (310 mg) in acetic acid (3 mL) and water (1.5 mL) was added N-chlorosuccinimide (776 mg), and the mixture was stirred at room temperature for 5 hr. The reaction mixture was concentrated under reduced pressure, toluene was added to the residue, the mixture was filtrated, and the filtrate was concentrated under reduced pressure to give crude 6-fluoropyridine-2-sulfonyl chloride (240 mg). To a solution of tert-butyl {[5-(2-fluoropyridin-3-yl)-4-fluoro-1H-pyrrol-3-yl]methyl}methylcarbamate (102 mg) in tetrahydrofuran (3 mL) was added sodium hydride (60% in oil, 37 mg) at 0° C., and the mixture was stirred at the same temperature for 15 min. 15-Crown-5 (0.19 mL), then a solution of crude 6-fluoropyridine-2-sulfonyl chloride (240 mg) in tetrahydrofuran (2 mL) were added at the same temperature, and the mixture was stirred at room temperature for 30 min. Water was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent: hexane-ethyl acetate=2:1) to give the title compound as a brown oil (yield 49 mg, 7% from 2-(benzylthio)-6-fluoropyridine).

$^1$H-NMR (CDCl$_3$) δ: 1.47 (9H, s), 2.88 (3H, s), 4.28 (2H, brs), 7.14-7.18 (1H, m), 7.26-7.30 (2H, m), 7.52-7.55 (1H, m), 7.83-7.98 (2H, m), 8.25-8.27 (1H, m).

Reference Example 156 tert-butyl ({4-fluoro-5-(2-fluoropyridin-3-yl)-1-[(6-methoxypyridin-2-yl)sulfonyl]-1H-pyrrol-3-yl}methyl)methylcarbamate To a solution of tert-butyl [5-(2-fluoropyridin-3-yl)-4-fluoro-1H-pyrrol-3-yl]methyl}methylcarbamate (91 mg) in tetrahydrofuran (3 mL) was added sodium hydride (60% in oil, 16 mg) at 0° C., and the mixture was stirred at the same temperature for 15 min. 15-Crown-5 (0.08 mL), then a solution of 6-methoxypyridine-2-sulfonyl chloride (75 mg) in tetrahydrofuran (2 mL) were added at the same temperature, and the mixture was stirred at room temperature for 15 min. Water was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by basic silica gel column chromatography (eluent: hexane-ethyl acetate=2:1) to give the title compound as a brown oil (yield 141 mg, 100%).

$^1$H-NMR (CDCl$_3$) δ: 1.47 (9H, s), 2.88 (3H, s), 3.83 (3H, s), 4.29 (2H, brs), 6.91 (1H, d, J=8.1 Hz), 7.15 (1H, d, J=7.2 Hz), 7.21-7.25 (1H, m), 7.34-7.36 (1H, m), 7.61 (1H, dd, J=8.1, 7.2 Hz), 7.78-7.83 (1H, m), 8.21-8.23 (1H, m).

Reference Example 157 tert-butyl ({4-fluoro-5-(2-fluoropyridin-3-yl)-1-[(6-methylpyridin-2-yl)sulfonyl]-1H-pyrrol-3-yl}methyl)methylcarbamate To a solution of tert-butyl [5-(2-fluoropyridin-3-yl)-4-fluoro-1H-pyrrol-3-yl]methyl}methylcarbamate (132 mg) in tetrahydrofuran (3 mL) was added sodium hydride (60% in oil, 35 mg) at 0° C., and the mixture was stirred at the same temperature for 15 min. 15-Crown-5 (0.18 mL), then a solution of 6-methylpyridine-2-sulfonyl chloride (158 mg) in tetrahydrofuran (2 mL) were added at the same temperature, and the mixture was stirred at room temperature for 30 min. Water was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent: hexane-ethyl acetate=1:1) to give the title compound as a brown oil (yield 180 mg, 91%).

¹H-NMR (CDCl₃) δ: 1.46 (9H, s), 2.53 (3H, s), 2.86 (3H, s), 4.26 (2H, brs), 7.23-7.32 (3H, m), 7.44 (1H, d, J=7.5 Hz), 7.65-7.70 (1H, m), 7.86-7.92 (1H, m), 8.24-8.25 (1H, m).

Example 1

1-[5-(2-fluoropyridin-3-yl)-1-(phenylsulfonyl)-1H-pyrrol-3-yl]-N-methylmethanamine fumarate 5-(2-Fluoropyridin-3-yl)-1-(phenylsulfonyl)-1H-pyrrole-3-carbaldehyde (160 mg) was dissolved in a mixture of 40% solution (188 mg) of methylamine in methanol and methanol (16 mL) at room temperature and the mixture was stirred for 5 min. Sodium borohydride (55 mg) was added and the mixture was stirred for 30 min. Saturated aqueous sodium hydrogen carbonate solution (40 mL) was added and the mixture was stirred for 5 min and extracted with ethyl acetate (80 mL). The obtained extract was washed with saturated brine (40 mL), dried over anhydrous magnesium sulfate, and concentrated under reduced pressure. The residue was purified by basic silica gel column chromatography (eluent: ethyl acetate-methanol (99:1)) and crystallized from a solution of fumaric acid (57 mg) in ethanol (5 mL) to give the title compound as colorless crystals (yield 92 mg, 41%).

¹H-NMR (DMSO-d₆) δ:2.39 (3H, s), 3.79 (2H, s), 6.48 (2H, s), 6.51 (1H, d, J=1.5 Hz), 7.38-7.42 (1H, m), 7.46-7.49 (2H, m), 7.54-7.60 (2H, m), 7.67-7.77 (3H, m), 8.30-8.33 (1H, m), 3H not detected.

melting point 191-192° C.

Example 2

1-{1-[(2-fluorophenyl)sulfonyl]-5-(2-fluoropyridin-3-yl)-1H-pyrrol-3-yl}-N-methylmethanamine fumarate 1-[(2-Fluorophenyl)sulfonyl]-5-(2-fluoropyridin-3-yl)-1H-pyrrole-3-carbaldehyde (120 mg) was dissolved in a mixture of 40% solution (268 mg) of methylamine in methanol and methanol (6 mL) at room temperature and the mixture was stirred for 5 min. Sodium borohydride (26 mg) was added and the mixture was stirred for 15 min. The reaction mixture was concentrated under reduced pressure at 25° C., and the residue was partitioned by adding saturated aqueous sodium hydrogen carbonate solution (40 mL) and ethyl acetate (80 mL). The obtained ethyl acetate layer was washed with saturated brine (40 mL), dried over anhydrous magnesium sulfate, and concentrated under reduced pressure. The residue was purified by basic silica gel column chromatography (eluent: ethyl acetate), dissolved in ethyl acetate (8 mL), and crystallized from a solution of fumaric acid (60 mg) in methanol (2 mL) to give the title compound as colorless crystals (yield 93 mg, 56%).

¹H-NMR (DMSO-d₆) δ:2.42 (3H, s), 3.84 (2H, s), 6.47 (2H, s), 6.56 (1H, d, J=1.9 Hz), 7.26-7.38 (3H, m), 7.45-7.52 (1H, m), 7.65-7.72 (2H, m), 7.78-7.86 (1H, m), 8.27-8.29 (1H, m), 3H not detected.

Example 3

1-[5-(2-fluoropyridin-3-yl)-1-(2-furylsulfonyl)-1H-pyrrol-3-yl]-N-methylmethanamine fumarate 5-(2-Fluoropyridin-3-yl)-1-(2-furylsulfonyl)-1H-pyrrole-3-carbaldehyde (250 mg) was dissolved in a mixture of 40% solution (303 mg) of methylamine in methanol and methanol (15 mL) at room temperature and the mixture was stirred for 5 min. Sodium borohydride (45 mg) was added and the mixture was stirred for 20 min. The reaction mixture was concentrated under reduced pressure at 25° C., and the residue was partitioned by adding saturated aqueous sodium hydrogen carbonate solution (40 mL) and ethyl acetate (80 mL). The obtained ethyl acetate layer was washed with saturated brine (40 mL), dried over anhydrous magnesium sulfate, and concentrated under reduced pressure. The residue was purified by basic silica gel column chromatography (eluent: ethyl acetate→ethyl acetate-methanol (49:1)), dissolved in ethyl acetate (12 mL), and crystallized from a solution of fumaric acid (91 mg) in methanol (3 mL) to give the title compound as colorless crystals (yield 234 mg, 66%).

¹H-NMR (DMSO-d₆) δ:2.41 (3H, s), 3.81 (2H, s), 6.48 (2H, s), 6.58 (1H, d, J=1.9 Hz), 6.72 (1H, d d, J=3.7 Hz, 1.8 Hz), 7.10 (1H, dd, J=3.7 Hz, 0.8 Hz), 7.40-7.44 (1H, m), 7.57 (1H, d, J=1.8 Hz), 7.78-7.84 (1H, m), 8.07 (1H, dd, J=1.8 Hz, 0.8 Hz), 8.30-8.33 (1H, m), 3H not detected.

Example 4

1-(5-(2-fluoropyridin-3-yl)-1-{[3-(methylsulfonyl)phenyl]sulfonyl}-1H-pyrrol-3-yl)-N-methylmethanamine fumarate 5-(2-Fluoropyridin-3-yl)-1-{[3-(methylsulfonyl)phenyl]sulfonyl}-1H-pyrrole-3-carbaldehyde (260 mg) was dissolved in a mixture of 40% solution (250 mg) of methylamine in methanol and methanol (15 mL) at room temperature and the mixture was stirred for 5 min. Sodium borohydride (36 mg) was added and the mixture was stirred for 15 min. The reaction mixture was concentrated under reduced pressure at 25° C., and the residue was partitioned by adding saturated aqueous sodium hydrogen carbonate solution (40 mL) and ethyl acetate (80 mL). The obtained ethyl acetate layer was washed with saturated brine (40 mL), dried over anhydrous magnesium sulfate, and concentrated under reduced pressure. The residue was purified by basic silica gel column chromatography (eluent: ethyl acetate→ethyl acetate-methanol (97:3)), dissolved in ethyl acetate (12 mL), and crystallized from a solution of fumaric acid (74 mg) in methanol (3 mL) to give the title compound as colorless crystals (yield 74 mg, 22%).

¹H-NMR (DMSO-d₆) δ:2.37 (3H, s), 3.30 (3H, s), 3.79 (2H, s), 6.49 (2H, s), 6.57 (1H, d, J=1.9 Hz), 7.39-7.44 (1H, m), 7.71-7.77 (2H, m), 7.84-7.85 (1H, m), 7.88-7.90 (2H, m), 8.29-8.35 (2H, m), 3H not detected.

Example 5

1-[5-(2-fluoropyridin-3-yl)-1-(2-thienylsulfonyl)-1H-pyrrol-3-yl]-N-methylmethanamine fumarate 5-(2-Fluoropyridin-3-yl)-1-(2-thienylsulfonyl)-1H-pyrrole-3-carbaldehyde (150 mg) was dissolved in a mixture of 40% solution (174 mg) of methylamine in methanol and methanol (30 mL) at room temperature and the mixture was stirred for 5 min. Sodium borohydride (26 mg) was added and the mixture was stirred for 15 min. The reaction mixture was concentrated under reduced pressure at 25° C., and the residue was partitioned by adding saturated aqueous sodium hydrogen carbonate solution (40 mL) and ethyl acetate (80 mL). The obtained ethyl acetate layer was washed with saturated brine (40 mL), dried over anhydrous magnesium sulfate, and concentrated under reduced pressure. The residue was purified by basic silica gel column chromatography (eluent: ethyl acetate→ethyl acetate-methanol (97:3)), dissolved in ethyl acetate (8 mL), and crystallized from a solution of fumaric acid (52 mg) in methanol (2 mL) to give the title compound as colorless crystals (yield 157 mg, 75%).

$^1$H-NMR (DMSO-$d_6$) δ:2.40 (3H, s), 3.80 (2H, s), 6.48 (2H, s), 6.55 (1H, d, J=1.5 Hz), 7.18 (1H, d d, J=4.9 Hz, 4.2 Hz), 7.40-7.45 (1H, m), 7.47 (1H, dd, J=4.0 Hz, 1.3 Hz), 7.62 (1H, d, J=1.5 Hz), 7.75-7.82 (1H, m), 8.11 (1H, dd, J=5.1 Hz, 1.3 Hz), 8.31-8.33 (1H, m), 3H not detected.

Example 6

1-[1-(1,3-benzodioxol-5-ylsulfonyl)-5-(2-fluoropyridin-3-yl)-1H-pyrrol-3-yl]-N-methylmethanamine fumarate 1-(1,3-Benzodioxol-5-ylsulfonyl)-5-(2-fluoropyridin-3-yl)-1H-pyrrole-3-carbaldehyde (220 mg) was dissolved in a mixture of 40% solution (230 mg) of methylamine in methanol and methanol (22 mL) at room temperature and the mixture was stirred for 5 min. Sodium borohydride (35 mg) was added and the mixture was stirred for 10 min. The reaction mixture was concentrated under reduced pressure at 30° C., and the residue was partitioned by adding saturated aqueous sodium hydrogen carbonate solution (40 mL) and ethyl acetate (80 mL). The obtained ethyl acetate layer was washed with saturated brine (40 mL), dried over anhydrous magnesium sulfate, and concentrated under reduced pressure. The residue was purified by basic silica gel column chromatography (eluent: ethyl acetate), dissolved in ethyl acetate (8 mL), and crystallized from a solution of fumaric acid (69 mg) in methanol (2 mL) to give the title compound as colorless crystals (yield 193 mg, 65%).

$^1$H-NMR (DMSO-$d_6$) δ:2.41 (3H, s), 3.80 (2H, s), 6.19 (2H, s), 6.48 (2H, s), 6.50 (1H, d, J=1.9 Hz), 6.94-7.05 (3H, m), 7.38-7.43 (1H, m), 7.64 (1H, d, J=1.5 Hz), 7.68-7.74 (1H, m), 8.31-8.32 (1H, m), 3H not detected.

Example 7

1-(4-chloro-5-(2-fluoropyridin-3-yl)-1-{[3-(methylsulfonyl)phenyl]sulfonyl}-1H-pyrrol-3-yl)-N-methylmethanamine fumarate 4-Chloro-5-(2-fluoropyridin-3-yl)-1-{[3-(methylsulfonyl)phenyl]sulfonyl}-1H-pyrrole-3-carbaldehyde (280 mg) was dissolved in a solution of methylamine hydrochloride (427 mg) in methanol (20 mL) and the mixture was stirred for 30 min. Sodium triacetoxyborohydride (536 mg) was added and the mixture was stirred for 30 min. The reaction mixture was concentrated under reduced pressure at 25° C., and the residue was partitioned by adding saturated aqueous sodium hydrogen carbonate solution (40 mL) and ethyl acetate (80 mL). The obtained ethyl acetate layer was washed with saturated brine (40 mL), dried over anhydrous magnesium sulfate, and concentrated under reduced pressure. The residue was purified by basic silica gel column chromatography (eluent: ethyl acetate→ethyl acetate-methanol (97:3)), and crystallized from a mixed solution of fumaric acid (75 mg), methanol (2 mL) and ethyl acetate (8 mL) to give the title compound as colorless crystals (yield 146 mg, 40%).

$^1$H-NMR (DMSO-$d_6$) δ:2.41 (3H, s), 3.31 (3H, s), 3.75 (2H, s), 6.55 (2H, s), 7.47-7.51 (1H, m), 7.82-7.95 (5H, m), 8.32-8.35 (1H, m), 8.40-8.42 (1H, m), 3H not detected.

Example 8

1-[4-fluoro-5-(2-fluoropyridin-3-yl)-1-(pyridin-3-ylsulfonyl)-1H-pyrrol-3-yl]-N-methylmethanamine fumarate 4-Fluoro-5-(2-fluoropyridin-3-yl)-1-(pyridin-3-ylsulfonyl)-1H-pyrrole-3-carbaldehyde (90 mg) was dissolved in a solution of methylamine hydrochloride (262 mg) in methanol (10 mL) and the mixture was stirred for 30 min. Sodium triacetoxyborohydride (330 mg) was added and the mixture was stirred for 1 hr. The reaction mixture was diluted with saturated aqueous sodium hydrogen carbonate solution (40 mL), and extracted with ethyl acetate (80 mL). The obtained extract was washed with saturated brine (40 mL), dried over anhydrous magnesium sulfate, and concentrated under reduced pressure. The residue was purified by basic silica gel column chromatography (eluent: ethyl acetate→ethyl acetate-methanol (19:1)) and crystallized from a mixed solution of fumaric acid (30 mg), methanol (1 mL) and ethyl acetate (9 mL) to give the title compound as colorless crystals (yield 54 mg, 44%).

$^1$H-NMR (DMSO-$d_6$) δ: 2.35 (3H, s), 3.69 (2H, s), 6.55 (2H, s), 7.47-7.52 (1H, m), 7.62-7.69 (2H, m), 7.88-7.94 (2H, m), 8.37-8.39 (1H, m), 8.63 (1H, d, J=2.3 Hz), 8.92 (1H, dd, J=4.9 Hz, 1.5 Hz), 3H not detected.

melting point 146-148° C.

Example 9

1-{5-(2-chloropyridin-3-yl)-1-[(6-methylpyridin-3-yl)sulfonyl]-1H-pyrrol-3-yl}-N-methylmethanamine fumarate 5-(2-Chloropyridin-3-yl)-1-[(6-methylpyridin-3-yl)sulfonyl]-1H-pyrrole-3-carbaldehyde (90 mg) was dissolved in a mixture of 40% solution (97 mg) of methylamine in methanol and methanol (9 mL) at room temperature and the mixture was stirred for 5 min. Sodium borohydride (15 mg) was added and the mixture was stirred for 30 min. The reaction mixture was concentrated under reduced pressure at 25° C., and the residue was partitioned by adding saturated aqueous sodium hydrogen carbonate solution (40 mL) and ethyl acetate (80 mL). The obtained ethyl acetate layer was washed with saturated brine (40 mL), dried over anhydrous magnesium sulfate, and concentrated under reduced pressure. The residue was purified by basic silica gel column chromatography (eluent: ethyl acetate-methanol=99:1→19:1), and crystallized from a mixed solution of fumaric acid (30 mg), methanol (1 mL) and ethyl acetate (9 mL) to give the title compound as colorless crystals (yield 75 mg, 61%).

$^1$H-NMR (DMSO-$d_6$) δ:2.43 (3H, s), 2.56 (3H, s), 3.86 (2H, s), 6.50 (2H, s), 6.52 (1H, d, J=1.7 Hz), 7.47-7.52 (2H, m), 7.68 (1H, dd, J=7.6 Hz, 2.0 Hz), 7.73 (1H, d, J=1.5 Hz), 7.80 (1H, dd, J=8.4 Hz, 2.5 Hz), 8.48-8.51 (2H, m), 3H not detected.

Example 10

3-{1-[(3-fluorophenyl)sulfonyl]-4-[(methylamino)methyl]-1H-pyrrol-2-yl}pyridine-2-carbonitrile fumarate 3-{1-[(3-Fluorophenyl)sulfonyl]-4-formyl-1H-pyrrol-2-yl}pyridine-2-carbonitrile (70 mg) was dissolved in a mixture of 40% solution (80 mg) of methylamine in methanol and methanol (10 mL) at room temperature and the mixture was stirred for 5 min. Sodium borohydride (15 mg) was added and the mixture was stirred for 10 min. The reaction mixture was concentrated under reduced pressure at 30° C., and the residue was partitioned by adding saturated aqueous sodium hydrogen carbonate solution (40 mL) and ethyl acetate (80 mL). The obtained ethyl acetate layer was washed with saturated brine (40 mL), dried over anhydrous magnesium sulfate, and concentrated under reduced pressure. The residue was purified by basic silica gel column chromatography (eluent: ethyl acetate-methanol=99:1→19:1), and crystallized from a mixed solution of fumaric acid (23 mg), methanol (1 mL) and ethyl acetate (9 mL) to give the title compound as colorless crystals (yield 55 mg, 57%).

$^1$H-NMR (DMSO-d$_6$) δ:2.39 (3H, s), 3.82 (2H, s), 6.49 (2H, s), 6.72 (1H, d, J=1.9 Hz), 7.26-7.32 (2H, m), 7.62-7.67 (2H, m), 7.78-7.82 (2H, m), 7.91-7.94 (1H, m), 8.81 (1H, dd, J=4.7 Hz, 1.7 Hz), 3H not detected.

Example 11

1-{5-(2-fluoropyridin-3-yl)-1-[(3-methoxyphenyl)sulfonyl]-1H-pyrrol-3-yl}-N-methylmethanamine fumarate tert-Butyl ({5-(2-fluoropyridin-3-yl)-1-[(3-methoxyphenyl)sulfonyl]-1H-pyrrol-3-yl}methyl)methylcarbamate (303 mg) was dissolved in ethyl acetate (1 mL) and methanol (1 mL) and 4 mol/L hydrogen chloride-ethyl acetate solution (3 mL) were added. The mixture was stirred at room temperature for 2 hr, and concentrated under reduced pressure. Saturated aqueous sodium hydrogen carbonate solution was added to the residue, and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=1:1→1:9) to give the title compound as a free base (149 mg). A solution of the obtained free base (149 mg) in ethyl acetate (2 mL) was added to a solution of fumaric acid (46 mg) in methanol (2 mL), and the mixture was concentrated under reduced pressure. The obtained crystals were recrystallized from a mixed solvent of ethanol-water=9:1 to give the title compound as colorless crystals (yield 138 mg, 44%).

$^1$H-NMR (DMSO-d$_6$) δ: 2.40 (3H, s), 3.75 (3H, s), 3.82 (2H, s), 6.47 (2H, s), 6.53 (1H, d, J=1.5 Hz), 6.86-6.88 (1H, m), 7.05-7.08 (1H, m), 7.27-7.31 (1H, m), 7.38-7.51 (2H, m), 7.69-7.75 (2H, m), 8.31-8.32 (1H, m), 3H not detected.

Example 12

1-{1-[(3-fluorophenyl)sulfonyl]-5-(2-fluoropyridin-3-yl)-1H-pyrrol-3-yl}-N-methylmethanamine hydrochloride To a solution of tert-butyl ({1-[(3-fluorophenyl)sulfonyl]-5-(2-fluoropyridin-3-yl)-1H-pyrrol-3-yl}methyl)methylcarbamate (194 mg) in ethanol (2 mL) was added 4 mol/L hydrogen chloride-ethyl acetate solution (4 mL), and the mixture was stirred at room temperature for 1 hr. The solvent was concentrated under reduced pressure, and the residue was recrystallized from ethanol to give the title compound (yield 90 mg, 54%).

$^1$H-NMR (DMSO-d$_6$) δ: 2.51 (3H, s), 3.99 (2H, s), 6.67 (1H, d, J=1.8 Hz), 7.33-7.36 (2H, m), 7.41-7.46 (1H, m), 7.65-7.76 (3H, m), 7.87 (1H, d, J=1.8 Hz), 8.34-8.36 (1H, m), 9.18 (2H, brs).

Example 13

1-[5-(2-fluoro-6-methylpyridin-3-yl)-1-(pyridin-3-ylsulfonyl)-1H-pyrrol-3-yl]-N-methylmethanamine fumarate tert-Butyl {[5-(2-fluoro-6-methylpyridin-3-yl)-1-(pyridin-3-ylsulfonyl)-1H-pyrrol-3-yl]methyl}methylcarbamate (400 mg) was dissolved in methanol (20 mL), 4 mol/L hydrogen chloride-ethyl acetate solution (2 mL) was added, and the mixture was stirred at 60° C. for 10 min. The reaction mixture was concentrated under reduced pressure, saturated aqueous sodium hydrogen carbonate solution was added, and the mixture was extracted with ethyl acetate. The obtained organic layer was washed with saturated brine, dried over anhydrous magnesium sulfate, and concentrated under reduced pressure. The residue was crystallized from a mixed solution of fumaric acid (101 mg), methanol (3 mL) and ethyl acetate (12 mL) to give the title compound as colorless crystals (yield 264 mg, 64%).

$^1$H-NMR (DMSO-d$_6$) δ: 2.40 (3H, s), 2.50 (3H, s), 3.81 (2H, s), 6.48 (2H, s), 6.53 (1H, d, J=1.5 Hz), 7.25-7.28 (1H, m), 7.57-7.73 (3H, m), 7.90-7.93 (1H, m), 8.63 (1H, d, J=2.5 Hz), 8.90 (1H, dd, J=4.7 Hz, 1.3 Hz), 3H not detected.

Example 14

3-{4-[(methylamino)methyl]-1-(pyridin-3-ylsulfonyl)-1H-pyrrol-2-yl}pyridine-2-carbonitrile fumarate By an operation similar to that in Example 11 and using tert-butyl 3-[5-(2-cyanopyridin-3-yl)-1-(pyridin-3-ylsulfonyl)-1H-pyrrol-3-yl]-2-methylcarbamate, the title compound was obtained as colorless crystals (yield 43.2 mg, 39%).

$^1$H-NMR (DMSO-d$_6$) δ: 2.39 (3H, s), 3.83 (2H, s), 6.48 (2H, s), 6.74 (1H, d, J=1.8 Hz), 7.60-7.65 (1H, m), 7.78-7.83 (2H, m), 7.88-7.95 (2H, m), 8.58-8.59 (1H, m), 8.80-8.82 (1H, m), 8.89-8.91 (1H, m), 3H not detected.

Example 15

1-[5-(2-chloropyridin-3-yl)-1-(phenylsulfonyl)-1H-pyrrol-3-yl]-N-methylmethanamine hydrochloride To a solution of tert-butyl {[5-(2-chloropyridin-3-yl)-1-(phenylsulfonyl)-1H-pyrrol-3-yl]methyl}methylcarbamate (259 mg) in ethanol (2 mL) was added 4 mol/L hydrogen chloride-ethyl acetate solution (2 mL), and the mixture was stirred at room temperature for 2 hr. The solvent was concentrated under reduced pressure, and the residue was recrystallized from ethanol to give the title compound (yield 124 mg, 56%).

$^1$H-NMR (DMSO-d$_6$) δ: 2.51 (3H, s), 4.00 (2H, s), 6.57-6.61 (1H, m), 7.46-7.52 (3H, m), 7.57-7.62 (3H, m), 7.74-7.83 (2H, m), 8.49-8.51 (1H, m), 9.04-9.23 (2H, m).

melting point 215-216° C.

Example 16

3-{4-[(methylamino)methyl]-1-(phenylsulfonyl)-1H-pyrrol-2-yl}pyridine-2-carbonitrile hydrochloride tert-Butyl {[5-(2-cyanopyridin-3-yl)-1-(phenylsulfonyl)-1H-pyrrol-3-yl]methyl}methylcarbamate (250 mg) was dissolved in ethyl acetate (5 mL) and methanol (3 mL), and 4 mol/L hydrogen chloride-ethyl acetate solution (3 mL) was added. The mixture was stirred at room temperature for 4 hr, and concentrated under reduced pressure. The obtained residue was recrystallized from ethanol to give the title compound as colorless crystals (yield 127 mg, 59%).

$^1$H-NMR (DMSO-d$_6$) δ: 2.49 (3H, s), 4.03 (2H, s), 6.80 (1H, d, J=1.8 Hz), 7.45-7.48 (2H, m), 7.56-7.61 (2H, m), 7.75-7.94 (4H, m), 8.81-8.83 (1H, m), 9.21 (2H, brs).

melting point 240-250° C. (decomposition)

Example 17

1-[5-(2-fluoropyridin-3-yl)-1-(3-thienylsulfonyl)-1H-pyrrol-3-yl]-N-methylmethanamine fumarate By an operation similar to that in Example 11 and using tert-butyl {[5-(2-fluoropyridin-3-yl)-1-(3-thienylsulfonyl)-1H-pyrrol-3-yl]methyl}methylcarbamate (433 mg), the title compound was obtained as colorless crystals (yield 283 mg, 63%).

$^1$H-NMR (DMSO-$d_6$) δ: 2.41 (3H, s), 3.81 (2H, s), 6.48 (2H, s), 6.53 (1H, d, J=1.8 Hz), 7.08-7.10 (1H, m), 7.38-7.42 (1H, m), 7.64-7.79 (3H, m), 8.08-8.10 (1H, m), 8.30-8.32 (1H, m), 3H not detected.

Example 18

3-({2-(2-fluoropyridin-3-yl)-4-[(methylamino)methyl]-1H-pyrrol-1-yl}sulfonyl)benzonitrile fumarate By an operation similar to that in Example 11 and using tert-butyl ({1-[(3-cyanophenyl)sulfonyl]-5-(2-fluoropyridin-3-yl)-1H-pyrrol-3-yl}methyl)methylcarbamate (447 mg), the title compound was obtained as colorless crystals (yield 202 mg, 44%).

$^1$H-NMR (DMSO-$d_6$) δ: 2.40 (3H, s), 3.82 (2H, s), 6.47 (2H, s), 6.57 (1H, d, J=1.8 Hz), 7.39-7.44 (1H, m), 7.71-7.81 (4H, m), 7.95-7.96 (1H, m), 8.21-8.24 (1H, m), 8.32-8.34 (1H, m), 3H not detected.

Example 19

1-[3-({2-(2-fluoropyridin-3-yl)-4-[(methylamino)methyl]-1H-pyrrol-1-yl}sulfonyl)phenyl]ethanone hydrochloride To a solution of tert-butyl ({1-[(3-acetylphenyl)sulfonyl]-5-(2-fluoropyridin-3-yl)-1H-pyrrol-3-yl}methyl)methylcarbamate (106 mg) in ethanol (2 mL) was added 4 mol/L hydrogen chloride-ethyl acetate solution (4 mL), and the mixture was stirred at room temperature for 1 hr. The solvent was concentrated under reduced pressure, and the residue was recrystallized from ethanol to give the title compound (yield 44.3 mg, 48%).

$^1$H-NMR (DMSO-$d_6$) δ: 2.50 (3H, s), 2.59 (3H, s), 3.97 (2H, s), 6.61-6.64 (1H, m), 7.40-7.44 (1H, m), 7.68-7.87 (5H, m), 8.29-8.35 (2H, m), 9.11 (2H, brs).

Example 20

1-{1-[(4-fluorophenyl)sulfonyl]-5-(2-fluoropyridin-3-yl)-1H-pyrrol-3-yl}-N-methylmethanamine fumarate By an operation similar to that in Example 11 and using tert-butyl ({1-[(4-fluorophenyl)sulfonyl]-5-(2-fluoropyridin-3-yl)-1H-pyrrol-3-yl}methyl)methylcarbamate (436 mg), the title compound was obtained as colorless crystals (yield 139 mg, 31%).

$^1$H-NMR (DMSO-$d_6$) δ: 2.41 (3H, s), 3.82 (2H, s), 6.47 (2H, s), 6.53 (1H, d, J=1.5 Hz), 7.34-7.45 (3H, m), 7.53-7.57 (2H, m), 7.68-7.71 (2H, m), 8.30-8.33 (1H, m), 3H not detected.

melting point 184-185° C.

Example 21

1-{1-[(2,3-difluorophenyl)sulfonyl]-5-(2-fluoropyridin-3-yl)-1H-pyrrol-3-yl}-N-methylmethanamine hydrochloride To a solution of tert-butyl ({1-[(2,3-difluorophenyl)sulfonyl]-5-(2-fluoropyridin-3-yl)-1H-pyrrol-3-yl}methyl)methylcarbamate (443 mg) in ethanol (4 mL) was added 4 mol/L hydrogen chloride-ethyl acetate solution (4 mL), and the mixture was stirred at room temperature for 2 hr. The solvent was concentrated under reduced pressure, and the residue was recrystallized from ethanol to give the title compound (yield 206 mg, 54%).

$^1$H-NMR (DMSO-$d_6$) δ: 2.51 (3H, s), 4.03 (2H, s), 6.74-6.76 (1H, m), 7.13-7.17 (1H, m), 7.34-7.41 (2H, m), 7.72-7.78 (1H, m), 7.83 (1H, s), 7.89-7.98 (1H, m), 8.31-8.32 (1H, m), 9.34 (2H, brs).

Example 22

1-{1-[(3,4-difluorophenyl)sulfonyl]-5-(2-fluoropyridin-3-yl)-1H-pyrrol-3-yl}-N-methylmethanamine hydrochloride To a solution of tert-butyl ({1-[(3,4-difluorophenyl)sulfonyl]-5-(2-fluoropyridin-3-yl)-1H-pyrrol-3-yl}methyl)methylcarbamate (468 mg) in ethanol (2 mL) was added 4 mol/L hydrogen chloride-ethyl acetate solution (2 mL), and the mixture was stirred at room temperature for 3 hr. The solvent was concentrated under reduced pressure, and the residue was recrystallized from ethanol to give the title compound (yield 210 mg, 52%).

$^1$H-NMR (DMSO-$d_6$) δ: 2.52 (3H, s), 3.99 (2H, s), 6.69 (1H, d, J=1.8 Hz), 7.37-7.46 (2H, m), 7.65-7.77 (3H, m), 7.87 (1H, d, J=1.8 Hz), 8.35-8.36 (1H, m), 9.24 (2H, brs).

Example 23

1-{1-[(3-fluoro-4-methylphenyl)sulfonyl]-5-(2-fluoropyridin-3-yl)-1H-pyrrol-3-yl}-N-methylmethanamine hydrochloride To a solution of tert-butyl ({1-[(3-fluoro-4-methylphenyl)sulfonyl]-5-(2-fluoropyridin-3-yl)-1H-pyrrol-3-yl}methyl)methylcarbamate (287 mg) in ethanol (2 mL) was added 4 mol/L hydrogen chloride-ethyl acetate solution (2 mL), and the mixture was stirred at room temperature for 2 hr. The solvent was concentrated under reduced pressure, and the residue was recrystallized from ethanol to give the title compound (yield 125 mg, 50%).

$^1$H-NMR (DMSO-$d_6$) δ: 2.30 (3H, s), 2.50 (3H, s), 3.98 (2H, s), 6.65-6.66 (1H, m), 7.23-7.29 (2H, m), 7.41-7.45 (1H, m), 7.51-7.56 (1H, m), 7.70-7.76 (1H, m), 7.84-7.85 (1H, m), 8.34-8.36 (1H, m), 9.15-9.21 (2H, m).

Example 24

1-{1-[(2,5-difluorophenyl)sulfonyl]-5-(2-fluoropyridin-3-yl)-1H-pyrrol-3-yl}-N-methylmethanamine hydrochloride tert-Butyl ({1-[(2,5-difluorophenyl)sulfonyl]-5-(2-fluoropyridin-3-yl)-1H-pyrrol-3-yl}methyl)methylcarbamate (160 mg) was dissolved in ethyl acetate (5 mL) and methanol (3 mL), and 4 mol/L hydrogen chloride-ethyl acetate solution (3 mL) was added. The mixture was stirred at room temperature for 2 hr, and concentrated under reduced pressure. Saturated aqueous sodium hydrogen carbonate solution was added to the residue, and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=1:1→1:9) to give the title compound as a free base. The free base was dissolved in ethyl acetate. 4 mol/L Hydrogen chloride-ethyl acetate solution was added and the solvent was evaporated under reduced pressure. The obtained residue was recrystallized from ethanol to give the title compound as colorless crystals (yield 45.9 mg, 33%).

$^1$H-NMR (DMSO-$d_6$) δ: 2.52 (3H, s), 4.01 (2H, s), 6.68 (1H, d, J=2.1 Hz), 7.08-7.13 (1H, m), 7.40-7.44 (1H, m), 7.58-7.66 (1H, m), 7.72-7.80 (3H, m), 8.32-8.34 (1H, m), 8.90 (2H, br).

Example 25

1-[5-(2-fluoropyridin-3-yl)-4-methyl-1-(pyridin-3-ylsulfonyl)-1H-pyrrol-3-yl]-N-methylmethanamine fumarate To a solution of 5-(2-fluoropyridin-3-yl)-4-methyl-1-(pyridin-3-ylsulfonyl)-1H-pyrrole-3-carbaldehyde (171 mg) in tetrahydrofuran (4 mL) were added 40% methylamine methanol solution (0.5 mL) and methanol (4 mL), and the mixture was stirred at room temperature for 30 min. Sodium borohydride (24 mg) was added and the mixture was further stirred for 30 min. The reaction mixture was concentrated under reduced pressure. Saturated aqueous sodium hydrogen carbonate solution was added to the residue, and the mixture was extracted with ethyl acetate. The extract was washed with saturated aqueous sodium hydrogen carbonate solution, water and saturated brine, and dried over anhydrous sodium sulfate, the solvent was evaporated under reduced pressure. The residue was purified by basic silica gel column chromatography (eluent: ethyl acetate) to give the title compound as a free base (yield 102 mg). To a solution of the obtained free base (101 mg) in ethyl acetate (2 mL) was added a solution of fumaric acid (33 mg) in ethanol (3 mL), and the mixture was stirred at room temperature for 1 hr. The reaction mixture was concentrated under reduced pressure, and the residue was recrystallized from ethanol to give the title compound as colorless crystals (yield 197 mg, 32%).

$^1$H-NMR (DMSO-$d_6$) δ: 1.76 (3H, s), 2.42 (3H, s), 3.75 (2H, s), 6.50 (2H, s), 7.42-7.46 (1H, m), 7.59-7.75 (3H, m), 7.84-7.88 (1H, m), 8.33-8.35 (1H, m), 8.56-8.57 (1H, m), 8.86-8.88 (1H, m), 3H not detected.

Example 26

1-[5-(2-fluoropyridin-3-yl)-4-methyl-1-(phenylsulfonyl)-1H-pyrrol-3-yl]-N-methylmethanamine hydrochloride To a solution of 5-(2-fluoropyridin-3-yl)-4-methyl-1-(phenylsulfonyl)-1H-pyrrole-3-carbaldehyde (219 mg) in tetrahydrofuran (3 mL) were added 40% methylamine methanol solution (0.7 mL) and methanol (3 mL), and the mixture was stirred at room temperature for 1 hr. Sodium borohydride (30 mg) was added at 0° C., and the mixture was further stirred at room temperature for 30 min and concentrated under reduced pressure. Saturated aqueous sodium hydrogen carbonate solution was added to the residue, and the mixture was extracted with ethyl acetate. The extract was washed with saturated aqueous sodium hydrogen carbonate solution, water and saturated brine, and dried over anhydrous sodium sulfate, and the solvent was evaporated under reduced pressure. The residue was purified by basic silica gel column chromatography (eluent: ethyl acetate) to give the title compound as a free base (yield 161 mg). To a solution of the obtained free base (159 mg) in ethanol (2 mL) was added 4 mol/L hydrogen chloride-ethyl acetate solution (2 mL), and the mixture was stirred at room temperature for 15 min. The solvent was concentrated under reduced pressure and the residue was recrystallized from ethanol to give the title compound as colorless crystals (yield 113 mg, 44%).

$^1$H-NMR (DMSO-$d_6$) δ: 1.70 (3H, s), 2.55 (3H, s), 3.98 (2H, s), 7.40-7.46 (3H, m), 7.53-7.66 (3H, m), 7.71-7.76 (1H, m), 7.84 (1H, s), 8.33-8.35 (1H, m), 9.06 (2H, brs).

Example 27

1-[4-fluoro-5-(2-fluoropyridin-3-yl)-1-(pyridin-3-ylsulfonyl)-1H-pyrrol-3-yl]-N-methylmethanamine To a solution of 1-(2,4-dimethoxyphenyl)-N-{[4-fluoro-5-(2-fluoropyridin-3-yl)-1-(pyridin-3-ylsulfonyl)-1H-pyrrol-3-yl]methyl}-N-methylmethanamine (5.68 g) in tetrahydrofuran (25 mL) was added a solution of 1-chloroethyl chlorocarbonate (1.58 g) in tetrahydrofuran (5 mL) at 0° C., and the mixture was stirred for 15 min. Triethylamine (4.63 mL) was added and the obtained mixture was stirred at 65° C. for 16 hr. The obtained solid was filtrated and the filtrate was concentrated under reduced pressure. Water was added to the residue, and the mixture was extracted with ethyl acetate. The extract was washed with water and saturated brine, dried over anhydrous magnesium sulfate, and concentrated under reduced pressure. Ethanol (25 mL) was added to the residue, and the mixture was refluxed for 1.5 hr, and concentrated under reduced pressure. Ethyl acetate was added to the residue, and the precipitated solid was filtrated. To the obtained solid were successively added ethyl acetate, 1 mol/L aqueous sodium hydroxide solution and saturated aqueous sodium hydrogen carbonate solution, and the mixture was stirred at room temperature for 10 min. The organic layer was separated, dried over anhydrous magnesium sulfate, and concentrated under reduced pressure. The residue was purified by basic silica gel column chromatography (eluent: hexane:ethyl acetate=1:1→1:4) to give the title compound as a colorless oil (yield 3.10 g, 77%).

$^1$H-NMR (CDCl$_3$) δ: 2.45 (3H, s), 3.64 (2H, s), 7.28-7.34 (2H, m), 7.38 (1H, ddd, J=8.1, 4.9, 0.6 Hz), 7.67 (1H, ddd, J=8.1, 2.3, 1.7 Hz), 7.81 (1H, ddd, J=9.2, 7.3, 1.9 Hz), 8.31 (1H, ddd, J=4.7, 1.9, 0.9 Hz), 8.67 (1H, d, J=2.3 Hz), 8.81 (1H, dd, J=4.9, 1.7 Hz), 1H not detected.

Example 28

1-[4-fluoro-5-(2-fluoropyridin-3-yl)-1-(pyridin-3-ylsulfonyl)-1H-pyrrol-3-yl]-N-methylmethanamine 0.5 fumarate To a solution of 1-[4-fluoro-5-(2-fluoropyridin-3-yl)-1-(pyridin-3-ylsulfonyl)-1H-pyrrol-3-yl]-N-methylmethanamine (6.88 g) in ethyl acetate (70 mL) was added a solution of fumaric acid (1.15 g) in ethanol (40 mL), and the mixture was stirred at room temperature for 30 min. The reaction mixture was concentrated under reduced pressure. The residue was recrystallized from ethanol-water-ethyl acetate to give the title compound as colorless crystals (yield 5.60 g, 70%).

$^1$H-NMR (DMSO-d$_6$) δ: 2.31 (3H, s), 3.64 (2H, s), 6.51 (1H, s), 7.50 (1H, ddd, J=7.4, 5.1, 1.9 Hz), 7.60-7.68 (1H, m), 7.66 (1H, d, J=5.3 Hz), 7.79-7.98 (2H, m), 8.39 (1H, ddd, J=4.9, 1.9, 1.1 Hz), 8.64 (1H, d, J=2.7 Hz), 8.92 (1H, dd, J=4.9, 1.5 Hz), 2H not detected.

melting point 186-188° C.

Example 29

1-[4-fluoro-5-(2-fluoropyridin-3-yl)-1-(phenylsulfonyl)-1H-pyrrol-3-yl]-N-methylmethanamine To a solution of 1-(2,4-dimethoxyphenyl)-N-{[4-fluoro-5-(2-fluoropyridin-3-yl)-1-(phenylsulfonyl)-1H-pyrrol-3-yl]methyl}-N-methylmethanamine (2.75 g) in tetrahydrofuran (10 mL) was added a solution of 1-chloroethyl chlorocarbonate (781 mg) in tetrahydrofuran (2 mL) at 0° C., and the mixture was stirred for 15 min. Triethylamine (2.3 mL) was added and the obtained mixture was refluxed for 16 hr. The reaction mixture was cooled to room temperature, water was added, and the mixture was extracted with ethyl acetate. The extract was washed with water and saturated brine, dried over anhydrous magnesium sulfate, and concentrated under reduced pressure. Ethanol (12 mL) was added to the residue, and the mixture was refluxed for 1.5 hr, and concentrated under reduced pressure. Saturated aqueous sodium hydrogen carbonate solution was added to the residue, and the mixture was extracted with ethyl acetate. The extract was washed with water and saturated brine, dried over anhydrous magnesium sulfate, and concentrated under reduced pressure. The residue was purified by basic silica gel column chromatography (eluent: ethyl acetate:methanol=9:1→1:1) to give the title compound as a yellow solid (yield 1.46 g, 75%).

$^1$H-NMR (CDCl$_3$) δ: 2.44 (3H, s), 3.63 (2H, s), 7.18-7.34 (2H, m), 7.33-7.47 (4H, m), 7.52-7.63 (1H, m), 7.81 (1H, ddd, J=9.3, 7.4, 1.9 Hz), 8.28 (1H, ddd, J=4.9, 1.9, 1.1 Hz), 1H not detected.

melting point 128° C.

Example 30

1-[4-fluoro-5-(2-fluoropyridin-3-yl)-1-(phenylsulfonyl)-1H-pyrrol-3-yl]-N-methylmethanamine 0.5 fumarate To a solution of 1-[4-fluoro-5-(2-fluoropyridin-3-yl)-1-(phenylsulfonyl)-1H-pyrrol-3-yl]-N-methylmethanamine (1.05 g) in ethyl acetate (20 mL) was added a solution of fumaric acid (342 mg) in ethanol (40 mL), and the mixture was stirred at room temperature for 1 hr. The reaction mixture was heated to 65° C., and water and ethanol were added to give a solution. At the same temperature, ethyl acetate was added to the solution, and the mixture was cooled to room temperature, and the obtained crystals were collected by filtration to give the title compound as colorless crystals (yield 974 mg, 80%).

$^1$H-NMR (DMSO-d$_6$) δ: 2.31 (3H, s), 3.63 (2H, s), 6.51 (1H, s), 7.42-7.51 (3H, m), 7.53-7.63 (3H, m), 7.72-7.79 (1H, m), 7.85 (1H, ddd, J=9.6, 7.3, 1.9 Hz), 8.36 (1H, ddd, J=4.9, 1.7, 0.9 Hz), 2H not detected.

melting point 187° C.

Example 31

1-{4-fluoro-1-(phenylsulfonyl)-5-[2-(trifluoromethyl)pyridin-3-yl]-1H-pyrrol-3-yl}-N-methylmethanamine hydrochloride To a solution of tert-butyl ({4-fluoro-1-(phenylsulfonyl)-5-[2-(trifluoromethyl)pyridin-3-yl]-1H-pyrrol-3-yl}methyl)methylcarbamate (389 mg) in ethanol (4 mL) was added 4 mol/L hydrogen chloride-ethyl acetate solution (4 mL), and the mixture was stirred at room temperature for 3 hr. The reaction mixture was concentrated under reduced pressure, and the residue was recrystallized from ethanol to give the title compound as a white solid (yield 188 mg, 55%).

$^1$H-NMR (CDCl$_3$) δ: 2.68 (3H, s), 4.03-4.27 (2H, m), 7.41-7.51 (4H, m), 7.57-7.63 (2H, m), 7.83-7.85 (1H, m), 8.03 (1H, d, J=5.4 Hz), 8.80-8.81 (1H, m), 10.06 (2H, brs).

Example 32

1-{4-fluoro-1-(pyridin-3-ylsulfonyl)-5-[2-(trifluoromethyl)pyridin-3-yl]-1H-pyrrol-3-yl}-N-methylmethanamine fumarate To a solution of tert-butyl ({4-fluoro-1-(pyridin-3-ylsulfonyl)-5-[2-(trifluoromethyl)pyridin-3-yl]-1H-pyrrol-3-yl}methyl)methylcarbamate (506 mg) in ethanol (5 mL) was added 4 mol/L hydrogen chloride-ethyl acetate solution (5 mL), and the mixture was stirred at room temperature for 4 hr. The reaction mixture was concentrated under reduced pressure. Saturated aqueous sodium hydrogen carbonate solution was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by basic silica gel column chromatography (eluent: ethyl acetate) to give the title compound as a free base (307 mg). To a solution of the obtained free base (229 mg) in ethyl acetate (3 mL) was added a solution of fumaric acid (65.1 mg) in ethanol (3 mL), and the mixture was stirred at room temperature for 15 min. The reaction mixture was concentrated under reduced pressure, and the residue was recrystallized from ethanol to give the title compound as a white solid (yield 209 mg, 39%).

$^1$H-NMR (DMSO-d$_6$) δ: 2.37 (3H, s), 3.73 (2H, s), 6.53 (2H, s), 7.63-7.67 (1H, m), 7.72-7.74 (1H, m), 7.79-7.87 (2H, m), 7.94-7.98 (1H, m), 8.65-8.66 (1H, m), 8.88-8.93 (2H, m), 3H not detected.

Example 33

1-[5-(2-chloropyridin-3-yl)-4-fluoro-1-(phenylsulfonyl)-1H-pyrrol-3-yl]-N-methylmethanamine fumarate To a solution of tert-butyl {[5-(2-chloropyridin-3-yl)-4-fluoro-1-(phenylsulfonyl)-1H-pyrrol-3-yl]methyl}methylcarbamate (439 mg) in ethanol (4 mL) was added 4 mol/L hydrogen chloride-ethyl acetate solution (4 mL), and the mixture was stirred at room temperature for 3 hr. The reaction mixture was concentrated under reduced pressure. Saturated aqueous sodium hydrogen carbonate solution was added to the residue, and the mixture was extracted with ethyl acetate. The extract washed with saturated aqueous sodium hydrogen carbonate solution, water and saturated brine, dried over anhydrous sodium sulfate, and concentrated under reduced pressure. The residue was purified by basic silica gel column chromatography (eluent: hexane:ethyl acetate=1:1) to give the title compound as a free base (267 mg). To a solution of the obtained free base (264 mg) in ethyl acetate (2 mL) was added a solution of fumaric acid (81.1 mg) in ethanol (2 mL), and the mixture was stirred at room temperature for 30 min. The reaction mixture was concentrated under reduced pressure, and the residue was recrystallized from ethanol-water to give the title compound as a white solid (yield 225 mg, 49%).

$^1$H-NMR (DMSO-$d_6$) δ: 2.37 (3H, s), 3.73 (2H, s), 6.53 (2H, s), 7.45-7.64 (6H, m), 7.72-7.78 (2H, m), 8.51-8.53 (1H, m), 3H not detected.

Example 34

3-[3-fluoro-4-[(methylamino)methyl]-1-(phenylsulfonyl)-1H-pyrrol-2-yl]pyridine-2-carbonitrile hydrochloride To a solution of tert-butyl {[5-(2-cyanopyridin-3-yl)-4-fluoro-1-(phenylsulfonyl)-1H-pyrrol-3-yl]methyl}methylcarbamate (433 mg) in ethanol (5 mL) was added 4 mol/L hydrogen chloride-ethyl acetate solution (5 mL), and the mixture was stirred at room temperature for 3 hr. The reaction mixture was concentrated under reduced pressure, and the residue was recrystallized from ethanol to give the title compound as a white solid (yield 175 mg, 47%).

$^1$H-NMR (DMSO-$d_6$) δ: 2.53 (3H, s), 4.03-4.13 (2H, m), 7.46-7.49 (2H, m), 7.55-7.61 (2H, m), 7.76-7.81 (1H, m), 7.85-7.89 (1H, m), 7.99-8.04 (2H, m), 8.85-8.87 (1H, m), 9.36 (2H, brs).

Example 35

1-{4-fluoro-5-(2-fluoropyridin-3-yl)-1-[(3-methoxyphenyl)sulfonyl]-1H-pyrrol-3-yl}-N-methylmethanamine hydrochloride Tert-butyl ({4-fluoro-5-(2-fluoropyridin-3-yl)-1-[(3-methoxyphenyl)sulfonyl]-1H-pyrrol-3-yl}methyl)methylcarbamate (551 mg) was dissolved in ethyl acetate (5 mL) and 2-propanol (3 mL), and 4 mol/L hydrogen chloride-ethyl acetate solution (5 mL) was added at room temperature. The reaction mixture was stirred for 4 hr and concentrated under reduced pressure. The residue was recrystallized from ethanol to give the title compound as colorless crystals (yield 327 mg, 76%).

$^1$H-NMR (DMSO-$d_6$) δ: 2.55 (3H, s), 3.76 (3H, s), 4.04 (2H, s), 6.87-6.88 (1H, m), 7.05-7.07 (1H, m), 7.32-7.35 (1H, m), 7.47-7.53 (2H, m), 7.83-7.92 (2H, m), 8.38-8.40 (1H, m), 9.15 (2H, brs).

Example 36

1-{4-fluoro-1-[(3-fluorophenyl)sulfonyl]-5-(2-fluoropyridin-3-yl)-1H-pyrrol-3-yl}-N-methylmethanamine hydrochloride Tert-butyl ({4-fluoro-1-[(3-fluorophenyl)sulfonyl]-5-(2-fluoropyridin-3-yl)-1H-pyrrol-3-yl}methyl)methylcarbamate (527 mg) was dissolved in ethyl acetate (5 mL) and 2-propanol (3 mL), and 4 mol/L hydrogen chloride-ethyl acetate solution (5 mL) was added at room temperature. The reaction mixture was stirred for 3 hr and concentrated under reduced pressure. The residue was recrystallized from ethanol to give the title compound as colorless crystals (yield 255 mg, 61%).

$^1$H-NMR (DMSO-$d_6$) δ: 2.56 (3H, s), 4.04 (2H, s), 7.32-7.36 (2H, m), 7.47-7.52 (1H, m), 7.65-7.70 (2H, m), 7.84-7.94 (2H, m), 8.38-8.40 (1H, m), 9.20 (2H, brs).

Example 37

1-{5-(2-chloropyridin-3-yl)-4-fluoro-1-[(3-methoxyphenyl)sulfonyl]-1H-pyrrol-3-yl}-N-methylmethanamine hydrochloride To a solution of tert-butyl ({5-(2-chloropyridin-3-yl)-4-fluoro-1-[(3-methoxyphenyl)sulfonyl]-1H-pyrrol-3-yl}methyl)methylcarbamate (501 mg) in ethyl acetate (3 mL) and 2-propanol (2 mL) was added 4 mol/L hydrogen chloride-ethyl acetate solution (3 mL), and the mixture was stirred at room temperature for 1 hr. The reaction mixture was concentrated under reduced pressure, and the residue was recrystallized from ethanol to give the title compound as a white solid (yield 321 mg, 73%).

$^1$H-NMR (DMSO-$d_6$) δ: 2.56 (3H, s), 3.76 (3H, s), 4.06 (2H, s), 6.87 (1H, t, J=2.1 Hz), 7.04-7.14 (1H, m), 7.30-7.39 (1H, m), 7.46-7.61 (2H, m), 7.80 (1H, dd, J=7.6, 2.0 Hz), 7.92 (1H, d, J=5.5 Hz), 8.56 (1H, dd, J=4.8, 2.0 Hz), 9.15 (2H, brs).

Example 38

1-[5-(2-chloropyridin-3-yl)-4-fluoro-1-(pyridin-3-ylsulfonyl)-1H-pyrrol-3-yl]-N-methylmethanamine fumarate To a solution of tert-butyl {[5-(2-chloropyridin-3-yl)-4-fluoro-1-(pyridin-3-ylsulfonyl)-1H-pyrrol-3-yl]methyl}methylcarbamate (465 mg) in ethyl acetate (3 mL), 2-propanol (2 mL) and methanol (3 mL) was added 4 mol/L hydrogen chloride-ethyl acetate solution (6 mL), and the mixture was stirred at room temperature for 3 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=1:1→1:9) to give a free base of the title compound as a pale-yellow oil (yield 297 mg). A solution of the obtained free base in ethyl acetate (5 mL) was added dropwise to a solution of fumaric acid (88 mg) in ethanol (5 mL) and concentrated under reduced pressure. The residue was recrystallized from ethanol to give the title compound as a white solid (yield 267 mg, 59%).

$^1$H-NMR (DMSO-$d_6$) δ: 2.37 (3H, s), 3.72 (2H, s), 6.54 (2H, s), 7.56 (1H, dd, J=7.6, 4.8 Hz), 7.61-7.76 (2H, m), 7.86 (1H, dd, J=7.5, 1.9 Hz), 7.89-7.98 (1H, m), 8.55 (1H, dd, J=4.8, 2.0 Hz), 8.63 (1H, d, J=1.9 Hz), 8.92 (1H, dd, J=4.9, 1.5 Hz), 3H not detected.

melting point 176-177° C.

Example 39

1-{5-(2-chloropyridin-3-yl)-4-fluoro-1-[(3-fluorophenyl)sulfonyl]-1H-pyrrol-3-yl}-N-methylmethanamine hydrochloride To a solution of tert-butyl ({5-(2-chloropyridin-3-yl)-4-fluoro-1-[(3-fluorophenyl)sulfonyl]-1H-pyrrol-3- yl}methyl)methylcarbamate (476 mg) in ethyl acetate (3 mL) and 2-propanol (2 mL) was added 4 mol/L hydrogen chloride-ethyl acetate solution (6 mL), and the mixture was stirred at room temperature for 3 hr. The reaction mixture was concentrated under reduced pressure, and the residue was recrystallized from ethanol to give the title compound as a white solid (yield 240 mg, 63%).

$^1$H-NMR (DMSO-d$_6$) δ: 2.56 (3H, s), 4.07 (2H, s), 7.19-7.43 (2H, m), 7.57 (1H, dd, J=7.6, 4.8 Hz), 7.62-7.75 (2H, m), 7.82 (1H, dd, J=7.6, 2.0 Hz), 7.96 (1H, d, J=5.5 Hz), 8.56 (1H, dd, J=4.8, 2.0 Hz), 9.32 (2H, brs).

Example 40

3-({2-(2-chloropyridin-3-yl)-3-fluoro-4-[(methylamino)methyl]-1H-pyrrol-1-yl}sulfonyl)benzonitrile 0.5 fumarate To a solution of tert-butyl ({5-(2-chloropyridin-3-yl)-1-[(3-cyanophenyl)sulfonyl]-4-fluoro-1H-pyrrol-3-yl}methyl)methylcarbamate (489 mg) in ethyl acetate (3 mL) and 2-propanol (2 mL) was added 4 mol/L hydrogen chloride-ethyl acetate solution (6 mL), and the mixture was stirred at room temperature for 6 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=1:1→1:9) to give a free base of the title compound as a pale-yellow oil (yield 152 mg, 39%). A solution of the obtained free base in ethyl acetate (2 mL) was added dropwise to a solution of fumaric acid (44 mg) in ethanol (4 mL) and the mixture was concentrated under reduced pressure. The residue was recrystallized from ethanol to give the title compound as a white solid (yield 127 mg, 28%).

$^1$H-NMR (DMSO-d$_6$) δ: 2.35 (3H, s), 3.68 (2H, s), 6.51 (1H, s), 7.56 (1H, dd, J=7.6, 4.8 Hz), 7.68 (1H, d, J=5.7 Hz), 7.77-7.83 (2H, m), 7.86 (1H, dd, J=7.6, 2.0 Hz), 7.97 (1H, q, J=1.4 Hz), 8.18-8.32 (1H, m), 8.55 (1H, dd, J=4.7, 1.9 Hz), 2H not detected.

Example 41

3-{3-fluoro-1-[(3-methoxyphenyl)sulfonyl]-4-[(methylamino)methyl]-1H-pyrrol-2-yl}pyridine-2-carbonitrile hydrochloride To a solution of tert-butyl ({5-(2-cyanopyridin-3-yl)-4-fluoro-1-[(3-methoxyphenyl)sulfonyl]-1H-pyrrol-3-yl}methyl)methylcarbamate (476 mg) in ethyl acetate (3 mL) and 2-propanol (2 mL) was added 4 mol/L hydrogen chloride-ethyl acetate solution (6 mL), and the mixture was stirred at room temperature for 3 hr. The reaction mixture was concentrated under reduced pressure, and the residue was recrystallized from ethanol to give the title compound as a white solid (yield 265 mg, 64%).

$^1$H-NMR (DMSO-d$_6$) δ: 2.55 (3H, s), 3.75 (3H, s), 4.09 (2H, d, J=2.6 Hz), 6.86 (1H, t, J=2.2 Hz), 6.96-7.09 (1H, m), 7.28-7.41 (1H, m), 7.51 (1H, t, J=8.1 Hz), 7.89 (1H, dd, J=8.1, 4.9 Hz), 7.98-8.09 (2H, m), 8.87 (1H, dd, J=4.7, 1.5 Hz), 9.22 (2H, brs).

Example 42

3-{3-fluoro-1-[(3-fluorophenyl)sulfonyl]-4-[(methylamino)methyl]-1H-pyrrol-2-yl}pyridine-2-carbonitrile hydrochloride To a solution of tert-butyl ({5-(2-cyanopyridin-3-yl)-4-fluoro-1-[(3-fluorophenyl)sulfonyl]-1H-pyrrol-3-yl}methyl)methylcarbamate (445 mg) in ethyl acetate (3 mL) and 2-propanol (2 mL) was added 4 mol/L hydrogen chloride-ethyl acetate solution (6 mL), and the mixture was stirred at room temperature for 3 hr. The reaction mixture was concentrated under reduced pressure, and the residue was recrystallized from a mixed solvent of ethanol and water to give the title compound as a white solid (yield 281 mg, 73%).

$^1$H-NMR (DMSO-d$_6$) δ: 2.55 (3H, s), 4.10 (2H, d, J=4.3 Hz), 7.30-7.41 (2H, m), 7.61-7.73 (2H, m), 7.90 (1H, dd, J=8.1, 4.7 Hz), 8.03 (1H, d, J=5.5 Hz), 8.06 (1H, dd, J=8.1, 1.5 Hz), 8.88 (1H, dd, J=4.8, 1.6 Hz), 9.25 (2H, brs).

Example 43

3-{1-[(3-cyanophenyl)sulfonyl]-3-fluoro-4-[(methylamino)methyl]-1H-pyrrol-2-yl}pyridine-2-carbonitrile hydrochloride To a solution of tert-butyl {[1-[(3-cyanophenyl)sulfonyl]-5-(2-cyanopyridin-3-yl)-4-fluoro-1H-pyrrol-3-yl]methyl}methylcarbamate (401 mg) in ethyl acetate (3 mL) and 2-propanol (2 mL) was added 4 mol/L hydrogen chloride-ethyl acetate solution (6 mL), and the mixture was stirred at room temperature for 17 hr. The reaction mixture was concentrated under reduced pressure, and the residue was recrystallized from a mixed solvent of ethanol and water to give the title compound as a white solid (yield 276 mg, 79%).

$^1$H-NMR (DMSO-d$_6$) δ: 2.55 (3H, s), 4.02-4.18 (2H, m), 7.81 (2H, dd, J=3.5, 1.6 Hz), 7.90 (1H, dd, J=8.0, 4.8 Hz), 7.98-8.13 (3H, m), 8.23-8.35 (1H, m), 8.90 (1H, dd, J=4.7, 1.5 Hz), 9.32 (2H, brs).

Example 44

3-[3-fluoro-4-[(methylamino)methyl]-1-(pyridin-3-ylsulfonyl)-1H-pyrrol-2-yl]pyridine-2-carbonitrile fumarate To a solution of tert-butyl {[5-(2-cyanopyridin-3-yl)-4-fluoro-1-(pyridine-3-sulfonyl)-1H-pyrrol-3-yl]methyl}methylcarbamate (421 mg) in ethyl acetate (3 mL) and 2-propanol (2 mL) was added 4 mol/L hydrogen chloride-ethyl acetate solution (6 mL), and the mixture was stirred at room temperature for 2 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=3:7→ethyl acetate) to give a free base of the title compound as a pale-yellow solid (yield 242 mg). A solution of the obtained free base in ethyl acetate (3 mL) was added dropwise to a solution of fumaric acid (74 mg) in ethanol (3 mL) and the mixture was concentrated under reduced pressure. The residue was recrystallized from a mixed solvent of ethanol and water to give the title compound as a white solid (yield 259 mg, 61%).

$^1$H-NMR (DMSO-d$_6$) δ: 2.37 (3H, s), 3.76 (2H, s), 6.55 (2H, s), 7.60-7.68 (1H, m), 7.81 (1H, d, J=5.5 Hz), 7.88 (1H, dd, J=8.1, 4.9 Hz), 7.91-7.96 (1H, m), 8.08 (1H, dd, J=8.1, 1.5 Hz), 8.63 (1H, d, J=2.1 Hz), 8.87 (1H, dd, J=4.8, 1.6 Hz), 8.94 (1H, dd, J=4.7, 1.5 Hz), 3H not detected.

Example 45

3-({3-fluoro-2-(2-fluoropyridin-3-yl)-4-[(methylamino)methyl]-1H-pyrrol-1-yl}sulfonyl)benzonitrile hydrochloride To a solution of tert-butyl {[1-[(3-cyanophenyl)sulfonyl]-4-fluoro-5-(2-fluoropyridin-3-yl)-1H-pyrrol-3-yl]methyl}methylcarbamate (435 mg) in ethyl acetate (3 mL) and 2-propanol (2 mL) was added 4 mol/L hydrogen chloride-ethyl acetate solution (6 mL), and the mixture was stirred at room temperature for 2 hr. The reaction mixture was concentrated under reduced pressure, and the residue was recrystallized from ethanol to give the title compound as a white solid (yield 245 mg, 65%).

$^1$H-NMR (DMSO-d$_6$) δ: 2.56 (3H, s), 4.04 (2H, s), 7.45-7.56 (1H, m), 7.81 (2H, d, J=5.3 Hz), 7.84-7.93 (1H, m), 7.94-8.02 (2H, m), 8.20-8.34 (1H, m), 8.37-8.46 (1H, m), 9.31 (2H, brs).

Example 46

1-(4-fluoro-5-(2-fluoropyridin-3-yl)-1-{[3-(methylsulfonyl)phenyl]sulfonyl}-1H-pyrrol-3-yl)-N-methylmethanamine hydrochloride To a solution of tert-butyl [(4-fluoro-5-(2-fluoropyridin-3-yl)-1-{[3-(methylsulfonyl)phenyl]sulfonyl}-1H-pyrrol-3-yl)methyl]methylcarbamate (504 mg) in ethyl acetate (3 mL) and 2-propanol (2 mL) was added 4 mol/L hydrogen chloride-ethyl acetate solution (6 mL), and the mixture was stirred at room temperature for 1 hr. The reaction mixture was concentrated under reduced pressure, and the residue was recrystallized from a mixed solvent of ethanol and water to give the title compound as a white solid (yield 358 mg, 78%).

$^1$H-NMR (DMSO-d$_6$) δ: 2.54 (3H, s), 3.33 (3H, s), 4.04 (2H, s), 7.46-7.55 (1H, m), 7.82-7.90 (2H, m), 7.90-7.96 (2H, m), 8.00 (1H, d, J=5.5 Hz), 8.35 (1H, dt, J=7.2, 1.8 Hz), 8.38-8.44 (1H, m), 9.30 (2H, brs).

Example 47

3-({3-fluoro-2-(2-fluoropyridin-3-yl)-4-[(methylamino)methyl]-1H-pyrrol-1-yl}sulfonyl)-N-(2-hydroxyethyl)benzamide hydrochloride To a solution of tert-butyl ({4-fluoro-5-(2-fluoropyridin-3-yl)-1-[(3-{[(2-hydroxyethyl)amino]carbonyl}phenyl)sulfonyl]-1H-pyrrol-3-yl}methyl)methylcarbamate (226 mg) in ethyl acetate (3 mL) and 2-propanol (2 mL) was added 4 mol/L hydrogen chloride-ethyl acetate solution (6 mL), and the mixture was stirred at room temperature for 2 hr. The reaction mixture was concentrated under reduced pressure, and the residue was recrystallized from ethanol to give the title compound as a white solid (yield 99 mg, 50%).

$^1$H-NMR (DMSO-d$_6$) δ: 2.53-2.59 (3H, m), 3.33-3.41 (1H, m), 3.53 (2H, q, J=6.0 Hz), 4.04 (2H, s), 4.78 (1H, t, J=5.6 Hz), 7.43-7.52 (1H, m), 7.58 (1H, d, J=8.1 Hz), 7.69 (1H, t, J=7.9 Hz), 7.83 (2H, ddd, J=9.5, 7.6, 1.8 Hz), 7.93 (1H, d, J=5.5 Hz), 8.01 (1H, t, J=1.6 Hz), 8.25 (1H, d, J=7.7 Hz), 8.39 (1H, d, J=4.9 Hz), 8.73-8.87 (1H, m), 9.04 (2H, brs).

Example 48

[3-({3-fluoro-2-(2-fluoropyridin-3-yl)-4-[(methylamino)methyl]-1H-pyrrol-1-yl}sulfonyl)phenyl]methanol 0.5 fumarate To a solution of tert-butyl [(4-fluoro-5-(2-fluoropyridin-3-yl)-1-{[3-(hydroxymethyl)phenyl]sulfonyl}-1H-pyrrol-3-yl)methyl]methylcarbamate (207 mg) in ethyl acetate (3 mL) and 2-propanol (2 mL) was added 4 mol/L hydrogen chloride-ethyl acetate solution (6 mL), and the mixture was stirred at room temperature for 2 hr. The solvent was concentrated under reduced pressure, diluted with ethyl acetate, and washed with saturated aqueous sodium hydrogen carbonate solution. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=4:1→ethyl acetate:methanol=32:1) (basic TLC:R$_f$=0.1 (ethyl acetate)) to give a free base of the title compound as a pale-yellow oil (yield 82.6 mg). A solution of the obtained free base in ethyl acetate (1 mL) was added dropwise to a solution of fumaric acid (24 mg) in ethanol (1 mL) and the mixture was concentrated under reduced pressure. The residue was recrystallized from ethanol to give the title compound as a white solid (yield 69 mg, 36%).

$^1$H-NMR (DMSO-d$_6$) δ: 2.32 (3H, s), 3.64 (2H, s), 4.50 (2H, s), 6.50 (1H, s), 7.27-7.41 (2H, m), 7.42-7.60 (3H, m), 7.66 (1H, d, J=7.5 Hz), 7.83 (1H, ddd, J=9.5, 7.5, 1.9 Hz), 8.32-8.42 (1H, m), 2H not detected.

Example 49

3-({3-fluoro-2-(2-fluoropyridin-3-yl)-4-[(methylamino)methyl]-1H-pyrrol-1-yl}sulfonyl)benzyl acetate fumarate To a solution of tert-butyl [(4-fluoro-5-(2-fluoropyridin-3-yl)-1-{[3-(hydroxymethyl)phenyl]sulfonyl}-1H-pyrrol-3-yl)methyl]methylcarbamate (207 mg) in ethyl acetate (3 mL) and 2-propanol (2 mL) was added 4 mol/L hydrogen chloride-ethyl acetate solution (6 mL), and the mixture was stirred at room temperature for 2 hr. The solvent was concentrated under reduced pressure, diluted with ethyl acetate, and washed with saturated aqueous sodium hydrogen carbonate solution. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=4:1→ethyl acetate:methanol=32:1) (basic TLC:R$_f$=0.4 (ethyl acetate)) to give a free base of the title compound as a pale-yellow oil (yield 61.1 mg). A solution of the obtained free base in ethyl acetate (1 mL) was added dropwise to a solution of fumaric acid (16 mg) in ethanol (1 mL) and the mixture was concentrated under reduced pressure. The residue was recrystallized from a mixed solvent of ethyl acetate and ethanol to give the title compound as a white solid (yield 58 mg, 25%).

$^1$H-NMR (DMSO-d$_6$) δ: 2.09 (3H, s), 2.36 (3H, s), 3.73 (2H, s), 5.08 (2H, s), 6.54 (2H, s), 7.39 (1H, s), 7.43-7.51 (2H, m), 7.60 (1H, t, J=7.8 Hz), 7.65 (1H, d, J=5.5 Hz), 7.75 (1H, d, J=7.7 Hz), 7.84 (1H, ddd, J=9.5, 7.4, 1.9 Hz), 8.38 (1H, d, J=4.9 Hz), 3H not detected.

Example 50

1-[4-fluoro-5-(2-fluoropyridin-3-yl)-1-(3-furylsulfonyl)-1H-pyrrol-3-yl]-N-methylmethanamine hydrochloride To a solution of tert-butyl {[4-fluoro-5-(2-fluoropyridin-3-yl)-1-(3-furylsulfonyl)-1H-pyrrol-3-yl]methyl}methylcarbamate (335 mg) in ethyl acetate (3 mL) and 2-propanol (2 mL) was added 4 mol/L hydrogen chloride-ethyl acetate solution (6 mL), and the mixture was stirred at room temperature for 2 hr. The reaction mixture was concentrated under reduced pressure, and the residue was recrystallized from ethanol to give the title compound as a white solid (yield 220 mg, 76%).
$^1$H-NMR (DMSO-$d_6$) δ: 2.57 (3H, s), 4.05 (2H, s), 6.72 (1H, dd, J=1.9, 0.8 Hz), 7.49 (1H, ddd, J=7.3, 5.0, 1.7 Hz), 7.85 (1H, d, J=5.7 Hz), 7.91 (1H, ddd, J=9.6, 7.5, 1.9 Hz), 7.96 (1H, t, J=1.9 Hz), 8.33 (1H, dd, J=1.5, 0.8 Hz), 8.36-8.41 (1H, m), 9.32 (2H, brs).
melting point 237-238° C.

Example 51

1-[5-(2-fluoropyridin-3-yl)-1-(3-furylsulfonyl)-1H-pyrrol-3-yl]-N-methylmethanamine hydrochloride To a solution of tert-butyl {[5-(2-fluoropyridin-3-yl)-1-(3-furylsulfonyl)-1H-pyrrol-3-yl]methyl}methylcarbamate (253 mg) in ethyl acetate (3 mL) and 2-propanol (2 mL) was added 4 mol/L hydrogen chloride-ethyl acetate solution (6 mL), and the mixture was stirred at room temperature for 2.5 hr. The reaction mixture was concentrated under reduced pressure, and the residue was recrystallized from a mixed solvent of ethyl acetate and ethanol to give the title compound as a white solid (yield 134 mg, 62%).
$^1$H-NMR (DMSO-$d_6$) δ: 2.53 (3H, s), 4.00 (2H, s), 6.63-6.67 (2H, m), 7.43 (1H, ddd, J=7.1, 5.0, 1.9 Hz), 7.75 (1H, d, J=1.9 Hz), 7.80 (1H, ddd, J=9.6, 7.5, 1.9 Hz), 7.94 (1H, t, J=1.9 Hz), 8.27-8.30 (1H, m), 8.31-8.37 (1H, m), 9.03 (2H, brs).

Example 52

1-[4-fluoro-5-(2-fluoropyridin-3-yl)-1-({3-[(methylsulfonyl)methyl]phenyl}sulfonyl)-1H-pyrrol-3-yl]-N-methylmethanamine hydrochloride To a solution of tert-butyl {[4-fluoro-5-(2-fluoropyridin-3-yl)-1-({3-[(methylsulfonyl)methyl]phenyl}sulfonyl)-1H-pyrrol-3-yl]methyl}methylcarbamate (266 mg) in ethyl acetate (3 mL) and 2-propanol (2 mL) was added 4 mol/L hydrogen chloride-ethyl acetate solution (6 mL), and the mixture was stirred at room temperature for 2.5 hr. The reaction mixture was concentrated under reduced pressure, and the residue was recrystallized from a mixed solvent of ethanol and water to give the title compound as a white solid (yield 187 mg, 79%).
$^1$H-NMR (DMSO-$d_6$) δ: 2.55 (3H, s), 2.94 (3H, s), 4.03 (2H, s), 4.65 (2H, s), 7.46 (1H, dt, J=7.2, 5.1, 1.7 Hz), 7.50-7.56 (1H, m), 7.60-7.68 (2H, m), 7.74-7.83 (2H, m), 7.92 (1H, d, J=5.5 Hz), 8.39 (1H, d, J=4.7 Hz), 9.30 (2H, brs).

Example 53

1-(4-fluoro-5-(2-fluoropyridin-3-yl)-1-{[3-(5-methyl-1,3,4-oxadiazol-2-yl)phenyl]sulfonyl}-1H-pyrrol-3-yl)-N-methylmethanamine fumarate To a solution of tert-butyl {[(4-fluoro-5-(2-fluoropyridin-3-yl)-1-{[3-(5-methyl-1,3,4-oxadiazol-2-yl)phenyl]sulfonyl}-1H-pyrrol-3-yl)methyl]methylcarbamate (83 mg) in ethyl acetate (2 mL) and 2-propanol (1 mL) was added 4 mol/L hydrogen chloride-ethyl acetate solution (3 mL), and the mixture was stirred at room temperature for 2 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. The combined organic layer was washed with saturated brine, dried over anhydrous magnesium sulfate, and concentrated under reduced pressure. A solution of the residue in ethyl acetate (2 mL) was added dropwise to a solution of fumaric acid (8.4 mg) in ethanol (2 mL) and the mixture was concentrated under reduced pressure. The residue was recrystallized from a mixed solvent of ethyl acetate and ethanol to give the title compound as a white solid (yield 21 mg, 38%).
$^1$H-NMR (DMSO-$d_6$) δ: 2.32 (3H, s), 2.63 (3H, s), 3.68 (2H, s), 6.54 (2H, s), 7.46-7.53 (1H, m), 7.68 (1H, d, J=5.7 Hz), 7.73-7.86 (3H, m), 7.87-7.95 (1H, m), 8.33 (1H, dt, J=7.4, 1.4 Hz), 8.39 (1H, d, J=5.7 Hz), 3H not detected.

Example 54

3-({2-(2-chloropyridin-3-yl)-4-[(methylamino)methyl]-1H-pyrrol-1-yl}sulfonyl)benzonitrile fumarate 3-{[2-(2-Chloropyridin-3-yl)-4-formyl-1H-pyrrol-1-yl]sulfonyl}benzonitrile (140 mg) was dissolved in a mixture of 40% solution (150 mg) of methylamine in methanol and methanol (14 mL) at room temperature, and the mixture was stirred for 5 min. Sodium borohydride (29 mg) was added and the mixture was stirred for 10 min. Saturated brine (40 mL) was added to the reaction mixture, and the mixture was extracted with ethyl acetate (80 mL). The obtained extract was washed with saturated brine (40 mL), dried over anhydrous magnesium sulfate, and concentrated under reduced pressure. The residue was purified by basic silica gel column chromatography (eluent:ethyl acetate-methanol (18:1), dissolved in ethyl acetate (8 mL), and crystallized from a solution of fumaric acid (66 mg) in methanol (2 mL) to give the title compound as colorless crystals (yield 45 mg, 24%).
$^1$H-NMR (DMSO-$d_6$) δ: 2.40 (3H, s), 3.80 (2H, s), 6.48 (2H, s), 6.52 (1H, d, J=1.7 Hz), 7.50 (1H, dd, J=7.5, 4.9 Hz), 7.69 (1H, dd, J=7.6, 2.0 Hz), 7.72 (1H, d, J=1.7 Hz), 7.76-7.82 (2H, m), 7.92-7.97 (1H, m), 8.22-8.26 (1H, m), 8.51 (1H, dd, J=4.9, 1.9 Hz), 3H not detected.

Example 55

1-[1-(cyclohexylsulfonyl)-4-fluoro-5-(2-fluoropyridin-3-yl)-1H-pyrrol-3-yl]-N-methylmethanamine hydrochloride tert-Butyl {[1-(cyclohexylsulfonyl)-4-fluoro-5-(2-fluoropyridin-3-yl)-1H-pyrrol-3-yl]methyl}methylcarbamate (420 mg) was dissolved in methanol (10 mL), 4 mol/L hydrogen chloride-ethyl acetate solution (2 mL) was added, and the mixture was stirred at 70° C. for 30 min. The reaction mixture was concentrated under reduced pressure, and the residue was crystallized from ethyl acetate to give the title compound as colorless crystals (yield 256 mg, 71%).

$^1$H-NMR (DMSO-d$_6$) δ: 0.98-1.40 (5H, m), 1.49-1.80 (5H, m), 2.58 (3H, s), 3.21-3.42 (1H, m), 4.06 (2H, s), 7.46-7.54 (1H, m), 7.64 (1H, d, J=5.3 Hz), 8.03-8.17 (1H, m), 8.33-8.40 (1H, m), 9.36 (2H, brs).

Example 56

1-[4-fluoro-5-(2-fluoropyridin-3-yl)-1-(piperidin-1-ylsulfonyl)-1H-pyrrol-3-yl]-N-methylmethanamine hydrochloride tert-Butyl {[4-fluoro-5-(2-fluoropyridin-3-yl)-1-(piperidin-1-ylsulfonyl)-1H-pyrrol-3-yl]methyl}methylcarbamate (210 mg) was dissolved in ethanol (5 mL), 4 mol/L hydrogen chloride-ethyl acetate solution (5 mL) was added, and the mixture was stirred at 50° C. for 15 min. The reaction mixture was concentrated under reduced pressure, and the residue was crystallized from ethyl acetate to give the title compound as colorless crystals (yield 145 mg, 80%).

$^1$H-NMR (DMSO-d$_6$) δ: 1.42 (6H, br), 2.59 (3H, s), 2.92 (4H, br), 4.05 (2H, s), 7.46-7.53 (1H, m), 7.67 (1H, d, J=5.7 Hz), 8.02-8.13 (1H, m), 8.30-8.39 (1H, m), 9.30 (2H, brs).

Example 57

1-{1-[(2,6-difluorophenyl)sulfonyl]-4-fluoro-5-(2-fluoropyridin-3-yl)-1H-pyrrol-3-yl}-N-methylmethanamine hydrochloride tert-Butyl ({1-[(2,6-difluorophenyl)sulfonyl]-4-fluoro-5-(2-fluoropyridin-3-yl)-1H-pyrrol-3-yl}methyl)methylcarbamate (430 mg) was dissolved in ethanol (5 mL), 4 mol/L hydrogen chloride-ethyl acetate solution (5 mL) was added, and the mixture was stirred at 50° C. for 20 min. The reaction mixture was concentrated under reduced pressure, and the residue was crystallized from ethyl acetate to give the title compound as colorless crystals (yield 283 mg, 75%).

$^1$H-NMR (DMSO-d$_6$) δ: 2.57 (3H, s), 4.08 (2H, s), 7.32 (2H, d, J=8.9 Hz), 7.41-7.48 (1H, m), 7.82-7.96 (3H, m), 8.35-8.41 (1H, m), 9.26 (2H, brs).

Example 58

1-{4-chloro-5-(2-fluoropyridin-3-yl)-1-[(1-methyl-1H-pyrazol-4-yl)sulfonyl]-1H-pyrrol-3-yl}-N-methylmethanamine fumarate 4-Chloro-5-(2-fluoropyridin-3-yl)-1-[(1-methyl-1H-pyrazol-4-yl)sulfonyl]-1H-pyrrole-3-carbaldehyde (160 mg) was dissolved in a solution of methylamine hydrochloride (293 mg) in methanol (15 mL), and the mixture was stirred for 5 min. Sodium triacetoxyborohydride (460 mg) was added and the mixture was stirred for 1 hr. The reaction mixture was concentrated under reduced pressure at 30° C., and the residue was partitioned by adding saturated aqueous sodium hydrogen carbonate solution and ethyl acetate. The ethyl acetate layer was washed with saturated brine, dried over anhydrous magnesium sulfate, and concentrated under reduced pressure. The residue was purified by basic silica gel column chromatography (eluent: ethyl acetate-methanol=99:1→95:5), and crystallized from a solution of fumaric acid (51 mg) in ethanol (5 mL) to give the title compound as colorless crystals (yield 68 mg, 31%).

$^1$H-NMR (DMSO-d$_6$) δ: 2.43 (3H, s), 3.73 (2H, s), 3.85 (3H, s), 6.54 (2H, s), 7.36-7.58 (1H, m), 7.62 (1H, d, J=0.6 Hz), 7.66 (1H, s), 7.82-7.94 (1H, m), 8.23 (1H, s), 8.34-8.44 (1H, m), 3H not detected.

Example 59

1-[4-fluoro-5-(2-fluoropyridin-3-yl)-1-(2-thienylsulfonyl)-1H-pyrrol-3-yl]-N-methylmethanamine hydrochloride To a mixed solution of tert-butyl {[4-fluoro-5-(2-fluoropyridin-3-yl)-1-(2-thienylsulfonyl)-1H-pyrrol-3-yl]methyl}methylcarbamate (276 mg) in ethyl acetate (2 mL) and 2-propanol (1 mL) was added 4 mol/L hydrogen chloride-ethyl acetate solution (5 mL), and the mixture was stirred at room temperature for 2 hr. The reaction mixture was concentrated under reduced pressure, and the residue was recrystallized from ethanol to give the title compound as a white solid (yield 168 mg, 70%).

$^1$H-NMR (DMSO-d$_6$) δ: 2.56 (3H, s), 4.05 (2H, s), 7.22 (1H, dd, J=5.1, 4.0 Hz), 7.48-7.56 (2H, m), 7.85 (1H, d, J=5.5 Hz), 7.93 (1H, ddd, J=9.5, 7.5, 2.0 Hz), 8.18 (1H, dd, J=4.9, 1.3 Hz), 8.40 (1H, dq, J=4.9, 0.9 Hz), 9.12 (2H, brs).

Example 60

1-[4-fluoro-5-(2-fluoropyridin-3-yl)-1-(2-furylsulfonyl)-1H-pyrrol-3-yl]-N-methylmethanamine hydrochloride To a mixed solution of tert-butyl {[4-fluoro-5-(2-fluoropyridin-3-yl)-1-(2-furylsulfonyl)-1H-pyrrol-3-yl]methyl}methylcarbamate (243 mg) in ethyl acetate (2 mL) and 2-propanol (1 mL) was added 4 mol/L hydrogen chloride-ethyl acetate solution (5 mL), and the mixture was stirred at room temperature for 2.5 hr. The reaction mixture was concentrated under reduced pressure, and the residue was recrystallized from ethanol to give the title compound as a white solid (yield 160 mg, 77%).

$^1$H-NMR (DMSO-d$_6$) δ: 2.58 (3H, s), 4.07 (2H, s), 6.77 (1H, dd, J=3.8, 1.7 Hz), 7.17 (1H, d, J=3.8 Hz), 7.50 (1H, ddd, J=7.1, 5.2, 1.4 Hz), 7.80 (1H, d, J=5.5 Hz), 7.94 (1H, ddd, J=9.3, 7.5, 1.6 Hz), 8.13 (1H, s), 8.40 (1H, d, J=4.3 Hz), 9.04 (2H, brs).

Example 61

1-[4-fluoro-5-(2-fluoropyridin-3-yl)-1-(3-thienylsulfonyl)-1H-pyrrol-3-yl]-N-methylmethanamine hydrochloride To a mixed solution of tert-butyl {[4-fluoro-5-(2-fluoropyridin-3-yl)-1-(3-thienylsulfonyl)-1H-pyrrol-3-yl]methyl}methylcarbamate (264 mg) in ethyl acetate (2 mL) and 2-propanol (1 mL) was added 4 mol/L hydrogen chloride-ethyl acetate solution (5 mL), and the mixture was stirred at room temperature for 3 hr. The reaction mixture was concentrated under reduced pressure, and the residue was recrystallized from ethanol to give the title compound as a white solid (yield 165 mg, 72%).

$^1$H-NMR (DMSO-d$_6$) δ: 2.56 (3H, s), 4.05 (2H, s), 7.13 (1H, dd, J=5.3, 1.5 Hz), 7.48 (1H, ddd, J=7.3, 5.1, 1.8 Hz), 7.76-7.92 (3H, m), 8.15 (1H, dd, J=3.0, 1.5 Hz), 8.38 (1H, dq, J=4.9, 0.9 Hz), 9.15 (2H, brs).

Example 62

1-{4-fluoro-5-(2-fluoropyridin-3-yl)-1-[(1-methyl-1H-pyrazol-4-yl)sulfonyl]-1H-pyrrol-3-yl}-N-methylmethanamine hydrochloride tert-Butyl ({4-fluoro-5-(2-fluoropyridin-3-yl)-1-[(1-methyl-1H-pyrazol-4-yl)sulfonyl]-1H-pyrrol-3-yl}methyl)methylcarbamate (460 mg) was dissolved in 2-propanol (5 mL), 4 mol/L hydrogen chloride-ethyl acetate solution (5 mL) was added, and the mixture was stirred at 50° C. for 20 min. The reaction mixture was concentrated under reduced pressure, and the residue was crystallized from ethanol to give the title compound as colorless crystals (yield 285 mg, 72%).

$^1$H-NMR (DMSO-d$_6$) δ: 2.57 (3H, s), 3.85 (3H, s), 4.04 (2H, brs), 7.46-7.53 (1H, m), 7.64 (1H, s), 7.79 (1H, d, J=5.7 Hz) 7.86-7.95 (1H, m), 8.31 (1H, s), 8.39 (1H, dd, J=4.9, 0.8 Hz), 9.25 (2H, brs).

Example 63

Methyl 5-({3-fluoro-2-(2-fluoropyridin-3-yl)-4-[(methylamino)methyl]-1H-pyrrol-1-yl}sulfonyl)-2-furoate hydrochloride To a solution of methyl 5-{[4-{[(tert-butoxycarbonyl)(methyl)amino]methyl}-3-fluoro-2-(2-fluoropyridin-3-yl)-1H-pyrrol-1-yl]sulfonyl}-2-furoate (260 mg) in ethyl acetate (2 mL) and 2-propanol (1 mL) was added 4 mol/L hydrogen chloride-ethyl acetate solution (3 mL), and the mixture was stirred at room temperature for 1 hr. The reaction mixture was concentrated under reduced pressure, and the residue was recrystallized from a mixed solvent of ethyl acetate-ethanol to give the title compound as a white solid (yield 177 mg, 78%).

$^1$H-NMR (DMSO-d$_6$) δ: 2.58 (3H, s), 3.88 (3H, s), 4.07 (2H, s), 7.36 (1H, d, J=4.0 Hz), 7.48 (1H, d, J=4.0 Hz), 7.52 (1H, ddd, J=7.3, 5.1, 1.8 Hz), 7.81 (1H, d, J=5.3 Hz), 8.00 (1H, ddd, J=9.6, 7.5, 2.0 Hz), 8.42 (1H, dq, J=4.9, 0.9 Hz), 8.92 (2H, brs).

Example 64

[5-({3-fluoro-2-(2-fluoropyridin-3-yl)-4-[(methylamino)methyl]-1H-pyrrol-1-yl}sulfonyl)-2-furyl]methanol 0.5 fumarate To a solution of tert-butyl [(4-fluoro-5-(2-fluoropyridin-3-yl)-1-{[5-(hydroxymethyl)-2-furyl]sulfonyl}-1H-pyrrol-3-yl)methyl]methylcarbamate (223 mg) in ethyl acetate (2 mL) and 2-propanol (1 mL) was added 4 mol/L hydrogen chloride-ethyl acetate solution (3 mL), and the mixture was stirred at room temperature for 1 hr. The solvent was concentrated under reduced pressure, the residue was diluted with ethyl acetate, and washed with saturated aqueous sodium hydrogen carbonate solution. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=2:3→ethyl acetate) to give the title compound as a free base (basic TLC:R$_f$=0.03 (hexane:ethyl acetate=1:1)) (yield 142 mg). A solution of the obtained free base (141 mg) in ethyl acetate (2 mL) was added dropwise to a solution of fumaric acid (43 mg) in ethanol (2 mL) and the mixture was concentrated under reduced pressure. The residue was recrystallized from a mixed solvent of ethyl acetate-ethanol to give the title compound as a white solid (yield 107 mg, 42%).

$^1$H-NMR (DMSO-d$_6$) δ: 2.33 (3H, s), 3.63 (2H, s), 4.41 (2H, s), 6.51 (1H, s), 6.53 (1H, d, J=3.8 Hz), 7.06 (1H, d, J=3.6 Hz), 7.41-7.51 (2H, m), 7.94 (1H, ddd, J=9.6, 7.5, 2.0 Hz), 8.36 (1H, ddd, J=4.9, 1.9, 0.9 Hz), 3H not detected.

Example 65

[5-({3-fluoro-2-(2-fluoropyridin-3-yl)-4-[(methylamino)methyl]-1H-pyrrol-1-yl}sulfonyl)-2-furyl]methyl acetate fumarate To a solution of tert-butyl [(4-fluoro-5-(2-fluoropyridin-3-yl)-1-{[5-(hydroxymethyl)-2-furyl]sulfonyl}-1H-pyrrol-3-yl)methyl]methylcarbamate (223 mg) in ethyl acetate (2 mL) and 2-propanol (1 mL) was added 4 mol/L hydrogen chloride-ethyl acetate solution (3 mL), and the mixture was stirred at room temperature for 1 hr. The solvent was concentrated under reduced pressure, the residue was diluted with ethyl acetate, and washed with saturated aqueous sodium hydrogen carbonate solution. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent:hexane-ethyl acetate=2:3→ethyl acetate) to give the title compound as a free base (basic TLC:R$_f$=0.22 (hexane:ethyl acetate=1:1)) (yield 42.2 mg). A solution of the obtained free base (42.2 mg) in ethyl acetate (2 mL) was added dropwise to a solution of fumaric acid (11.5 mg) in ethanol (2 mL) and the mixture was concentrated under reduced pressure. The residue was recrystallized from a mixed solvent of ethyl acetate-ethanol to give the title compound as a white solid (yield 37.4 mg, 23%).

$^1$H-NMR (DMSO-d$_6$) δ: 2.27 (3H, s), 2.56 (3H, s), 3.89 (2H, s), 5.25 (2H, s), 6.74 (2H, s), 6.95 (1H, d, J=3.8 Hz), 7.35 (1H, d, J=3.4 Hz), 7.62-7.73 (2H, m), 8.16 (1H, ddd, J=9.5, 7.7, 1.9 Hz), 8.57 (1H, dt, J=4.8, 0.9 Hz), 3H not detected.

Example 66

1-[4-fluoro-1-{[5-(fluoromethyl)-2-furyl]sulfonyl}-5-(2-fluoropyridin-3-yl)-1H-pyrrol-3-yl]-N-methylmethanamine fumarate To a solution of tert-butyl {[4-fluoro-1-{[5-(fluoromethyl)-2-furyl]sulfonyl}-5-(2-fluoropyridin-3-yl)-1H-pyrrol-3-yl]methyl}methylcarbamate (165 mg) in ethyl acetate (2 mL) and 2-propanol (1 mL) was added 4 mol/L hydrogen chloride-ethyl acetate solution (3 mL), and the mixture was stirred at room temperature for 3 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. The combined organic layer was washed with saturated brine, dried over anhydrous magnesium sulfate, and concentrated under reduced pressure. The residue was purified by basic silica gel column chromatography (eluent: hexane-ethyl acetate=1:1→ethyl acetate) to give a free base of the title compound as a colorless oil (yield 114 mg, 87%). A solution of the obtained free base (114 mg) in ethyl acetate (2 mL) was added dropwise to a solution of fumaric acid (34.4 mg) in ethanol (2 mL) and the mixture was concentrated under reduced pressure. The residue was recrystallized from ethanol to give the title compound as a white solid (yield 94.6 mg, 56%).

$^1$H-NMR (DMSO-d$_6$) δ: 2.36 (3H, s), 3.71 (2H, s), 5.39 (2H, d, J=48.0 Hz), 6.54 (2H, s), 6.92 (1H, t, J=4.1 Hz), 7.17 (1H, dd, J=3.6, 1.1 Hz), 7.49 (1H, ddd, J=7.2, 5.0, 1.9 Hz), 7.53 (1H, d, J=5.5 Hz), 7.91-8.00 (1H, m), 8.38 (1H, ddd, J=4.9, 1.9, 0.9 Hz), 3H not detected.

Example 67

5-({3-fluoro-2-(2-fluoropyridin-3-yl)-4-[(methylamino)methyl]-1H-pyrrol-1-yl}sulfonyl)-2-furamide 0.5 fumarate To a solution of tert-butyl {{[1-{[5-(aminocarbonyl)-2-furyl]sulfonyl}-4-fluoro-5-(2-fluoropyridin-3-yl)-1H-pyrrol-3-yl]methyl}methylcarbamate (40.4 mg) in ethyl acetate (1 mL) and 2-propanol (0.5 mL) was added 4 mol/L hydrogen chloride-ethyl acetate solution (1.5 mL), and the mixture was stirred at room temperature for 2 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. The combined organic layer was washed with saturated brine, dried over anhydrous magnesium sulfate, and concentrated under reduced pressure to give a free base of the title compound as a pale-yellow oil (yield 32.3 mg, 99%). A solution of the obtained free base (32.3 mg) in ethyl acetate (1 mL) was added dropwise to a solution of fumaric acid (9.4 mg) in ethanol (1 mL) and the mixture was concentrated under reduced pressure. The residue was recrystallized from a mixed solvent of ethanol-water to give the title compound as a white solid (yield 26.6 mg, 71%).

$^1$H-NMR (DMSO-d$_6$) δ: 2.32 (3H, s), 3.65 (2H, s), 6.51 (1H, s), 7.17 (1H, d, J=3.4 Hz), 7.25 (1H, d, J=3.8 Hz), 7.47 (1H, ddd, J=7.1, 5.1, 1.5 Hz), 7.54 (1H, d, J=5.5 Hz), 7.84 (1H, s), 8.00 (1H, ddd, J=9.3, 7.4, 1.8 Hz), 8.12 (1H, s), 8.36 (1H, dt, J=4.9, 0.8 Hz), 2H not detected.

Example 68

5-({3-fluoro-2-(2-fluoropyridin-3-yl)-4-[(methylamino)methyl]-1H-pyrrol-1-yl}sulfonyl)-2-furonitrile fumarate To a solution of tert-butyl {[1-[(5-cyano-2-furyl)sulfonyl]-4-fluoro-5-(2-fluoropyridin-3-yl)-1H-pyrrol-3-yl]methyl}methylcarbamate (253 mg) in ethyl acetate (2 mL) and 2-propanol (1 mL) was added 4 mol/L hydrogen chloride-ethyl acetate solution (3 mL), and the mixture was stirred at room temperature for 1 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. The combined organic layer was washed with saturated brine, dried over anhydrous magnesium sulfate, and concentrated under reduced pressure. A solution of the residue in ethyl acetate (2 mL) was added dropwise to a solution of fumaric acid (27.6 mg) in ethanol (2 mL) and the mixture was concentrated under reduced pressure. The residue was recrystallized from ethanol to give the title compound as a white solid (yield 59.3 mg, 23%).

$^1$H-NMR (DMSO-d$_6$) δ: 2.36 (3H, s), 3.69 (2H, s), 6.55 (2H, s), 7.46 (1H, d, J=4.0 Hz), 7.47-7.52 (1H, m), 7.55 (1H, d, J=5.7 Hz), 7.81 (1H, d, J=4.0 Hz), 8.02 (1H, ddd, J=9.6, 7.5, 2.0 Hz), 8.39 (1H, dq), 3H not detected.

Example 69

1-[1-{[5-(difluoromethyl)-2-furyl]sulfonyl}-4-fluoro-5-(2-fluoropyridin-3-yl)-1H-pyrrol-3-yl]-N-methylmethanamine hydrochloride To a solution of tert-butyl {[1-{[5-(difluoromethyl)-2-furyl]sulfonyl}-4-fluoro-5-(2-fluoropyridin-3-yl)-1H-pyrrol-3-yl]methyl}methylcarbamate (154 mg) in ethyl acetate (2 mL) and 2-propanol (1 mL) was added 4 mol/L hydrogen chloride-ethyl acetate solution (3 mL), and the mixture was stirred at room temperature for 1.5 hr. The reaction mixture was concentrated under reduced pressure, and the residue was recrystallized from a mixed solution of ethyl acetate-ethanol to give the title compound as a white solid (yield 96.3 mg, 72%).

$^1$H-NMR (DMSO-d$_6$) δ: 2.57 (3H, s), 4.06 (2H, s), 6.96-7.39 (1H, m), 7.14-7.23 (1H, m), 7.30-7.38 (1H, m), 7.51 (1H, ddd, J=7.3, 5.1, 1.9 Hz), 7.83 (1H, d, J=5.7 Hz), 7.96 (1H, ddd, J=9.5, 7.5, 1.9 Hz), 8.41 (1H, ddd, J=4.9, 1.8, 0.8 Hz), 9.02 (2H, brs).

Example 70

1-[5-({3-fluoro-2-(2-fluoropyridin-3-yl)-4-[(methylamino)methyl]-1H-pyrrol-1-yl}sulfonyl)-2-furyl] ethanol hydrochloride To a solution of tert-butyl [(4-fluoro-5-(2-fluoropyridin-3-yl)-1-{[5-(1-hydroxyethyl)-2-furyl]sulfonyl}-1H-pyrrol-3-yl)methyl]methylcarbamate (176 mg) in tetrahydrofuran (2 mL) was added 4 mol/L hydrogen chloride-dioxane solution (3 mL), and the mixture was stirred at room temperature for 6 hr. The reaction mixture was concentrated under reduced pressure, and the residue was recrystallized from a mixed solvent of ethyl acetate-ethanol to give the title compound as a white solid (yield 95.5 mg, 62%).

$^1$H-NMR (DMSO-d$_6$) δ: 1.32 (3H, d, J=6.6 Hz), 2.57 (3H, s), 4.07 (2H, s), 4.69 (1H, dq, J=6.2 Hz), 5.68 (1H, d, J=5.3 Hz), 6.52 (1H, dd, J=3.6, 0.8 Hz), 7.12 (1H, d, J=3.8 Hz), 7.50 (1H, ddd, J=7.3, 5.1, 1.8 Hz), 7.78 (1H, d, J=5.5 Hz), 7.95 (1H, ddd, J=9.5, 7.5, 2.0 Hz), 8.40 (1H, ddd, J=4.9, 1.9, 0.8 Hz), 9.09 (2H, brs).

Example 71

1-[5-({3-fluoro-2-(2-fluoropyridin-3-yl)-4-[(methylamino)methyl]-1H-pyrrol-1-yl}sulfonyl)-2-furyl] ethanone hydrochloride To a solution of tert-butyl {[1-[(5-acetyl-2-furyl)sulfonyl]-4-fluoro-5-(2-fluoropyridin-3-yl)-1H-pyrrol-3-yl]methyl}methylcarbamate (180 mg) in ethyl acetate (2 mL) and 2-propanol (1 mL) was added 4 mol/L hydrogen chloride-ethyl acetate solution (3 mL), and the mixture was stirred at room temperature for 2 hr. The reaction mixture was concentrated under reduced pressure, and the residue was recrystallized from a mixed solvent of ethyl acetate-ethanol to give the title compound as a white solid (yield 82.8 mg, 53%).

$^1$H-NMR (DMSO-d$_6$) δ: 2.46 (3H, s), 2.58 (3H, s), 4.07 (2H, s), 7.39 (1H, d, J=3.8 Hz), 7.52 (1H, ddd, J=7.3, 5.1, 1.9 Hz), 7.59 (1H, d, J=4.0 Hz), 7.84 (1H, d, J=5.5 Hz), 8.02 (1H, ddd, J=9.6, 7.5, 2.0 Hz), 8.42 (1H, ddd, J=4.9, 1.9, 0.9 Hz), 9.04 (2H, brs).

Example 72

1-{4-fluoro-5-(2-fluoropyridin-3-yl)-1-[(2-methylfuran-3-yl)sulfonyl]-1H-pyrrol-3-yl}-N-methylmethanamine hydrochloride tert-Butyl ({4-fluoro-5-(2-fluoropyridin-3-yl)-1-[(2-methyl-3-furyl)sulfonyl]-1H-pyrrol-3-yl}methyl)methylcarbamate (187 mg) was dissolved in ethyl acetate (1 mL) and ethanol (1 mL), and 4 mol/L hydrogen chloride-ethyl acetate solution (2 mL) was added. The mixture was stirred at room temperature for 2 hr, and the reaction mixture was concentrated under reduced pressure. The residue was recrystallized from a mixed solvent of ethyl acetate-ethanol=3:1 to give the title compound as colorless crystals (yield 125 mg, 78%).

$^1$H-NMR (DMSO-$d_6$) δ: 2.09 (3H, s), 2.57 (3H, s), 4.06 (2H, s), 6.49 (1H, d, J=2.3 Hz), 7.48-7.54 (1H, m), 7.77 (1H, d, J=2.1 Hz), 7.86 (1H, d, J=5.5 Hz), 7.89-7.96 (1H, m), 8.38-8.42 (1H, m), 9.25 (2H, brs).

melting point 211-213° C.

Example 73

1-[1-[(5-chloro-2-thienyl)sulfonyl]-4-fluoro-5-(2-fluoropyridin-3-yl)-1H-pyrrol-3-yl]-N-methylmethanamine hydrochloride To a solution of tert-butyl {[1-[(5-chloro-2-thienyl)sulfonyl]-4-fluoro-5-(2-fluoropyridin-3-yl)-1H-pyrrol-3-yl]methyl}methylcarbamate (229 mg) in ethyl acetate (2 mL) and 2-propanol (1 mL) was added 4 mol/L hydrogen chloride-ethyl acetate solution (3 mL), and the mixture was stirred at room temperature for 1 hr. The reaction mixture was concentrated under reduced pressure, and the residue was recrystallized from a mixed solvent of ethyl acetate-ethanol to give the title compound as a white solid (yield 130 mg, 65%).

$^1$H-NMR (DMSO-$d_6$) δ: 2.57 (3H, s), 4.05 (2H, s), 7.35 (1H, d, J=4.1 Hz), 7.47-7.56 (2H, m), 7.85 (1H, d, J=5.5 Hz), 7.99 (1H, ddd, J=9.5, 7.5, 2.0 Hz), 8.37-8.45 (1H, m), 9.11 (2H, brs).

Example 74

1-[1-[(5-bromo-2-thienyl)sulfonyl]-4-fluoro-5-(2-fluoropyridin-3-yl)-1H-pyrrol-3-yl]-N-methylmethanamine hydrochloride To a solution of tert-butyl {[1-[(5-bromo-2-thienyl)sulfonyl]-4-fluoro-5-(2-fluoropyridin-3-yl)-1H-pyrrol-3-yl]methyl}methylcarbamate (248 mg) in ethyl acetate (2 mL) and 2-propanol (1 mL) was added 4 mol/L hydrogen chloride-ethyl acetate solution (3 mL), and the mixture was stirred at room temperature for 1.5 hr. The reaction mixture was concentrated under reduced pressure, and the residue was recrystallized from a mixed solvent of ethyl acetate-ethanol to give the title compound as a white solid (yield 121 mg, 55%).

$^1$H-NMR (DMSO-$d_6$) δ: 2.58 (3H, s), 4.06 (2H, s), 7.41 (1H, d, J=4.2 Hz), 7.44 (1H, d, J=4.2 Hz), 7.53 (1H, ddd, J=7.2, 5.1, 1.7 Hz), 7.81 (1H, d, J=5.3 Hz), 7.99 (1H, ddd, J=9.6, 7.5, 1.9 Hz), 8.41 (1H, d, J=4.9 Hz), 8.98 (2H, brs).

Example 75

1-[1-[(4-bromo-3-thienyl)sulfonyl]-4-fluoro-5-(2-fluoropyridin-3-yl)-1H-pyrrol-3-yl]-N-methylmethanamine hydrochloride To a solution of tert-butyl {[1-[(4-bromo-3-thienyl)sulfonyl]-4-fluoro-5-(2-fluoropyridin-3-yl)-1H-pyrrol-3-yl] methyl}methylcarbamate (195 mg) in ethyl acetate (2 mL) and 2-propanol (1 mL) was added 4 mol/L hydrogen chloride-ethyl acetate solution (3 mL), and the mixture was stirred at room temperature for 4 hr. The reaction mixture was concentrated under reduced pressure, and the residue was recrystallized from a mixed solvent of ethyl acetate-ethanol to give the title compound as a white solid (yield 114 mg, 66%).

$^1$H-NMR (DMSO-$d_6$) δ: 2.58 (3H, s), 4.08 (2H, s), 7.37 (1H, d, J=5.3 Hz), 7.47 (1H, ddd, J=7.3, 5.1, 1.9 Hz), 7.88 (1H, ddd, J=9.5, 7.5, 2.0 Hz), 7.94 (1H, d, J=5.7 Hz), 8.14 (1H, d, J=5.3 Hz), 8.36 (1H, ddd, J=4.9, 1.9, 0.9 Hz), 9.10 (2H, brs).

Example 76

4-({3-fluoro-2-(2-fluoropyridin-3-yl)-4-[(methylamino)methyl]-1H-pyrrol-1-yl}sulfonyl)thiophene-3-carbonitrile hydrochloride To a solution of tert-butyl {[1-[(4-cyano-3-thienyl)sulfonyl]-4-fluoro-5-(2-fluoropyridin-3-yl)-1H-pyrrol-3-yl] methyl}methylcarbamate (181 mg) in ethyl acetate (2 mL) and 2-propanol (1 mL) was added 4 mol/L hydrogen chloride-ethyl acetate solution (3 mL), and the mixture was stirred at room temperature for 1 hr. The reaction mixture was concentrated under reduced pressure, and the residue was recrystallized from a mixed solvent of ethyl acetate-ethanol to give the title compound as a white solid (yield 116 mg, 74%).

$^1$H-NMR (DMSO-$d_6$) δ: 2.58 (3H, s), 4.09 (2H, s), 7.52 (1H, ddd, J=7.3, 5.1, 1.9 Hz), 7.76 (1H, d, J=5.1 Hz), 7.90 (1H, d, J=5.5 Hz), 7.99 (1H, ddd, J=9.6, 7.5, 2.0 Hz), 8.35 (1H, d, J=5.1 Hz), 8.41 (1H, ddd, J=4.9, 1.9, 0.9 Hz), 9.06 (2H, brs).

Example 77

Methyl 3-({3-fluoro-2-(2-fluoropyridin-3-yl)-4-[(methylamino)methyl]-1H-pyrrol-1-yl}sulfonyl) thiophene-2-carboxylate fumarate To a solution of methyl 3-{[4-{[(tert-butoxycarbonyl)(methyl)amino]methyl}-3-fluoro-2-(2-fluoropyridin-3-yl)-1H-pyrrol-1-yl]sulfonyl}thiophene-2-carboxylate (155 mg) in ethyl acetate (2 mL) and 2-propanol (1 mL) was added 4 mol/L hydrogen chloride-ethyl acetate solution (3 mL), and the mixture was stirred at room temperature for 1 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. The combined organic layer was washed with saturated brine, dried over anhydrous magnesium sulfate, and concentrated under reduced pressure to give a free base of the title compound as a colorless oil (yield 124 mg, 98%). A solution of the obtained free base (124 mg) in ethyl acetate (2 mL) was added dropwise to a solution of fumaric acid (32.9 mg) in ethanol (2 mL) and the mixture was concentrated under reduced pressure. The residue was recrystallized from a mixed solvent of ethyl acetate and ethanol to give the title compound as a white solid (yield 134 mg, 85%).

$^1$H-NMR (DMSO-$d_6$) δ: 2.42 (3H, s), 3.76 (2H, s), 3.81 (3H, s), 6.53 (2H, s), 6.61 (1H, d, J=5.3 Hz), 7.40 (1H, ddd, J=7.3, 5.1, 1.9 Hz), 7.62 (1H, d, J=5.7 Hz), 7.83 (1H, ddd, J=9.5, 7.4, 1.9 Hz), 7.92 (1H, d, J=5.3 Hz), 8.31 (1H, ddd, J=4.9, 1.9, 0.8 Hz), 3H not detected.

Example 78

1-{5-(2-fluoropyridin-3-yl)-1-[(5-isoxazol-5-yl-2-thienyl)sulfonyl]-1H-pyrrol-3-yl}-N-methylmethanamine hydrochloride tert-Butyl ({5-(2-fluoropyridin-3-yl)-1-[(5-isoxazol-5-yl-2-thienyl)sulfonyl]-1H-pyrrol-3-yl}methyl)methylcarbamate (80 mg) was dissolved in ethanol (5 mL), 4 mol/L hydrogen chloride-ethyl acetate solution (5 mL) was added, and the mixture was stirred at 50° C. for 30 min. The reaction mixture was concentrated under reduced pressure, and the residue was crystallized from a mixed solvent of ethyl acetate-diethyl ether (1:1) to give the title compound as colorless crystals (yield 23 mg, 33%).

$^1$H-NMR (DMSO-$d_6$) δ: 2.54 (3H, brs), 4.02 (2H, brs), 6.69 (1H, d, J=1.9 Hz), 7.21 (1H, d, J=1.9 Hz), 7.44-7.51 (1H, m), 7.64 (1H, d, J=4.2 Hz), 7.78 (1H, d, J=4.2 Hz), 7.82 (1H, d, J=1.9 Hz), 7.83-7.91 (1H, m), 8.35-8.39 (1H, m), 8.78 (1H, d, J=1.9 Hz), 8.97 (2H, brs).

Example 79

1-{1-[(1-ethyl-1H-pyrazol-4-yl)sulfonyl]-4-fluoro-5-(2-fluoropyridin-3-yl)-1H-pyrrol-3-yl}-N-methylmethanamine hydrochloride tert-Butyl {[1-[(1-ethyl-1H-pyrazol-4-yl)sulfonyl]-4-fluoro-5-(2-fluoropyridin-3-yl)-1H-pyrrol-3-yl]methyl}methylcarbamate (290 mg) was dissolved in ethanol (5 mL), 4 mol/L hydrogen chloride-ethyl acetate solution (5 mL) was added, and the mixture was stirred at 40° C. for 30 min. The reaction mixture was concentrated under reduced pressure, and the residue was crystallized from ethyl acetate to give the title compound as colorless crystals (yield 196 mg, 78%).

$^1$H-NMR (DMSO-$d_6$) δ: 1.34 (3H, t, J=7.2 Hz), 2.57 (3H, s), 4.05 (2H, s), 4.14 (2H, q, J=7.2 Hz), 7.46-7.53 (1H, m), 7.66 (1H, s), 7.79 (1H, d, J=5.7 Hz), 7.84-7.94 (1H, m), 8.30 (1H, s), 8.37-8.42 (1H, m), 9.19 (2H, brs).

Example 80

1-{1-[(1,5-dimethyl-1H-pyrazol-4-yl)sulfonyl]-4-fluoro-5-(2-fluoropyridin-3-yl)-1H-pyrrol-3-yl}-N-methylmethanamine hydrochloride tert-Butyl {[1-[(1,5-dimethyl-1H-pyrazol-4-yl)sulfonyl]-4-fluoro-5-(2-fluoropyridin-3-yl)-1H-pyrrol-3-yl]methyl}methylcarbamate (290 mg) was dissolved in ethanol (5 mL), 4 mol/L hydrogen chloride-ethyl acetate solution (5 mL) was added, and the mixture was stirred at 40° C. for 30 min. The reaction mixture was concentrated under reduced pressure, and the residue was crystallized from ethyl acetate to give the title compound as colorless crystals (yield 178 mg, 71%).

$^1$H-NMR (DMSO-$d_6$) δ: 2.14 (3H, s), 2.57 (3H, s), 3.74 (3H, s), 4.04 (2H, s), 7.38 (1H, s), 7.45-7.52 (1H, m), 7.83 (1H, d, J=5.7 Hz), 7.85-7.92 (1H, m), 8.36-8.41 (1H, m), 9.19 (2H, brs).

Example 81

1-[1-{[1-(difluoromethyl)-1H-pyrazol-4-yl]sulfonyl}-4-fluoro-5-(2-fluoropyridin-3-yl)-1H-pyrrol-3-yl]-N-methylmethanamine hydrochloride tert-Butyl {[1-{[1-(difluoromethyl)-1H-pyrazol-4-yl]sulfonyl}-4-fluoro-5-(2-fluoropyridin-3-yl)-1H-pyrrol-3-yl]methyl}methylcarbamate (380 mg) was dissolved in ethanol (10 mL), 4 mol/L hydrogen chloride-ethyl acetate solution (10 mL) was added, and the mixture was stirred at 40° C. for 30 min. The reaction mixture was concentrated under reduced pressure, and the residue was crystallized from ethyl acetate to give the title compound as colorless crystals (yield 240 mg, 72%).

$^1$H-NMR (DMSO-$d_6$) δ: 2.57 (3H, s), 4.06 (2H, s), 7.47-7.54 (1H, m), 7.67-8.07 (3H, m), 8.11 (1H, s), 8.37-8.42 (1H, m), 8.94 (1H, s), 9.32 (2H, brs).

melting point 205-207° C.

Example 82

1-{4-fluoro-5-(2-fluoropyridin-3-yl)-1-[(1-methyl-1H-imidazol-2-yl)sulfonyl]-1H-pyrrol-3-yl}-N-methylmethanamine hydrochloride tert-Butyl ({4-fluoro-5-(2-fluoropyridin-3-yl)-1-[(1-methyl-1H-imidazol-2-yl)sulfonyl]-1H-pyrrol-3-yl}methyl)methylcarbamate (229 mg) was dissolved in ethyl acetate (1 mL) and ethanol (1 mL), 4 mol/L hydrogen chloride-ethyl acetate solution (2 mL) was added, and the mixture was stirred at room temperature for 2 hr. The reaction mixture was concentrated under reduced pressure, and the residue was recrystallized from a mixed solvent of ethyl acetate-ethanol=1:10 to give the title compound as colorless crystals (yield 174 mg, 88%).

$^1$H-NMR (DMSO-$d_6$) δ: 2.58 (3H, s), 3.61 (3H, s), 4.07 (2H, s), 7.13-7.15 (1H, m), 7.43-7.49 (1H, m), 7.56-7.59 (1H, m), 7.76-7.84 (1H, m), 7.87 (1H, d, J=5.3 Hz), 8.34-8.42 (1H, m), 9.15 (2H, brs).

Example 83

1-[4-fluoro-5-(2-fluoropyridin-3-yl)-1-(1,3-thiazol-2-ylsulfonyl)-1H-pyrrol-3-yl]-N-methylmethanamine hydrochloride tert-Butyl {[4-fluoro-5-(2-fluoropyridin-3-yl)-1-(1,3-thiazol-2-ylsulfonyl)-1H-pyrrol-3-yl]methyl}methylcarbamate (220 mg) was dissolved in ethyl acetate (2 mL) and ethanol (2 mL), and 4 mol/L hydrogen chloride-ethyl acetate solution (4 mL) was added. After stirring at room temperature for 2 hr, the reaction mixture was concentrated under reduced pressure, and the residue was recrystallized from a mixed solvent of ethyl acetate-ethanol=1:2 to give the title compound as colorless crystals (yield 82.8 mg, 44%).

$^1$H-NMR (DMSO-$d_6$) δ: 2.56 (3H, s), 4.06 (2H, s), 7.41-7.53 (1H, m), 7.87-7.92 (1H, m), 7.92-8.00 (1H, m), 8.17 (1H, d, J=3.0 Hz), 8.36 (1H, d, J=3.0 Hz), 8.37-8.42 (1H, m), 9.15 (2H, brs).

Example 84

1-{4-fluoro-5-(2-fluoropyridin-3-yl)-1-[(6-methoxypyridin-3-yl)sulfonyl]-1H-pyrrol-3-yl}-N-methylmethanamine fumarate tert-Butyl ({4-fluoro-5-(2-fluoropyridin-3-yl)-1-[(6-methoxypyridin-3-yl)sulfonyl]-1H-pyrrol-3-yl}methyl)methylcarbamate (124 mg) was dissolved in ethyl acetate (1 mL) and ethanol (1 mL), and 4 mol/L hydrogen chloride-ethyl acetate solution (2 mL) was added. After stirring at room temperature for 2 hr, the reaction mixture was concentrated under reduced pressure. Saturated aqueous sodium hydrogen carbonate solution was added to the residue and the mixture was extracted with ethyl acetate. The extract was washed with saturated brine, dried over anhydrous sodium sulfate, and concentrated under reduced pressure to give the title compound as a free base (57.1 mg). A solution of the obtained free base (57.1 mg) in ethyl acetate (2 mL) was added dropwise to a solution of fumaric acid (24 mg) in ethanol (2 mL), and the mixture was concentrated under reduced pressure. The obtained crystal was recrystallized from a mixed solvent of ethanol-water=20:1 to give the title compound as colorless crystals (yield 24.4 mg, 33%).

$^1$H-NMR (DMSO-$d_6$) δ: 2.38 (3H, s), 3.72 (2H, brs), 3.94 (3H, s), 6.53 (2H, s), 6.99 (1H, d, J=8.7 Hz), 7.46-7.53 (1H, m), 7.66 (1H, d, J=5.7 Hz), 7.74 (1H, dd, J=8.9, 2.8 Hz), 7.87-7.95 (1H, m), 8.25 (1H, d, J=2.7 Hz), 8.36-8.41 (1H, m), 3H not detected.

Example 85

1-[4-fluoro-5-(2-fluoropyridin-3-yl)-1-(pyridin-2-ylsulfonyl)-1H-pyrrol-3-yl]-N-methylmethanamine hydrochloride tert-Butyl {[4-fluoro-5-(2-fluoropyridin-3-yl)-1-(pyridin-2-ylsulfonyl)-1H-pyrrol-3-yl]methyl}methylcarbamate (221 mg) was dissolved in ethyl acetate (2 mL) and ethanol (2 mL), and 4 mol/L hydrogen chloride-ethyl acetate solution (4 mL) was added. After stirring at room temperature for 2 hr, the reaction mixture was concentrated under reduced pressure, and the residue was recrystallized from a mixed solvent of ethyl acetate-ethanol=3:1 to give the title compound as colorless crystals (yield 175 mg, 92%).

$^1$H-NMR (DMSO-$d_6$) δ: 2.56 (3H, s), 4.06 (2H, s), 7.42-7.48 (1H, m), 7.72-7.92 (4H, m), 8.07-8.15 (1H, m), 8.33-8.38 (1H, m), 8.70-8.74 (1H, m), 9.18 (2H, brs).

melting point 187-188° C.

Example 86

1-[1-[(2-chloropyridin-3-yl)sulfonyl]-4-fluoro-5-(2-fluoropyridin-3-yl)-1H-pyrrol-3-yl]-N-methylmethanamine hydrochloride tert-Butyl {[1-[(2-chloropyridin-3-yl)sulfonyl]-4-fluoro-5-(2-fluoropyridin-3-yl)-1H-pyrrol-3-yl]methyl}methylcarbamate (100 mg) was dissolved in ethyl acetate (1 mL) and ethanol (1 mL), and 4 mol/L hydrogen chloride-ethyl acetate solution (2 mL) was added. After stirring at room temperature for 2 hr, the reaction mixture was concentrated under reduced pressure, and the residue was recrystallized from a mixed solvent of ethyl acetate-ethanol=1:5 to give the title compound as colorless crystals (yield 78 mg, 90%).

$^1$H-NMR (DMSO-$d_6$) δ: 2.59 (3H, s), 4.09 (2H, s), 7.40-7.48 (1H, m), 7.52 (1H, dd, J=8.0, 4.5 Hz), 7.72-7.79 (1H, m), 7.81-7.91 (1H, m), 7.93-8.02 (1H, m), 8.32-8.36 (1H, m), 8.75 (1H, dd, J=4.7, 1.7 Hz), 9.21 (2H, brs).

Example 87

2-({3-fluoro-2-(2-fluoropyridin-3-yl)-4-[(methylamino)methyl]-1H-pyrrol-1-yl}sulfonyl)benzonitrile hydrochloride tert-Butyl {[1-[(2-cyanophenyl)sulfonyl]-4-fluoro-5-(2-fluoropyridin-3-yl)-1H-pyrrol-3-yl]methyl}methylcarbamate (238 mg) was dissolved in ethyl acetate (1 mL) and ethanol (1 mL), and 4 mol/L hydrogen chloride-ethyl acetate solution (2 mL) was added. After stirring at room temperature for 2 hr, the reaction mixture was concentrated under reduced pressure, and the residue was recrystallized from a mixed solvent of ethyl acetate-ethanol=3:1 to give the title compound as colorless crystals (yield 186 mg, 90%).

$^1$H-NMR (DMSO-$d_6$) δ: 2.58 (3H, s), 4.08 (2H, s), 7.42-7.49 (1H, m), 7.51-7.57 (1H, m), 7.80-7.89 (2H, m), 7.94-8.01 (2H, m), 8.19 (1H, dd, J=7.6, 1.2 Hz), 8.34-8.39 (1H, m), 9.23 (2H, brs).

Example 88

4-({3-fluoro-2-(2-fluoropyridin-3-yl)-4-[(methylamino)methyl]-1H-pyrrol-1-yl}sulfonyl)phenol hydrochloride tert-Butyl ({4-fluoro-5-(2-fluoropyridin-3-yl)-1-[(4-hydroxyphenyl)sulfonyl]-1H-pyrrol-3-yl}methyl)methylcarbamate (300 mg) was dissolved in ethanol (5 mL), 4 mol/L hydrogen chloride-ethyl acetate solution (5 mL) was added, and the mixture was stirred at 40° C. for 30 min. The reaction mixture was concentrated under reduced pressure, and the residue was crystallized from ethyl acetate, and further recrystallized from a mixed solvent of ethyl acetate-methanol (4:1) to give the title compound as colorless crystals (yield 208 mg, 81%).

$^1$H-NMR (DMSO-$d_6$) δ: 2.55 (3H, brs), 4.03 (2H, brs), 6.79-6.94 (2H, m), 7.17-7.35 (2H, m), 7.41-7.54 (1H, m), 7.75-7.91 (2H, m), 8.38 (1H, dd, J=4.7, 1.0 Hz), 9.24 (2H, brs), 11.13 (1H, s).

Example 89

1-[4-fluoro-5-(2-fluoropyridin-3-yl)-1-(morpholin-4-ylsulfonyl)-1H-pyrrol-3-yl]-N-methylmethanamine hydrochloride tert-Butyl {[4-fluoro-5-(2-fluoropyridin-3-yl)-1-(morpholin-4-ylsulfonyl)-1H-pyrrol-3-yl]methyl}methylcarbamate (370 mg) was dissolved in ethanol (5 mL), 4 mol/L hydrogen chloride-ethyl acetate solution (5 mL) was added, and the mixture was stirred at 50° C. for 30 min. The reaction mixture was concentrated under reduced pressure, and the residue was crystallized from a mixed solvent of ethyl acetate-ethanol (9:1) to give the title compound as colorless crystals (yield 105 mg, 33%).

$^1$H-NMR (DMSO-$d_6$) δ: 2.60 (3H, brs), 2.86-3.05 (4H, m), 3.45-3.62 (4H, m), 4.07 (2H, brs), 7.45-7.55 (1H, m), 7.67 (1H, d, J=5.7 Hz), 8.05-8.20 (1H, m), 8.29-8.44 (1H, m), 9.21 (2H, brs).

Example 90

1-[4-fluoro-5-(2-fluoropyridin-3-yl)-1-(pyrrolidin-1-ylsulfonyl)-1H-pyrrol-3-yl]-N-methylmethanamine hydrochloride tert-Butyl {[4-fluoro-5-(2-fluoropyridin-3-yl)-1-(pyrrolidin-1-ylsulfonyl)-1H-pyrrol-3-yl]methyl}methylcarbamate (260 mg) was dissolved in ethanol (5 mL), 4 mol/L hydrogen chloride-ethyl acetate solution (5 mL) was added, and the mixture was stirred at 40° C. for 30 min. The reaction mixture was concentrated under reduced pressure, and the residue was crystallized from ethyl acetate to give the title compound as colorless crystals (yield 148 mg, 66%).

¹H-NMR (DMSO-d₆) δ: 1.67-1.78 (4H, m), 2.58 (3H, s), 2.95-3.10 (4H, m), 4.05 (2H, s), 7.42-7.58 (1H, m), 7.68 (1H, d, J=5.3 Hz), 8.06-8.14 (1H, m), 8.34-8.40 (1H, m), 9.18 (2H, brs).

Example 91

1-[5-(2-fluoropyridin-3-yl)-1-(1,3-thiazol-2-ylsulfonyl)-1H-pyrrol-3-yl]-N-methylmethanamine hydrochloride tert-Butyl {[5-(2-fluoropyridin-3-yl)-1-(1,3-thiazol-2-yl-sulfonyl)-1H-pyrrol-3-yl]methyl}methylcarbamate (168 mg) was dissolved in ethyl acetate (2 mL) and ethanol (2 mL), and 4 mol/L hydrogen chloride-ethyl acetate solution (4 mL) was added. After stirring at room temperature for 2 hr, the reaction mixture was concentrated under reduced pressure, and the residue was recrystallized from a mixed solvent of ethyl acetate-ethanol=1:3 to give the title compound as colorless crystals (yield 101 mg, 70%).
¹H-NMR (DMSO-d₆) δ: 2.52 (3H, s), 4.02 (2H, s), 6.72 (1H, d, J=1.9 Hz), 7.40-7.47 (1H, m), 7.78-7.85 (2H, m), 8.15 (1H, d, J=3.0 Hz), 8.33 (1H, d, J=3.0 Hz), 8.34-8.36 (1H, m), 8.98 (2H, brs).

Example 92

3-{1-(2-furylsulfonyl)-4-[(methylamino)methyl]-1H-pyrrol-2-yl}pyridine-2-carbonitrile hydrochloride To a solution of tert-butyl {[5-(2-cyanopyridin-3-yl)-1-(2-furylsulfonyl)-1H-pyrrol-3-yl]methyl}methylcarbamate (193 mg) in ethyl acetate (2 mL) and 2-propanol (1 mL) was added 4 mol/L hydrogen chloride-ethyl acetate solution (3 mL), and the mixture was stirred at room temperature for 2 hr. The reaction mixture was concentrated under reduced pressure, and the residue was recrystallized from ethanol to give the title compound as a white solid (yield 127 mg, 77%).
¹H-NMR (DMSO-d₆) δ: 2.52 (3H, s), 4.05 (2H, s), 6.75 (1H, dd, J=3.8, 1.9 Hz), 6.83 (1H, d, J=1.9 Hz), 7.14 (1H, dd, J=3.7, 0.8 Hz), 7.78-7.85 (2H, m), 7.98 (1H, dd, J=8.0, 1.6 Hz), 8.11 (1H, dd, J=1.8, 0.8 Hz), 8.83 (1H, dd, J=4.7, 1.5 Hz), 8.97 (2H, brs).

Example 93

3-{1-(3-furylsulfonyl)-4-[(methylamino)methyl]-1H-pyrrol-2-yl}pyridine-2-carbonitrile hydrochloride To a solution of tert-butyl {[5-(2-cyanopyridin-3-yl)-1-(3-furylsulfonyl)-1H-pyrrol-3-yl]methyl}methylcarbamate (175 mg) in ethyl acetate (2 mL) and 2-propanol (1 mL) was added 4 mol/L hydrogen chloride-ethyl acetate solution (3 mL), and the mixture was stirred at room temperature for 2 hr. The reaction mixture was concentrated under reduced pressure, and the residue was recrystallized from ethanol to give the title compound as a white solid (yield 126 mg, 84%).
¹H-NMR (DMSO-d₆) δ: 2.53 (3H, s), 4.04 (2H, s), 6.67 (1H, dd, J=2.1, 0.9 Hz), 6.80 (1H, d, J=1.7 Hz), 7.80 (1H, dd, J=8.1, 4.7 Hz), 7.84 (1H, d, J=1.7 Hz), 7.91-7.98 (2H, m), 8.28 (1H, dd, J=1.6, 0.8 Hz), 8.82 (1H, dd, J=4.7, 1.5 Hz), 9.04 (2H, brs).

Example 94

3-[4-[(methylamino)methyl]-1-(2-thienylsulfonyl)-1H-pyrrol-2-yl]pyridine-2-carbonitrile hydrochloride To a solution of tert-butyl {[5-(2-cyanopyridin-3-yl)-1-(2-thienylsulfonyl)-1H-pyrrol-3-yl]methyl}methylcarbamate (195 mg) in ethyl acetate (2 mL) and 2-propanol (1 mL) was added 4 mol/L hydrogen chloride-ethyl acetate solution (3 mL), and the mixture was stirred at room temperature for 2 hr. The reaction mixture was concentrated under reduced pressure, and the residue was recrystallized from ethanol to give the title compound as a white solid (yield 140 mg, 84%).
¹H-NMR (DMSO-d₆) δ: 2.49 (3H, s), 4.04 (2H, s), 6.80 (1H, d, J=1.7 Hz), 7.20 (1H, dd, J=4.9, 4.0 Hz), 7.48 (1H, dd, J=3.9, 1.4 Hz), 7.82 (1H, dd, J=8.0, 4.8 Hz), 7.87 (1H, d, J=1.7 Hz), 7.96 (1H, dd, J=8.0, 1.6 Hz), 8.17 (1H, dd, J=5.0, 1.4 Hz), 8.83 (1H, dd, J=4.7, 1.5 Hz), 8.96 (2H, brs).

Example 95

3-[4-[(methylamino)methyl]-1-(3-thienylsulfonyl)-1H-pyrrol-2-yl]pyridine-2-carbonitrile hydrochloride To a solution of tert-butyl {[5-(2-cyanopyridin-3-yl)-1-(3-thienylsulfonyl)-1H-pyrrol-3-yl]methyl}methylcarbamate (201 mg) in ethyl acetate (2 mL) and 2-propanol (1 mL) was added 4 mol/L hydrogen chloride-ethyl acetate solution (3 mL), and the mixture was stirred at room temperature for 2 hr. The reaction mixture was concentrated under reduced pressure, and the residue was recrystallized from a mixed solvent of ethanol-water to give the title compound as a white solid (yield 134 mg, 78%).
¹H-NMR (DMSO-d₆) δ: 2.52 (3H, s), 4.05 (2H, s), 6.76 (1H, d, J=1.5 Hz), 7.10 (1H, dd, J=5.1, 1.3 Hz), 7.76-7.83 (2H, m), 7.84-7.91 (2H, m), 8.09 (1H, dd, J=2.8, 1.3 Hz), 8.82 (1H, dd, J=4.7, 1.7 Hz), 8.96 (2H, brs).

Example 96

3-{1-[(2,6-difluorophenyl)sulfonyl]-4-[(methylamino)methyl]-1H-pyrrol-2-yl}pyridine-2-carbonitrile hydrochloride To a solution of tert-butyl ({5-(2-cyanopyridin-3-yl)-1-[(2,6-difluorophenyl)sulfonyl]-1H-pyrrol-3-yl}methyl)methylcarbamate (213 mg) in ethyl acetate (2 mL) and 2-propanol (1 mL) was added 4 mol/L hydrogen chloride-ethyl acetate solution (3 mL), and the mixture was stirred at room temperature for 2 hr. The reaction mixture was concentrated under reduced pressure, and the residue was recrystallized from ethanol to give the title compound as a white solid (yield 160 mg, 86%).
¹H-NMR (DMSO-d₆) δ: 2.53 (3H, s), 4.08 (2H, s), 6.83 (1H, d, J=1.5 Hz), 7.31 (2H, t, J=8.9 Hz), 7.78 (1H, dd, J=8.1, 4.7 Hz), 7.84-7.97 (3H, m), 8.81 (1H, dd, J=4.9, 1.5 Hz), 8.97 (2H, brs).

Example 97

3-{1-[(2,4-difluorophenyl)sulfonyl]-4-[(methylamino)methyl]-1H-pyrrol-2-yl}pyridine-2-carbonitrile hydrochloride To a solution of tert-butyl ({5-(2-cyanopyridin-3-yl)-1-[(2,4-difluorophenyl)sulfonyl]-1H-pyrrol-3-yl}methyl)methylcarbamate (208 mg) in ethyl acetate (2 mL) and 2-propanol (1 mL) was added 4 mol/L hydrogen chloride-ethyl acetate solution (3 mL), and the mixture was stirred at room temperature for 2 hr. The reaction mixture was concentrated under reduced pressure, and the residue was recrystallized from ethanol to give the title compound as a white solid (yield 134 mg, 74%).

¹H-NMR (DMSO-d$_6$) δ: 2.52 (3H, s), 4.07 (2H, s), 6.82 (1H, d, J=1.9 Hz), 7.20-7.28 (1H, m), 7.28-7.38 (1H, m), 7.69 (1H, ddd, J=11.1, 9.0, 2.3 Hz), 7.75-7.82 (1H, m), 7.86-7.93 (2H, m), 8.81 (1H, dd, J=4.9, 1.5 Hz), 9.03 (2H, brs).

Example 98

3-{4-[(methylamino)methyl]-1-[(2-methylphenyl)sulfonyl]-1H-pyrrol-2-yl}pyridine-2-carbonitrile hydrochloride To a solution of tert-butyl ({5-(2-cyanopyridin-3-yl)-1-[(2-methylphenyl)sulfonyl]-1H-pyrrol-3-yl}methyl)methylcarbamate (202 mg) in ethyl acetate (2 mL) and 2-propanol (1 mL) was added 4 mol/L hydrogen chloride-ethyl acetate solution (3 mL), and the mixture was stirred at room temperature for 2 hr. The reaction mixture was concentrated under reduced pressure, and the residue was recrystallized from a mixed solvent of ethanol-water to give the title compound as a white solid (yield 157 mg, 90%).

¹H-NMR (DMSO-d$_6$) δ: 2.30 (3H, s), 2.55 (3H, s), 4.09 (2H, s), 6.78 (1H, d, J=1.9 Hz), 7.04 (1H, dd, J=8.0, 1.5 Hz), 7.14 (1H, t, J=8.0 Hz), 7.44 (1H, d, J=7.6 Hz), 7.62 (1H, ddd, J=7.6, 1.5 Hz), 7.69-7.76 (1H, m), 7.84 (1H, dd, J=8.1, 1.7 Hz), 7.96 (1H, d, J=1.9 Hz), 8.71 (1H, dd, J=4.7, 1.7 Hz), 8.94 (2H, brs).

Example 99

3-{1-[(2-chlorophenyl)sulfonyl]-4-[(methylamino)methyl]-1H-pyrrol-2-yl}pyridine-2-carbonitrile hydrochloride To a solution of tert-butyl {[1-[(2-chlorophenyl)sulfonyl]-5-(2-cyanopyridin-3-yl)-1H-pyrrol-3-yl]methyl}methylcarbamate (211 mg) in ethyl acetate (2 mL) and 2-propanol (1 mL) was added 4 mol/L hydrogen chloride-ethyl acetate solution (3 mL), and the mixture was stirred at room temperature for 2 hr. The reaction mixture was concentrated under reduced pressure, and the residue was recrystallized from a mixed solvent of ethanol-water to give the title compound as a white solid (yield 144 mg, 78%).

¹H-NMR (DMSO-d$_6$) δ: 2.54 (3H, s), 4.09 (2H, s), 6.79 (1H, d, J=1.9 Hz), 7.18-7.25 (1H, m), 7.28-7.39 (1H, m), 7.67-7.80 (3H, m), 7.80-7.88 (1H, m), 7.96 (1H, d, J=1.9 Hz), 8.74 (1H, dd, J=4.7, 1.7 Hz), 8.91 (2H, brs).

Example 100

3-{1-[(2-fluorophenyl)sulfonyl]-4-[(methylamino)methyl]-1H-pyrrol-2-yl}pyridine-2-carbonitrile hydrochloride To a solution of tert-butyl {[1-[(2-fluorophenyl)sulfonyl]-5-(2-cyanopyridin-3-yl)-1H-pyrrol-3-yl]methyl}methylcarbamate (218 mg) in ethyl acetate (2 mL) and 2-propanol (1 mL) was added 4 mol/L hydrogen chloride-ethyl acetate solution (3 mL), and the mixture was stirred at room temperature for 2.5 hr. The reaction mixture was concentrated under reduced pressure, and the residue was recrystallized from ethanol to give the title compound as a white solid (yield 147 mg, 78%).

¹H-NMR (DMSO-d$_6$) δ: 2.54 (3H, s), 4.08 (2H, brs), 6.81 (1H, d, J=1.5 Hz), 7.19-7.27 (1H, m), 7.27-7.35 (1H, m), 7.51 (1H, dd, J=10.6, 8.3 Hz), 7.73-7.81 (1H, m), 7.81-7.93 (3H, m), 8.79 (1H, dd, J=4.5, 1.5 Hz), 9.01 (2H, brs).

Example 101

3-{1-[(2-cyanophenyl)sulfonyl]-4-[(methylamino)methyl]-1H-pyrrol-2-yl}pyridine-2-carbonitrile hydrochloride tert-Butyl {[1-[(2-cyanophenyl)sulfonyl]-5-(2-cyanopyridin-3-yl)-1H-pyrrol-3-yl]methyl}methylcarbamate (239 mg) was dissolved in ethyl acetate (2 mL) and ethanol (2 mL), and 4 mol/L hydrogen chloride-ethyl acetate solution (4 mL) was added. After stirring at room temperature for 2 hr, the reaction mixture was concentrated under reduced pressure, and the residue was recrystallized from ethanol to give the title compound (yield 185 mg, yield 89%).

¹H-NMR (DMSO-d$_6$) δ: 2.53 (3H, s), 4.08 (2H, s), 6.84 (1H, d, J=1.9 Hz), 7.42-7.47 (1H, m), 7.75-7.84 (2H, m), 7.89-8.01 (3H, m), 8.16-8.21 (1H, m), 8.80 (1H, dd, J=4.7, 1.7 Hz), 8.95 (2H, br).

Example 102

3-{1-[(6-methoxypyridin-3-yl)sulfonyl]-4-[(methylamino)methyl]-1H-pyrrol-2-yl}pyridine-2-carbonitrile hydrochloride tert-Butyl ({5-(2-cyanopyridin-3-yl)-1-[(6-methoxypyridin-3-yl)sulfonyl]-1H-pyrrol-3-yl}methyl)methylcarbamate (235 mg) was dissolved in ethyl acetate (2 mL) and ethanol (2 mL), and 4 mol/L hydrogen chloride-ethyl acetate solution (4 mL) was added. After stirring at room temperature for 2 hr, the reaction mixture was concentrated under reduced pressure, and the residue was recrystallized from ethanol to give the title compound as colorless crystals (yield 161 mg, 79%).

¹H-NMR (DMSO-d$_6$) δ: 2.51 (3H, s), 3.93 (3H, s), 4.03 (2H, s), 6.79 (1H, d, J=1.9 Hz), 7.00 (1H, d, J=9.1 Hz), 7.76 (1H, dd, J=9.1, 2.7 Hz), 7.80-7.86 (1H, m), 7.90-7.97 (2H, m), 8.20 (1H, d, J=2.7 Hz), 8.84 (1H, dd, J=4.9, 1.5 Hz), 9.06 (2H, brs).

Example 103

1-methyl-3-{4-[(methylamino)methyl]-1-(phenylsulfonyl)-1H-pyrrol-2-yl}pyridin-2(1H)-one hydrochloride tert-Butyl methyl{[5-(1-methyl-2-oxo-1,2-dihydropyridin-3-yl)-1-(phenylsulfonyl)-1H-pyrrol-3-yl]methyl}carbamate (9.9 mg) was dissolved in ethyl acetate (0.5 mL) and ethanol (0.5 mL), and 4 mol/L hydrogen chloride-ethyl acetate solution (1 mL) was added. After stirring at room temperature for 2 hr, the reaction mixture was concentrated under reduced pressure. The residue was solidified with diisopropyl ether to give the title compound as a pale-gray solid (yield 5.7 mg, 78%).

¹H-NMR (DMSO-d$_6$) δ: 2.50 (3H, s), 3.40 (3H, s), 3.95 (2H, brs), 6.24 (1H, t, J=6.8 Hz), 6.36 (1H, d, J=1.9 Hz), 7.18 (1H, dd, J=6.8, 2.1 Hz), 7.55-7.77 (6H, m), 7.80 (1H, dd, J=6.8, 2.1 Hz), 8.91 (2H, brs).

Example 104

3-{4-[(dimethylamino)methyl]-1-(phenylsulfonyl)-1H-pyrrol-2-yl}-1-methylpyridin-2(1H)-one hydrochloride To a solution (8 mL) of tert-butyl {[5-(2-fluoropyridin-3-yl)-1-(phenylsulfonyl)-1H-pyrrol-3-yl]methyl}methylcarbamate (214 mg) in 1,2-dichloroethane was added dropwise dimethyl sulfate (0.27 mL) under ice-cooling, and the mixture was stirred at 80° C. for 18 hr. The reaction mixture was cooled to room temperature, triethylamine (1.41 mL), acetic acid (0.94 mL) and ethanol (0.94 mL) were added and the mixture was heated under reflux for 2 hr. After cooling, the mixture was diluted with ethyl acetate and saturated aqueous sodium hydrogen carbonate solution, and extracted with ethyl acetate. The separated aqueous layer was extracted again with ethyl acetate. The combined organic layer was washed with saturated brine, dried over anhydrous sodium sulfate, and concentrated under reduced pressure. The residue was purified by basic silica gel column chromatography (eluent: methanol-ethyl acetate=1:99→3:17) (basic TLC:$R_f$=0.2 (chloroform:methanol=10:1)) to give a free base of the title compound as a pale-yellow oil (yield 34.9 mg). The obtained free base (34.9 mg) was dissolved in ethyl acetate (1 mL) and ethanol (1 mL), and 4 mol/L hydrogen chloride-ethyl acetate solution (2 mL) was added. After stirring at room temperature for 2 hr, the reaction mixture was concentrated under reduced pressure. The residue was solidified with diisopropyl ether to give the title compound as a white solid (yield 20.8 mg, 11%).

$^1$H-NMR (DMSO-$d_6$) δ: 2.63 (6H, s), 3.40 (3H, s), 4.08 (2H, s), 6.24 (1H, t, J=6.8 Hz), 6.44 (1H, d, J=1.7 Hz), 7.15-7.24 (1H, m), 7.53-7.77 (6H, m), 7.81 (1H, dd, J=6.7, 2.0 Hz), 10.65 (1H, brs).

Example 105

3-[4-[(methylamino)methyl]-1-(phenylsulfonyl)-1H-pyrrol-2-yl]pyridin-2(1H)-one hydrochloride A suspension of tert-butyl {[5-(2-fluoropyridin-3-yl)-1-(phenylsulfonyl)-1H-pyrrol-3-yl]methyl}methylcarbamate (240 mg) in 6 mol/L hydrochloric acid (6 mL) was stirred for 3 hr under heated reflux. After cooling, the reaction mixture was concentrated under reduced pressure, and the residue was recrystallized from a mixed solvent of ethyl acetate-ethanol=1:4 to give the title compound as a pale-gray solid (yield 181 mg, 88%).

$^1$H-NMR (DMSO-$d_6$) δ: 2.49 (3H, brs), 3.94 (2H, s), 6.19 (1H, t, J=6.6 Hz), 6.36 (1H, d, J=1.9 Hz), 7.17 (1H, dd, J=6.8, 2.3 Hz), 7.46 (1H, d, J=5.3 Hz), 7.54-7.64 (3H, m), 7.67-7.77 (3H, m), 8.86 (2H, brs), 11.76 (1H, brs).

Example 106

1-{4-fluoro-5-(2-fluoropyridin-3-yl)-1-[(6-fluoropyridin-2-yl)sulfonyl]-1H-pyrrol-3-yl}-N-methyl-methanamine hydrochloride To a solution of tert-butyl ({4-fluoro-5-(2-fluoropyridin-3-yl)-1-[(6-fluoropyridin-2-yl)sulfonyl]-1H-pyrrol-3-yl}methyl)methylcarbamate (48 mg) in ethanol (2 mL) was added 4 mol/L hydrogen chloride-ethyl acetate solution (2 mL), and the mixture was stirred at room temperature for 1 hr. The reaction mixture was concentrated under reduced pressure, and the residue was recrystallized from a mixed solvent of ethyl acetate-ethanol to give the title compound as a white solid (yield 22 mg, 53%).

$^1$H-NMR (DMSO-$d_6$) δ: 2.58 (3H, s), 4.08 (2H, s), 7.44-7.48 (1H, m), 7.65-7.78 (3H, m), 7.87-8.92 (1H, m), 8.25-8.38 (2H, m), 8.85 (2H, brs).

Example 107

1-{4-fluoro-5-(2-fluoropyridin-3-yl)-1-[(6-methoxy-pyridin-2-yl)sulfonyl]-1H-pyrrol-3-yl}-N-methyl-methanamine hydrochloride To a solution of tert-butyl ({4-fluoro-5-(2-fluoropyridin-3-yl)-1-[(6-methoxypyridin-2-yl)sulfonyl]-1H-pyrrol-3-yl}methyl)methylcarbamate (136 mg) in 2-propanol (2 mL) was added 4 mol/L hydrogen chloride-ethyl acetate solution (2 mL), and the mixture was stirred at room temperature for 2 hr. The reaction mixture was concentrated under reduced pressure, and the residue was recrystallized from ethanol to give the title compound as a white solid (yield 62 mg, 51%).

$^1$H-NMR (DMSO-$d_6$) δ: 2.58 (3H, s), 3.79 (3H, s), 4.08 (2H, s), 7.21 (1H, d, J=8.4 Hz), 7.32 (1H, d, J=6.9 Hz), 7.42-7.46 (1H, m), 7.81-7.89 (2H, m), 7.94 (1H, dd, J=8.4, 6.9 Hz), 8.33-8.35 (1H, m), 8.96 (2H, brs).

Example 108

1-{4-fluoro-5-(2-fluoropyridin-3-yl)-1-[(6-methylpyridin-2-yl)sulfonyl]-1H-pyrrol-3-yl}-N-methyl-methanamine hydrochloride To a solution of tert-butyl ({4-fluoro-5-(2-fluoropyridin-3-yl)-1-[(6-methylpyridin-2-yl)sulfonyl]-1H-pyrrol-3-yl}methyl)methylcarbamate (173 mg) in 2-propanol (2 mL) was added 4 mol/L hydrogen chloride-ethyl acetate solution (2 mL), and the mixture was stirred at room temperature for 5 hr. The reaction mixture was concentrated under reduced pressure, and the residue was recrystallized from ethanol to give the title compound as a white solid (yield 79 mg, 53%).

$^1$H-NMR (DMSO-$d_6$) δ: 2.49 (3H, s), 2.54 (3H, s), 4.04 (2H, s), 7.43-7.48 (1H, m), 7.58-7.64 (2H, m), 7.79 (1H, d, J=5.4 Hz), 7.88-7.99 (2H, m), 8.34-8.35 (1H, m), 9.21 (2H, brs).

The structures of the compounds described in Reference Examples are shown in Tables 1-14.

TABLE 1

| Ref. No. | $R^a$ | $R^b$ | $R^c$ | $R^d$ | $R^e$ |
|---|---|---|---|---|---|
| 1 | H | Br | H | CHO | H |
| 2 | phenyl-SO$_2$ | Br | H | CHO | H |

TABLE 1-continued

| Ref. No. | R$^a$ | R$^b$ | R$^c$ | R$^d$ | R$^e$ |
|---|---|---|---|---|---|
| 3 | phenyl-SO$_2$- | 2-fluoro-3-methylpyridin-yl | H | CHO | H |
| 4 | H | 2-fluoro-3-methylpyridin-yl | H | CHO | H |
| 5 | 2-fluorophenyl-SO$_2$- | 2-fluoro-3-methylpyridin-yl | H | CHO | H |
| 6 | furan-3-yl-SO$_2$- | 2-fluoro-3-methylpyridin-yl | H | CHO | H |
| 7 | 3-(MeO$_2$S)phenyl-SO$_2$- | 2-fluoro-3-methylpyridin-yl | H | CHO | H |
| 8 | thiophen-2-yl-SO$_2$- | 2-fluoro-3-methylpyridin-yl | H | CHO | H |
| 9 | benzo[1,3]dioxol-5-yl-SO$_2$- | 2-fluoro-3-methylpyridin-yl | H | CHO | H |
| 10 | H | 2-fluoro-3-methylpyridin-yl | Cl | CHO | H |
| 11 | 3-(MeO$_2$S)phenyl-SO$_2$- | 2-fluoro-3-methylpyridin-yl | Cl | CHO | H |
| 12 | H | 2-fluoro-3-methylpyridin-yl | F | CHO | H |

TABLE 1-continued
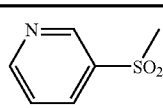
| Ref. No. | $R^a$ | $R^b$ | $R^c$ | $R^d$ | $R^e$ |
|---|---|---|---|---|---|
| 13 | 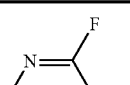 | 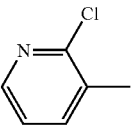 | F | CHO | H |
TABLE 2
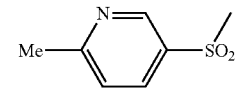
| Ref. No. | $R^a$ | $R^b$ | $R^c$ | $R^d$ | $R^e$ |
|---|---|---|---|---|---|
| 14 | H | 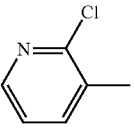 | H | CHO | H |
| 15 | 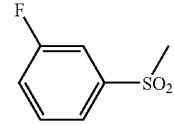 | 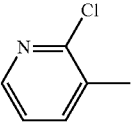 | H | CHO | H |
| 16 | 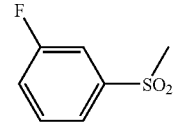 | 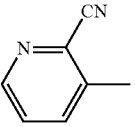 | H | CHO | H |
| 17 |  | 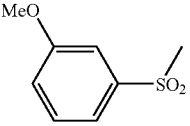 | H | CHO | H |
| 18 | H | Br | H |  | H |
| 19 | 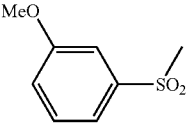 | Br | H | 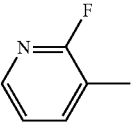 | H |
| 20 |  |  | H |  | H |

TABLE 2-continued

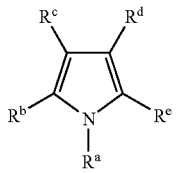

| Ref. No. | R$^a$ | R$^b$ | R$^c$ | R$^d$ | R$^e$ |
|---|---|---|---|---|---|
| 21 | 3-F-C$_6$H$_4$-SO$_2$- | Br | H | CH$_2$N(Me)Boc | H |
| 22 | 3-F-C$_6$H$_4$-SO$_2$- | 2-F-3-Me-pyridin-3-yl | H | CH$_2$N(Me)Boc | H |
| 23 | pyridin-3-yl-SO$_2$- | Br | H | CH$_2$N(Me)Boc | H |
| 24 | pyridin-3-yl-SO$_2$- | 2-F-3-Me-6-Me-pyridin-3-yl | H | CH$_2$N(Me)Boc | H |
| 25 | pyridin-3-yl-SO$_2$- | 2-Cl-3-Me-pyridin-3-yl | H | CH$_2$N(Me)Boc | H |
| 26 | pyridin-3-yl-SO$_2$- | 2-CN-3-Me-pyridin-3-yl | H | CH$_2$N(Me)Boc | H |

TABLE 3

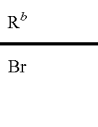

| Ref. No. | R$^a$ | R$^b$ | R$^c$ | R$^d$ | R$^e$ |
|---|---|---|---|---|---|
| 27 | C$_6$H$_5$-SO$_2$- | Br | H | CH$_2$N(Me)Boc | H |
| 28 | C$_6$H$_5$-SO$_2$- | 2-Cl-3-Me-pyridin-3-yl | H | CH$_2$N(Me)Boc | H |

TABLE 3-continued

| Ref. No. | $R^a$ | $R^b$ | $R^c$ | $R^d$ | $R^e$ |
|---|---|---|---|---|---|
| 29 | phenyl-SO2 | 3-methyl-2-cyanopyridin-... | H | CH2N(Me)Boc | H |
| 30 | pyridin-3-yl-SO2 | 2-fluoro-3-methylpyridin-... | H | CH2N(Me)Boc | H |
| 31 | H | 2-fluoro-3-methylpyridin-... | H | CH2N(Me)Boc | H |
| 32 | thien-3-yl-SO2 | 2-fluoro-3-methylpyridin-... | H | CH2N(Me)Boc | H |
| 33 | 3-cyanophenyl-SO2 | 2-fluoro-3-methylpyridin-... | H | CH2N(Me)Boc | H |
| 34 | 3-acetylphenyl-SO2 | 2-fluoro-3-methylpyridin-... | H | CH2N(Me)Boc | H |
| 35 | 4-fluorophenyl-SO2 | 2-fluoro-3-methylpyridin-... | H | CH2N(Me)Boc | H |
| 36 | 2,3-difluorophenyl-SO2 | 2-fluoro-3-methylpyridin-... | H | CH2N(Me)Boc | H |
| 37 | 3,4-difluorophenyl-SO2 | 2-fluoro-3-methylpyridin-... | H | CH2N(Me)Boc | H |

TABLE 3-continued

![Pyrrole structure with R^a on N, R^b, R^c, R^d, R^e substituents]

| Ref. No. | R^a | R^b | R^c | R^d | R^e |
|---|---|---|---|---|---|
| 38 | 3-F-4-Me-phenyl-SO_2- | 2-F-3-pyridyl | H | CH_2N(Me)Boc | H |
| 39 | 2,5-diF-phenyl-SO_2- | 2-F-3-pyridyl | H | CH_2N(Me)Boc | H |

TABLE 4

![Pyrrole structure with R^a on N, R^b, R^c, R^d, R^e substituents]

| Ref. No. | R^a | R^b | R^c | R^d | R^e |
|---|---|---|---|---|---|
| 44 | H | 2-F-3-pyridyl | Me | COOEt | Cl |
| 45 | H | 2-F-3-pyridyl | Me | COOEt | H |
| 46 | H | 2-F-3-pyridyl | Me | CH_2OH | H |
| 47 | H | 2-F-3-pyridyl | Me | CHO | H |
| 48 | 3-pyridyl-SO_2- | 2-F-3-pyridyl | Me | CHO | H |

TABLE 4-continued

![Pyrrole structure with R^a on N, R^b, R^c, R^d, R^e substituents]

| Ref. No. | R^a | R^b | R^c | R^d | R^e |
|---|---|---|---|---|---|
| 49 | phenyl-SO_2- | 2-F-3-pyridyl | Me | CHO | H |

Structural Formulas of Ref. Nos. 40-43

40

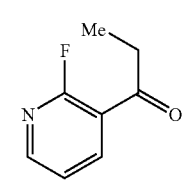

41

147
-continued
42 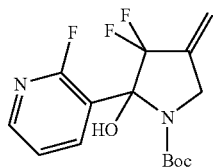
43 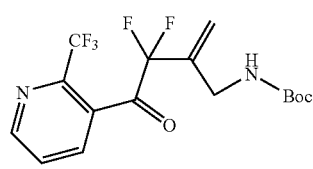
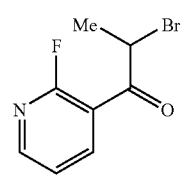
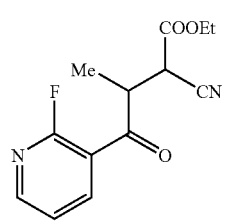
Structural Formulas of Ref. Nos. 50-59
50 
51 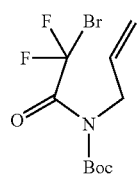
52 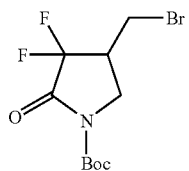
53 
148
-continued
54
55
56 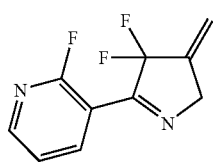
57 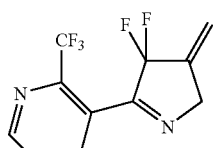
58 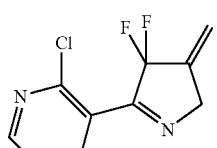
59 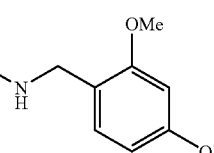
TABLE 5
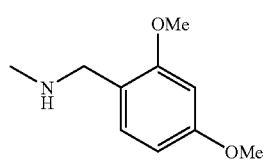
| Ref. No. | $R^a$ | $R^b$ | $R^c$ | $R^d$ | $R^e$ |
|---|---|---|---|---|---|
| 60 | H | | F | Me CH₂N DMB | H |

TABLE 5-continued

| Ref. No. | R$^a$ | R$^b$ | R$^c$ | R$^d$ | R$^e$ |
|---|---|---|---|---|---|
| 61 | H | 2-CF$_3$-3-methyl-pyridin-3-yl | F | CH$_2$N(Me)(DMB) | H |
| 62 | H | 2-Cl-3-methyl-pyridin-3-yl | F | CH$_2$N(Me)(DMB) | H |
| 63 | pyridin-3-yl-SO$_2$- | 2-F-3-methyl-pyridin-3-yl | F | CH$_2$N(Me)(DMB) | H |
| 64 | Ph-SO$_2$- | 2-F-3-methyl-pyridin-3-yl | F | CH$_2$N(Me)(DMB) | H |
| 65 | Ph-SO$_2$- | 2-CF$_3$-3-methyl-pyridin-3-yl | F | CH$_2$N(Me)(DMB) | H |
| 66 | Ph-SO$_2$- | 2-Cl-3-methyl-pyridin-3-yl | F | CH$_2$N(Me)(DMB) | H |
| 67 | Ph-SO$_2$- | 2-CF$_3$-3-methyl-pyridin-3-yl | F | CH$_2$N(Me)(Boc) | H |
| 68 | Ph-SO$_2$- | 2-Cl-3-methyl-pyridin-3-yl | F | CH$_2$N(Me)(Boc) | H |
| 69 | Ph-SO$_2$- | 2-CN-3-methyl-pyridin-3-yl | F | CH$_2$N(Me)(Boc) | H |
| 70 | H | 2-CF$_3$-3-methyl-pyridin-3-yl | F | CH$_2$N(Me)(Boc) | H |

TABLE 5-continued

| Ref. No. | R$^a$ | R$^b$ | R$^c$ | R$^d$ | R$^e$ |
|---|---|---|---|---|---|
| 71 | H | 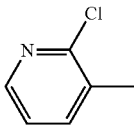 2-Cl-3-methylpyridin-yl | F |  CH$_2$N(Me)Boc | H |
| 72 | H | 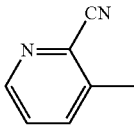 2-CN-3-methylpyridin-yl | F |  CH$_2$N(Me)Boc | H |

TABLE 6

| Ref. No. | R$^a$ | R$^b$ | R$^c$ | R$^d$ | R$^e$ |
|---|---|---|---|---|---|
| 73 | 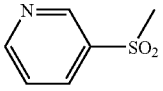 pyridin-3-yl-SO$_2$ | 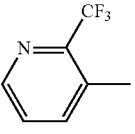 2-CF$_3$-3-methylpyridin-yl | F |  CH$_2$N(Me)Boc | H |
| 74 | 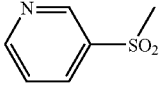 pyridin-3-yl-SO$_2$ | 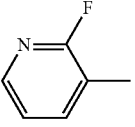 2-F-3-methylpyridin-yl | F |  CH$_2$N(Me)Boc | H |
| 75 | H | 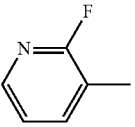 2-F-3-methylpyridin-yl | F |  CH$_2$N(Me)Boc | H |
| 76 | 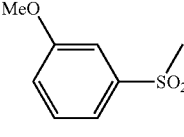 3-MeO-phenyl-SO$_2$ | 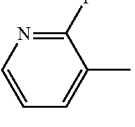 2-F-3-methylpyridin-yl | F |  CH$_2$N(Me)Boc | H |
| 77 | 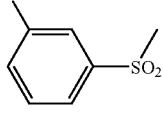 3-F-phenyl-SO$_2$ | 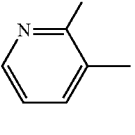 2-F-3-methylpyridin-yl | F |  CH$_2$N(Me)Boc | H |

TABLE 6-continued
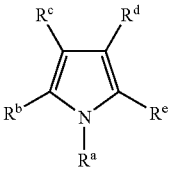
| Ref. No. | $R^a$ | $R^b$ | $R^c$ | $R^d$ | $R^e$ |
|---|---|---|---|---|---|
| 78 | 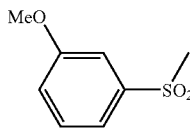 | 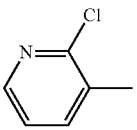 | F |  | H |
| 79 | 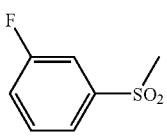 | 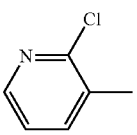 | F |  | H |
| 80 | 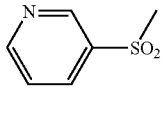 |  | F |  | H |
| 81 | 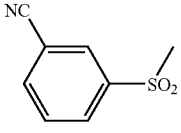 | 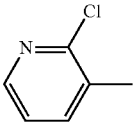 | F |  | H |
| 82 | 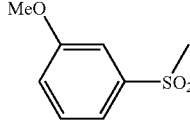 | 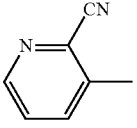 | F |  | H |
| 83 | 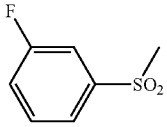 | 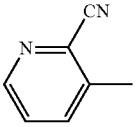 | F |  | H |
| 84 | 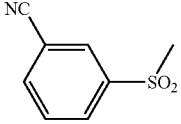 | 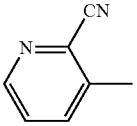 | F |  | H |
| 85 | 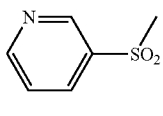 | 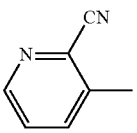 | F |  | H |

TABLE 7

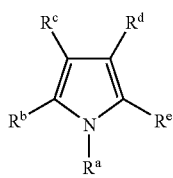

| Ref. No. | $R^a$ | $R^b$ | $R^c$ | $R^d$ | $R^e$ |
|---|---|---|---|---|---|
| 86 | NC–C₆H₄–SO₂– | 2-F-3-Me-pyridin-4-yl | F | CH₂N(Me)Boc | H |
| 87 | MeO₂S–C₆H₄–SO₂– | 2-F-3-Me-pyridin-4-yl | F | CH₂N(Me)Boc | H |
| 88 | BnOOC–C₆H₄–SO₂– | 2-F-3-Me-pyridin-4-yl | F | CH₂N(Me)Boc | H |
| 89 | HOOC–C₆H₄–SO₂– | 2-F-3-Me-pyridin-4-yl | F | CH₂N(Me)Boc | H |
| 90 | HOCH₂CH₂NHC(O)–C₆H₄–SO₂– | 2-F-3-Me-pyridin-4-yl | F | CH₂N(Me)Boc | H |
| 91 | HOCH₂–C₆H₄–SO₂– | 2-F-3-Me-pyridin-4-yl | F | CH₂N(Me)Boc | H |
| 92 | ClCH₂–C₆H₄–SO₂– | 2-F-3-Me-pyridin-4-yl | F | CH₂N(Me)Boc | H |
| 93 | MeSCH₂–C₆H₄–SO₂– | 2-F-3-Me-pyridin-4-yl | F | CH₂N(Me)Boc | H |
| 94 | MeO₂SCH₂–C₆H₄–SO₂– | 2-F-3-Me-pyridin-4-yl | F | CH₂N(Me)Boc | H |

TABLE 7-continued

| Ref. No. | R$^a$ | R$^b$ | R$^c$ | R$^d$ | R$^e$ |
|---|---|---|---|---|---|
| 95 | furan-3-yl-SO$_2$- | 2-fluoro-3-methylpyridin-4-yl | F | CH$_2$N(Me)Boc | H |
| 96 | furan-3-yl-SO$_2$- | 2-fluoro-3-methylpyridin-4-yl | H | CH$_2$N(Me)Boc | H |
| 97 | 2-methyl-1,3,4-oxadiazol-5-yl-(3-SO$_2$-phenyl)- | 2-fluoro-3-methylpyridin-4-yl | F | CH$_2$N(Me)Boc | H |

TABLE 8

| Ref. No. | R$^a$ | R$^b$ | R$^c$ | R$^d$ | R$^e$ |
|---|---|---|---|---|---|
| 98 | 3-cyanophenyl-SO$_2$- | 2-chloro-3-methylpyridin-4-yl | H | CHO | H |
| 99 | cyclohexyl-SO$_2$- | 2-fluoro-3-methylpyridin-4-yl | F | CH$_2$N(Me)Boc | H |
| 100 | piperidin-1-yl-SO$_2$- | 2-fluoro-3-methylpyridin-4-yl | F | CH$_2$N(Me)Boc | H |
| 101 | 2,6-difluorophenyl-SO$_2$- | 2-fluoro-3-methylpyridin-4-yl | F | CH$_2$N(Me)Boc | H |

TABLE 8-continued

| Ref. No. | $R^a$ | $R^b$ | $R^c$ | $R^d$ | $R^e$ |
|---|---|---|---|---|---|
| 102 | 1-methyl-pyrazol-4-yl-SO₂- | 2-fluoro-3-methyl-pyridin-4-yl | Cl | CHO | H |
| 103 | thien-2-yl-SO₂- | 2-fluoro-3-methyl-pyridin-4-yl | F | CH₂N(Me)Boc | H |
| 104 | fur-2-yl-SO₂- | 2-fluoro-3-methyl-pyridin-4-yl | F | CH₂N(Me)Boc | H |
| 105 | thien-3-yl-SO₂- | 2-fluoro-3-methyl-pyridin-4-yl | F | CH₂N(Me)Boc | H |
| 106 | 1-methyl-pyrazol-4-yl-SO₂- | 2-fluoro-3-methyl-pyridin-4-yl | F | CH₂N(Me)Boc | H |

TABLE 9

| Ref. No. | $R^a$ | $R^b$ | $R^c$ | $R^d$ | $R^e$ |
|---|---|---|---|---|---|
| 107 | 5-(MeOOC)-fur-2-yl-SO₂- | 2-fluoro-3-methyl-pyridin-4-yl | F | CH₂N(Me)Boc | H |
| 108 | 5-(HOCH₂)-fur-2-yl-SO₂- | 2-fluoro-3-methyl-pyridin-4-yl | F | CH₂N(Me)Boc | H |

TABLE 9-continued

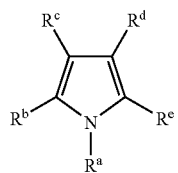

| Ref. No. | R$^a$ | R$^b$ | R$^c$ | R$^d$ | R$^e$ |
|---|---|---|---|---|---|
| 109 | 5-(fluoromethyl)furan-2-SO$_2$- | 2-fluoro-3-methylpyridin-3-yl | F | CH$_2$N(Me)Boc | H |
| 110 | 5-(carbamoyl)furan-2-SO$_2$- | 2-fluoro-3-methylpyridin-3-yl | F | CH$_2$N(Me)Boc | H |
| 111 | 5-cyanofuran-2-SO$_2$- | 2-fluoro-3-methylpyridin-3-yl | F | CH$_2$N(Me)Boc | H |
| 112 | 5-(1,3-dioxolan-2-yl)furan-2-SO$_2$- | 2-fluoro-3-methylpyridin-3-yl | F | CH$_2$N(Me)Boc | H |
| 113 | 5-formylfuran-2-SO$_2$- | 2-fluoro-3-methylpyridin-3-yl | F | CH$_2$N(Me)Boc | H |
| 114 | 5-(difluoromethyl)furan-2-SO$_2$- | 2-fluoro-3-methylpyridin-3-yl | F | CH$_2$N(Me)Boc | H |
| 115 | 5-(1-hydroxyethyl)furan-2-SO$_2$- | 2-fluoro-3-methylpyridin-3-yl | F | CH$_2$N(Me)Boc | H |

TABLE 10
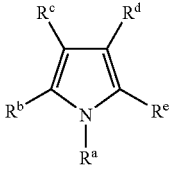
| Ref. No. | R$^a$ | R$^b$ | R$^c$ | R$^d$ | R$^e$ |
|---|---|---|---|---|---|
| 116 | 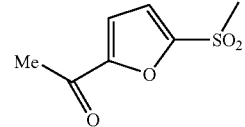 | 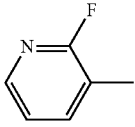 | F | CH$_2$N(Me)Boc | H |
| 117 | 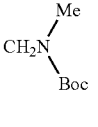 | 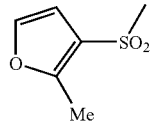 | F | CH$_2$N(Me)Boc | H |
| 118 | 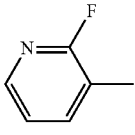 | 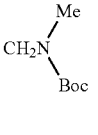 | F | CH$_2$N(Me)Boc | H |
| 119 | 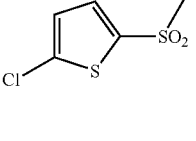 | 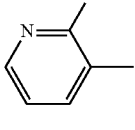 | F | CH$_2$N(Me)Boc | H |
| 120 | 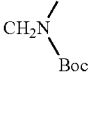 | 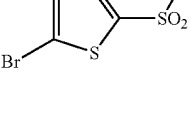 | F | CH$_2$N(Me)Boc | H |
| 121 | 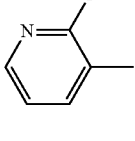 | 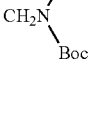 | F | CH$_2$N(Me)Boc | H |
| 122 | 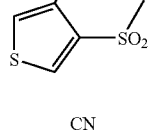 | 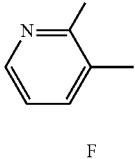 | F | CH$_2$N(Me)Boc | H |
| 123 | 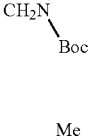 | 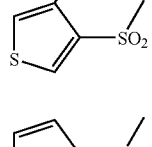 | F | CH$_2$N(Me)Boc | H |
| 124 | 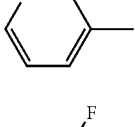 | 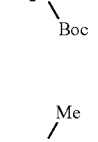 | F | CH$_2$N(Me)Boc | H |

TABLE 11

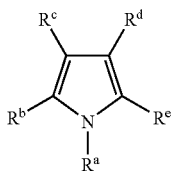

| Ref. No. | R$^a$ | R$^b$ | R$^c$ | R$^d$ | R$^e$ |
|---|---|---|---|---|---|
| 125 | 1,5-dimethyl-pyrazol-4-yl-SO$_2$- | 2-fluoro-3-methyl-pyridin-3-yl | F | CH$_2$N(Me)Boc | H |
| 126 | 1-(difluoromethyl)-pyrazol-4-yl-SO$_2$- | 2-fluoro-3-methyl-pyridin-3-yl | F | CH$_2$N(Me)Boc | H |
| 127 | 1-methyl-pyrrol-2-yl-SO$_2$- | 2-fluoro-3-methyl-pyridin-3-yl | F | CH$_2$N(Me)Boc | H |
| 128 | thiazol-2-yl-SO$_2$- | 2-fluoro-3-methyl-pyridin-3-yl | F | CH$_2$N(Me)Boc | H |
| 129 | 6-methoxy-pyridin-3-yl-SO$_2$- | 2-fluoro-3-methyl-pyridin-3-yl | F | CH$_2$N(Me)Boc | H |
| 130 | pyridin-2-yl-SO$_2$- | 2-fluoro-3-methyl-pyridin-3-yl | F | CH$_2$N(Me)Boc | H |
| 131 | 2-chloro-pyridin-3-yl-SO$_2$- | 2-fluoro-3-methyl-pyridin-3-yl | F | CH$_2$N(Me)Boc | H |
| 132 | 2-cyano-phenyl-SO$_2$- | 2-fluoro-3-methyl-pyridin-3-yl | F | CH$_2$N(Me)Boc | H |
| 133 | 4-benzyloxy-phenyl-SO$_2$- | 2-fluoro-3-methyl-pyridin-3-yl | F | CH$_2$N(Me)Boc | H |

TABLE 12

[Pyrrole core structure with substituents R$^a$ (N), R$^b$, R$^c$, R$^d$, R$^e$]

| Ref. No. | R$^a$ | R$^b$ | R$^c$ | R$^d$ | R$^e$ |
|---|---|---|---|---|---|
| 134 | 4-HO-C$_6$H$_4$-SO$_2$- | 2-F-pyridin-3-yl | F | CH$_2$N(Me)Boc | H |
| 135 | morpholine-N-SO$_2$- | 2-F-pyridin-3-yl | F | CH$_2$N(Me)Boc | H |
| 136 | pyrrolidine-N-SO$_2$- | 2-F-pyridin-3-yl | F | CH$_2$N(Me)Boc | H |
| 137 | thiazol-2-yl-SO$_2$- | 2-F-pyridin-3-yl | F | CH$_2$N(Me)Boc | H |
| 138 | furan-2-yl-SO$_2$- | 2-CN-pyridin-3-yl | H | CH$_2$N(Me)Boc | H |
| 139 | furan-3-yl-SO$_2$- | 2-CN-pyridin-3-yl | H | CH$_2$N(Me)Boc | H |
| 140 | thien-2-yl-SO$_2$- | 2-CN-pyridin-3-yl | H | CH$_2$N(Me)Boc | H |
| 141 | thien-3-yl-SO$_2$- | 2-CN-pyridin-3-yl | H | CH$_2$N(Me)Boc | H |
| 142 | 2,6-difluorophenyl-SO$_2$- | 2-CN-pyridin-3-yl | H | CH$_2$N(Me)Boc | H |

TABLE 12-continued

[Pyrrole core structure with substituents R$^a$ (N), R$^b$, R$^c$, R$^d$, R$^e$]

| Ref. No. | R$^a$ | R$^b$ | R$^c$ | R$^d$ | R$^e$ |
|---|---|---|---|---|---|
| 143 | 2,4-difluorophenyl-SO$_2$- | 3-methyl-2-cyanopyridin-yl | H | CH$_2$N(Me)Boc | H |

TABLE 13

[Pyrrole core structure with substituents R$^a$ (N), R$^b$, R$^c$, R$^d$, R$^e$]

| Ref. No. | R$^a$ | R$^b$ | R$^c$ | R$^d$ | R$^e$ |
|---|---|---|---|---|---|
| 144 | 2-methylphenyl-SO$_2$- | 3-methyl-2-cyanopyridin-yl | H | CH$_2$N(Me)Boc | H |
| 145 | 2-chlorophenyl-SO$_2$- | 3-methyl-2-cyanopyridin-yl | H | CH$_2$N(Me)Boc | H |
| 146 | 2-fluorophenyl-SO$_2$- | 3-methyl-2-cyanopyridin-yl | H | CH$_2$N(Me)Boc | H |
| 147 | 2-cyanophenyl-SO$_2$- | 3-methyl-2-cyanopyridin-yl | H | CH$_2$N(Me)Boc | H |
| 148 | 6-methoxypyridin-3-yl-SO$_2$- | 3-methyl-2-cyanopyridin-yl | H | CH$_2$N(Me)Boc | H |
| 149 | phenyl-SO$_2$- | 1-methyl-3-methyl-2-oxopyridin-yl | H | CH$_2$N(Me)Boc | H |

TABLE 14
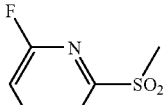
| Ref. No. | $R^a$ | $R^b$ | $R^c$ | $R^d$ | $R^e$ |
|---|---|---|---|---|---|
| 155 | 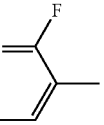 | 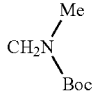 | F | CH$_2$N(Me)Boc | H |
| 156 | 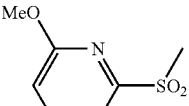 | 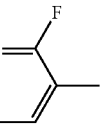 | F | CH$_2$N(Me)Boc | H |
| 157 | 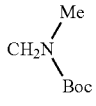 | 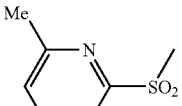 | F | CH$_2$N(Me)Boc | H |
The structures of the compounds described in Examples are shown in Tables 15-25.
TABLE 15
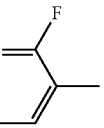
| Ex. No. | $R^a$ | $R^b$ | $R^c$ | $R^d$ | I | addition salt |
|---|---|---|---|---|---|---|
| 1 | 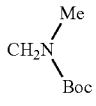 | 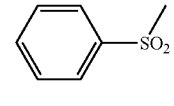 | H | CH$_2$NHMe | H | 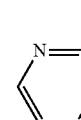 |
| 2 | 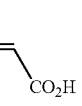 | 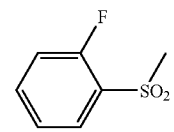 | H | CH$_2$NHMe | H | 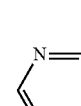 |
| 3 | 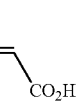 | 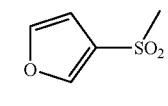 | H | CH$_2$NHMe | H | 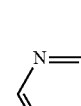 |
| 4 | 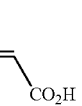 | 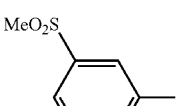 | H | CH$_2$NHMe | H | 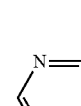 |

TABLE 15-continued

| Ex. No. | $R^a$ | $R^b$ | $R^c$ | $R^d$ | I | addition salt |
|---|---|---|---|---|---|---|
| 5 | 2-(methylsulfonyl)thiophene | 2-fluoro-3-methylpyridin-3-yl | H | CH$_2$NHMe | H | fumaric acid |
| 6 | benzo[1,3]dioxol-5-ylsulfonyl | 2-fluoro-3-methylpyridin-3-yl | H | CH$_2$NHMe | H | fumaric acid |
| 7 | 3-(methylsulfonyl)phenylsulfonyl (MeO$_2$S) | 2-fluoro-3-methylpyridin-3-yl | Cl | CH$_2$NHMe | H | fumaric acid |
| 8 | pyridin-3-ylsulfonyl | 2-fluoro-3-methylpyridin-3-yl | F | CH$_2$NHMe | H | fumaric acid |
| 9 | 6-methylpyridin-3-ylsulfonyl | 2-chloro-3-methylpyridin-3-yl | H | CH$_2$NHMe | H | fumaric acid |
| 10 | 3-fluorophenylsulfonyl | 2-cyano-3-methylpyridin-3-yl | H | CH$_2$NHMe | H | fumaric acid |
| 11 | 3-methoxyphenylsulfonyl | 2-fluoro-3-methylpyridin-3-yl | H | CH$_2$NHMe | H | fumaric acid |
| 12 | 3-fluorophenylsulfonyl | 2-fluoro-3-methylpyridin-3-yl | H | CH$_2$NHMe | H | HCl |
| 13 | pyridin-3-ylsulfonyl | 2-fluoro-6-methyl-5-methylpyridin-3-yl | H | CH$_2$NHMe | H | fumaric acid |

TABLE 16

| Ex. No. | R$^a$ | R$^b$ | R$^c$ | R$^d$ | addition salt |
|---|---|---|---|---|---|
| 14 | pyridin-3-yl-SO₂- | 2-cyano-3-methylpyridin-... | H | CH₂NHMe | H | HO₂C-CH=CH-CO₂H |
| 15 | phenyl-SO₂- | 2-chloro-3-methylpyridin-... | H | CH₂NHMe | H | HCl |
| 16 | phenyl-SO₂- | 2-cyano-3-methylpyridin-... | H | CH₂NHMe | H | HCl |
| 17 | thiophen-3-yl-SO₂- | 2-fluoro-3-methylpyridin-... | H | CH₂NHMe | H | HO₂C-CH=CH-CO₂H |
| 18 | 3-cyanophenyl-SO₂- | 2-fluoro-3-methylpyridin-... | H | CH₂NHMe | H | HO₂C-CH=CH-CO₂H |
| 19 | 3-acetylphenyl-SO₂- | 2-fluoro-3-methylpyridin-... | H | CH₂NHMe | H | HCl |
| 20 | 4-fluorophenyl-SO₂- | 2-fluoro-3-methylpyridin-... | H | CH₂NHMe | H | HO₂C-CH=CH-CO₂H |
| 21 | 2,3-difluorophenyl-SO₂- | 2-fluoro-3-methylpyridin-... | H | CH₂NHMe | H | HCl |
| 22 | 3,4-difluorophenyl-SO₂- | 2-fluoro-3-methylpyridin-... | H | CH₂NHMe | H | HCl |

TABLE 16-continued

[Pyrrole core structure with substituents $R^a$ (on N), $R^b$, $R^c$, $R^d$, $R^e$]

| Ex. No. | $R^a$ | $R^b$ | $R^c$ | $R^d$ | addition salt |
|---|---|---|---|---|---|
| 23 | 3-fluoro-4-methylphenyl-SO$_2$-CH$_2$- | 2-fluoro-3-methylpyridin-yl | H | CH$_2$NHMe | H | HCl |
| 24 | 2,5-difluorophenyl-SO$_2$-CH$_2$- | 2-fluoro-3-methylpyridin-yl | H | CH$_2$NHMe | H | HCl |
| 25 | pyridin-3-yl-SO$_2$-CH$_2$- | 2-fluoro-3-methylpyridin-yl | Me | CH$_2$NHMe | H | fumarate (HO$_2$C-CH=CH-CO$_2$H) |
| 26 | phenyl-SO$_2$-CH$_2$- | 2-fluoro-3-methylpyridin-yl | Me | CH$_2$NHMe | H | HCl |

TABLE 17

[Pyrrole core structure with substituents $R^a$ (on N), $R^b$, $R^c$, $R^d$, $R^e$]

| Ex. No. | $R^a$ | $R^b$ | $R^c$ | $R^d$ | addition salt |
|---|---|---|---|---|---|
| 27 | pyridin-3-yl-SO$_2$-CH$_2$- | 2-fluoro-3-methylpyridin-yl | F | CH$_2$NHMe | H | |
| 28 | pyridin-3-yl-SO$_2$-CH$_2$- | 2-fluoro-3-methylpyridin-yl | F | CH$_2$NHMe | H | 0.5 fumarate (HO$_2$C-CH=CH-CO$_2$H) |
| 29 | phenyl-SO$_2$-CH$_2$- | 2-fluoro-3-methylpyridin-yl | F | CH$_2$NHMe | H | |

TABLE 17-continued

| Ex. No. | R$^a$ | R$^b$ | R$^c$ | R$^d$ | addition salt |
|---|---|---|---|---|---|
| 30 | phenyl-SO$_2$-Me | 2-F,3-methyl pyridin-3-yl | F | CH$_2$NHMe | H | 0.5 fumaric acid |
| 31 | phenyl-SO$_2$-Me | 2-CF$_3$,3-methyl pyridin-3-yl | F | CH$_2$NHMe | H | HCl |
| 32 | pyridin-3-yl-SO$_2$-Me | 2-CF$_3$,3-methyl pyridin-3-yl | F | CH$_2$NHMe | H | fumaric acid |
| 33 | phenyl-SO$_2$-Me | 2-Cl,3-methyl pyridin-3-yl | F | CH$_2$NHMe | H | fumaric acid |
| 34 | phenyl-SO$_2$-Me | 2-CN,3-methyl pyridin-3-yl | F | CH$_2$NHMe | H | HCl |
| 35 | 3-MeO-phenyl-SO$_2$-Me | 2-F,3-methyl pyridin-3-yl | F | CH$_2$NHMe | H | HCl |
| 36 | 3-F-phenyl-SO$_2$-Me | 2-F,3-methyl pyridin-3-yl | F | CH$_2$NHMe | H | HCl |
| 37 | 3-MeO-phenyl-SO$_2$-Me | 2-Cl,3-methyl pyridin-3-yl | F | CH$_2$NHMe | H | HCl |

TABLE 17-continued

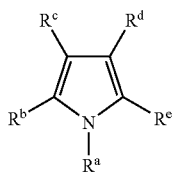

| Ex. No. | R$^a$ | R$^b$ | R$^c$ | R$^d$ | addition salt |
|---|---|---|---|---|---|
| 38 | 3-pyridyl-SO$_2$- | 2-chloro-3-methylpyridin-yl | F | CH$_2$NHMe | H | HO$_2$C-CH=CH-CO$_2$H |
| 39 | 3-F-phenyl-SO$_2$- | 2-chloro-3-methylpyridin-yl | F | CH$_2$NHMe | H | HCl |

TABLE 18

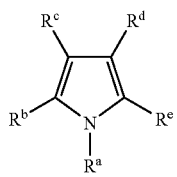

| Ex. No. | R$^a$ | R$^b$ | R$^c$ | R$^d$ | addition salt |
|---|---|---|---|---|---|
| 40 | 3-NC-phenyl-SO$_2$- | 2-chloro-3-methylpyridin-yl | F | CH$_2$NHMe | H | 0.5 HO$_2$C-CH=CH-CO$_2$H |
| 41 | 3-MeO-phenyl-SO$_2$- | 2-CN-3-methylpyridin-yl | F | CH$_2$NHMe | H | HCl |
| 42 | 3-F-phenyl-SO$_2$- | 2-CN-3-methylpyridin-yl | F | CH$_2$NHMe | H | HCl |
| 43 | 3-NC-phenyl-SO$_2$- | 2-CN-3-methylpyridin-yl | F | CH$_2$NHMe | H | HCl |
| 44 | 3-pyridyl-SO$_2$- | 2-CN-3-methylpyridin-yl | F | CH$_2$NHMe | H | HO$_2$C-CH=CH-CO$_2$H |

TABLE 18-continued
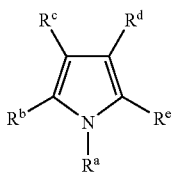
| Ex. No. | Rª | Rᵇ | Rᶜ | Rᵈ | | addition salt |
|---|---|---|---|---|---|---|
| 45 | 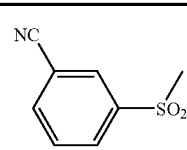 | 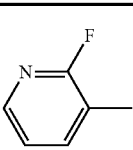 | F | CH₂NHMe | H | HCl |
| 46 | 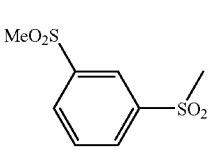 | 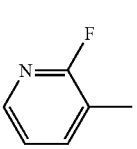 | F | CH₂NHMe | H | HCl |
| 47 | 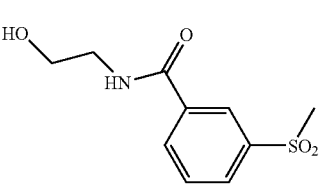 |  | F | CH₂NHMe | H | HCl |
| 48 | 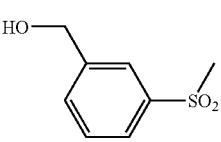 |  | F | CH₂NHMe | H | 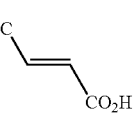 0.5 |
| 49 | 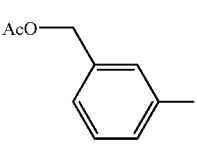 | 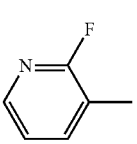 | F | CH₂NHMe | H | 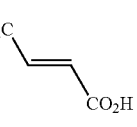 |
| 50 | 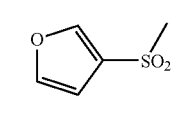 | 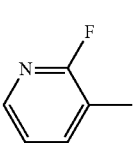 | F | CH₂NHMe | H | HCl |
| 51 | 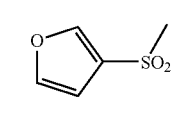 | 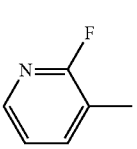 | H | CH₂NHMe | H | HCl |
| 52 | 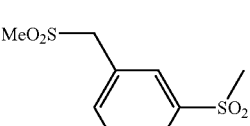 | 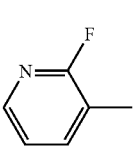 | F | CH₂NHMe | H | HCl |

TABLE 19

| Ex. No. | $R^a$ | $R^b$ | $R^c$ | $R^d$ | $R^e$ | addition salt |
|---|---|---|---|---|---|---|
| 53 | 2-methyl-1,3,4-oxadiazol-5-yl-(3-methylsulfonyl)phenyl | 2-fluoro-3-methylpyridin-4-yl | F | CH$_2$NHMe | H | fumaric acid |
| 54 | 3-cyano-(methylsulfonyl)phenyl | 2-chloro-3-methylpyridin-4-yl | H | CH$_2$NHMe | H | fumaric acid |
| 55 | cyclohexyl-CH$_2$-SO$_2$- | 2-fluoro-3-methylpyridin-4-yl | F | CH$_2$NHMe | H | HCl |
| 56 | piperidin-1-yl-SO$_2$-CH$_2$- | 2-fluoro-3-methylpyridin-4-yl | F | CH$_2$NHMe | H | HCl |
| 57 | 2,6-difluorophenyl-CH$_2$-SO$_2$- | 2-fluoro-3-methylpyridin-4-yl | F | CH$_2$NHMe | H | HCl |
| 58 | 1-methyl-1H-pyrazol-4-yl-SO$_2$-CH$_2$- | 2-fluoro-3-methylpyridin-4-yl | Cl | CH$_2$NHMe | H | fumaric acid |
| 59 | thiophen-2-yl-SO$_2$-CH$_2$- | 2-fluoro-3-methylpyridin-4-yl | F | CH$_2$NHMe | H | HCl |
| 60 | oxazol-2-yl-SO$_2$-CH$_2$- | 2-fluoro-3-methylpyridin-4-yl | F | CH$_2$NHMe | H | HCl |
| 61 | thiophen-3-yl-SO$_2$-CH$_2$- | 2-fluoro-3-methylpyridin-4-yl | F | CH$_2$NHMe | H | HCl |

TABLE 19-continued
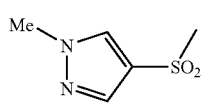
| Ex. No. | $R^a$ | $R^b$ | $R^c$ | $R^d$ | $R^e$ | addition salt |
|---|---|---|---|---|---|---|
| 62 | 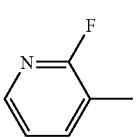 | 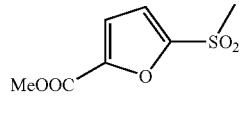 | F | CH$_2$NHMe | H | HCl |
TABLE 20
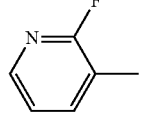
| Ex. No. | $R^a$ | $R^b$ | $R^c$ | $R^d$ | $R^e$ | addition salt |
|---|---|---|---|---|---|---|
| 63 | 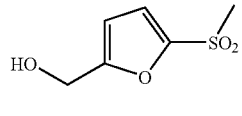 | 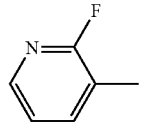 | F | CH$_2$NHMe | H | HCl |
| 64 | 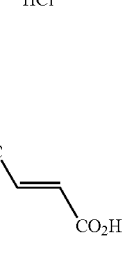 | 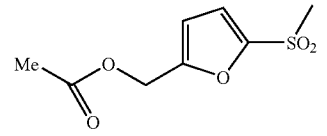 | F | CH$_2$NHMe | H | 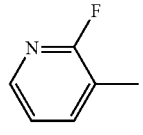 0.5 |
| 65 | 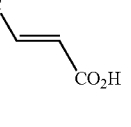 | 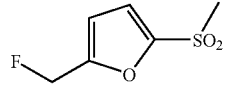 | F | CH$_2$NHMe | H | 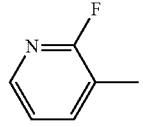 |
| 66 | 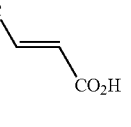 | 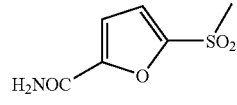 | F | CH$_2$NHMe | H | 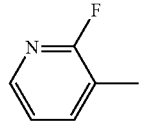 |
| 67 | 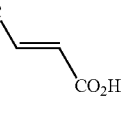 | 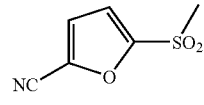 | F | CH$_2$NHMe | H | 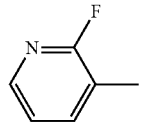 |
| 68 | 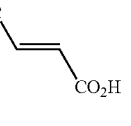 | | F | CH$_2$NHMe | H | |

TABLE 20-continued
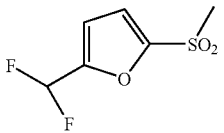
| Ex. No. | R$^a$ | R$^b$ | R$^c$ | R$^d$ | R$^e$ | addition salt |
|---|---|---|---|---|---|---|
| 69 |  | 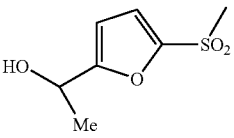 | F | CH$_2$NHMe | H | HCl |
| 70 | 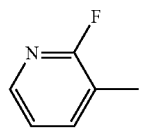 | 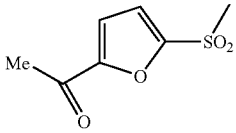 | F | CH$_2$NHMe | H | HCl |
TABLE 21
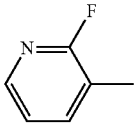
| Ex. No. | R$^a$ | R$^b$ | R$^c$ | R$^d$ | R$^e$ | addition salt |
|---|---|---|---|---|---|---|
| 71 | 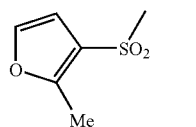 | 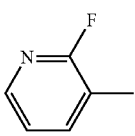 | F | CH$_2$NHMe | H | HCl |
| 72 | 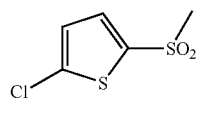 | 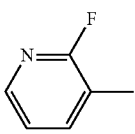 | F | CH$_2$NHMe | H | HCl |
| 73 | 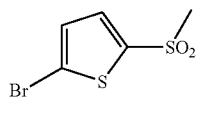 | 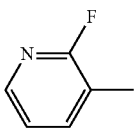 | F | CH$_2$NHMe | H | HCl |
| 74 | 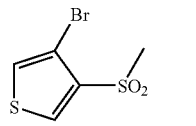 | 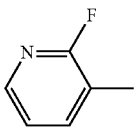 | F | CH$_2$NHMe | H | HCl |
| 75 |  |  | F | CH$_2$NHMe | H | HCl |

TABLE 21-continued

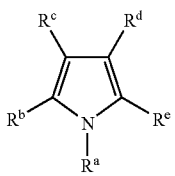

| Ex. No. | $R^a$ | $R^b$ | $R^c$ | $R^d$ | $R^e$ | addition salt |
| --- | --- | --- | --- | --- | --- | --- |
| 76 | thiophene-CN/SO₂Me | 2-F-3-Me-pyridyl | F | CH₂NHMe | H | HCl |
| 77 | thiophene-COOMe/SO₂Me | 2-F-3-Me-pyridyl | F | CH₂NHMe | H | HO₂C—CH=CH—CO₂H |
| 78 | isoxazole-thiophene-SO₂Me | 2-F-3-Me-pyridyl | F | CH₂NHMe | H | HCl |
| 79 | 1-Et-pyrazole-SO₂Me | 2-F-3-Me-pyridyl | F | CH₂NHMe | H | HCl |

TABLE 22

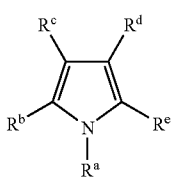

| Ex. No. | $R^a$ | $R^b$ | $R^c$ | $R^d$ | $R^e$ | addition salt |
| --- | --- | --- | --- | --- | --- | --- |
| 80 | 1,5-diMe-pyrazole-SO₂Me | 2-F-3-Me-pyridyl | F | CH₂NHMe | H | HCl |
| 81 | 1-CHF₂-pyrazole-SO₂Me | 2-F-3-Me-pyridyl | F | CH₂NHMe | H | HCl |
| 82 | 1-Me-imidazole-SO₂Me | 2-F-3-Me-pyridyl | F | CH₂NHMe | H | HCl |

TABLE 22-continued

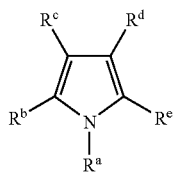

| Ex. No. | $R^a$ | $R^b$ | $R^c$ | $R^d$ | $R^e$ | addition salt |
|---|---|---|---|---|---|---|
| 83 | thiazol-2-yl-SO₂-Me | 2-F, 3-Me pyridin-4-yl | F | CH₂NHMe | H | HCl |
| 84 | 6-MeO-pyridin-3-yl-SO₂-Me | 2-F, 3-Me pyridin-4-yl | F | CH₂NHMe | H | HO₂C-CH=CH-CO₂H |
| 85 | pyridin-2-yl-SO₂-Me | 2-F, 3-Me pyridin-4-yl | F | CH₂NHMe | H | HCl |
| 86 | 2-Cl-pyridin-3-yl-SO₂-Me | 2-F, 3-Me pyridin-4-yl | F | CH₂NHMe | H | HCl |
| 87 | 2-CN-phenyl-SO₂-Me | 2-F, 3-Me pyridin-4-yl | F | CH₂NHMe | H | HCl |
| 88 | 4-HO-phenyl-SO₂-Me | 2-F, 3-Me pyridin-4-yl | F | CH₂NHMe | H | HCl |

TABLE 23

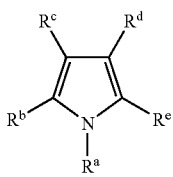

| Ex. No. | $R^a$ | $R^b$ | $R^c$ | $R^d$ | $R^e$ | addition salt |
|---|---|---|---|---|---|---|
| 89 | morpholin-4-yl-SO₂-Me | 2-F, 3-Me pyridin-4-yl | F | CH₂NHMe | H | HCl |

TABLE 23-continued

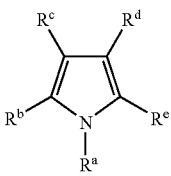

| Ex. No. | $R^a$ | $R^b$ | $R^c$ | $R^d$ | $R^e$ | addition salt |
|---|---|---|---|---|---|---|
| 90 | pyrrolidine-N-SO₂- | 2-F,3-methyl-pyridin-4-yl | F | CH₂NHMe | H | HCl |
| 91 | thiazol-2-yl-SO₂- | 2-F,3-methyl-pyridin-4-yl | H | CH₂NHMe | H | HCl |
| 92 | furan-2-yl-SO₂- | 2-CN,3-methyl-pyridin-4-yl | H | CH₂NHMe | H | HCl |
| 93 | furan-3-yl-SO₂- | 2-CN,3-methyl-pyridin-4-yl | H | CH₂NHMe | H | HCl |
| 94 | thien-2-yl-SO₂- | 2-CN,3-methyl-pyridin-4-yl | H | CH₂NHMe | H | HCl |
| 95 | thien-3-yl-SO₂- | 2-CN,3-methyl-pyridin-4-yl | H | CH₂NHMe | H | HCl |
| 96 | 2,6-difluorophenyl-SO₂- | 2-CN,3-methyl-pyridin-4-yl | H | CH₂NHMe | H | HCl |
| 97 | 2,4-difluorophenyl-SO₂- | 2-CN,3-methyl-pyridin-4-yl | H | CH₂NHMe | H | HCl |

TABLE 24

| Ex. No. | R$^a$ | R$^b$ | R$^c$ | R$^d$ | R$^e$ | addition salt |
|---|---|---|---|---|---|---|
| 98 | 2-Me-C$_6$H$_4$-SO$_2$- | 2-CN-pyridin-3-yl | H | CH$_2$NHMe | H | HCl |
| 99 | 2-Cl-C$_6$H$_4$-SO$_2$- | 2-CN-pyridin-3-yl | H | CH$_2$NHMe | H | HCl |
| 100 | 2-F-C$_6$H$_4$-SO$_2$- | 2-CN-pyridin-3-yl | H | CH$_2$NHMe | H | HCl |
| 101 | 2-CN-C$_6$H$_4$-SO$_2$- | 2-CN-pyridin-3-yl | H | CH$_2$NHMe | H | HCl |
| 102 | 6-MeO-pyridin-3-yl-SO$_2$- | 2-CN-pyridin-3-yl | H | CH$_2$NHMe | H | HCl |
| 103 | C$_6$H$_5$-SO$_2$- | 1-Me-2-oxo-1,2-dihydropyridin-3-yl | H | CH$_2$NHMe | H | HCl |
| 104 | C$_6$H$_5$-SO$_2$- | 1-Me-2-oxo-1,2-dihydropyridin-3-yl | H | CH$_2$NHMe | H | HCl |
| 105 | C$_6$H$_5$-SO$_2$- | 2-oxo-1,2-dihydropyridin-3-yl | H | CH$_2$NHMe | H | HCl |

TABLE 25

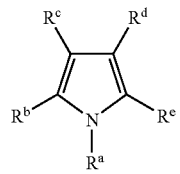

| Ex. No. | $R^a$ | $R^b$ | $R^c$ | $R^d$ | $R^e$ | addition salt |
|---|---|---|---|---|---|---|
| 106 | F-pyridine-SO$_2$- | F-pyridine-Me | F | CH$_2$NHMe | H | HCl |
| 107 | MeO-pyridine-SO$_2$- | F-pyridine-Me | F | CH$_2$NHMe | H | HCl |
| 108 | Me-pyridine-SO$_2$- | F-pyridine-Me | F | CH$_2$NHMe | H | HCl |

Experimental Example 1

Proton Potassium-Adenosine Triphosphatase ($H^+,K^+$-ATPase) Inhibitory Activity Test According to the method [*Biochim. Biophys. Acta,* 728, 31 (1983)] of Wallmark et al., a gastric mucous membrane microsomal fraction was prepared from the stomach of swine. First, the stomach was removed, washed with tap water, immersed in 3 mol/L brine, and the surface of the mucous membrane was wiped with a paper towel. The gastric mucous membrane was detached, chopped, and homogenized in a 0.25 mol/L saccharose solution (pH 6.8) containing 1 mmol/L EDTA and 10 mmol/L tris-hydrochloric acid using polytron (Kinematica). The obtained homogenate was centrifuged at 20,000×g for 30 min and the supernatant was centrifuged at 100,000×g for 90 min. The precipitate was suspended in 0.25 mol/L saccharose solution, superimposed on a 0.25 mol/L saccharose solution containing 7.5% Ficoll, and centrifuged at 100,000×g for 5 hr. The fraction containing the interface between the both layers was recovered, and centrifugally washed with 0.25 mol/L saccharose solution.

The obtained microsomal fraction was used as a proton, potassium-adenosine triphosphatase standard product.

To 40 µL of a 50 mmol/L HEPES-tris buffer (5 mmol/L magnesium chloride, 10 mmol/L potassium chloride, 10 µmol/L valinomycin, pH=6.5) containing 2.5 µg/mL (based on the protein concentration) of the enzyme standard product was added a test compound (5 µL) dissolved in a 10% aqueous dimethyl sulfoxide solution, and the mixture was incubated at 37° C. for 30 min. The enzyme reaction was started by adding 5 µL of a 2 mmol/L adenosine triphosphate tris salt solution (50 mmol/L HEPES-tris buffer (5 mmol/L magnesium chloride, pH 6.5)). The enzyme reaction was carried out at 37° C. for 20 min, and 15 µL of a malachite green solution (0.12% malachite green solution in sulfuric acid (2.5 mol/L), 7.5% ammonium molybdate and 11% Tween 20 were mixed at a ratio of 100:25:2) was added to quench the reaction. After allowing to stand at room temperature for 15 min, the resulting reaction product of inorganic phosphorus with malachite green was calorimetrically determined at a wavelength of 610 nm. In addition, the amount of the inorganic phosphoric acid in the reaction solution free of potassium chloride was measured in the same manner, which was subtracted from the inorganic phosphoric acid amount in the presence of potassium chloride to determine the proton, potassium-adenosine triphosphatase activity. The inhibitory rate (%) was determined from the activity value of the control and the activity values of various concentrations of the test compound, and the 50% inhibitory concentration ($IC_{50}$) of the proton, potassium-adenosine triphosphatase was determined. The results are shown in Table 26.

Experimental Example 2

ATP Content Test

Human liver cancer-derived cell line HepG2 (ATCC No. HB-8065) was passaged using Dulbecco's Modified Eagle medium (DMEM; Invitrogen) containing 10% fetal bovine serum (FBS; TRACE SCIENTIFIC LTD.), 1 mmol/L sodium pyruvate (Invitrogen), 2 mmol/L L-glutamine (Invitrogen), 50 IU/mL penicillin (Invitrogen) and 50 µg/mL streptomycin (Invitrogen) at 5% $CO_2$, 37° C. The test reagent was prepared with DMSO to 10 mM, and further diluted with DMEM medium containing 0.5% FBS, 1 mmol/L sodium pyruvate, 2 mmol/L L-glutamine, 50 IU/mL penicillin and 50 µg/mL streptomycin to a final concentration of DMSO of 0.1%. HepG2 (2×10⁴ cells/well) was cultured on a 96 well white plate (Costar) with the test reagent at 5% $CO_2$, 37° C. After culture for one day, the intracellular ATP content was measured using ATPLite™ (PerkinElmer Life Sciences). The results are shown in Table 26 (n≥3, average value±SD) as a relative value (%) to control (without addition of drug) at 30 μM.

Experimental Example 3

Caspase-3/7 Activity Test

The Caspase-3/7 activity in the cells cultured for one day by a method similar to that in Experimental Example 2 was measured using Caspase-Glo 3/7 Assay (Promega). The results are shown in Table 26 (n≥3, average value±SD) as relative activity (%) of each reagent based on the maximum value of Caspase-3/7 activity when exposed to Staurosporine (100%), and the activity without addition of a test reagent (0%).

TABLE 26

| Example No. | $H^+/K^+$-ATPase inhibitory activity ($IC_{50}$, nM) | ATP content (%, 30 μM) | Caspase-3/7 activity (%, 30 μM) |
| --- | --- | --- | --- |
| 1 | 26 | 88.1 | −1.3 |
| 3 | 59 | 91.4 | −0.5 |
| 8 | 90 | 103.9 | 0.2 |
| 13 | 120 | 87.7 | 0.2 |
| 15 | 43 | 90.4 | −0.8 |
| 16 | 120 | 97.1 | 0 |
| 20 | 57 | 86.6 | −0.2 |
| 26 | 110 | 85.2 | −0.2 |
| 28 | 71 | — | — |
| 30 | 26 | 97.3 | −0.6 |
| 38 | 130 | 93.4 | −0.4 |
| 48 | 130 | 92.7 | −0.8 |
| 50 | 60 | 99.8 | −0.3 |
| 54 | 65 | 96.8 | −0.4 |
| 58 | 300 | 98.0 | −1.9 |
| 64 | 190 | 102.2 | −0.1 |
| 66 | 140 | 94.8 | −0.2 |
| 68 | 170 | 83.4 | 3.6 |
| 72 | 93 | 88.1 | −0.5 |
| 81 | 300 | 101.7 | −0.2 |
| 83 | 180 | 96.6 | 0.3 |
| 85 | 98 | 102.0 | −0.6 |
| 99 | 270 | 82.7 | 0.0 |
| 101 | 230 | 97.3 | −0.5 |

From the results of Table 26, it is clear that compound (I) of the present invention has a superior $H^+/K^+$-ATPase inhibitory activity, and further shows low cytotoxicity.

INDUSTRIAL APPLICABILITY

Compound (I) of the present invention shows a superior proton pump inhibitory effect. Conventional proton pump inhibitors such as omeprazole, lansoprazole and the like are converted to active forms in an acidic environment of stomach wall cells and form a covalent bond with a cysteine residue of $H^+/K^+$-ATPase, and irreversibly inhibit the enzyme activity. In contrast, compound (I) inhibits proton pump ($H^+/K^+$-ATPase) activity in a reversible and $K^+$ antagonist-like inhibitory manner, and consequently suppresses acid secretion. Therefore, it is sometimes called a potassium-competitive acid blocker (P-CAB), or an acid pump antagonist (APA). Compound (I) rapidly expresses the action and shows the maximum efficacy from the initial administration. Furthermore, it characteristically shows less influence of metabolic polymorphism (variation between patients), low cytotoxicity, weak cytochrome P450 (CYP) inhibitory activity and weak hERG inhibitory activity, and long duration of action. Accordingly, the present invention can provide a clinically useful agent for the prophylaxis or treatment of peptic ulcer (e.g., gastric ulcer, duodenal ulcer, anastomotic ulcer, ulcer caused by non-steroidal anti-inflammatory agent, ulcer due to postoperative stress etc.), Zollinger-Ellison syndrome, gastritis, erosive esophagitis, reflux esophagitis, symptomatic gastroesophageal reflux disease (Symptomatic GERD), Barrettesophagus, functional dyspepsia, gastric cancer, stomach MALT lymphoma or hyperacidity; or a suppressant of upper gastrointestinal hemorrhage due to peptic ulcer, acute stress ulcer, hemorrhagic gastritis or invasive stress; and the like. Since compound (I) shows low toxicity and is superior in water-solubility, in vivo kinetics and efficacy expression, it is useful as a pharmaceutical composition. Since compound (I) is stable even under acidic conditions, it can be administered orally as a conventional tablet and the like without formulating into an enteric-coated preparation. This has an advantageous consequence that the preparation (tablet and the like) can be made smaller, and can be easily swallowed by patients having difficulty in swallowing, particularly the elderly and children. In addition, since it is free of a sustained release effect afforded by enteric-coated preparations, a gastric acid secretion-suppressive action is expressed rapidly, and symptoms such as pain and the like can be alleviated rapidly.

This application is based on patent application Nos. 2007-050326 and 2007-256273 filed in Japan, the contents of which are incorporated in full herein by this reference.

The invention claimed is:
1. A compound represented by the formula (I)

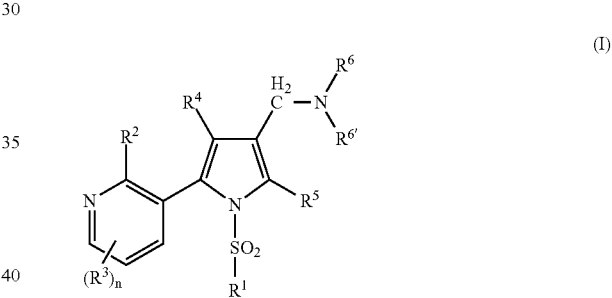

wherein $R^1$ is a pyridyl group which may optionally be substituted by 1 to 5 substituents selected from (1) a halogen atom, (2) nitro, (3) cyano, (4) hydroxy, (5) $C_{1-6}$ alkoxy optionally having 1 to 5 halogen atoms, (6) $C_{6-14}$ aryloxy, (7) $C_{7-16}$ aralkyloxy, (8) mercapto, (9) $C_{1-6}$ alkylthio optionally having 1 to 5 halogen atoms, (10) $C_{6-14}$ arylthio, (11) $C_{7-16}$ aralkylthio, (12) amino, (13) mono-$C_{1-6}$ alkylamino, (14) mono-$C_{6-14}$ arylamino, (15) mono-$C_{7-16}$ aralkylamino, (16) di-$C_{1-6}$ alkylamino, (17) di-$C_{6-14}$ arylamino, (18) di-$C_{7-16}$ aralkylamino, (19) formyl, (20) $C_{1-6}$ alkyl-carbonyl, (21) $C_{6-14}$ aryl-carbonyl, (22) carboxyl, (23) $C_{1-6}$ alkoxy-carbonyl, (24) $C_{6-14}$ aryloxy-carbonyl, (25) carbamoyl, (26) thiocarbamoyl, (27) mono-$C_{1-6}$ alkyl-carbamoyl optionally substituted by hydroxyl, (28) di-$C_{1-6}$ alkyl-carbamoyl, (29) $C_{6-14}$ aryl-carbamoyl, (30) $C_{1-6}$ alkylsulfonyl, (31) $C_{6-14}$ arylsulfonyl, (32) $C_{1-6}$ alkylsulfinyl, (33) $C_{6-14}$ arylsulfinyl, (34) formylamino, (35) $C_{1-6}$ alkyl-carbonylamino, (36) $C_{6-14}$ aryl-carbonylamino, (37) $C_{1-6}$ alkoxy-carbonylamino, (38) $C_{1-6}$ alkylsulfonylamino, (39) $C_{6-14}$ arylsulfonylamino, (40) $C_{1-6}$ alkyl-carbonyloxy, (41) $C_{6-14}$ aryl-carbonyloxy, (42) $C_{1-6}$ alkoxy-carbonyloxy, (43) mono-$C_{1-6}$ alkyl-carbamoyloxy, (44) di-$C_{1-6}$ alkyl-carbamoyloxy, (45) $C_{6-14}$ aryl-carbamoyloxy, (46) $C_{1-3}$ alkylenedioxy, (47) $C_{3-7}$ cycloalkyl, (48) a $C_{1-6}$ alkyl group optionally having 1 to 5 halogen atoms or hydroxy, (49) a $C_{2-6}$ alkenyl group optionally having 1 to 5 halogen atoms, (50) $C_{2-6}$ alkynyl group, (51) a $C_{6-14}$ aryl group optionally having 1 to 5 halogen atoms, (52) $C_{7-16}$ aralkyl optionally having 1 to 5 halogen atoms, and (53) oxo, $R^2$ is (i) a halogen atom, (ii) a cyano group, (iii)(I) a group represented by the formula —S(O)$_p$—$R^7$ wherein p is 1 or 2, and $R^7$ is a hydroxyl group, (II) a group represented by the formula —COOR$^8$ wherein $R^8$ is a hydrogen atom, (III) a group represented by the formula —CONR$^9$R$^{10}$ wherein $R^9$ and $R^{10}$ are a hydrogen atom, (IV) a group represented by the formula —SO$_2$NH—$R^{11}$ wherein $R^{11}$ is a hydrogen atom, (V) a group represented by the formula —CO—$R^{12}$ wherein $R^{12}$ is a hydrogen atom, (iv) a halogenoalkyl group, (v) a $C_{1-6}$ alkyl group, (vi) a $C_{1-6}$ alkylthio group, (vii) a $C_{1-6}$ alkoxy group, or (viii) a group represented by the —NR$^{13}$R$^{14}$ wherein $R^{13}$ and $R^{14}$ are the same or different and each is a hydrogen atom or an alkyl group, $R^3$ is an alkyl group optionally substituted by halogen, a halogen atom, a cyano group or a nitro group, $R^4$ and $R^5$ are the same or different and each is a hydrogen atom, an alkyl group optionally substituted by halogen, a halogen atom, a cyano group or a nitro group, $R^6$ is an alkyl group, $R^{6'}$ is a hydrogen atom, and n is an integer of 0 to 3, provided that 1-[5-(2-fluoropyridin-3-yl)-1-(pyridin-3-ylsulfonyl)-1H-pyrrol-3-yl]-N-methylmethanamine, 1-[5-(2-chloropyridin-3-yl)-1-(pyridin-3-ylsulfonyl)-1H-pyrrol-3-yl]-N-methylmethanamine, 1-{5-(2-fluoropyridin-3-yl)-1-[(6-methoxypyridin-3-yl)sulfonyl]-1H-pyrrol-3-yl}-N-methylmethanamine, N-methyl-1-[5-(2-methylpyridin-3-yl)-1-(pyridin-3-ylsulfonyl)-1H-pyrrol-3-yl]methanamine, 1-{5-(2-fluoropyridin-3-yl)-1-[(6-methylpyridin-3-yl)sulfonyl]-1H-pyrrol-3-yl}-N-methylmethanamine, and 1-[4-chloro-5-(2-fluoropyridin-3-yl)-1-(pyridin-3-ylsulfonyl)-1H-pyrrol-3-yl]-N-methylmethanamine are excluded, or a salt thereof.

2. The compound of claim 1, wherein the substituent for $R^2$ is (i) a halogen atom, (ii) a cyano group, (iii)(I) a group represented by the formula —S(O)$_p$—$R^7$ wherein p is 1 or 2, and $R^7$ is a hydroxyl group, (II) a group represented by the formula —COOR$^8$ wherein $R^8$ is a hydrogen atom, (III) a group represented by the formula —CONR$^9$R$^{10}$ wherein $R^9$ and $R^{10}$ are a hydrogen atom, (IV) a group represented by the formula —SO$_2$NH—$R^{11}$ wherein $R^{11}$ is a hydrogen atom, (V) a group represented by the formula —CO—$R^{12}$ wherein $R^{12}$ is a hydrogen atom, or (iv) a halogenoalkyl group.

3. The compound of claim 2, wherein the substituent for $R^2$ is (i) a halogen atom, (ii) a cyano group, (iii) (I) a group represented by the formula —S(O)—$R^7$ wherein p is 1 or 2, and $R^7$ is a hydroxyl group, (II) a group represented by the formula —COOR$^8$ wherein $R^8$ is a hydrogen atom, (III) a group represented by the formula —CONR$^9$R$^{10}$ wherein $R^9$ and $R^{10}$ are a hydrogen atom, (IV) a group represented by the formula —SO$_2$NH—$R^{11}$ wherein $R^{11}$ is a hydrogen atom, (V) a group represented by the formula —CO—$R^{12}$ wherein $R^{12}$ is a hydrogen atom, or (iv) a trifluoromethyl group.

4. The compound of claim 1, wherein $R^4$ and $R^5$ are the same or different and each is a hydrogen atom or a halogen atom.

5. The compound of claim 1, wherein $R^6$ is a methyl group.

6. The compound of claim 1, wherein n is 0.

7. A pharmaceutical composition comprising the compound of claim 1 and a pharmaceutically acceptable carrier.

8. 1-[4-Fluoro-5-(2-fluoropyridin-3-yl)-1-(pyridin-3-ylsulfonyl)-1H-pyrrol-3-yl]-N-methylmethanamine or a salt thereof.

9. 1-[4-Fluoro-5-(2-fluoropyridin-3-yl)-1-(pyridin-2-ylsulfonyl)-1H-pyrrol-3-yl]-N-methylmethanamine or a salt thereof.

* * * * *